US008822185B2

(12) United States Patent
Hong et al.

(10) Patent No.: US 8,822,185 B2
(45) Date of Patent: Sep. 2, 2014

(54) PEROXISOME BIOGENESIS FACTOR PROTEIN (PEX) DISRUPTIONS FOR ALTERING POLYUNSATURATED FATTY ACIDS AND TOTAL LIPID CONTENT IN OLEAGINOUS EUKARYOTIC ORGANISMS

(71) Applicant: E I Du Pont De Nemours and Company, Wilmington, DE (US)

(72) Inventors: Seung-Pyo Hong, Hockessin, DE (US); Pamela L Sharpe, Wilmington, DE (US); Zhixiong Xue, Chadds Ford, PA (US); Narendra S Yadav, Wilmington, DE (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/780,532

(22) Filed: Feb. 28, 2013

(65) Prior Publication Data

US 2013/0230891 A1 Sep. 5, 2013

Related U.S. Application Data

(63) Continuation of application No. 12/244,950, filed on Oct. 3, 2008, now abandoned.

(60) Provisional application No. 60/977,174, filed on Oct. 3, 2007, provisional application No. 60/977,177, filed on Oct. 3, 2007.

(51) Int. Cl.

| | |
|---|---|
| *C12P 7/64* | (2006.01) |
| *C12P 1/00* | (2006.01) |
| *C12N 9/10* | (2006.01) |
| *C12N 9/02* | (2006.01) |
| *C12N 15/81* | (2006.01) |

(52) U.S. Cl.
CPC ............ *C12P 7/6427* (2013.01); *C12N 9/1029* (2013.01); *C12N 9/0083* (2013.01); *C12N 15/815* (2013.01); *C12P 7/6472* (2013.01)
USPC ............................................ 435/134; 435/41

(58) Field of Classification Search
None
See application file for complete search history.

(56) References Cited

U.S. PATENT DOCUMENTS 7,238,482 B2 7/2007 Picataggio et al.
7,932,077 B2 * 4/2011 Damude et al. ............ 435/254.2

(Continued)

FOREIGN PATENT DOCUMENTS

| | | | |
|---|---|---|---|
| WO | WO2005003322 | | 1/2005 |
| WO | WO/2005/047485 | * | 5/2005 |
| WO | WO2006033723 | | 3/2006 |
| WO | WO/2006/052870 | * | 5/2006 |

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim

(57) ABSTRACT

Methods of increasing the amount of polyunsaturated fatty acids (PUFAs) in the total lipid fraction and in the oil fraction of PUFA-producing, oleaginous eukaryotes, accomplished by modifying the activity of peroxisome biogenesis factor (Pex) proteins, are disclosed. Disruptions of a chromosomal Pex3 gene, Pex10p gene or Pex16p gene in a PUFA-producing, oleaginous eukaryotic strain resulted in an increased amount of PUFAs, as a percent of total fatty acids and as a percent of dry cell weight, in the total lipid fraction and in the oil fraction of the strain, as compared to the parental strain whose native Pex protein was not disrupted.

14 Claims, 16 Drawing Sheets

(56) References Cited

U.S. PATENT DOCUMENTS

Figure 1A:
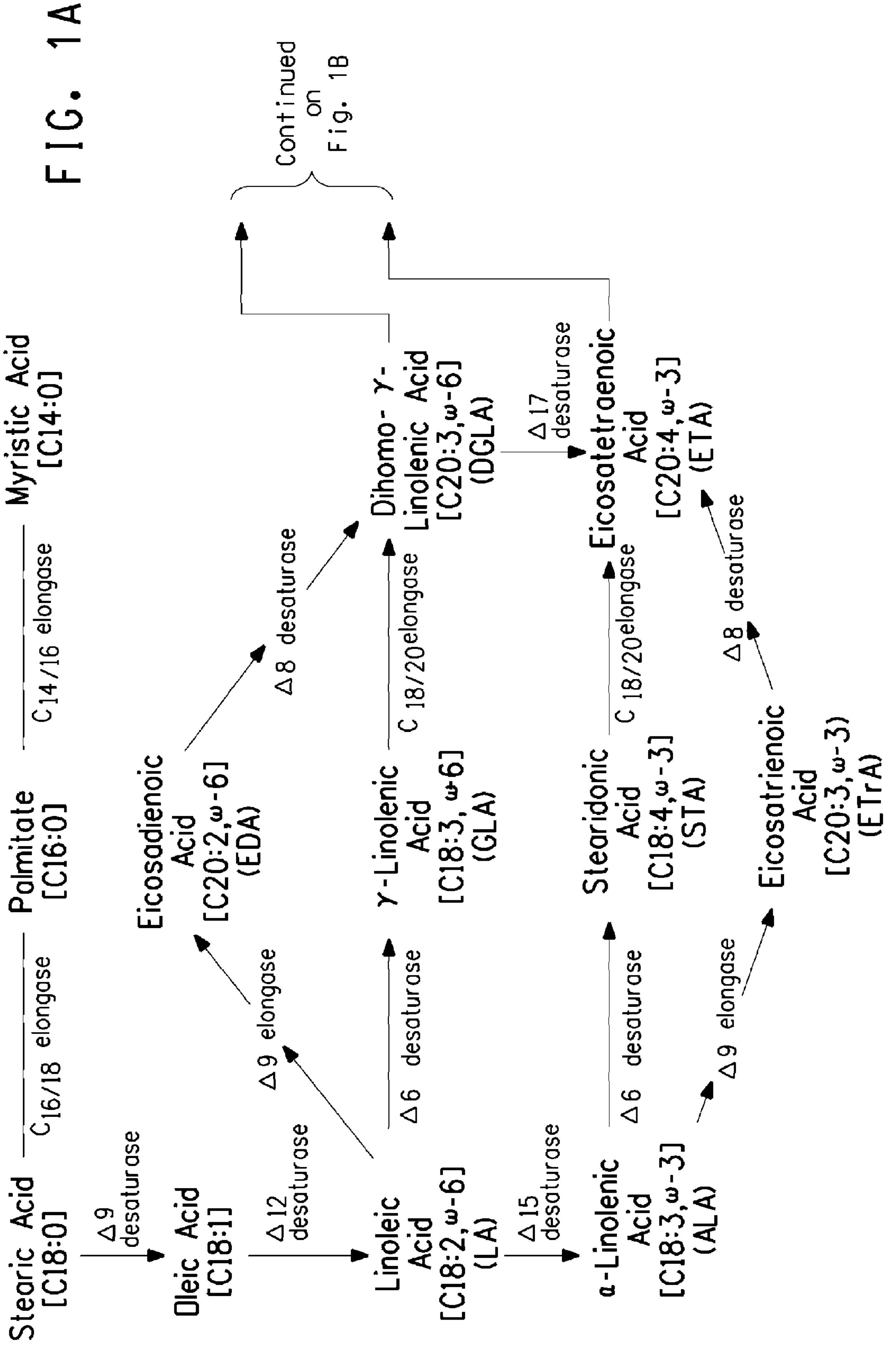

| | | | | |
|---|---|---|---|---|
| 8,313,911 | B2 * | 11/2012 | Jackson et al. | 435/6.15 |
| 2005/0043527 | A1 | 2/2005 | Yadav et al. | |
| 2006/0094092 | A1 | 5/2006 | Damude et al. | |
| 2006/0110806 | A1 | 5/2006 | Damude et al. | |
| 2006/0115881 | A1 | 6/2006 | Damude et al. | |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Lin, Plant Physiology, 135:814-827 (2004).

Binns, et al., J. Cell Biol., 173(5):719-731 (2006).

International Search Report and Written Opinion of corresponding PCT/US2008/078671 mailed Dec. 18, 2008.

Sumita et al., FEMS Microbiology Letters, 214(1):31-38 (2002).

Eitzen et al., Journal of Cell Biology, 137(6):1265-1278 (1997).

Bascom et al., Molecular Biology of the Cell, 14(3):939-957 (2003).

* cited by examiner

```
327 G T L G L S - - - - - - - - - - - - -                    (AA 327-364 of SEQ ID NO:10 [YlPex10p])
266 G A I G F R D E E Q E G G A S H Y S T                    (AA 266-323 of SEQ ID NO:2 [YlPex2p])
342 C P L G S K - - - - - - - - - - - - -                    (AA 342-391 of SEQ ID NO:11 [YlPex12p])
       *                      *

333 Y I S A R A C T P C G H F C W D C L S E W                (AA 327-364 of SEQ ID NO:10 [YlPex10p])
288 D V T N P Y Q A D C G H V Y C L V T K                    (AA 266-323 of SEQ ID NO:2 [YlPex2p])
348 E L V N P T V I E S G Y V F C N T Y R H                  (AA 342-391 of SEQ ID NO:11 [YlPex12p])
              *           *       *       *

355 V R E K P E - - - C P L - - - C C C *                    (AA 327-364 of SEQ ID NO:10 [YlPex10p])
310 H A Q G D G - C W N C Y R - - - - - -                    (AA 266-323 of SEQ ID NO:2 [YlPex2p])
370 E D G D F T G C R E V T G Q K L L G                      (AA 342-391 of SEQ ID NO:11 [YlPex12p])
           *       *         *
```

PEROXISOME BIOGENESIS FACTOR PROTEIN (PEX) DISRUPTIONS FOR ALTERING POLYUNSATURATED FATTY ACIDS AND TOTAL LIPID CONTENT IN OLEAGINOUS EUKARYOTIC ORGANISMS

This application is a continuation of pending application Ser. No. 12/244,950, filed Oct. 3, 2008, which claims the benefit of U.S. Provisional Application Nos. 60/977,174 and No. 60/977,177, both filed Oct. 3, 2007, all of which prior applications are incorporated herein by reference in their entirety.

FIELD OF THE INVENTION

This invention is in the field of biotechnology. More specifically, this invention pertains to methods useful for manipulating the polyunsaturated fatty acid (PUFA) composition and lipid content of eukaryotic organisms, based on disruption of peroxisome biogenesis factor (Pex) proteins.

BACKGROUND OF THE INVENTION

The health benefits associated with polyunsaturated fatty acids ["PUFAs"], especially ω-3 and ω-6 PUFAs, have been well documented. In order to find ways to produce large-scale quantities of ω-3 and ω-6 PUFAs, researchers have directed their work toward the discovery of genes and the understanding of the encoded biosynthetic pathways that result in lipids and fatty acids.

One effort to produce these PUFAs has introduced ω-3/ω-6 PUFA biosynthetic pathways into organisms that do not natively produce ω-3/ω-6 PUFAs. One such organism that has been extensively manipulated is the non-oleaginous yeast, *Saccharomyces cerevisiae*. However, none of the preliminary results demonstrating limited production of linoleic acid ["LA"], γ-linolenic acid ["GLA"], α-linolenic acid ["ALA"], stearidonic acid ["STA"] and/or eicosapentaenoic acid ["EPA"] are suitable for commercial exploitation.

Other efforts to produce large-scale quantities of ω-3/ω-6 PUFAs have cultivated microbial organisms that natively produce the fatty acid of choice, e.g., heterotrophic diatoms *Cyclotella* sp. and *Nitzschia* sp., *Pseudomonas, Alteromonas* or *Shewanella* species, filamentous fungi of the genus *Pythium*, or *Mortierella elongata, M. exigua* or *M. hygrophila*.

All these efforts suffer from an inability to substantially improve the yield of oil or to control the characteristics of the oil composition produced, since the fermentations rely on the natural abilities of the microbes themselves.

Commonly owned U.S. Pat. No. 7,238,482 describes the use of the oleaginous yeast *Yarrowia lipolytica* as a production host for the production of PUFAs. Oleaginous yeast are defined as those yeast that are naturally capable of oil synthesis and accumulation, where greater than 25% of the cellular dry weight is typical. Optimization of the production host has been described in the art (see for example Int'l App. Pub. No. WO 2006/033723, U.S. Pat. App. Pub. No. 2006-0094092, U.S. Pat. App. Pub. No. 2006-0115881, and U.S. Pat. App. Pub. No. 2006-0110806). The recombinant strains described therein comprise various chimeric genes expressing multiple copies of heterologous desaturases, elongases and acyltransferases and optionally comprise various native desaturase and acyltransferase knockouts to enable PUFA synthesis and accumulation. Further optimization of the host cell is needed for commercial production of PUFAs.

Lin Y. et al suggest that peroxisomes are required for both catabolic and anabolic lipid metabolism (*Plant Physiology*, 135:814-827 (2004)). However, this hypothesis was based on studies with a homolog of Pex16p in *Arabidopsis* mutants that had both abnormal peroxisome biogenesis and fatty acid synthesis (i.e., a reduction of oil to approximately 10-16% of wild type in sse1 seeds was reported). Binns, D. et al. (*J. Cell Biol.*, 173(5):719-731 (2006)) also document an intimate collaboration between peroxisomes and lipid bodies in *Saccharomyces cerevisiae*. But, previous studies of Pex knockouts have not been performed in a PUFA-producing organism.

Applicants have solved the stated problem of optimizing host cells for commercial production of PUFAs by the unpredictable mechanism of disruption of peroxisome biogenesis factor proteins in a PUFA-producing organism, which leads to the unpredictable result of an increase in the amount of PUFAs, as a percent of total fatty acids, in a recombinant PUFA-producing strain of *Y. lipolytica*. Novel strains containing disruptions in peroxisome biogenesis factor proteins are described herein.

SUMMARY OF THE INVENTION

Described herein are methods of increasing the weight percent of at least one polyunsaturated fatty acid ["PUFA"] relative to the weight percent of total fatty acids ["TFAs"] in an oleaginous eukaryotic organism having a total lipid content, a total lipid fraction and an oil fraction, comprising:

a) providing an oleaginous eukaryotic organism comprising:
   1) genes encoding a functional polyunsaturated fatty acid biosynthetic pathway; and
   2) a disruption in a native gene encoding a peroxisome biogenesis factor protein, thereby providing a PEX-disrupted organism, and
b) growing the PEX-disrupted organism under conditions as to increase the weight percent of at least one polyunsaturated fatty acid relative to the weight percent of total fatty acids in the total lipid fraction or in the oil fraction, when compared to the weight percent of the at least one polyunsaturated fatty acid relative to the weight percent of total fatty acids in the total lipid fraction or in the oil fraction in the oleaginous eukaryotic organism in which no native gene encoding a peroxisome biogenesis factor protein has been disrupted.

This method of increasing may also be used to increase the percent of at least one polyunsaturated fatty acid ["PUFA"] relative to the dry cell weight MOM by applying the same steps (a) and (b).

In some of the methods described here, the weight percent of the PUFA relative to the weight percent of the TFAs is increased at least 1.3 fold.

In some of the described methods, the total lipid content in the PEX-disrupted organism may be increased or decreased compared with that of an oleaginous eukaryote having no disruption in a native PEX gene.

In any of these methods, the increased PUFA may be a single PUFA or a combination of PUFAs. In either case, the increased PUFA or increased combination of PUFAs can include linoleic acid, conjugated linoleic acid, γ-linolenic acid, dihomo-γ-linolenic acid, arachidonic acid, docosatetraenoic acid, ω-6 docosapentaenoic acid, α-linolenic acid, stearidonic acid, eicosatetraenoic acid, eicosapentaenoic acid, ω-3 docosapentaenoic acid, eicosadienoic acid, eicosatrienoic acid, docosahexaenoic acid, hydroxylated or expoxy fatty acids of these, a $C_{18}$ polyunsaturated fatty acid or a combination of these, a $C_{20}$ polyunsaturated fatty acid or a combination of these, a combination of $C_{20-22}$ polyunsaturated fatty acids and a $C_{22}$ polyunsaturated fatty acid or a combination of these.

In any of these methods, the PEX-disrupted organism may be a member of the following: *Yarrowia, Candida, Rhodotorula, Rhodosporidium, Cryptococcus, Trichosporon, Lipomyces, Mortierella Thraustochytrium, Schizochytrium*, and *Saccharomyces* having the property of oleaginy. And, in any of the described methods, the PUFA biosynthetic pathway includes genes that encodes any or a combination of the following enzymes: Δ9 desaturase, Δ12 desaturase, Δ6 desaturase, Δ5 desaturase, Δ17 desaturase, Δ8 desaturase, Δ15 desaturase, Δ4 desaturase, $C_{14/16}$ elongase, $C_{16/18}$ elongase, $C_{18/20}$ elongase, $C_{20/22}$ elongase and Δ9 elongase.

The disruption may occur in a PEX gene that encodes a peroxisome biogenesis factor protein that includes the following: Pex1p, Pex 2p, Pex3p, Pex3Bp, Pex4p, Pex5p, Pex5Bp, Pex5Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21Bp, Pex22p, Pex22p-like and Pex26p. And in any of these methods, the disruption may be a gene knockout or a deletion in a portion of the gene that encodes the C-terminal portion of the protein. In some of these methods, the deletion is in the portion of the gene encoding the C-terminal portion of the $C_3HC_4$ zinc ring finger motif of the protein.

Also described herein is the oil fraction or the total lipid fraction in a PEX-disrupted organism, which has experienced an increase in the weight percent of at least one PUFA accomplished by the method of Claim 1. Described herein is also a PEX-disrupted *Yarrowia lipolytica*, having a disruption in a native gene encoding Pex3p or Pex10p or Pex16p. This *Y. lipolytica* may have ATCC designation ATCC PTA-8614 (strain Y4128).

Biological Deposits

The following biological materials have been deposited with the American Type Culture Collection (ATCC), 10801 University Boulevard, Manassas, Va. 20110-2209, and bear the following designations, accession numbers and dates of deposit.

| Biological Material | Accession No. | Date of Deposit |
|---|---|---|
| *Yarrowia lipolytica* Y2047 | ATCC PTA-7186 | Oct. 26, 2005 |
| *Yarrowia lipolytica* Y2201 | ATCC PTA-7185 | Oct. 26, 2005 |
| *Yarrowia lipolytica* Y2096 | ATCC PTA-7184 | Oct. 26, 2005 |
| *Yarrowia lipolytica* Y3000 | ATCC PTA-7187 | Oct. 26, 2005 |
| *Yarrowia lipolytica* Y4128 | ATCC PTA-8614 | Aug. 23, 2007 |
| *Yarrowia lipolytica* Y4127 | ATCC PTA-8802 | Nov. 29, 2007 |

The biological materials listed above were deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE LISTINGS

Figure 1B:
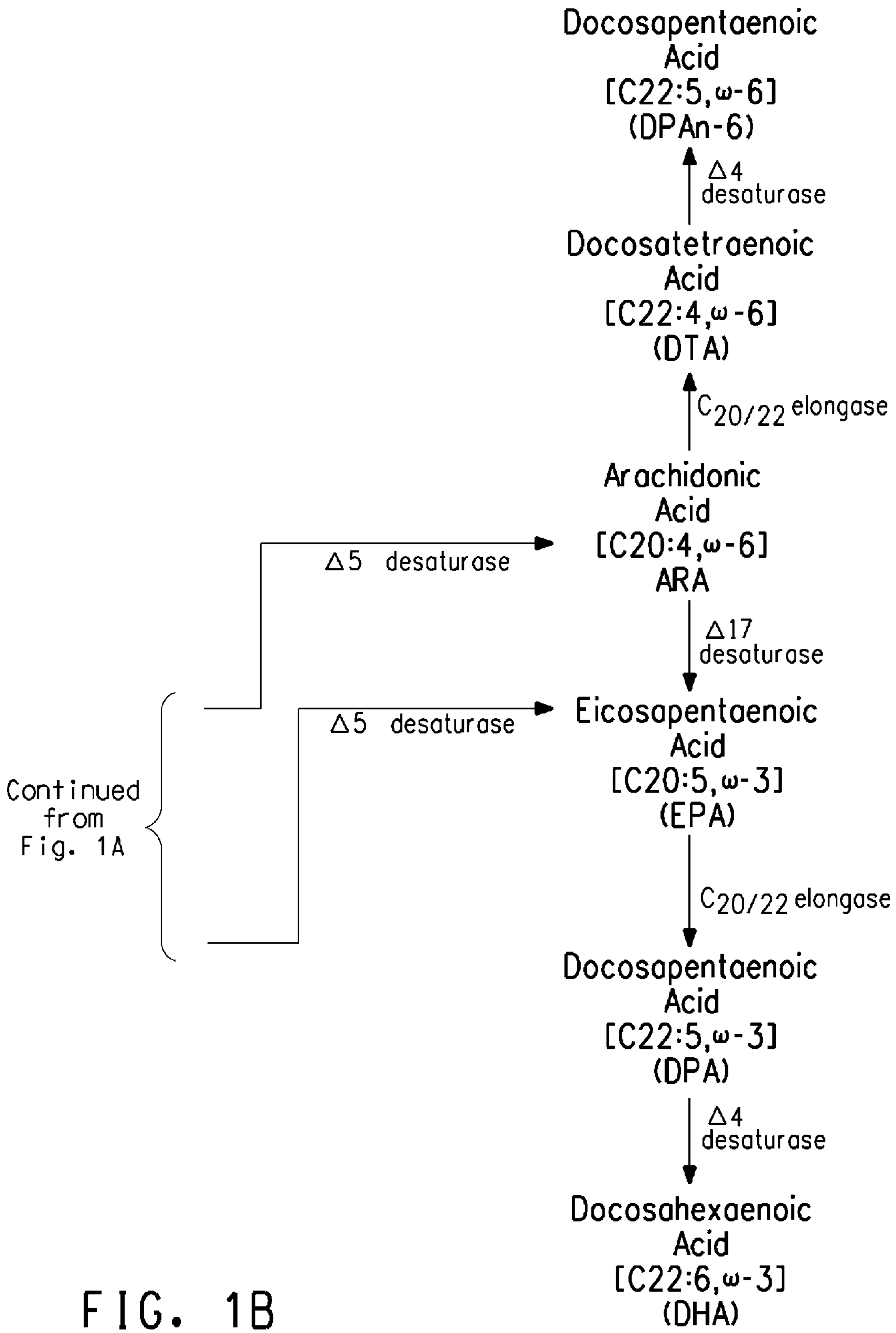

FIG. 1 consists of FIG. 1A and FIG. 1B, which together illustrate the ω-3/ω-6 fatty acid biosynthetic pathway, and should be viewed together when considering the description of this pathway below.

Figure 2A:
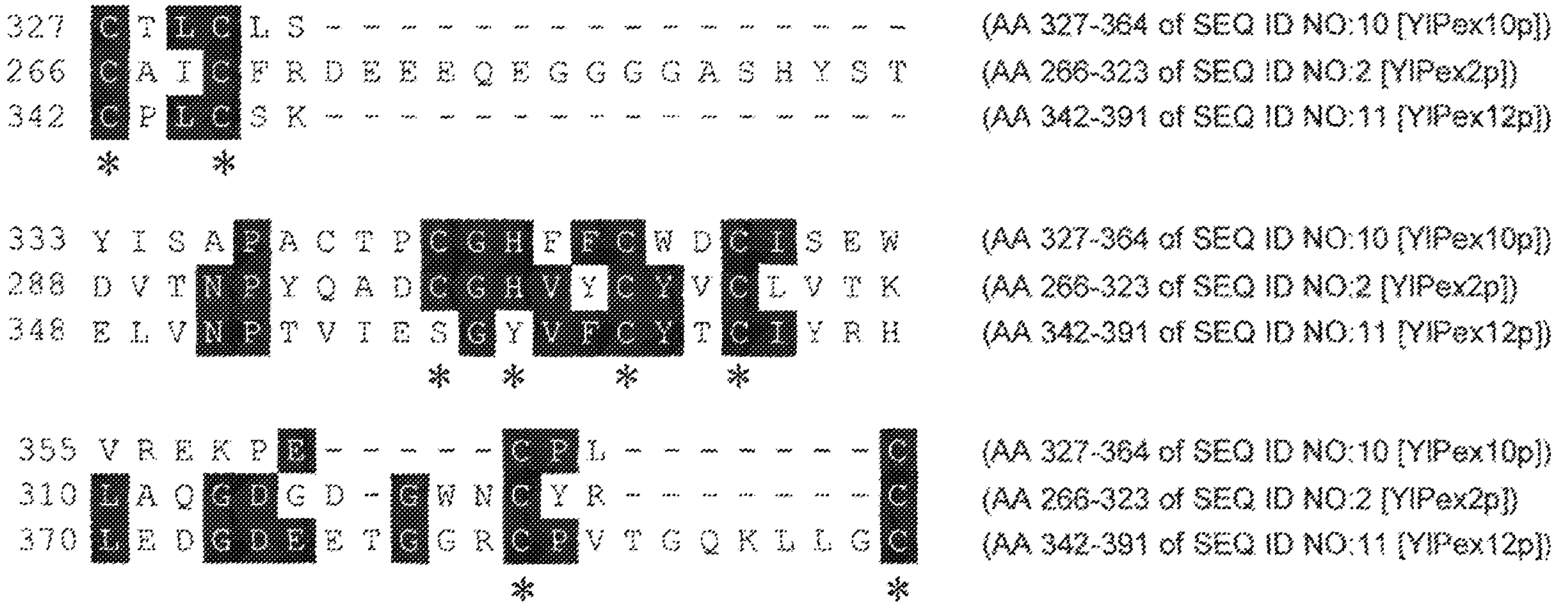

FIG. 2A provides an alignment of the $C_3HC_4$ zinc ring finger motifs of the *Yarrowia lipolytica* Pex10p (i.e., amino acids 327-364 of SEQ ID NO:10 [GenBank Accession No. CAG81606]), the *Yarrowia lipolytica* Pex2p (i.e., amino acids 266-323 of SEQ ID NO:2 [GenBank Accession No. CAG77647]) and the *Yarrowia lipolytica* Pex12p (i.e., amino acids 342-391 of SEQ ID NO:11 [GenBank Accession No. CAG81532]), with cysteine and histidine residues of the conserved $C_3HC_4$ zinc ring finger motif indicated by asterisks.

Figure 2B:
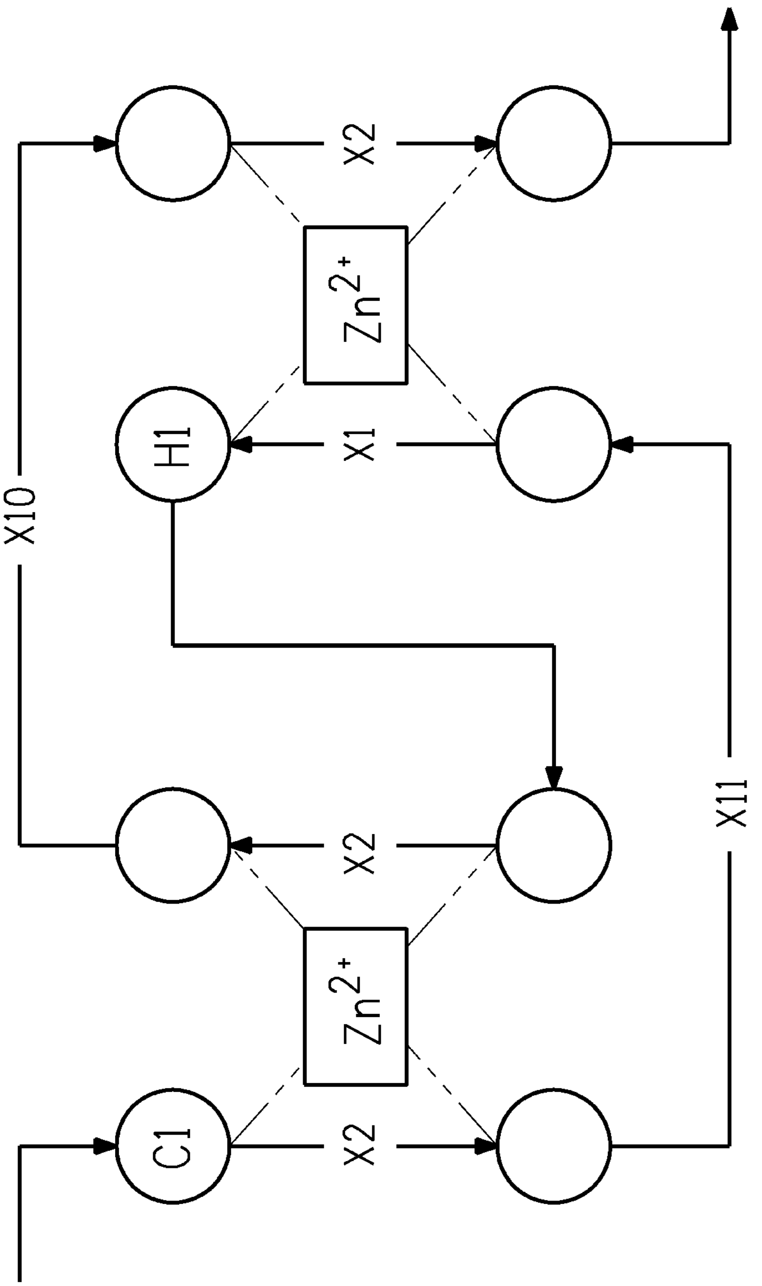

FIG. 2B schematically illustrates the proposed interaction between various amino acid residues of the *Y. lipolytica* Pex10p $C_3HC_4$ finger motif and the two zinc ions to which they bind.

Figure 3A:
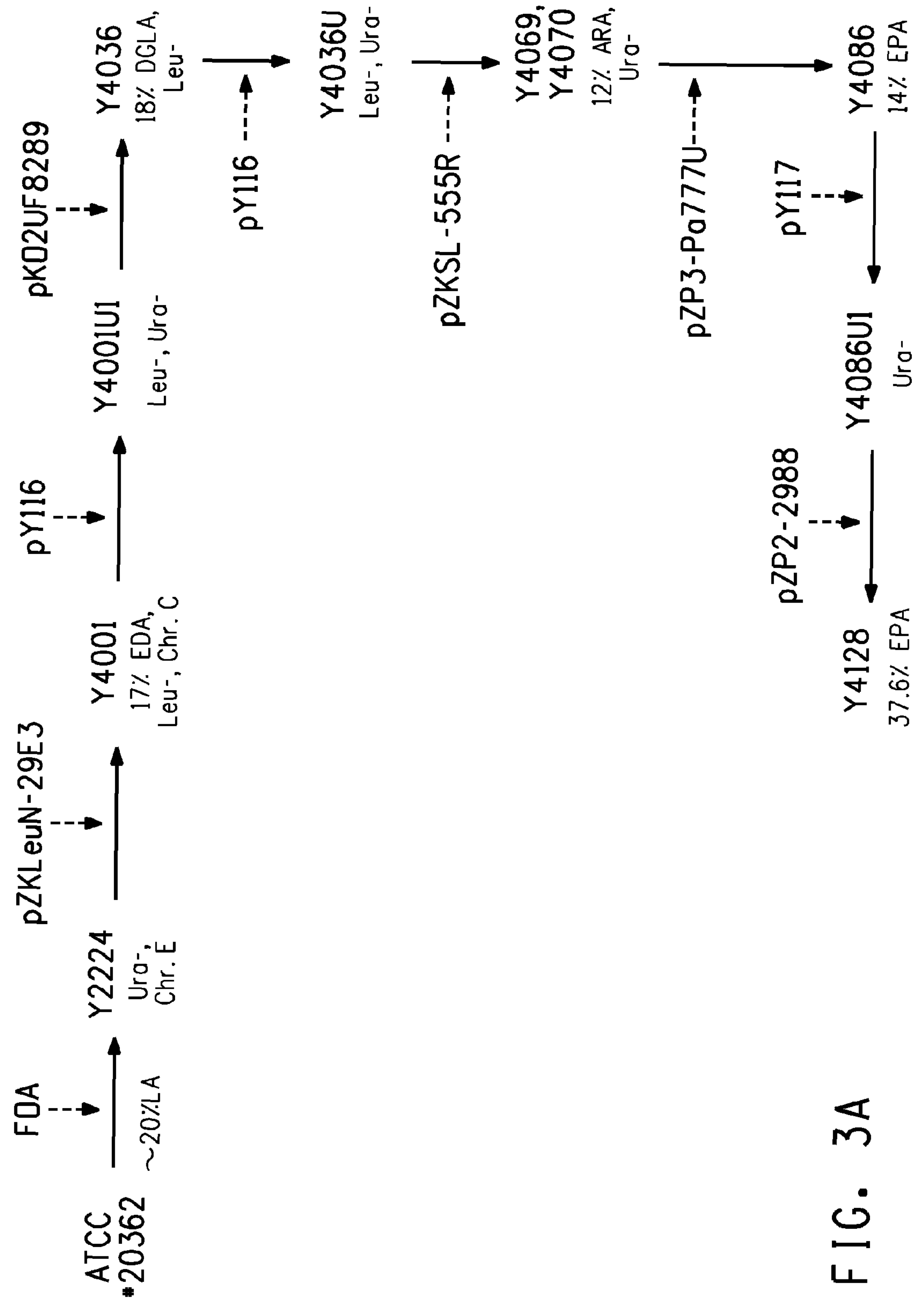

FIG. 3A diagrams the development of *Yarrowia lipolytica* strain Y4128, producing 37.6% EPA in the total lipid fraction.

Figure 3B:
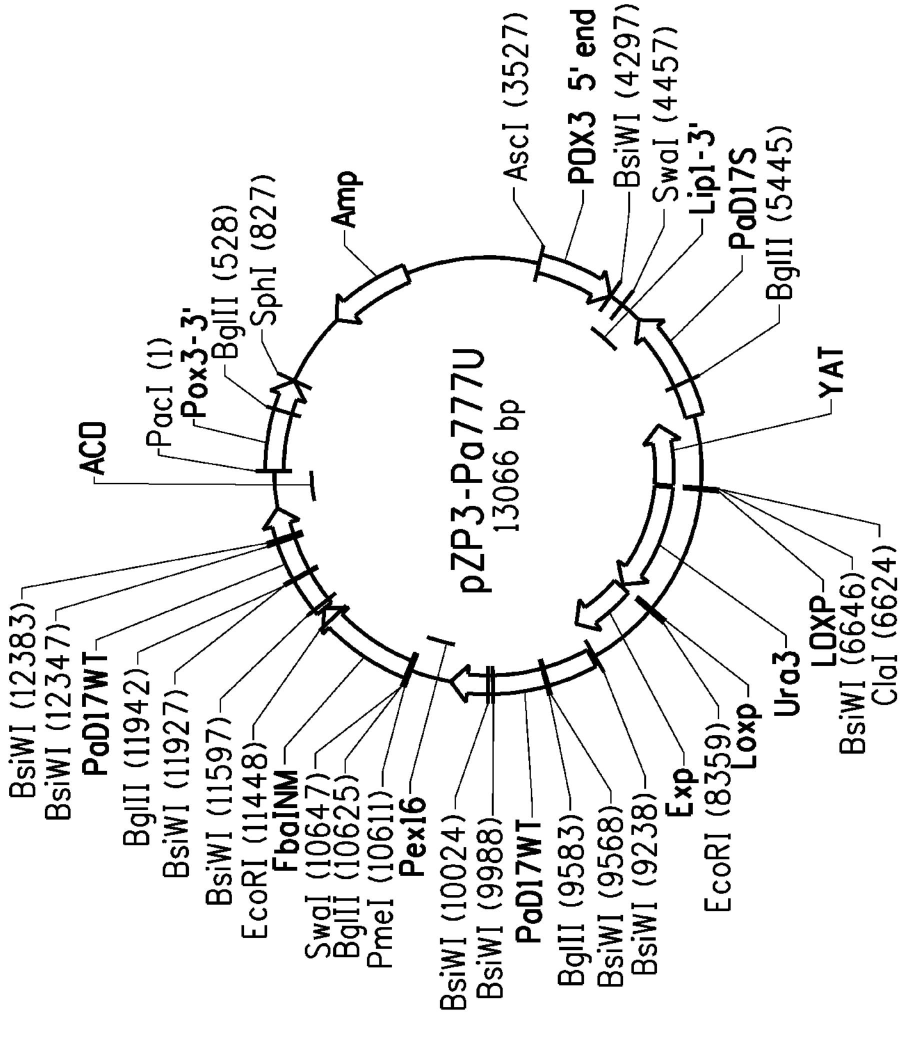

FIG. 3B provides a plasmid map for pZP3-Pa777U.

FIG. 4 provides plasmid maps for the following: (A) pY117; and, (B) pZP2-2988.

FIG. 5 provides plasmid maps for the following: (A) pZKUE3S; and, (B) pFBAIN-MOD-1.

FIG. 6 provides plasmid maps for the following: (A) pFBAIN-PEX10; and, (B) pEXP-MOD-1.

Figure 7A:
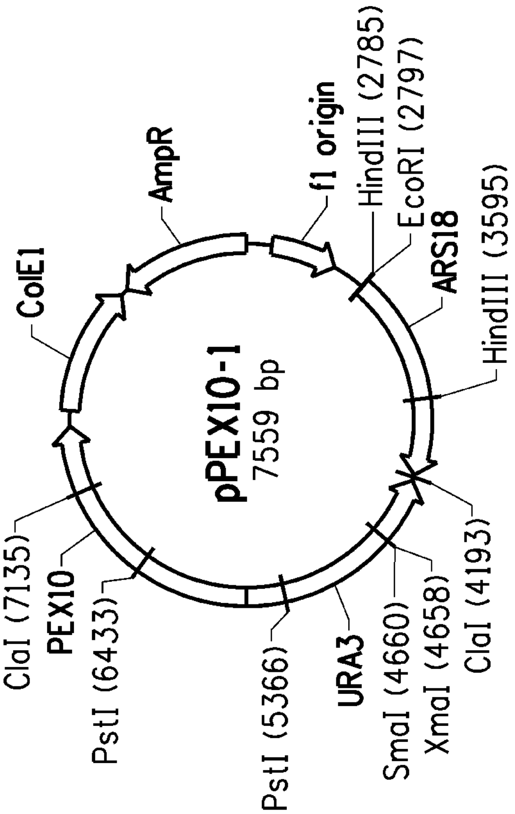
Figure 7B:
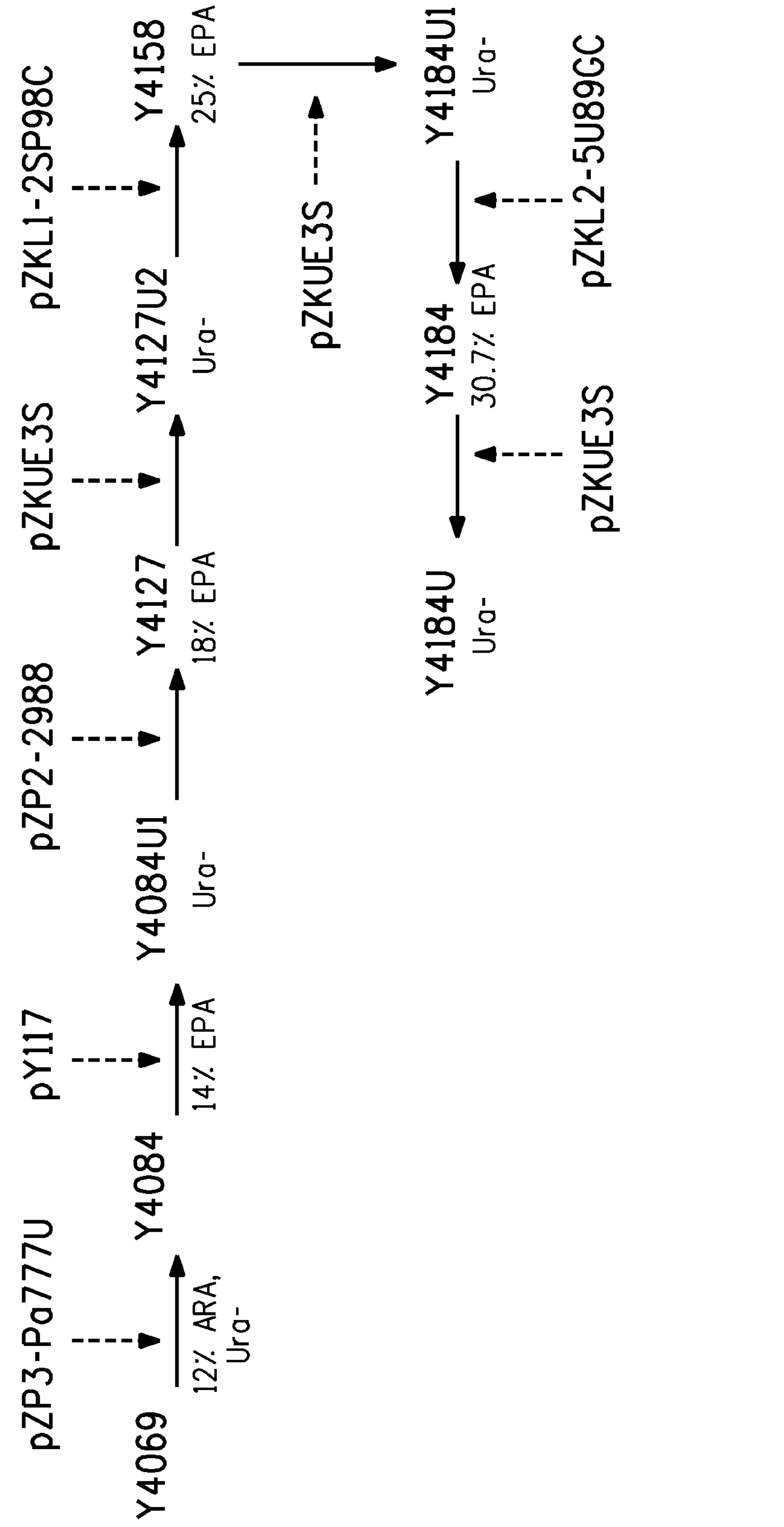

FIG. 7A provides a plasmid map for pPEX10-1. FIG. 7B diagrams the development of *Yarrowia lipolytica* strain Y4184U.

FIG. 8 provides plasmid maps for the following: (A) pZKL1-2SP98C; and, (B) pZKL2-5U89GC.

FIG. 9 provides plasmid maps for the following: (A) pYPS161; and, (B) pYRH13.

Figure 10:
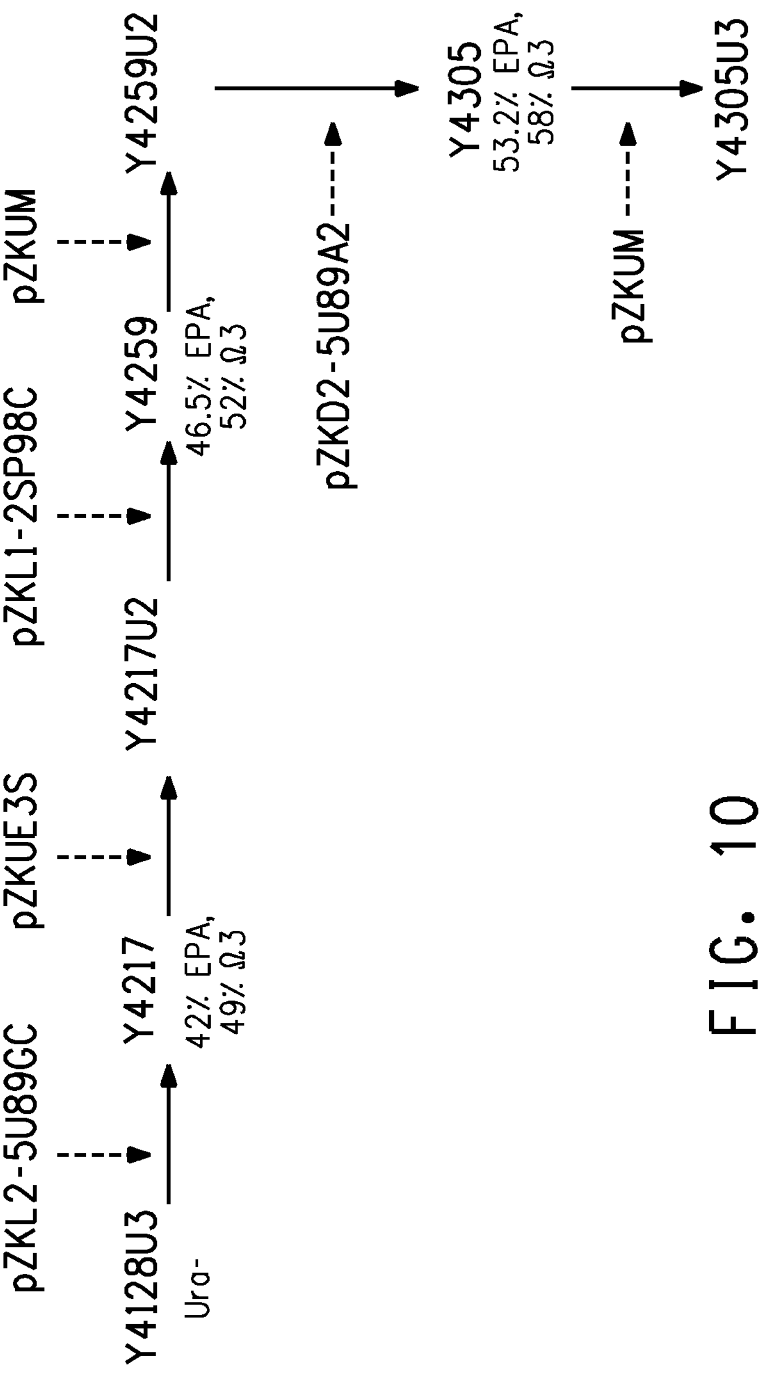

FIG. 10 diagrams the development of *Yarrowia lipolytica* strain Y4305U3.

FIG. 11 provides plasmid maps for the following: (A) pZKUM; and, (B) pZKD2-5U89A2.

Figure 12A:
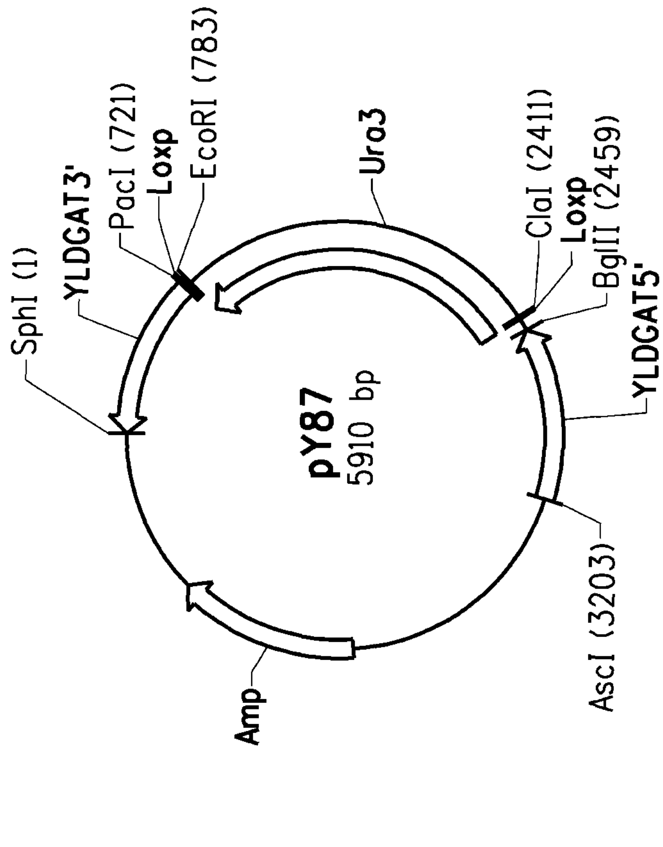

FIG. 12 provides plasmid maps for the following: (A) pY87; and, (B) pY157.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-86 are primers, ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Yarrowia lipolytica* Pex1p (GenBank Accession No. CAG82178) | — | 1 (1024 AA) |
| *Yarrowia lipolytica* Pex2p (GenBank Accession No. CAG77647) | — | 2 (381 AA) |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| *Yarrowia lipolytica* Pex3p (GenBank Accession No. CAG78565) | — | 3 (431 AA) |
| *Yarrowia lipolytica* Pex3Bp (GenBank Accession No. CAG83356) | — | 4 (395 AA) |
| *Yarrowia lipolytica* Pex4p (GenBank Accession No. CAG79130) | — | 5 (153 AA) |
| *Yarrowia lipolytica* Pex5p (GenBank Accession No. CAG78803) | — | 6 (598 AA) |
| *Yarrowia lipolytica* Pex6p (GenBank Accession No. CAG82306) | — | 7 (1024 AA) |
| *Yarrowia lipolytica* Pex7p (GenBank Accession No. CAG78389) | — | 8 (356 AA) |
| *Yarrowia lipolytica* Pex8p (GenBank Accession No. CAG80447) | — | 9 (671 AA) |
| *Yarrowia lipolytica* Pex10p (GenBank Accession No. CAG81606) | — | 10 (377 AA) |
| *Yarrowia lipolytica* Pex12p (GenBank Accession No. CAG81532) | — | 11 (408 AA) |
| *Yarrowia lipolytica* Pex13p (GenBank Accession No. CAG81789) | — | 12 (412 AA) |
| *Yarrowia lipolytica* Pex14p (GenBank Accession No. CAG79323) | — | 13 (380 AA) |
| *Yarrowia lipolytica* Pex16p (GenBank Accession No. CAG79622) | — | 14 (391 AA) |
| *Yarrowia lipolytica* Pex17p (GenBank Accession No. CAG84025) | — | 15 (225 AA) |
| *Yarrowia lipolytica* Pex19p (GenBank Accession No. AAK84827) | — | 16 (324 AA) |
| *Yarrowia lipolytica* Pex20p (GenBank Accession No. CAG79226) | — | 17 (417 AA) |
| *Yarrowia lipolytica* Pex22p (GenBank Accession No. CAG77876) | — | 18 (195 AA) |
| *Yarrowia lipolytica* Pex26p (GenBank Accession No. NC_006072, antisense translation of nucleotides 117230-118387) | — | 19 (386 AA) |
| Contig comprising *Yarrowia lipolytica* Pex10 gene encoding peroxisomal biogenesis factor protein (Pex10p) (GenBank Accession No. AB036770) | 20 (3387 bp) | — |
| *Yarrowia lipolytica* Pex10 (GenBank Accession No. AB036770, nucleotides 1038-2171) (the protein sequence is 100% identical to SEQ ID NO: 10) | 21 (1134 bp) | 22 (377 AA) |
| *Yarrowia lipolytica* Pex10 (GenBank Accession No. AJ012084, which corresponds to nucleotides 1107-2171 of GenBank Accession No. AB036770) (the first 23 amino acids are truncated with respect to the protein sequences of SEQ ID NOs: 10 and 22) | 23 (1065 bp) | 24 (354 AA) |
| *Yarrowia lipolytica* Pex10p $C_3HC_4$ zinc ring finger motif (i.e., amino acids 327-364 of SEQ ID NO: 10) | — | 25 (38 AA) |
| *Yarrowia lipolytica* truncated Pex10p (GenBank Accession No. CAG81606 [SEQ ID NO: 10], with C-terminal 32 amino acid deletion) | — | 26 (345 AA) |
| *Yarrowia lipolytica* mutant acetohydroxyacid synthase (AHAS) gene comprising a W497L mutation | 27 (2987 bp) | — |
| Plasmid pZP3-Pa777U | 28 (13,066 bp) | — |
| Plasmid pY117 | 29 (9570 bp) | — |
| Plasmid pZP2-2988 | 30 (15,743 bp) | — |
| Plasmid pZKUE3S | 31 (6303 bp) | — |
| Primer pZP-GW-5-1 | 32 | — |
| Primer pZP-GW-5-2 | 33 | — |
| Primer pZP-GW-5-3 | 34 | — |
| Primer pZP-GW-5-4 | 35 | — |
| Primer pZP-GW-3-1 | 36 | — |
| Primer pZP-GW-3-2 | 37 | — |
| Primer pZP-GW-3-3 | 38 | — |
| Primer pZP-GW-3-4 | 39 | — |
| Genome Walker adaptor [top strand] | 40 | — |
| Genome Walker adaptor [bottom strand] | 41 | — |
| Nested adaptor primer | 42 | — |
| Primer Per10 F1 | 43 | — |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| Primer ZPGW-5-5 | 44 | — |
| Primer Per10 R | 45 | — |
| Plasmid pFBAIN-MOD-1 | 46 (7222 bp) | — |
| Plasmid pFBAIn-PEX10 | 47 (8133 bp) | — |
| Primer PEX10-R-BsiWI | 48 | — |
| Primer PEX10-F1-SalI | 49 | — |
| Primer PEX10-F2-SalI | 50 | — |
| Plasmid pEXP-MOD1 | 51 (7277 bp) | — |
| Plasmid pPEX10-1 | 52 (7559 bp) | — |
| Plasmid pPEX10-2 | 53 (8051 bp) | — |
| Plasmid pZKL1-2SP98C | 54 (15,877 bp) | — |
| Plasmid pZKL2-5U89GC | 55 (15,812 bp) | — |
| Plasmid pYPS161 | 56 (7966 bp) | — |
| Primer Pex-10del1 3'.Forward | 57 | — |
| Primer Pex-10del2 5'.Reverse | 58 | — |
| Plasmid pYRH13 | 59 (8673 bp) | — |
| Primer PEX16Fii | 60 | — |
| Primer PEX16Rii | 61 | — |
| Primer 3UTR-URA3 | 62 | — |
| Primer Pex16-conf | 63 | — |
| Real time PCR primer ef-324F | 64 | — |
| Real time PCR primer ef-392R | 65 | — |
| Real time PCR primer Pex16-741F | 66 | — |
| Real time PCR primer Pex16-802R | 67 | — |
| Nucleotide portion of TaqMan probe ef-345T | 68 | — |
| Nucleotide portion of TaqMan probe PEX16-760T | 69 | — |
| Plasmid pZKUM | 70 (4313 bp) | — |
| Plasmid pZKD2-5U89A2 | 71 (15,966 bp) | — |
| *Yarrowia lipolytica* diacylglycerol acyltransferase (DGAT2) (U.S. Pat. No. 7,267,976) | 72 (2119 bp) | 73 (514 AA) |
| Synthetic Δ12 desaturase derived from *Fusarium moniliforme*, codon-optimized for expression in *Yarrowia lipolytica* ("FmD12S") | 74 (1434 bp) | 75 (477 AA) |
| Synthetic mutant Δ8 desaturase ("EgD8M"), derived from *Euglena gracilis* ("EgD8S"; U.S. Pat. No. 7,256,033) | 76 (1272 bp) | 77 (422 AA) |
| Synthetic Δ9 elongase derived from *Eutreptiella* sp. CCMP389 codon-optimized for expression in *Yarrowia lipolytica* ("E389D9eS") | 78 (792 bp) | 79 (263 AA) |
| Synthetic Δ5 desaturase derived from *Euglena gracilis*, codon-optimized for expression in *Yarrowia lipolytica* ("EgD5S") | 80 (1350 bp) | 81 (449 AA) |
| Plasmid pY157 | 82 (6356 bp) | — |
| Plasmid pY87 | 83 (5910 bp) | — |
| *Escherichia coli* LoxP recombination site, recognized by a Cre recombinase enzyme | 84 (34 bp) | — |
| Primer UP 768 | 85 | — |
| Primer LP 769 | 86 | — |

DETAILED DESCRIPTION OF THE INVENTION

Described herein are generalized methods to manipulate the concentration (as a percent of total fatty acids) and content (as a percent of the dry cell weight) of long-chain polyunsaturated fatty acids ["LC-PUFAs"] in PUFA-producing eukaryotic organisms. These methods rely on disruption of a native peroxisome biogenesis factor ["Pex"] protein within the host and will have wide-spread applicability to a variety of eukaryotic organisms having native or genetically-engineered ability to produce PUFAs, including algae, fungi, oomycetes, yeast, euglenoids, stramenopiles, plants and some mammalian systems.

PUFAs, or derivatives thereof, are used as dietary substitutes, or supplements, particularly infant formulas, for patients undergoing intravenous feeding or for preventing or treating malnutrition. For example, PUFAs may be incorporated into cooking oils, fats or margarines and ingested as part of a consumer's typical diet, thereby giving the consumer desired dietary supplementation. Further, PUFAs may also be incorporated into infant formulas, nutritional supplements or other food products and may find use as anti-inflammatory or cholesterol lowering agents. Optionally, the compositions may be used for pharmaceutical use, either human or veterinary.

DEFINITIONS

In this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

The term "invention" or "present invention" as used herein is not meant to be limiting but applies generally to any of the inventions defined in the claims or described herein.

The term "peroxisomes" refers to ubiquitous organelles found in all eukaryotic cells. They have a single lipid bilayer membrane that separates their contents from the cytosol and that contains various membrane proteins essential to the functions described below. Peroxisomes selectively import proteins via an "extended shuttle mechanism". More specifically, there are at least 32 known peroxisomal proteins, also known as peroxins, which participate in the process of importing proteins by means of ATP hydrolysis through the peroxisomal membrane. Some peroxins comprise a specific protein signal, i.e., a peroxisomal targeting signal or "PTS", at either the N-terminus or C-terminus to signal that importation through the peroxisomal membrane should occur. Once cellular proteins are imported into the peroxisome, they are typically subjected to some means of degradation. For example, peroxisomes contain oxidative enzymes, such as catalase, D-amino acid oxidase and uric acid oxidase, that enable degradation of substances that are toxic to the cell. Alternatively, peroxisomes breakdown fatty acid molecules to produce free molecules of acetyl-CoA which are exported back to the cytosol, in a process called β-oxidation.

The terms "peroxisome biogenesis factor protein", "peroxin" and "Pex protein" are interchangeable and refer to proteins involved in peroxisome biogenesis and/or that participate in the process of importing cellular proteins by means of ATP hydrolysis through the peroxisomal membrane. The acronym of a gene that encodes any of these proteins is "Pex gene". A system for nomenclature of Pex genes is described by Distel et al., *J. Cell Biol.,* 135:1-3 (1996). At least 32 different Pex genes have been identified so far in various eukaryotic organisms. Many Pex genes have been isolated from the analysis of mutants that demonstrated abnormal peroxisomal functions or structures. Based on a review by Kiel, J. A. K. W., et al. (*Traffic,* 7:1291-1303 (2006)), wherein in silico analysis of the genomic sequences of 17 different fungal species was performed, the following Pex proteins were identified: Pex1p, Pex2p, Pex3p, Pex3Bp, Pex4p, Pex5p, Pex5Bp, Pex5Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21Bp, Pex22p, Pex22p-like and Pex26p. Thus, each of these proteins is referred to herein as a "Pex protein", a "peroxin" or a "peroxisome biogenesis factor protein", and is encoded by at least one "Pex gene".

The term "conserved domain" or "motif" refers to a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Of relevance herein, Pex2p, Pex10p and Pex12p all share a cysteine-rich motif near their carboxyl termini, known as a $C_3HC_4$ zinc ring finger motif. This motif appears to be required for their activities, involved in protein docking and translocation into the peroxisome (Kiel, J. A. K. W., et al., *Traffic,* 7:1291-1303 (2006)).

The term "$C_3HC_4$ zinc ring finger motif" or "$C_3HC_4$ motif" generically refers to a conserved cysteine-rich motif that binds two zinc ions, identified by the presence of a sequence of amino acids as set forth in Formula I:

$$CX_2CX_{9-27}CX_{1-3}HX_2CX_2CX_{4-48}CX_2C \quad \text{Formula I}$$

The $C_3HC_4$ zinc ring finger motif within the *Yarrowia lipolytica* gene encoding the peroxisome biogenesis factor 10 protein, i.e., YlPex10p, is located between amino acids 327-364 of SEQ ID NO:10 and is defined by a $CX_2CX_{11}CX_1HX_2CX_2CX_{10}CX_2C$ motif (SEQ ID NO:25). The $C_3HC_4$ zinc ring finger motif within the *Y. lipolytica* gene encoding the peroxisome biogenesis factor 2 protein, i.e., YlPex2p, is located between amino acids 266-323 of SEQ ID NO:2. The *Y. lipolytica* peroxisome biogenesis factor 12 protein, i.e., YlPex12p, contains an imperfect $C_3HC_4$ ring-finger motif located between amino acids 342-391 of SEQ ID NO:11. The protein sequences corresponding to the $C_3HC_4$ zinc ring finger motif of YlPex10, YlPex2 and YlPex12 are aligned in FIG. 2A; asterisks denote the conserved cysteine or histidine residues of the motif.

YlPex10, YlPex2 and YlPex12 are thought to form a ring finger complex by protein-protein interaction. The proposed interaction between the cystine and histidine residues of the YlPex10p $C_3HC_4$ finger motif with two zinc residues is schematically diagrammed in FIG. 2B.

The term "Pex10" refers to the gene encoding the peroxisome biogenesis factor 10 protein or peroxisomal assembly protein Peroxin 10, wherein the peroxin protein is hereinafter referred to as "Pex10p". The function of Pex10p has not been clearly elucidated, although studies in other organisms have revealed that Pex10 products are localized in the peroxisomal membrane and are essential to the normal functioning of the organelle. A $C_3HC_4$ zinc ring finger motif appears to be conserved in the C-terminal region of Pex10p (Kalish, J. E. et al., *Mol. Cell Biol.,* 15:6406-6419 (1995); Tan, X. et al., *J. Cell Biol.,* 128:307-319 (1995); Warren, D. S., et al., *Am. J. Hum. Genet.,* 63:347-359 (1998)) and is required for enzymatic activity.

The term "YlPex10" refers to the *Yarrowia lipolytica* gene encoding the peroxisome biogenesis factor 10 protein, wherein the protein is hereinafter referred to as "YlPex10p". This particular peroxin was recently studied by Sumita et al. (*FEMS Microbiol. Lett.,* 214:31-38 (2002)). The nucleotide sequence of YlPex10 was registered in GenBank under multiple accession numbers, including GenBank Accession No. CAG81606 (SEQ ID NO:10), No. AB036770 (SEQ ID NOs: 20, 21 and 22) and No. AJ012084 (SEQ ID NOs:23 and 24). The YlPex10p sequence set forth in SEQ ID NO:24 is 354 amino acids in length. In contrast, the YlPex10p sequences set forth in SEQ ID NO:10 and SEQ ID NO:22 are each 377 amino acids in length, as the 100% identical sequences possess an additional 23 amino acids at the N-terminus of the protein (corresponding to a different start codon than that identified in GenBank Accession No. AJ012084 (SEQ ID NO:24)).

The term "Pex3" refers to the gene encoding the peroxisome biogenesis factor 3 protein or peroxisomal assembly protein Peroxin 3, wherein the peroxin protein is hereinafter referred to as "Pex3p". Although mechanistic details concerning the function of Pex3p have not been clearly resolved, it is clear that Pex3p is a peroxisomal integral membrane protein required early in peroxisome biogenesis for formation of the peroxisomal membrane (see, e.g., Baerends, R. J. et al., *J. Biol. Chem.,* 271:8887-8894 (1996); Bascom, R. A. et al, *Mol. Biol. Cell,* 14:939-957 (2003)).

The term "YlPex3" refers to the *Yarrowia lipolytica* gene encoding the peroxisome biogenesis factor 3 protein, wherein the protein is hereinafter referred to as "YlPex3p". The nucleotide sequence of YlPex3 was registered in GenBank as Accession No. CAG78565 (SEQ ID NO:3). The term "Pex16" refers to the gene encoding the peroxisome biogenesis factor 16 protein or peroxisomal assembly protein Peroxin 16, wherein the peroxin protein is hereinafter referred to as "Pex16p". The function of Pex16p has not been clearly elucidated, although studies in various organisms have revealed that Pex16 products play a role in the formation of the peroxisomal membrane and regulation of peroxisomal proliferation (Platta, H. W. and R. Erdmann, *Trends Cell Biol.,* 17(10):474-484 (2007)).

The term "YlPex16" refers to the *Yarrowia lipolytica* gene encoding the peroxisome biogenesis factor 16 protein, wherein the protein is hereinafter referred to as "YlPex16p". This particular peroxin was described by Elizen G. A., et al. (*J. Cell Biol.,* 137:1265-1278 (1997)) and Titorenko, V. I. et al. (*Mol. Cell Biol.,* 17:5210-5226 (1997)). The nucleotide sequence of YlPex16 was registered in GenBank as Accession No. CAG79622 (SEQ ID NO:14).

The term "disruption" in or in connection with a native Pex gene refers to an insertion, deletion, or targeted mutation within a portion of that gene, that results in either a complete gene knockout such that the gene is deleted from the genome and no protein is translated or a translated Pex protein having an insertion, deletion, amino acid substitution or other targeted mutation. The location of the disruption in the protein may be, for example, within the N-terminal portion of the protein or within the C-terminal portion of the protein. The disrupted Pex protein will have impaired activity with respect to the Pex protein that was not disrupted, and can be non-functional. A disruption in a native gene encoding a Pex protein also includes alternate means that result in low or lack of expression of the Pex protein, such as could result via manipulating the regulatory sequences, transcription and translation factors and/or signal transduction pathways or by use of sense, antisense or RNAi technology, etc.

As used herein, the term "Pex-disrupted organism" refers to any oleaginous eukaryotic organism comprising genes that encode a functional polyunsaturated fatty acid biosynthetic pathway and having a disruption, as defined above, in a native gene that encodes a peroxisome biogenesis factor protein, The term "'lipids" refer to any fat-soluble (i.e., lipophilic), naturally-occurring molecule. Lipids are a diverse group of compounds that have many key biological functions, such as structural components of cell membranes, energy storage sources and intermediates in signaling pathways. Lipids may be broadly defined as hydrophobic or amphiphilic small molecules that originate entirely or in part from either ketoacyl or isoprene groups. A general overview of lipids, based on the Lipid Metabolites and Pathways Strategy (LIPID MAPS) classification system (National Institute of General Medical Sciences, Bethesda, Md.), is shown below in Table 2.

TABLE 2

Overview Of Lipid Classes

| Structural Building Block | Lipid Category | Examples Of Lipid Classes |
|---|---|---|
| Derived from condensation of ketoacyl subunits | Fatty Acyls | Includes fatty acids, eicosanoids, fatty esters and fatty amides |
| | Glycerolipids | Includes mainly of mono-, di- and tri-substituted glycerols, the most well-known being the fatty acid esters of glycerol ["triacylglycerols"] |
| | Glycero-phospholipids or Phospholipids | Includes phosphatidylcholine, phosphatidylethanolamine, phosphatidylserine, phosphatidylinositols and phosphatidic acids |
| | Sphingolipids | Includes ceramides, phospho-sphingolipids (e.g., sphingomyelins), glycosphingolipids (e.g., gangliosides), sphingosine, cerebrosides |
| | Saccharolipids | Includes acylaminosugars, acylamino-sugar glycans, acyltrehaloses, acyltrehalose glycans |
| | Polyketides | Includes halogenated acetogenins, polyenes, linear tetracyclines, polyether antibiotics, flavonoids, aromatic polyketides |
| Derived from condensation of isoprene subunits | Sterol Lipids | Includes sterols (e.g., cholesterol), C18 steroids (e.g., estrogens), C19 steroids (e.g., androgens), C21 steroids (e.g., progestogens, glucocorticoids and mineral-ocorticoids), secosteroids, bile acids |
| | Prenol Lipids | Includes isoprenoids, carotenoids, quinones, hydroquinones, polyprenols, hopanoids |

The term "total lipid fraction" of cells herein refers to all esterified fatty acids of the cell. Various subfractions within the total lipid fraction can be isolated, including the triacylglycerol ["oil"] fraction, phosphatidylcholine fraction and the phosphatidylethanolamine fraction, although this is by no means inclusive of all sub-fractions.

"Lipid bodies" refer to lipid droplets that are bound by a monolayer of phospholipid and, usually, by specific proteins. These organelles are sites where most organisms transport/store neutral lipids. Lipid bodies are thought to arise from microdomains of the endoplasmic reticulum that contain TAG biosynthesis enzymes. Their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The terms "triacylglycerols" ["TAGs"] and "oil" are interchangeable and refer to neutral lipids composed of three fatty acyl residues esterified to a glycerol molecule. TAGs can contain long chain PUFAs, as well as shorter saturated and unsaturated fatty acids and longer chain saturated fatty acids. The TAG fraction of cells is also referred to as the "oil fraction", and "oil biosynthesis" generically refers to the synthesis of TAGs in the cell. The oil or TAG fraction is a sub-fraction of the total lipid fraction, although also it constitutes a major part of the total lipid content, measured as the weight of total fatty acids in the cell as a percent of the dry cell weight [see below], in oleaginous organisms. The fatty acid composition in the oil ["TAG"] fraction and the fatty acid composition of the total lipid fraction are generally similar. Thus, an increase or decrease in the concentration of PUFAs in the total lipid fraction will correspond with an increase or decrease in the concentration of PUFAs in the oil ["TAG"] fraction, and vice versa.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the total lipid fraction or the oil fraction, for example. Thus, total fatty acids include fatty acids from neutral and polar lipid fractions, including the phosphatidylcholine fraction, the phosphatidylethanolamine fraction and the diacylglycerol, monoacylglycerol and triacylglycerol ["TAG or oil"] fractions but not free fatty acids.

The term "total lipid content" of cells is a measure of TFAs as a percent of the dry cell weight ["DCW"]. Thus, total lipid content ["TFAs DCW"] is equivalent to, e.g., milligrams of total fatty acids per 100 milligrams of DCW.

Generally, the concentration of a fatty acid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its percent of the dry cell weight ["% DCW"]. Thus, for example, eicosapentaenoic acid % DCW would be determined according to the following formula: (eicosapentaenoic acid % TFAs)*(TFA % DCW)]/100.

The terms "lipid profile" and "lipid composition" are interchangeable and refer to the amount of an individual fatty acid contained in a particular lipid fraction, such as in the total lipid fraction or the oil ["TAG"] fraction, wherein the amount is expressed as a percent of TFAs. The sum of each individual fatty acid present in the mixture should be 100.

As used herein, the term "fold increase" refers to an increase obtained by multiplying by a number. For example, multiplying by 1.3 a quantity, an amount, a concentration, a weight percent, etc. provides a 1.3 fold increase.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 3. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that are used throughout the specification and the chemical name of each compound.

TABLE 3

Nomenclature of Polyunsaturated Fatty Acids And Precursors

| Common Name | Abbreviation | Chemical Name | Shorthand Notation |
|---|---|---|---|
| Myristic | — | Tetradecanoic | 14:0 |
| Palmitic | Palmitate | Hexadecanoic | 16:0 |
| Palmitoleic | — | 9-hexadecenoic | 16:1 |
| Stearic | — | Octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosatrienoic | DRA | cis-10,13,16-docosatrienoic | 22:3 ω-3 |
| Docosa-tetraenoic | DTA | cis-7,10,13,16-docosatetraenoic | 22:4 ω-3 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

Although the ω-3/ω-6 PUFAs listed in Table 3 are the most likely to be accumulated in the oil fractions of oleaginous yeast using the methods described herein, this list should not be construed as limiting or as complete.

As used herein, the terms "a combination of polyunsaturated fatty acids" or "any combination of polyunsaturated fatty acids" refers to a mixture of any two or more of the polyunsaturated fatty acids listed above in Table 3. Such combination has the attributes of a concentration and of a weight percent that can be measured relative to a variety of concentrations or weight percents in the cell, including relative to the weight percent of the total fatty acids in the cell.

A metabolic pathway, or biosynthetic pathway, in a biochemical sense, can be regarded as a series of chemical reactions occurring in order within a cell, catalyzed by enzymes, to achieve either the formation of a metabolic product to be used or stored by the cell, or the initiation of another metabolic pathway, which is termed "flux generating step". Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature. See e.g., Int'. App. Pub. No. WO 2006/052870. Briefly, this process involves elongation of the carbon chain through the addition of carbon atoms and desaturation of the elongated molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode them) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

The term "ω-3/ω-6 fatty acid biosynthetic pathway" refers to a set of genes which, when expressed under the appropriate conditions, encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions, such that one portion generates only ω-3 fatty acids and the other portion, only ω-6 fatty acids. That portion that generates only ω-3 fatty acids is referred to herein as the ω-3 fatty acid biosynthetic pathway, whereas that portion that generates only ω-6 fatty acids is referred to herein as the ω-6 fatty acid biosynthetic pathway.

The term "functional" as used herein relating to the ω-3/ω-6 fatty acid biosynthetic pathway, means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all of the genes listed in the above paragraph are required, as a number of fatty acid products require only the expression of a subset of the genes of this pathway.

The term "Δ6 desaturase/Δ6 elongase pathway" refers to a PUFA biosynthetic pathway that minimally includes at least one Δ6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" refers to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "desaturase" refers to a polypeptide that can desaturate adjoining carbons in a fatty acid by removing a hydrogen from one of the adjoining carbons and thereby introducing a double bond between them. Desaturation produces a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: 1) Δ5 desaturases that catalyze the conversion of the substrate fatty acid, DGLA, to ARA and/or of the substrate fatty acid, ETA, to EPA; 2) Δ17 desaturases that desaturate a fatty acid between the 17th and 18th carbon atom numbered from the carboxyl-terminal end of the molecule and which, for example, catalyze the conversion of the substrate fatty acid, ARA, to EPA and/or the conversion of the substrate fatty acid, DGLA, to ETA; 3) Δ6 desaturases that catalyze the conversion of the substrate fatty acid, LA, to GLA and/or the conversion of the substrate fatty acid, ALA, to STA; 4) Δ12 desaturases that catalyze the conversion of the substrate fatty acid, oleic acid, to LA; 5) Δ15 desaturases that catalyze the conversion of the substrate fatty acid, LA, to ALA and/or the conversion of the substrate fatty acid, GLA, to STA; 6) Δ4 desaturases that catalyze the conversion of the substrate fatty acid, DPA, to DHA and/or the conversion of the substrate fatty acid, DTA, to DPAn-6; 7) Δ8 desaturases that catalyze the conversion of the substrate fatty acid, EDA, to DGLA and/or the conversion of the substrate fatty acid, ETrA, to ETA; and, 8) Δ9 desaturases that catalyze the conversion of the substrate fatty acid, palmitate, to palmitoleic acid (16:1) and/or the conversion of the substrate fatty acid, stearic acid, to oleic acid. Δ15 and Δ17 desaturases are also occasionally referred to as "omega-3 desaturases", "w-3 desaturases", and/or "ω-3 desaturases", based on their ability to convert ω-6 fatty acids into their ω-3 counterparts (e.g., conversion of LA into ALA and ARA into EPA, respectively). It may be desirable to empirically determine the specificity of a particular fatty acid desaturase by transforming a suitable host with the gene for the fatty acid desaturase and determining its effect on the fatty acid profile of the host.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in U.S. Pat. App. Pub. No. 2005/0132442 and Int'l App. Pub. No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase utilizes a $C_{14}$ substrate e.g., myristic acid, a $C_{16/18}$ elongase utilizes a $C_{16}$ substrate e.g., palmitate, a $C_{18/20}$ elongase [also known as a Δ6 elongase as the terms can be used interchangeably] utilizes a $C_{18}$ substrate e.g., GLA or STA, and a $C_{20/22}$ elongase utilizes a $C_{20}$ substrate e.g., EPA. In like manner, a Δ9 elongase is able to catalyze the conversion of LA and ALA to EDA and ETrA, respectively. It is important to note that some elongases have broad specificity and thus a single enzyme may be capable of catalyzing several elongase reactions. For example a single enzyme may thus act as both a $C_{16/18}$ elongase and a $C_{18/20}$ elongase.

The terms "conversion efficiency" and "percent substrate conversion" refer to the efficiency by which a particular enzyme, such as a desaturase, can convert substrate to product. The conversion efficiency is measured according to the following formula: ([product]/[substrate+product])*100, where 'product' includes the immediate product and all products in the pathway derived from it.

The term "oleaginous" refers to those organisms that tend to store their energy source in the form of oil (Weete, In: Fungal Lipid Biochemistry, 2$^{nd}$ Ed., Plenum, 1980).

The term "oleaginous yeast" refers to those microorganisms classified as yeasts that can make oil, that is, TAGs. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)). Oleaginous microorganisms as referred to herein typically accumulate in excess of about 25% of their dry cell weight as oil or TAGs. Examples of oleaginous yeast include, but are not limited to, the following genera: *Yarrowia, Candida, Rhodotorula, Rhodosporidium, Cryptococcus, Trichosporon* and *Lipomyces.*

As used herein, the terms "isolated nucleic acid fragment" and "isolated nucleic acid molecule" are used interchangeably and refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), which is hereby incorporated herein by reference, particularly Chapter 11 and Table 11.1.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or of thirty or more contiguous nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation, such as in situ hybridization of microbial colonies or bacteriophage plaques. In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the Pex nucleic acid fragments described herein, such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, such as 0.5×SSC, 0.1% SDS, 60° C., with the sequences exemplified herein, or to any portion of the nucleotide sequences disclosed herein and which are functionally equivalent thereto.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Int'l. App. Pub. No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA derived from nucleic acid fragments. Expression may also refer to translation of mRNA into a polypeptide.

"Mature" protein refers to a post-translationally processed polypeptide, i.e., one from which any pre- or pro-peptides present in the primary translation product have been removed. "Precursor" protein refers to the primary product of translation of mRNA, i.e., with pre- and pro-peptides still present. Pre- and pro-peptides may be, but are not limited to, intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence, i.e., open reading frame ["ORF"] and, 3) a 3' untranslated region, i.e., a terminator that in eukaryotes usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "percent identity" refers to a relationship between two or more polypeptide sequences or two or more polynucleotide sequences, as determined by comparing the sequences. "Identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ v6.1 program of the LASERGENE bioinformatics computing suite (DNASTAR Inc.). After alignment of the sequences using either Clustal program, it is possible to obtain a "percent identity" by viewing the "sequence distances" table in the program.

It is well understood by one skilled in the art that various measures of sequence percent identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing suitable nucleic acid fragments (isolated polynucleotides) encoding polypeptides in methods and host cells described herein, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In some cases, suitable nucleic acid fragments (isolated polynucleotides) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" means any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238,482. Palmitate is the precursor of longer-chain saturated and unsaturated fatty acid derivates, which are formed through the action of elongases and desaturases (FIG. 1).

TAGs, the primary storage unit for fatty acids, are formed by a series of reactions that involve: 1) esterification of one molecule of acyl-CoA to glycerol-3-phosphate via an acyltransferase to produce lysophosphatidic acid; 2) esterification of a second molecule of acyl-CoA via an acyltransferase to yield 1,2-diacylglycerol phosphate, commonly identified as phosphatidic acid; 3) removal of a phosphate by phosphatidic acid phosphatase to yield 1,2-diacylglycerol ["DAG"]; and, 4) addition of a third fatty acid by the action of an acyltransferase to form the TAG.

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases include: capric (10:0), lauric (12:0), myristic (14:0), palmitic (16:0), palmitoleic (16:1), stearic (18:0), oleic (18:1), vaccenic (18:1), LA (18:2), eleostearic (18:3), GLA (18:3), ALA (18:3), STA (18:4), arachidic (20:0), EDA (20:2), DGLA (20:3), ETrA (20:3), ARA (20:4), ETA (20:4), EPA (20:5), behenic (22:0), DPA (22:5), DHA (22:6), lignoceric (24:0), nervonic (24:1), cerotic (26:0) and montanic (28:0) fatty acids. In the methods and host cells described herein, incorporation of "long-chain" PUFAs into TAGs may be most desirable, wherein long-chain PUFAs include any fatty acid derived from an 18:1 substrate having at least 18 carbons in length, i.e., $C_{18}$ or greater. This also includes hydroxylated fatty acids, expoxy fatty acids and conjugated linoleic acid.

Although most PUFAs are incorporated into TAGs as neutral lipids and are stored in lipid bodies, it is important to note that a measurement of the total PUFAs within an oleaginous organism should include those PUFAs that are located in the phosphatidylcholine fraction, phosphatidyl-ethanolamine fraction, and triacylglycerol, also known as the TAG or oil, fraction.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, FIG. 1 depicts the pathways described below. All pathways require the initial conversion of oleic acid to linoleic acid ["LA"], the first of the ω-6 fatty acids, by a Δ12 desaturase. Then, using the "Δ6 desaturase/Δ6 elongase pathway" and LA as substrate, long-chain ω-6 fatty acids are formed as follows: 1) LA is converted to γ-linolenic acid

["GLA"] by a Δ6 desaturase; 2) GLA is converted to dihomo-γ-linolenic acid ["DGLA"] by a $C_{18/20}$ elongase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase.

Alternatively, the "Δ6 desaturase/Δ6 elongase pathway" can use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to stearidonic acid ["STA"] by a Δ6 desaturase; 3) STA is converted to eicosatetraenoic acid ["ETA"] by a $C_{18/20}$ elongase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity.

Alternate pathways for the biosynthesis of ω-3/ω-6 fatty acids utilize Δ9 elongase and Δ8 desaturase, that is, the "Δ9 elongase/Δ8 desaturase pathway". More specifically, LA and ALA may be converted to EDA and ETrA, respectively, by a Δ9 elongase. A Δ8 desaturase then converts EDA to DGLA and/or ETrA to ETA. Downstream PUFAs are subsequently formed as described above.

The host organism herein must possess the ability to produce PUFAs, either naturally or via techniques of genetic engineering. Although many microorganisms can synthesize PUFAs (including ω-3/ω-6 fatty acids) in the ordinary course of cellular metabolism, some of whom could be commercially cultured, few to none of these organisms produce oils having a desired oil content and composition for use in pharmaceuticals, dietary substitutes, medical foods, nutritional supplements, other food products, industrial oleochemicals or other end-use applications. Thus, there is increasing emphasis on the ability to engineer microorganisms for production of "designer" lipids and oils, wherein the fatty acid content and composition are carefully specified by genetic engineering. On this basis, it is expected that the host likely comprises heterologous genes encoding a functional PUFA biosynthetic pathway but not necessarily.

If the host organism does not natively produce the desired PUFAs or possess the desired lipid profile, one skilled in the art is familiar with the considerations and techniques necessary to introduce one or more expression cassettes encoding appropriate enzymes for PUFA biosynthesis into the host organism of choice. Numerous teachings are provided in the literature to one of skill for so introducing such expression cassettes into various host organisms. Some references using the host organism *Yarrowia lipolytica* are provided as follows: U.S. Pat. No. 7,238,482, Int'l. App. Pub. No. WO 2006/033723, Pat. Appl. Pub. No. US-2006-0094092, Pat. Appl. Pub. No. US-2006-0115881-A1 and Pat. Appl. Pub. No. US-2006-0110806-A1. This list is not exhaustive and should not be construed as limiting.

Briefly, a variety of ω-3/ω-6 PUFA products can be produced prior to their transfer to TAGs, depending on the fatty acid substrate and the particular genes of the ω-3/ω-6 fatty acid biosynthetic pathway that are present in or transformed into the host cell. As such, production of the desired fatty acid product can occur directly or indirectly. Direct production occurs when the fatty acid substrate is converted directly into the desired fatty acid product without any intermediate steps or pathway intermediates. Indirect production occurs when multiple genes encoding the PUFA biosynthetic pathway may be used in combination such that a series of reactions occur to produce a desired PUFA. Specifically, it may be desirable to transform an oleaginous yeast with an expression cassette comprising a Δ12 desaturase, Δ6 desaturase, a $C_{18/20}$ elongase, a Δ5 desaturase and a Δ17 desaturase for the overproduction of EPA. See U.S. Pat. No. 7,238,482 and Int'l. App. Pub. No. WO 2006/052870. As is well known to one skilled in the art, various other combinations of genes encoding enzymes of the PUFA biosynthetic pathway may be useful to express in an oleaginous organism (see FIG. 1). The particular genes included within a particular expression cassette depend on the host organism, its PUFA profile and/or desaturase/elongase profile, the availability of substrate and the desired end product(s).

A number of candidate genes having the desired desaturase and/or elongase activities can be identified according to publicly available literature, such as GenBank, the patent literature, and experimental analysis of organisms having the ability to produce PUFAs. Useful desaturase and elongase sequences may be derived from any source, e.g., isolated from a natural source such as from bacteria, algae, fungi, oomycete, yeast, plants, animals, etc., produced via a semi-synthetic route or synthesized de novo. Following the identification of these candidate genes, considerations for choosing a specific polypeptide having desaturase or elongase activity include: 1) the substrate specificity of the polypeptide; 2) whether the polypeptide or a component thereof is a rate-limiting enzyme; 3) whether the desaturase or elongase is essential for synthesis of a desired PUFA; 4) co-factors required by the polypeptide; and/or, 5) whether the polypeptide is modified after its production, such as by a kinase or a prenyltransferase.

The expressed polypeptide preferably has parameters compatible with the biochemical environment of its location in the host cell. See U.S. Pat. No. 7,238,482. It may also be useful to consider the conversion efficiency of each particular desaturase and/or elongase. More specifically, since each enzyme rarely functions with 100% efficiency to convert substrate to product, the final lipid profile of un-purified oils produced in a host cell is typically a mixture of various PUFAs consisting of the desired ω-3/ω-6 fatty acid, as well as various upstream intermediary PUFAs. Thus, the conversion efficiency of each enzyme is also a variable to consider when optimizing biosynthesis of a desired fatty acid.

Peroxisome Biogenesis and Pex Genes

As previously described, peroxisomes are ubiquitous organelles found in all eukaryotic cells. Their primary role is the degradation of various substances within a localized organelle of the cell, such as toxic compounds, fatty acids, etc. For example, the process of β-oxidation, wherein fatty acid molecules are broken down to ultimately produce free molecules of acetyl-CoA (which are exported back to the cytosol), can occur in peroxisomes. Although the process of β-oxidation in mitochondria results in ATP synthesis, β-oxidation in peroxisomes causes the transfer of high-potential electrons to $O_2$ and results in the formation of $H_2O_2$, which is subsequently converted to water and $O_2$ by peroxisome catalases. Very long chain, such as $C_{18}$ to $C_{22}$, fatty acids undergo initial β-oxidation in peroxisomes, followed by mitochondrial β-oxidation.

The proteins responsible for importing proteins by means of ATP hydrolysis through the peroxisomal membrane are known as peroxisome biogenesis factor proteins, or "peroxins". These peroxisome biogenesis factor proteins also include those proteins involved in peroxisome biogenesis/assembly. The gene acronym for peroxisome biogenesis factor proteins is Pex; and, a system for nomenclature is described by Distel et al., *J. Cell Biol.,* 135:1-3 (1996). At least 32 different Pex genes have been identified so far in various eukaryotic organisms. In fungi, however, the recent review of Kiel et al. (*Traffic,* 7:1291-1303 (2006)) suggests that the minimal requirement for peroxisome biogenesis/matrix protein import is numbered as 17, thereby requiring only Pex1p, Pex2p, Pex3p, Pex4p, Pex5p, Pex6p, Pex7p, Pex8p, Pex10p, Pex12p, Pex13p, Pex14p, Pex17p, Pex19p, Pex20p, Pex22p and Pe26p. These proteins act in a coordinated fashion to proliferate (duplicate) peroxisomes and import proteins via translocation into peroxisomes (reviewed in Waterham, H. R. and J. M. Cregg. *BioEssays.* 19(1):57-66 (1996)).

Many Pex genes were initially isolated from the analysis of mutants that demonstrated abnormal peroxisomal functions or structures. With the availability of complete genome sequences, however, it is becoming increasingly easy to identify Pex genes via computer sequence searches based on homology. Kiel et al. (*Traffic,* 7:1291-1303 (2006)) cite strong conservation of the peroxisome biogenesis machinery, despite occasional low sequence similarity. More specifically, within the yeast and filamentous fungi, their data indicate that almost all Pex proteins identified thus far are conserved. Table 4, below, shows peroxisome biogenesis factor proteins identified by Kiel et al. (supra) in *Saccharomyces cerevisiae, Candida glabrata, Ashbya gossypii, Kluyveromyces lactis, Candida albicans, Debaryomyces hansenii, Pichia pastoris, Hansenula polymorpha, Yarrowia lipolytica, Aspergillus fumigatus, Aspergillus nidulans, Penicillium chrysogenum, Magnaporthe grisea, Neurospora crassa, Gibberella zeae, Ustilago maydis, Cryptococcus neoformans* var. *neoformans* and *Schizosaccharomyces pombe*.

TABLE 4

GenBank Accession Numbers Of Fungal Peroxisome Biogenesis Factor Proteins
[Recreated From Table 2 of Kiel et al., (Traffic, 7:1291-1303 (2006))]

| | *Saccharomyces cerevisiae* | *Candida glabrata* | *Ashbya gossypii* | *Kluyveromyces lactis* | *Candida albicans* | *Debaryomyces hansenii* | *Pichia pastoris* | *Hansenula polymorpha* | *Yarrowia lipolytica* |
|---|---|---|---|---|---|---|---|---|---|
| Pex1p | CAA82041 | CAG60131 | AAS53742 | CAH02218 | EAL02496 | CAG89689 | CAA85450 | AAD52811 | CAG82178 |
| Pex2p | CAA89508 | CAG60461 | AAS50677 | CAH00186 | EAK95929 | CAG85956 | CAA65646 | AAT97412 | CAG77647 |
| Pex3p | AAB64764 | CAG62379 | AAS52217 | CAG99801 | EAK94771 | CAG89890 | CAA96530 | AAC49471 | CAG78565 |
| Pex3Bp | — | — | — | — | — | — | na | — | CAG83356 |
| Pex4p | CAA97146 | CAG60639 | AAS53685 | CAG99212 | EAL03336 | CAG87262 | AAA53634 | AAC16238 | CAG79130 |
| Pex5p | CAA89730 | CAG61665 | AAS53824 | CAH01742 | EAK94251 | CAG89098 | AAB40613 | AAC49040 | CAG78803 |
| Pex5Bp | — | CAG61076 | — | — | — | — | na | — | — |
| Pex5Cp | CAA89120 (Ymr018wp) | — | — | — | — | — | na | — | — |
| Pex5/20p | — | — | — | — | — | — | na | — | — |
| Pex5Rp | — | — | — | — | — | — | na | — | — |
| Pex6p | AAA16574 | CAG58438 | AAS54884 | CAG99125 | EAK95956 | CAG87108 | CAA80278 | AAD52812 | CAG82306 |
| Pex7p | CAA57183 | CAG57936 | AAS54301 | CAG99215 | EAK95226 | CAG87150 | AAC08303 | ABA64462 | CAG78389 |
| Pex8p | CAA97079 | CAG61238 | AAS52889 | CAH01253 | EAK91777, EAK91778* | CAG89446 | AAC41653 | CAA82928 | CAG80447 |
| Pex9p | ORF wrongly identified | — | — | — | — | — | — | — | — |
| Pex10p | AAB64453 | CAG62699 | AAS53069 | CAG99788 | Translation of AACQ-01000128, nucleotides 37281-36306 (contains intron) | CAG89101 | AAB09086 | CAA86101 | CAG81606 |
| Pex12p | CAA89129 | CAG62649 | AAS50837 | CAG99378 | EAL00707 | CAG84342 | AAC49402 | AAM66157 | CAG81532 |
| Pex13p | AAB46885 | CAG57840 | AAS51456 | CAG99931 | EAK97421 | CAG86337 | AAB09087 | DQ345349 | CAG81789 |
| Pex14p | AAS56829 | CAG58828 | AAS54871 | CAG99440 | EAK90926 | CAG91028 | AAG28574 | AAB40596 | CAG79323 |
| Pex15p | CAA99046 | CAG58938 | AAS51506 | CAG98135 | — | — | na | — | — |
| Pex16p | — | — | — | — | — | — | na | — | CAG79622 |
| Pex17p | CAA96116 | CAG61398 | AAS50595 | CAH01010 | EAK95385 | CAG86168 | AAF19606 | DQ345350 | CAG84025 |
| Pex14/17p | — | — | — | — | — | — | na | — | — |
| Pex18p | AAB68992 | — | — | — | — | — | na | — | — |
| Pex19p | CAA98630 | CAG58359 | AAS52741 | CAG99258 | EAK97275 | CAG84799 | AAD43507 | AAK84070 | AAK84827 |
| Pex20p | — | — | — | — | EAK91603, EAK94766* | CAG87898 | AAX11696 | AAX14715 | CAG79226 |
| Pex21p | CAA97267 | CAG59241 | AAS51769 | CAG99735 | — | — | na | — | — |
| Pex21Bp | — | CAG60281 | — | — | — | — | na | — | — |
| Pex22p | AAC04978 | CAG60970 | AAS52329 | CAG97800 | EAK91040 | CAG88727 | AAD45664 | DQ384616 | CAG77876 |
| Pex22p-like | — | — | — | — | — | na | — | — | EAL90994 |
| Pex26p | — | — | — | — | EAK91093 | CAG88929 | na | DQ645588 | Antisense translation of NC_006072, nucleotides 117230-118387 |

TABLE 4-continued

GenBank Accession Numbers Of Fungal Peroxisome Biogenesis Factor Proteins
[Recreated From Table 2 of Kiel et al., (Traffic, 7:1291-1303 (2006))]

| | *Aspergillus fumigatus* | *Aspergillus nidulans* | *Penicillium chrysogenum* | *Magna-porthe grisea* | *Neurospora crassa* | *Gibberella zeae* | *Ustilago maydis* | *Cryptococcus neoformans* var. *neoformans* | *Schizo-saccharo-myces pombe* |
|---|---|---|---|---|---|---|---|---|---|
| Pex1p | EAL93310 | EAA57740 | AAG09748 | XP_364454 | EAA34641 | EAA76787 | EAK85195 | AAW43248 | CAA19256 |
| Pex2p | EAL88068 | EAA58944 | DQ793192 | XP_368589 | EAA35361 | EAA70670 | EAK81310 | AAW40683 | CAA16981 |
| Pex3p | EAL91965 | EAA64392 | DQ793193 | XP_369909 | EAA33751 | EAA76989 | EAK87104 | AAW42444 | CAB10141 |
| Pex3Bp | — | — | — | — | — | — | — | — | — |
| Pex4p | EAL87211 | Translation of AACD0-1000130, nucleotides 150195-150738 (contains intron) | DQ793194 | XP_369064 | EAA34737 | EAA76379 | Translation of AACP0-1000006, nucleotides 97041-96550 (contains intron) | — | CAB91184 |
| Pex5p | EAL85289 | EAA63772 | AAR12222 | XP_360528 | EAA36111 | EAA68640 | EAK83659 | AAW46349 | CAA22179 |
| Pex5Bp | — | — | — | — | — | — | — | — | — |
| Pex5Cp | — | — | — | — | — | — | — | — | — |
| Pex5/20p | — | — | — | — | — | — | EAK82973 | AAW41849 | — |
| Pex5Rp | — | — | — | — | — | — | — | — | — |
| Pex6p | EAL92776 | EAA63496 | AAG09749 | XP_368715 | EAA36040 | EAA73732 | EAK83459 | AAW45333 | CAB11501 |
| Pex7p | EAL90870 | EAA65909 | DQ793195 | XP_363555 | AAN39560 | EAA74171 | EAK84499 | AAW41119 | P78798 |
| Pex8p | EAL93137 | EAA57947 | DQ793196 | XP_359449 | EAA27783 | EAA77627 | EAK83936 | AAW43468 | CAB53406 |
| Pex9p | — | — | — | — | — | — | — | — | — |
| Pex10p | EAL87045 | EAA62774 | DQ793197 | XP_369099 | EAA34967 | EAA76761 | EAK83811 | AAW45079 | CAB51769 |
| Pex12p | EAL93972 | EAA61357 | DQ793198 | XP_363845 | EAA32773 | EAA76413 | EAK81282 | AAW46724 | CAD27496 |
| Pex13p | EAL85282 | EAA63824 | DQ793199 | XP_369087 | EAA35785 | EAA68396 | EAK84395 | AAW42381 | CAB16740 |
| Pex14p | EAL92562 | EAA61046 | DQ793200 | XP_368216 | EAA28304 | EAA76904 | EAK83123 | AAW46857 | CAA18656 |
| Pex15p | — | — | — | — | — | — | — | — | — |
| Pex16p | EAL88469 | EAA62294 | DQ793201 | XP_364166 | EAA34648 | EAA71849 | EAK82801 | AAW43797 | CAA22819 |
| Pex17p | See Pex14/17p | — | — | — | — | — | — | — | — |
| Pex14/17p | EAL93590 | EAA58642 | DQ793202 | XP_368163 | EAA27748 | EAA73655 | EAK81127 | — | — |
| Pex18p | — | — | — | — | — | — | — | — | — |
| Pex19p | EAL92487 | EAA60977 | DQ793203 | XP_368273 | EAA31855 | EAA70162 | EAK86072 | AAW42876 | CAA97344 |
| Pex20p | EAL90176 | EAA60479 | DQ793204 | XP_368606 | AAN39561 | EAA76911 | — | — | — |
| Pex21p | — | — | — | — | — | — | — | — | — |
| Pex21Bp | — | — | — | — | — | — | — | — | — |
| Pex22p | — | — | — | — | — | — | — | — | — |
| Pex22p-like | EAL90994 | EAA66006 | DQ793205 | XP_365689 | EAA26537 | Translation of AACM0-1000080, nucleotides 4362-3039 (contains intron) | — | — | — |
| Pex26p | EAL93994 | EAA61336 | DQ793206 | XP_359606 | EAA28582 | EAA76391 | — | — | — |

*Partial ORFs encoded on non-overlapping contigs.

Mutations of Pex genes leading to impaired peroxisome biogenesis result in severe metabolic and developmental disturbances in yeasts, humans and plants (Eckert, J. H. and R. Erdmann, *Rev. Physiol. Biochem Pharmacol.,* 147:75-121 (2003); Weller, S. et al., *Annual Review of Genomics and Human Genetics,* 4:165-211 (2003); Wanders, R. J., *Am. J. Med. Genet.,* 126A:355-375 (2004); Mano, S. and M. Nishimura, *Vitam Horm.,* 72:111-154 (2005); Wanders, J. A., and H. R. Waterham, *Annu. Rev. Biochem.,* 75:295-332 (2006); Fujiki, Yukio. Peroxisome Biogenesis Disorders. In, *Encyclopedia of Life Sciences*. John Wiley & Sons, 2006). For example, X-linked adrenoleukodystrophy ["X-ALD"] and Zellweger syndrome, as well as several less severe forms of the disease, can result from single enzyme deficiencies and/or peroxisomal biogenesis disorders.

Within the yeast, *Yarrowia lipolytica*, a variety of different Pex genes have been isolated and characterized, as identified in Table 4 above. More specifically, Bascom, R. A. et al. (*Mol. Biol. Cell,* 14:939-957 (2003)) describe YlPex3p; Szilard, R. K. et al. (*J. Cell Biol.,* 131:1453-1469 (1995)) describe YlPex5p; Nuttley, W. M. et al. (*J. Biol. Chem.,* 269:556-566 (1994)) describe YlPex6p; Elizen G. A., et al. (*J. Biol. Chem.,* 270:1429-1436 (1995)) describe YlPex9p; Elizen G. A., et al. (*J. Cell Biol.,* 137:1265-1278 (1997)) and Titorenko, V. I. et al. (*Mol. Cell Biol.,* 17:5210-5226 (1997)) describe YlPex16p; Lambkin, G. R. and R. A. Rachubinski (*Mol. Biol. Cell.,* 12(11):3353-3364 (2001)) describe YlPex19; and Titorenko V. I., et al. (*J. Cell Biol.,* 142:403-420 (1998)) and Smith J. J. and R. A. Rachubinski (*J. Cell Biol.,* 276:1618-1625 (2001)) describe YlPex20p.

Of initial interest herein was YlPex10p (GenBank Accession No. CAG81606, No. AB036770 and No. AJ012084). It was demonstrated in Sumita et al. (*FEMS Microbiol. Lett.,* 214:31-38 (2002) that: 1) YlPex10p functions as a component of the peroxisome; and, 2) the $C_3HC_4$ zinc ring finger motif of YlPex10p was essential for the protein's function as determined via creation of C341S, C346S and H343W point mutations, followed by analysis of growth.

Studies of the $C_3HC_4$ zinc ring finger motif of Pex10 have been done in other organisms with similar results. For example, point mutations that alter conserved residues in the Pex10p $C_3HC_4$ motif of *Pichia pastoris* were found to abolish function of the protein (Kalish, J. E. et al., *Mol. Cell Biol.,* 15:6406-6419 (1995)). Similarly, after functional complementation assays in fibroblast cell lines, Warren D. S., et al. (*Hum. Mutat.,* 15(6):509-521 (2000)) concluded that the $C_3HC_4$ motif was critical for Pex10p function. Several studies show that loss of function of Pex10p in *Arabidopsis* causes embryo lethality at the heart stage (Hu, J., et al., *Science,* 297:405-409 (2002); Schmumann, U. et al., *Proc. Natl. Acad. Sci. U.S.A.,* 100:9626-9631 (2003); Sparkes, I. A., et al., *Plant Physiol.,* 133:1809-1819 (2003); Fan, J. et al., *Plant Physiol.,* 139:231-239 (2005)). In follow-up research, Schemann, U. et al. (*Proc. Natl. Acad. Sci. U.S.A.,* 104:1069-1074 (2007)) investigated the function of Pex10p in nonlethal partial loss-of-function *Arabidopsis* mutants. Specifically, four T-DNA insertion lines expressing Pex10p with a dysfunctional $C_3HC_4$ motif were created in an *Arabidopsis* wildtype background. Mutant plants demonstrated impaired leaf peroxisomes and the authors suggest that inactivation of the ring finger motif in Pex10p eliminated protein interaction required for attachment of peroxisomes to chloroplasts and movement of metabolites between peroxisomes and chloroplasts.

Although studies have not identified essential domains in other Pex proteins, research has looked at the effect of various Pex mutants to learn the strategies and the molecular mechanisms evolutionarily diverse organisms use for assembling, maintaining, propagating and inheriting the peroxisome, an organelle known for its role in lipid metabolism. For example, Bascom, R. A. et al. has performed knockout and overexpression of the *Yarrowia lipolytica* Pex3p (*Mol. Biol. Cell,* 14:939-957 (2003)). The knockout cells did not contain wild-type perixosomes but instead had numerous small vesicles; overexpression resulted in cells with fewer, larger and clustered peroxisomes. They hypothesized that Pex3p is involved in the initiation of peroxisome assembly by sequestering components of peroxisome biogenesis, i.e., peroxisome targeting signal (PTS) 1 and 2 import machineries. Similarly, for Guo, T. et al., knockout of the *Y. lipolytica* Pex16p resulted in excessive proliferation of immature peroxisomal vesicles and significantly decreased the rate and efficiency of their conversion to mature peroxisomes (*J. Cell Biol.,* 162:1255-1266 (2003)), while overexpression resulted in few but enlarged peroxisomes (Eitzen et al., *J. Cell Biol.,* 137:1265-1278 (1997)). Guo et al. concluded Pex16p negatively regulated the membrane scission event required for division of early peroxisomal precursors.

Despite the advances summarized above, many details concerning the roles of various Pex proteins, their interaction with one another and the biogenesis/assembly mechanism in peroxisomes remains to be elucidated. As such, the data described in the Application, wherein mutation within the $C_3HC_4$ motif of YlPex10p or knockout of YlPex3p, YlPex10p or YlPex16p results in creation of a *Yarrowia lipolytica* mutant that has an increased capacity to incorporate PUFAs, especially long-chain PUFAs such as $C_{20}$ to $C_{22}$ molecules, into the total lipid fraction and in the oil fraction in the cell, is a novel observation that does not yet find validation in studies with other plants or animals.

It has been suggested that peroxisomes are required for both catabolic and anabolic lipid metabolism (Lin, Y. et al., *Plant Physiology,* 135:814-827 (2004)); however, this hypothesis was based on studies with a homolog of Pex16p. More specifically, Lin, Y. et al. (supra) reported that *Arabidopsis* Shrunken Seed 1 (sse1) mutants had both abnormal peroxisome biogenesis and fatty acid synthesis, based on a reduction of oil to approximately 10-16% of wild type in sse1 seeds. Binns, D. et al. (*J. Cell Biol.,* 173(5):719-731 (2006)) examined the peroxisome-lipid body interactions in *Saccharomyces cerevisiae* and determined that extensive physical contact between the two organelles promotes coupling of lipolysis within lipid bodies with peroxisomal fatty acid oxidation. More specifically, ratios of free fatty acids to TAGs were examined in various Pex knockouts and found to be increased relative to the wildtype. Clearly, further investigation will be necessary to understand the metabolic roles of peroxisomes and in particular of Pex3p, Pex10p and Pex16p proteins.

Without wishing to be held to any particular explanation or theory, it is hypothesized that disruption or knockout of a Pex gene within an oleaginous yeast cell affects both the catabolic and anabolic lipid metabolism that naturally occurs in peroxisomes or is affected by peroxisomes. Disruption or knockout results in an increase in the amount of PUFAs in the total lipid fraction and in the oil fraction, as a percent of total fatty acids, as compared with an oleaginous yeast whose native peroxisome biogenesis factor protein has not been disrupted. In some cases, an increase in the amount of PUFAs in the total lipid fraction and in the oil fraction as a percent of dry cell weight, and/or an increase in the total lipid content as a percent of dry cell weight, is also observed. It is hypothesized that this generalized mechanism is applicable within all eukaryotic organisms, such as algae, fungi, oomycetes, yeast, euglenoids, stramenopiles, plants and some mammalian systems, since all comprise peroxisomes.

Identification and Isolation of Pex Homologs

When the sequence of a particular Pex gene or protein within a preferred host organism is not known, one skilled in the art recognizes that it will be most desirable to identify and isolate these genes, or portions of them, prior to regulating the activity of the encoded proteins, which regulation in turn facilitates altering the amount, as a percent of total fatty acids, of PUFAs incorporated into the total lipid fraction and in the oil fraction of the eukaryote. Sequence knowledge of the preferred host's Pex genes also facilitates disruption of the homologous chromosomal genes by targeted disruption.

The Pex sequences in Table 4, or portions of them, may be used to search for Pex homologs in the same or other algal, fungal, oomycete, euglenoid, stramenopiles, yeast or plant species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.* 25:3389-3402 (1997)), is well-known for comparing any Pex protein in Table 4 against a database of nucleic or protein sequences and thereby identifying similar known sequences within a preferred host organism.

Use of a software algorithm to comb through databases of known sequences is particularly suitable for the isolation of homologs having a relatively low percent identity to publicly available Pex sequences, such as those described in Table 4. It is predictable that isolation would be relatively easier for Pex homologs of at least about 70%-85% identity to publicly available Pex sequences. Further, those sequences that are at least about 85%-90% identical would be particularly suitable for isolation and those sequences that are at least about 90%-95% identical would be the most facilely isolated.

Some Pex homologs have also been isolated by the use of motifs unique to the Pex enzymes. For example, it is well known that Pex2p, Pex10p and Pex12p all share a cysteine-rich motif near their carboxyl termini, known as a $C_3HC_4$ zinc ring finger motif (FIG. 2A). This region of "conserved domain" corresponds to a set of amino acids that are highly conserved at specific positions and likely represents a region of the Pex protein that is essential to the structure, stability or activity of the protein. Motifs are identified by their high degree of conservation in aligned sequences of a family of protein homologues. As unique "signatures", they can determine if a protein with a newly determined sequence belongs to a previously identified protein family. These motifs are useful as diagnostic tools for the rapid identification of novel Pex2, Pex10 and/or Pex12 genes, respectively.

Alternatively, the publicly available Pex sequences or their motifs may be hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are hybridizable to the nucleic acid sequence to be detected. Although probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well known. Typically the probe and the sample must be mixed under conditions that permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and the sample nucleic acid occurs. The concentration of probe or target in the mixture determine the time necessary for hybridization to occur. The higher the concentration of the probe or target, the shorter the hybridization incubation time needed. Optionally, a chaotropic agent may be added, such as guanidinium chloride, guanidinium thiocyanate, sodium thiocyanate, lithium tetrachloroacetate, sodium perchlorate, rubidium tetrachloroacetate, potassium iodide or cesium trifluoroacetate. If desired, one can add formamide to the hybridization mixture, typically 30-50% (v/v) ["by volume"].

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution are unlabeled carrier nucleic acids from about 0.1 to 5 mg/mL, fragmented nucleic DNA such as calf thymus or salmon sperm DNA or yeast RNA, and optionally from about 0.5 to 2% wt/vol ["weight by volume"] glycine. Other additives may be included, such as volume exclusion agents that include polar water-soluble or swellable agents (e.g., polyethylene glycol), anionic polymers (e.g., polyacrylate or polymethylacrylate) and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed or covalently coupled to it immobilized nucleic acid probe that is unlabeled and complementary to one portion of the sequence.

Any of the Pex nucleic acid fragments or any identified homologs may be used to isolate genes encoding homologous proteins from the same or other algal, fungal, oomycete, euglenoid, stramenopiles, yeast or plant species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683,202); ligase chain reaction ["LCR"] (Tabor, S. et al., *Proc. Natl. Acad. Sci. U.S.A.,* 82:1074 (1985)); or strand displacement amplification ["SDA"] (Walker, et al., *Proc. Natl. Acad. Sci. U.S.A.,* 89:392 (1992)); and, 3) methods of library construction and screening by complementation.

For example, genes encoding proteins or polypeptides similar to publicly available Pex genes or their motifs could be isolated directly by using all or a portion of those publicly available nucleic acid fragments as DNA hybridization probes to screen libraries from any desired organism using well known methods. Specific oligonucleotide probes based upon the publicly available nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part or the full length of the publicly available sequences or their motifs. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of available Pex sequences may be used in PCR protocols to amplify longer nucleic acid fragments encoding homologous genes from DNA or RNA. PCR may also be performed on a library of cloned nucleic acid fragments wherein the sequence of one primer is derived from the available nucleic acid fragments or their motifs. The sequence of the other primer takes advantage of the presence of the polyadenylic acid tracts to the 3' end of the mRNA precursor encoding genes.

Alternatively, the second primer sequence may be based upon sequences derived from the cloning vector. For example, the skilled artisan can follow the RACE protocol (Frohman et al., *Proc. Natl. Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the available sequences. Using commercially available 3' RACE or 5' RACE systems (e.g., BRL, Gaithersburg, Md.), specific 3' or 5' cDNA fragments can be isolated (Ohara et al., *Proc. Natl. Acad. Sci. U.S.A.,* 86:5673 (1989); Loh et al., *Science,* 243:217 (1989)).

Based on any of these well-known methods just discussed, it would be possible to identify and/or isolate Pex gene homologs in any preferred eukaryotic organism of choice. The activity of any putative Pex gene can readily be confirmed by targeted disruption of the endogenous gene within the PUFA-producing host organism, since the lipid profiles of the total lipid fraction and of the oil fraction are modified relative to those within an organism lacking the targeted Pex gene disruption.

Increasing the Amount of PUFAs in the Total Lipid Fraction and in the Oil Fraction Via Disruption of a Native Peroxisome Biogenesis Factor Protein As noted above, the present disclosure relates to the following described methods for increasing the weight percent of one PUFA or a combination of PUFAs in an oleaginous eukaryotic organism, comprising:

a) providing an oleaginous eukaryotic organism comprising a disruption in a native gene encoding a peroxisome biogenesis factor protein, which creates a PEX-disruption organism; and genes encoding a functional PUFA biosynthetic pathway; and, b) growing the eukaryotic organism of (a) under conditions wherein the weight percent of one PUFA or a combination of PUFAs is increased in the total lipid fraction and in the oil fraction relative to the weight percent of the total fatty acids, when compared with those weight percents in an oleaginous eukaryotic organism whose native peroxisome biogenesis factor protein has not been disrupted.

The amount of PUFAs that increases as a percent of total fatty acids can be: 1) the PUFA that is the desired end product of a functional PUFA biosynthetic pathway, as opposed to PUFA intermediates or by-products; 2) $C_{20}$ to $C_{22}$ PUFAs; and/or, 3) total PUFAs.

In addition to the increase in the weight percent of one or a combination of PUFAs relative to the weight percent of the total fatty acids, in some cases, the total lipid content (TFA % DCW) of the cell may be increased or decreased. What this means is that regardless of whether the disruption in the PEX gene causes the amount of total lipids in the PEX-disrupted cell to increase or decrease, the disruption always causes the weight percent of a PUFA or of a combination of PUFAs to increase.

Another method provided herein relates to a disruption in a native gene encoding a peroxisome biogenesis factor protein, wherein said disruption can result in an increase in the percent of one PUFA or a combination of PUFAs relative to the dry cell weight when compared to that percent in a parental strain whose native Pex protein had not been disrupted or that was expressing a "replacement" copy of the disrupted native Pex protein.

In preferred aspects of the method above, the disruption in a native gene encoding a peroxisome biogenesis factor protein results in an increase in the amount of the PUFA that is the desired end product of a functional PUFA biosynthetic pathway, as opposed to PUFA intermediates or by-products, as a percent of dry cell weight relative to the parental strain whose native Pex protein had not been disrupted or the parental strain that was expressing a "replacement" copy of the disrupted native Pex protein. In some cases, the increase in the percent of a combination of PUFAs relative to the dry cell weight is a combination of $C_{20}$ to $C_{22}$ PUFAs or the total PUFAs.

Also described herein are organisms produced by these methods, comprising a disruption of at least one peroxisome biogenesis factor protein. Lipids and oils obtained from these organisms, products obtained from the processing of the lipids and oil, use of these lipids and oil in foods, animal feeds or industrial applications and/or use of the by-products in foods or animal feeds are also described.

Preferred eukaryotic organisms in the methods described above include algae, fungi, oomycetes, yeast, euglenoids, stramenopiles, plants and some mammalian systems.

The peroxisome biogenesis factor protein for any of these methods may be selected from the group consisting of: Pex1p, Pex2p, Pex3p, Pex3Bp Pex4p, Pex5p, Pex5Bp, Pex5Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21B, Pex22p, Pex22p-like and Pex26p (and protein homologs thereof). In some preferred methods described herein, the disrupted peroxisome biogenesis factor protein is selected from the group consisting of: Pex2p, Pex3p, Pex10p, Pex12p and/or Pex16p. In some more preferred methods, however, the disrupted peroxisome biogenesis factor protein is selected from the group consisting of: Pex3p, Pex10p and/or Pex16p.

The disruption in the native gene encoding a peroxisome biogenesis factor protein can be an insertion, deletion, or targeted mutation within a portion of the gene, such as within the N-terminal portion of the protein or within the C-terminal portion of the protein. Alternatively, the disruption can result in a complete gene knockout such that the gene is eliminated from the host cell genome. Or, the disruption could be a targeted mutation that results in a non-functional protein.

Disruption Methodologies

The invention includes disruption in a native gene encoding a peroxisome biogenesis factor protein within a preferred host cell. Although numerous techniques are available to one of skill in the art to achieve disruption, generally the endogenous activity of a particular gene can be reduced or eliminated by the following techniques, for example: 1) disrupting the gene through insertion, substitution and/or deletion of all or part of the target gene; or 2) manipulating the regulatory sequences controlling the expression of the protein. Both of these techniques are discussed below. However, one skilled in the art appreciates that these are well described in the existing literature and are not limiting to the methods, host cells, and products described herein. One skilled in the art also appreciates the most appropriate technique for use with any particular oleaginous yeast.

Disruption Via Insertion, Substitution and/or Deletion:

For gene disruption, a foreign DNA fragment, typically a selectable marker gene, is inserted into the structural gene. This interrupts the coding sequence of the structural gene and causes inactivation of that gene. Transformation of the disruption cassette into the host cell results in replacement of the functional native gene by homologous recombination with the non-functional disrupted gene. See, for example: Hamilton et al., *J. Bacteriol.,* 171:4617-4622 (1989); Balbas et al., *Gene,* 136:211-213 (1993); Gueldener et al., *Nucleic Acids Res.,* 24:2519-2524 (1996); and Smith et al., *Methods Mol. Cell. Biol.,* 5:270-277 (1996). One skilled in the art appreciates the many variations of the general method of gene targeting, which admits of positive or negative selection, creation of gene knockouts, and insertion of exogenous DNA sequences into specific genome sites in mammalian systems, plant cells, filamentous fungi, algae, oomycetes, euglenoids, stramenopiles, yeast and/or microbial systems.

In contrast, a non-specific method of gene disruption is the use of transposable elements or transposons. Transposons are genetic elements that insert randomly into DNA but can be later retrieved on the basis of sequence to determine the locus of insertion. Both in vivo and in vitro transposition techniques are known and involve the use of a transposable element in combination with a transposase enzyme. When the transposable element or transposon is contacted with a nucleic acid fragment in the presence of the transposase, the transposable element randomly inserts into the nucleic acid fragment. The technique is useful for random mutagenesis and for gene isolation, since the disrupted gene may be identified on the basis of the sequence of the transposable element. Kits for in vitro transposition are commercially available and include: the Primer Island Transposition Kit, available from Perkin Elmer Applied Biosystems, Branchburg, N.J., based upon the yeast Ty1 element; the Genome Priming System, available from New England Biolabs, Beverly, Mass., based upon the bacterial transposon Tn7; and EZ::TN Transposon Insertion Systems, available from Epicentre Technologies, Madison, Wis., based upon the Tn5 bacterial transposable element.

Manipulation of Pex Regulatory Sequences:

As is well known in the art, the regulatory sequences associated with a coding sequence include transcriptional and translational "control" nucleotide sequences located upstream (5' non-coding sequences), within, or downstream (3' non-coding sequences) of the coding sequence, and which influence the transcription, RNA processing or stability, or translation of the associated coding sequence. Thus, manipulation of a Pex gene's regulatory sequences may refer to manipulation of the promoters, silencers, 5' untranslated leader sequences (between the transcription start site and the translation initiation codon), introns, enhancers, initiation control regions, polyadenylation recognition sequences, RNA processing sites, effector binding sites and stem-loop structures of the particular Pex gene. In all cases, however, the result of the manipulation is down-regulation of the Pex gene's expression, which promotes increased amount of PUFAs in the total lipid fraction and in the oil fraction, as a percent of total fatty acids, as compared with an oleaginous yeast whose native peroxisome biogenesis factor protein has not been disrupted.

For example, the promoter of a Pex10 gene could be deleted or disrupted. Alternatively, the native promoter driving expression of a Pex10 gene may be substituted with a heterologous promoter having diminished promoter activity with respect to that of the native promoter. Methods useful for manipulating regulatory sequences are well known.

The skilled person is able to use these and other well known techniques to disrupt a native peroxisome biogenesis factor protein within the preferred host cells described herein, such as mammalian systems, plant cells, filamentous fungi, algae, oomycetes, euglenoids, stramenopiles and yeast.

One skilled in the art is able to discern the optimum means to disrupt the native Pex gene to achieve an increased amount of PUFAs that accumulate in the total lipid fraction and in the oil fraction, as a percent of total fatty acids, as compared with a eukaryotic organisms whose native peroxisome biogenesis factor protein has not been disrupted.

Metabolic Engineering of ω-3 and/or ω-6 Fatty Acid Biosynthesis

In addition to the methods described herein for disruption of a native peroxisome biogenesis factor protein, it may also be useful to manipulate ω-3 and/or ω-6 fatty acid biosynthesis. This may require metabolic engineering directly within the PUFA biosynthetic pathway or additional manipulation of pathways that contribute carbon to the PUFA biosynthetic pathway.

Techniques useful for up-regulating desirable biochemical pathways and down-regulating undesirable biochemical pathways are well known in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means, such as antisense mRNA and zinc-finger targeting technologies.

The following discuss altering the PUFA biosynthetic pathway as a means to increase GLA, ARA, EPA or DHA, respectively, and desirable manipulations in the TAG biosynthetic pathway and in the TAG degradation pathway: Int'l. App. Pub. No. WO 2006/033723, Int'l. App. Pub. No. WO 2006/055322 [U.S. Pat. Appl. Pub. No. 2006-0094092-A1], Int'l. App. Pub. No. WO 2006/052870 [U.S. Pat. Appl. Pub. No. 2006-0115881-A1] and Int'l. App. Pub. No. WO 2006/052871 [U.S. Pat. Appl. Pub. No. 2006-0110806-A1], respectively.

Expression Systems, Cassettes, Vectors and Transformation of Host Cells

It may be necessary to create and introduce a recombinant construct into the preferred eukaryotic host, such as e.g., mammalian systems, plant cells, filamentous fungi, algae, oomycetes, euglenoids, stramenopiles and yeast, to result in disruption of a native peroxisome biogenesis factor protein and/or introduction of genes encoding a PUFA biosynthetic pathway. One of skill in the art appreciates standard resource materials that describe: 1) specific conditions and procedures for construction, manipulation and isolation of macromolecules, such as DNA molecules, plasmids, etc.; 2) generation of recombinant DNA fragments and recombinant expression constructs; and 3) screening and isolating of clones. See Sambrook et al., *Molecular Cloning: A Laboratory Manual, 2nd* ed., Cold Spring Harbor Laboratory: Cold Spring Harbor, N.Y. (1989); Maliga et al., Methods in Plant Molecular Biology, Cold Spring Harbor, N.Y. (1995); Birren et al., Genome Analysis: Detecting Genes, v. 1, Cold Spring Harbor, N.Y. (1998); Birren et al., Genome Analysis Analyzing DNA, v. 2, Cold Spring Harbor: NY (1998); *Plant Molecular Biology: A Laboratory Manual*, Clark, ed. Springer: NY (1997).

In general, the choice of sequences included in the construct depends on the desired expression products, the nature of the host cell and the proposed means of separating transformed cells versus non-transformed cells. The skilled artisan is well aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, and a region 3' of the DNA fragment that controls transcriptional termination, i.e., a terminator. It is most preferred when both control regions are derived from genes from the transformed host cell.

Initiation control regions or promoters useful for driving expression of heterologous genes or portions of them in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter (i.e., native, synthetic, or chimeric) capable of directing expression of these genes in the selected host cell is suitable. Expression in a host cell can occur in an induced or constitutive fashion. Induced expression occurs by inducing the activity of a regulatable promoter operably linked to the Pex gene of interest. Constitutive expression occurs by the use of a constitutive promoter operably linked to the gene of interest.

When the host cell is, for example, yeast, transcriptional and translational regions functional in yeast cells are provided, particularly from the host species. See Int'l. App. Pub. No. WO 2006/052870 for preferred transcriptional initiation regulatory regions for use in *Yarrowia lipolytica*. Any of a number of regulatory sequences may be used, depending on whether constitutive or induced transcription is desired, the efficiency of the promoter in expressing the ORF of interest, the ease of construction, etc.

3' non-coding sequences encoding transcription termination signals, i.e., a "termination region", must be provided in a recombinant construct and may be from the 3' region of the gene from which the initiation region was obtained or from a different gene. A large number of termination regions are known and function satisfactorily in a variety of hosts when utilized in both the same and different genera and species from which they were derived. The termination region is selected more for convenience rather than for any particular property. Termination regions may also be derived from various genes native to the preferred hosts.

Particularly useful termination regions for use in yeast are those derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may comprise a selectable and/or scorable marker, in addition to the regulatory elements described above. Preferably, the marker gene is an antibiotic resistance gene such that treating cells with the antibiotic causes inhibition of growth, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histine or leucine being particularly useful.

Merely inserting a gene into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene and whether the gene is plasmid-borne or integrated into the genome of the host cell, the final cellular location of the synthesized foreign protein, the efficiency of translation and correct folding of the protein in the host organism, the intrinsic stability of the mRNA and protein of the cloned gene within the host cell and the codon usage within the cloned gene, such that its frequency approaches the frequency of preferred codon usage of the host cell. Each of these may be used in the methods and host cells described herein to further optimize expression of PUFA biosynthetic pathway genes and to diminish expression of a native Pex gene.

After a recombinant construct is created, e.g., comprising a chimeric gene comprising a promoter, ORF and terminator, suitable for disruption or knock out of a native peroxisome biogenesis factor protein and/or expression of genes encoding a PUFA biosynthetic pathway activity, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation, e.g., lithium acetate transformation (*Methods in Enzymology,* 194:186-187 (1991)), protoplast fusion, biolistic impact, electroporation, microinjection, vacuum filtration or any other method that introduces the gene of interest into the host cell.

For convenience, a host cell that has been manipulated by any method to take up a DNA sequence, for example, in an expression cassette, is referred to herein as "transformed" or "recombinant". The transformed host will have at least one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity (e.g., β-galactosidase can convert the substrate X-gal ["5-bromo-4-chloro-3-indolyl-β-D-galactopyranoside"] to a colored product; luciferase can convert luciferin to a light-emitting product) or its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as fluorescence-activated cell sorting or panning using antibodies.

Regardless of the selected host or expression construct, multiple transformants must be screened to obtain a strain or plant line displaying the desired expression level, regulation and pattern, as different independent transformation events result in different levels and patterns of expression (Jones et al., *EMBO J.,* 4:2411-2418 (1985); De Almeida et al., *Mol. Gen. Genetics,* 218:78-86 (1989)). Such screening may be accomplished by Southern analysis of DNA blots (Southern, *J. Mol. Biol.,* 98:503 (1975)), Northern analysis of mRNA expression (Kroczek, *J. Chromatogr. Biomed. Appl.,* 618(1-2):133-145 (1993)), Western and/or Elisa analyses of protein expression, phenotypic analysis or GC analysis of the PUFA products.

Preferred Eukaryotic Host Organisms

A variety of eukaryotic organisms are suitable as host herein, to thereby yield a transformant host organism comprising a disruption in a native peroxisome biogenesis factor protein and genes encoding a PUFA biosynthetic pathway, wherein the transformed eukaryotic host organism has an increased amount of PUFAs incorporated into the total lipid fraction and in the oil fraction, as a percent of total fatty acids, as compared to a eukaryotic organism whose native peroxisome biogenesis factor protein has not been disrupted. Various mammalian systems, plant cells, fungi, algae, oomycetes, yeasts, stramenopiles and/or euglenoids may be useful hosts. Although oleaginous organisms are preferred, non-oleaginous organisms also have utility herein such that, when one of their native PEX genes is disrupted, an increase in the weight percent of at least one polyunsaturated fatty acid relative to the weight percent of total fatty acids in the total lipid fraction or in the oil fraction will be experienced and may lead to a 1.3 fold increase in the PUFA. Additionally, the percent of the PUFA may be increased relative to the dry cell weight in the non-oleaginous organism. In alternate embodiments, a non-oleaginous organism can be genetically modified to become oleaginous, e.g., yeast such as *Saccharomyces cerevisiae.*

Oleaginous organisms are naturally capable of oil synthesis and accumulation, wherein the total oil content typically comprises greater than about 25% of the cellular dry weight. Various algae, moss, fungi, yeast, stramenopiles and plants are naturally classified as oleaginous.

Preferred oleaginous microbes include those algal, stramenopile and fungal organisms that naturally produce ω-3/ω-6 PUFAs. For example, ARA, EPA and/or DHA is produced via *Cyclotella* sp., *Nitzschia* sp., *Pythium, Thraustochytrium* sp., *Schizochytrium* sp. and *Mortierella*. The method of transformation of *M. alpina* is described by Mackenzie et al. (*Appl. Environ. Microbiol.,* 66:4655 (2000)). Similarly, methods for transformation of Thraustochytriales microorganisms (e.g., *Thraustochytrium, Schizochytrium*) are disclosed in U.S. Pat. No. 7,001,772.

More preferred are oleaginous yeast, including those that naturally produce and those genetically engineered to produce ω-3/ω-6 PUFAs. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.,* 82(1):43-9 (2002)).

Specific teachings relating to transformation of *Yarrowia lipolytica* include U.S. Pat. No. 4,880,741 and U.S. Pat. No. 5,071,764 and Chen, D. C. et al. (*Appl. Microbiol. Biotechnol.,* 48(2):232-235 (1997)), while suitable selection techniques are described in U.S. Pat. No. 7,238,482 and Int'l. App. Pub. Nos. WO 2005/003310 and WO 2006/052870.

The preferred method of expressing genes in *Yarrowia lipolytica* is by integration of linear DNA into the genome of the host. Integration into multiple locations within the genome can be particularly useful when high level expression of genes are desired, such as in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244 or Aco3: GenBank Accession No. AJ001301), the Δ12 desaturase gene locus (U.S. Pat. No. 7,214,491), the Lip1 gene locus (GenBank Accession No. Z50020), the Lip2 gene locus (GenBank Accession No. AJ012632), the SCP2 gene locus (GenBank Accession No. AJ431362), the Pex3 gene locus (GenBank Accession No. CAG78565), the Pex16 gene locus (GenBank Accession No. CAG79622) and/or the Pex10 gene locus (GenBank Accession No. CAG81606).

Preferred selection methods for use in *Yarrowia lipolytica* are resistance to kanamycin, hygromycin and the amino glycoside G418, as well as ability to grow on media lacking uracil, leucine, lysine, tryptophan or histidine. 5-fluoroorotic acid [5-fluorouracil-6-carboxylic acid monohydrate or "5-FOA"] may also be used for selection of yeast $Ura^-$ mutants. This compound is toxic to yeast cells that possess a functioning URA3 gene encoding orotidine 5'-monophosphate decarboxylase [OMP decarboxylase]; thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997; see also Int'l. App. Pub. No. WO 2006/052870 for 5-FOA use in *Yarrowia*).

An alternate preferred selection method for use in *Yarrowia* relies on a dominant, non-antibiotic marker for *Yarrowia lipolytica* based on sulfonylurea (chlorimuron ethyl; E. I. duPont de Nemours & Co., Inc., Wilmington, Del.) resistance. More specifically, the marker gene is a native acetohydroxyacid synthase ("AHAS" or acetolactate synthase; E.C. 4.1.3.18) that has a single amino acid change, i.e., W497L, that confers sulfonyl urea herbicide resistance (Int'l App. Pub. No. WO 2006/052870). AHAS is the first common enzyme in the pathway for the biosynthesis of branched-chain amino acids, i.e., valine, leucine, isoleucine, and it is the target of the sulfonylurea and imidazolinone herbicides.

Fermentation Processes for Polyunsaturated Fatty Acid Production

The transformed host cell is grown under conditions that optimize expression of PUFA biosynthetic genes and produce the greatest and most economical yield of desired PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Oleaginous yeast of interest, such as *Yarrowia lipolytica*, are generally grown in a complex medium such as yeast extract-peptone-dextrose broth (YPD) or a defined minimal media that lacks a component necessary for growth and forces selection of the desired expression cassettes (e.g., Yeast Nitrogen Base (DIFCO Laboratories, Detroit, Mich.)).

Fermentation media for the methods and host cells described herein must contain a suitable carbon source such as are taught in U.S. Pat. No. 7,238,482. Suitable sources of carbon encompass a wide variety of sources, with sugars, glycerol and/or fatty acids being preferred. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous yeast and the promotion of the enzymatic pathways of PUFA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of the transformant host cells is well known in microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of increased amounts of PUFAs and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. This approach is described in U.S. Pat. No. 7,238,482, as are various suitable fermentation process designs (i.e., batch, fed-batch and continuous) and considerations during growth.

Purification and Processing of PUFA Oils

Fatty acids, including PUFAs, may be found in the host organisms as free fatty acids or in esterified forms such as acylglycerols, phospholipids, sulfolipids or glycolipids. These fatty acids may be extracted from the host cells through a variety of means well-known in the art. One review of extraction techniques, quality analysis and acceptability standards for yeast lipids is that of Z. Jacobs (*Critical Reviews in Biotechnology,* 12(5/6):463-491 (1992)). A brief review of downstream processing is also available by A. Singh and O. Ward (*Adv. Appl. Microbiol.,* 45:271-312 (1997)).

In general, means for the purification of fatty acids (including PUFAs) may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. See U.S. Pat. No. 7,238,482.

Oils for Use in Foodstuffs, Health Food Products, Pharmaceuticals and Animal Feeds The market place contains many food and feed products, incorporating ω-3 and/or ω-6 fatty acids, particularly ALA, GLA, ARA, EPA, DPA and DHA. It is contemplated that the microbial biomass comprising long-chain PUFAs, partially purified microbial biomass comprising PUFAs, purified microbial oil comprising PUFAs, and/or purified PUFAs made by the methods and host cells described herein impart health benefits, upon ingestion of foods or feed improved by their addition. These oils can be added to food analogs, drinks, meat products, cereal products, baked foods, snack foods and dairy products, to name a few. See U.S. Pat. App. Pub. No. 2006/0094092, hereby incorporated herein by reference.

These compositions may impart health benefits by being added to medical foods including medical nutritionals, dietary supplements, infant formula and pharmaceuticals. The skilled artisan will appreciate the amount of the oils to be added to food, feed, dietary supplements, nutriceuticals, pharmaceuticals, and other ingestible products as to impart health benefits. Health benefits from ingestion of these oils are described in the art, known to the skilled artisan and continuously investigated. Such an amount is referred to herein as an "effective" amount and depends on, among other things, the nature of the ingested products containing these oils and the physical conditions they are intended to address.

DESCRIPTION OF PREFERRED EMBODIMENTS

As demonstrated in the Examples and summarized in Table 5, infra, disruptions in the C-terminal portion of the $C_3HC_4$ zinc ring finger motif of YlPex10p, deletion of the entire chromosomal YlPex10 gene or of the entire chromosomal YlPex16 gene, deletion of both the entire chromosomal YlPex10 and the YlPex16 gene, and deletion of the entire chromosomal YlPex3 gene all resulted in an engineered PUFA-producing strain of *Yarrowia lipolytica* that had an increased weight percent of PUFAs as a percent of total fatty acids, relative to the parental strain whose native Pex protein had no disruption. Expression of an extrachromosomal YlPex10p in an engineered EPA-producing strain of *Yarrowia lipolytica* that possessed a disruption in the genomic Pex10p and an increased amount of PUFAs in the total lipid fraction and in the oil fraction reversed the effect.

Table 5 compiles data from Examples 3, 4, 5, 7, 9, 11 and 12, such that trends concerning total lipid content ["TFAs % DCW"], concentration of a given fatty acid(s) expressed as a weight percent of total fatty acids ["% TFAs"], and content of a given fatty acid(s) as its percent of the dry cell weight ["% DCW"] can be deduced, based on the presence/absence of a Pex disruption or knockout. "Desired PUFA % TFAs" and "Desired PUFA % DCW" quantify the particular concentration or content, respectively, of the desired PUFA product (i.e., DGLA or EPA) that the engineered PUFA biosynthetic pathway was designed to produce. "All PUFAs" includes LA, ALA, EDA, DGLA, ETrA, ETA and EPA, while "C20 PUFAs" is limited to EDA, DGLA, ETrA, ETA and EPA.

TABLE 5

PUFA % TFAs and % DCW In *Yarrowia lipolytica* Strains With Mutant Pex Genes

| Example | Strain | Genomic Pex Gene | TFA % DCW | % TFAs Desired PUFA | % TFAs All PUFAs | % TFAs C20 PUFAs | % DCW Desired PUFA | % DCW All PUFAs | % DCW C20 PUFAs |
|---|---|---|---|---|---|---|---|---|---|
| 3, 4 | Y4086 | Wildtype Pex10 | 28.6 | 9.8 [EPA] | 60.1 | 25.2 | 2.8 [EPA] | 17.2 | 7.2 |
| | Y4128 | Mutant* Pex10 | 11.2 | 42.8 [EPA] | 79.3 | 57.9 | 4.8 [EPA] | 8.9 | 6.4 |
| 5 | Y4128U1 + pFBAIn-PEX10 | Mutant* Pex10 + Plasmid Wildtype Pex10 within chimeric FBAINm::Pex10::Pex20 gene | 29.2 | 10.8 [EPA] | 60 | 27.3 | 3.1 [EPA] | 17.5 | 8.0 |
| | Y4128U1 + pPEX10-1 | Mutant* Pex10 + Plasmid Wildtype Pex10 within Pex10-5' (500 bp)::Pex10::Pex10-3' gene | 27.1 | 10.7 [EPA] | 60.1 [EPA] | 26.7 | 2.9 [EPA] | 16.2 | 7.2 |
| | Y4128U1 + pPEX10-2 | Mutant* Pex10 + Plasmid Wildtype Pex10 within Pex10-5' (991 bp)::Pex10::Pex10-3' gene | 28.5 | 10.8 [EPA] | 59 [EPA] | 26.9 | 3.1 [EPA] | 16.8 | 7.7 |
| | Y4128U1 + control | Mutant* Pex10 | 22.8 | 27.7 [EPA] | 62.6 | 42.3 | 6.3 [EPA] | 14.2 | 9.6 |
| 7 | Y4184U | Wildtype Pex10 | 11.8 | 20.6 [EPA] | nq♦ | nq♦ | 2.4 [EPA] | nq♦ | nq♦ |
| | | | 8.8 | 23.2 [EPA] | nq♦ | nq♦ | 2.0 [EPA] | nq♦ | nq♦ |
| | Y4184U ΔPex10 | Mutant Pex10 | 17.6 | 43.2 [EPA] | nq♦ | nq♦ | 7.6 [EPA] | nq♦ | nq♦ |
| | | | 13.2 | 46.1 [EPA] | nq♦ | nq♦ | 6.1 [EPA] | nq♦ | nq♦ |
| 9 | Y4036 (avg) | Wildtype Pex16 | Nq♦ | 23.4 [DGLA] | 61.5 | 33.7 | nq♦ | nq♦ | nq♦ |
| | Y4036 (ΔPex16) (avg) | Mutant Pex16 | Nq♦ | 43.4 [DGLA] | 69.1 | 49.1 | nq♦ | nq♦ | nq♦ |
| 11 | Y4305U (Δpex10) (avg) | Mutant Pex10 and Wildtype Pex16 | 30 | 44.7 [EPA] | 76.6 | 55.4 | 13.4 [EPA] | 23.0 | 16.6 |
| | Y4305 (ΔPex10, ΔPex16) (avg) | Mutant Pex10, Mutant Pex16 | 30 | 48.3 [EPA] | 79.0 | 57.7 | 14.5 [EPA] | 23.7 | 17.3 |
| 12 | Y4036 | Wildtype Pex3 | 4.7 | 19 [DGLA] | 57 | 27 | 0.9 [DGLA] | 2.7 | 1.3 |
| | Y4036 (ΔPex3) | Mutant Pex3 | 6.1 | 46 [DGLA] | 68 | 56 | 2.8 [DGLA] | 4.4 | 3.4 |
| | | | 5.9 | 46 [DGLA] | 68 | 56 | 2.7 [DGLA] | 4.0 | 3.3 |

*Pex10 disruption in Y4128 results in a truncated protein, wherein the last 32 amino acids of the C-terminus (corresponding to the C-terminal portion of the $C_3HC_4$ zinc ring finger motif) are not present.
♦nq = not quantified Although data cannot be directly compared between Examples, as a result of different *Yarrowia* strains and growth conditions, the following conclusions can be drawn (relative to the parental strain whose native Pex protein had not been disrupted or the parental strain that was expressing a "replacement" copy of the disrupted native Pex protein):

1) Pex disruption in a PUFA-producing *Yarrowia* results in an increase in the weight percent of a single PUFA, for example EPA or DLGA, relative to the weight percent of total fatty acids (% TFAs) in the total lipid fraction and in the oil fraction;

2) Pex disruption in a PUFA-producing *Yarrowia* results in an increase in the weight percent of $C_{20}$ PUFAs relative to the weight percent of total fatty acids in the total lipid fraction and in the oil fraction;

3) By the extension of point 1), Pex disruption in a PUFA-producing *Yarrowia* results in an increase in the amount of any and all combinations of PUFAs relative to the weight percent of total fatty acids in the total lipid fraction and in the oil fraction; and 4) Pex disruption in a PUFA-producing *Yarrowia* results in an increase in the percent of a single PUFA, for example EPA or DLGA, relative to the dry cell weight.

Variable results are observed when comparing the effects of Pex disruptions in "All PUFAs % DCW", "C20 PUFAs % DCW" and TFA % DCW. Specifically, in some cases, the Pex disruption in the PUFA-producing *Yarrowia* results in an increased amount of $C_{20}$ PUFAs or All PUFAs, as a percent of dry cell weight, in the total lipid fraction and in the oil fraction (relative to the parental strain whose native Pex protein had not been disrupted). In other cases, there is a diminished amount of $C_{20}$ PUFAs or All PUFAs, as a percent of dry cell weight, in the total lipid fraction and in the oil fraction (relative to the parental strain whose native Pex protein had not been disrupted). Similar results are observed with respect to the total lipid content (TFA % DCW), in that the effect of the Pex disruption can either result in an increase in total lipid content or a decrease.

Although each of the above generalizations are of interest, it is particularly useful to examine the effect of the Pex disruptions on the ratio of the desired PUFA which the organism was engineered to produce relative to the amount of total PUFAs.

For example, 54% of the PUFAs (as a % TFAs) were EPA in strain Y4128 containing the Pex10 disruption that resulted in truncation of the last 32 amino acids of the C-terminus, while only 16.3% of the PUFAs (as a % TFAs) were EPA in the parent strain, Y4086. Thus, the disruption was responsible for a 3.3-fold increase in the amount of the desired PUFA (as % TFAs) (Examples 3, 4). In a similar manner, 62.8% of the PUFAs (as a % TFAs) were DGLA in strain Y4036 (ΔPex16), while only 38.1% the PUFAs (as a % TFAs) were DGLA in Y4036—a 1.65 fold increase (Example 9). And, 67.7% of the PUFAs (as a % TFAs) were DGLA in strain Y4036 (ΔPex3), while only 33.3% the PUFAs (as a % TFAs) were DGLA in Y4036—a 2.0 fold increase (Example 12). These results support the hypothesis that the Pex disruption results in a selective increase in the amount, as a % TFAs, of the desired PUFA which the organism was engineered to produce in the total lipid and oil fractions.

Less significant selectivity is observed when examining the effect of Pex disruptions on the ratio of C20 PUFAs relative to the amount of total PUFAs. For example, 73% of the PUFAs (as a % TFAs) were C20 PUFAs in strain Y4128 containing the Pex10 disruption, while only 42% of the PUFAs (as a % TFAs) were C20 PUFAs in strain Y4086. Thus, the disruption was responsible for a 1.7-fold increase in the amount of C20 PUFAs that accumulated in the total lipid and oil fractions, relative to the total PUFAs (Examples 3, 4). In a similar manner, 71% of the PUFAs (as a % TFAs) were C20 PUFAs in strain Y4036 (ΔPex16), while only 54.8% the PUFAs (as a % TFAs) were C20 PUFAs in Y4036—a 1.3 fold increase (Example 9). And, 82.4% of the PUFAs (as a % TFAs) were C20 PUFAs in strain Y4036 (ΔPex3), while only 47.4% the PUFAs (as a % TFAs) were C20 PUFAs in Y4036—a 1.7 fold increase (Example 12).

On the basis of the teachings and results described herein, it is expected that the feasibility and commercial utility of utilizing various disruptions in native genes encoding peroxisome biogenesis factor proteins as a means to increase the amount of PUFAs produced in a PUFA-producing eukaryotic organism will be appreciated. The PUFA-producing eukaryotic organism can synthesize a variety of ω-3 and/or ω-6 PUFAs, using either the Δ9 elongase/Δ8 desaturase pathway or the Δ6 desaturase/Δ6 elongase pathway.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and Methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Unless otherwise indicated herein comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Nomenclature for Expression Cassettes:

The structure of an expression cassette is represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco], and 20 g of glucose.

Basic Minimal Media (MM) (per liter): 20 g glucose, 1.7 g yeast nitrogen base without amino acids, 1.0 g proline, and pH 6.1 (not adjusted).

Minimal Media+Uracil (MM+uracil or MMU) (per liter): Prepare MM media as above and add 0.1 g uracil and 0.1 g uridine.

Minimal Media+Uracil+Sulfonylurea (MMU+SU) (per liter): Prepare MMU media as above and add 280 mg sulfonylurea.

Minimal Media+Leucine+Lysine (MMLeuLys) (per liter): Prepare MM media as above and add 0.1 g leucine and 0.1 g lysine.

Minimal Media+5-Fluoroorotic Acid (MM+5-FOA) (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

High Glucose Media (HGM) (per liter): 80 glucose, 2.58 g $KH_2PO_4$ and 5.36 g $K_2HPO_4$, pH 7.5 (do not need to adjust).

Fermentation medium without Yeast Extract (FM without YE) (per liter): 6.70 g Yeast Nitrogen base, 6.00 g $KH_2PO_4$, 2.00 g $K_2HPO_4$, 1.50 g $MgSO_4*7H_2O$ and 20 g Glucose.

Fermentation medium (FM) (per liter): Prepare FM without YE media as above and add 5.00 g Yeast extract (BBL).

Synthetic Dextrose Media (SD) (per liter): 6.7 g Yeast Nitrogen base with ammonium sulfate and without amino acids; and 20 g glucose.

Complete Minimal Glucose Broth Minus Uracil (CSM-Ura): Catalog No. C8140, Teknova, Hollister, Calif. (0.13% amino acid dropout powder minus uracil. 0.17% yeast nitrogen base, 0.5% $(NH_4)_2SO_4$, 2.0% glucose).

Transformation of *Y. lipolytica* was performed according to the method of Chen, D. C. et al. (*Appl. Microbiol. Biotechnol.,* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; and 0.125 mL of 2 M DTT. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters ["FAMEs"] were prepared by transesterification of the lipid extract with sodium methoxide (Roughan, G., and Nishida I., *Arch Biochem Biophys.,* 276 (1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Generation of *Yarrowia lipolytica* Strain Y4086 to Produce about 14% EPA of Total Lipids Via the Δ9 Elongase/Δ8 Desaturase Pathway The present Example describes the construction of strain Y4086, derived from *Yarrowia lipolytica* ATCC #20362, capable of producing about 14% EPA relative to the total lipids via expression of a Δ9 elongase/Δ8 desaturase pathway (FIG. 3A).

The development of strain Y4086 required the construction of strain Y2224 (a FOA resistant mutant from an autonomous mutation of the Ura3 gene of wildtype *Yarrowia* strain ATCC #20362), strain Y4001 (producing 17% EDA with a Leu− phenotype), strain Y4001U (Leu− and Ura− phenotype), strain Y4036 (producing 18% DGLA with a Leu− phenotype), strain Y4036U (Leu− and Ura− phenotype) and strain Y4070 (producing 12% ARA with a Ura− phenotype). Further details regarding the construction of strains Y2224, Y4001, Y4001U, Y4036, Y4036U and Y4070 are described in Example 7 of Int'l. App. Pub. No. WO 2008/073367, hereby incorporated herein by reference.

The final genotype of strain Y4070 with respect to wildtype *Yarrowia lipolytica* ATCC #20362 was Ura3−, unknown 1−, unknown 3−, Leu+, Lys+, GPD::FmD12::Pex20, YAT1::FmD12::OCT, YAT1::ME3S::Pex16, GPAT::EgD9e::Lip2, EXP1::EgD9eS::Lip1, FBAINm::EgD9eS::Lip2, FBAINm::EgD8M::Pex20, EXP1::EgD8M::Pex16, FBAIN::EgD5::Aco, EXP1::EgD5S::Pex20, YAT1::RD5S::OCT (wherein FmD12 is a *Fusarium moniliforme* Δ12 desaturase gene [Int'l. App. Pub. No. WO 2005/047485]; ME3S is a codon-optimized $C_{16/18}$ elongase gene, derived from *Mortierella alpina* [Int'l. App. Pub. No. WO 2007/046817]; EgD9e is a *Euglena gracilis* Δ9 elongase gene [Int'l. App. Pub. No. WO 2007/061742]; EgD9eS is a codon-optimized Δ9 elongase gene, derived from *Euglena gracilis* [Int'l. App. Pub. No. WO 2007/061742]; EgD8M is a synthetic mutant Δ8 desaturase [Int'l. App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. US 2007-0292924-A1]; EgD5S is a codon-optimized Δ5 desaturase gene, derived from *Euglena gracilis* [U.S. Pat. App. Pub. No. 2007-0292924]; and RD5S is a codon-optimized Δ5 desaturase, derived from *Peridinium* sp. CCMP626 [U.S. Pat. App. Pub. No. 2007-0271632]).

Generation of Y4086 Strain to Produce about 14% EPA of Total Lipids

Construct pZP3-Pa777U (FIG. 3B; SEQ ID NO:28), described in Table 19 of Int'l. App. Pub. No. WO 2008/073367, hereby incorporated herein by reference, was generated to integrate three Δ17 desaturase genes into the Pox3 loci (GenBank Accession No. AJ001301) of strain Y4070, to thereby enable production of EPA. The Δ17 desaturase genes were PaD17, a *Pythium aphanidermatum* Δ17 desaturase (Int'l. App. Pub. No. WO 2008/054565), and PaD17S, a codon-optimized Δ17 desaturase derived from *Pythium aphanidermatum* (Int'l. App. Pub. No. WO 2008/054565).

The pZP3-Pa777U plasmid was digested with AscI/SphI, and then used for transformation of strain Y4070 according to the General Methods. The transformant cells were plated onto MM plates and maintained at 30° C. for 2 to 3 days. Single colonies were re-streaked onto MM plates, and then inoculated into liquid MMLeuLys at 30° C. and shaken at 250 rpm/min for 2 days. The cells were collected by centrifugation, lipids were extracted, and FAMEs were prepared by trans-esterification, and subsequently analyzed with a Hewlett-Packard 6890 GC.

GC analyses showed the presence of EPA in the transformants containing the 3 chimeric genes of pZP3-Pa777U, but not in the parent Y4070 strain. Most of the selected 96 strains produced 10-13% EPA of total lipids. There were 2 strains (i.e., #58 and #79) that produced about 14.2% and 13.8% EPA of total lipids. These two strains were designated as Y4085 and Y4086, respectively.

The final genotype of strain Y4086 with respect to wildtype *Yarrowia lipolytica* ATCC #20362 was Ura3+, Leu+, Lys+, unknown 1−, unknown 2−, YALI0F24167g−, GPD::FmD12::Pex20, YAT1::FmD12::OCT, YAT1::ME3S::Pex16, GPAT::EgD9e::Lip2, EXP1::EgD9eS::Lip1, FBAINm::EgD9eS::Lip2, FBAINm::EgD8M::Pex20, EXP1::EgD8M::Pex16, FBAIN::EgD5::Aco, EXP1::EgD5S::Pex20, YAT1::RD5S::OCT, YAT1::PaD17S::Lip1, EXP1::PaD17::Pex16, FBAINm::PaD17::Aco.

Example 2

Generation of *Yarrowia lipolytica* Strain Y4128 to Produce about 37% EPA of Total Lipids Via the Δ9 Elongase/Δ8 Desaturase Pathway The present Example describes the construction of strain Y4128, derived from *Yarrowia lipolytica* ATCC #20362, capable of producing about 37.6% EPA relative to the total lipids (i.e., greater than a 2-fold increase in EPA concentration as percent of total fatty acids with respect to Y4086; FIG. 3A).

The development of strain Y4128 required the construction of strains Y2224, Y4001, Y4001U, Y4036, Y4036U, Y4070 and Y4086 (described in Example 1), as well as construction of strain Y4086U1 (Ura−).

Generation of Strain Y4086U1 (Ura−)

Figure 4B:
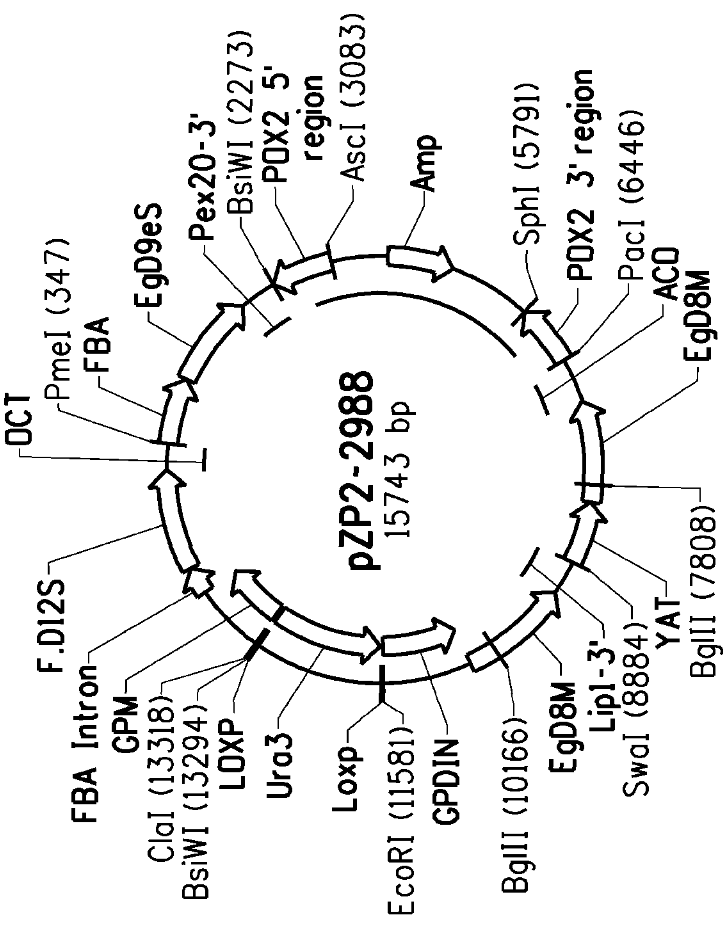
Figure 4A:
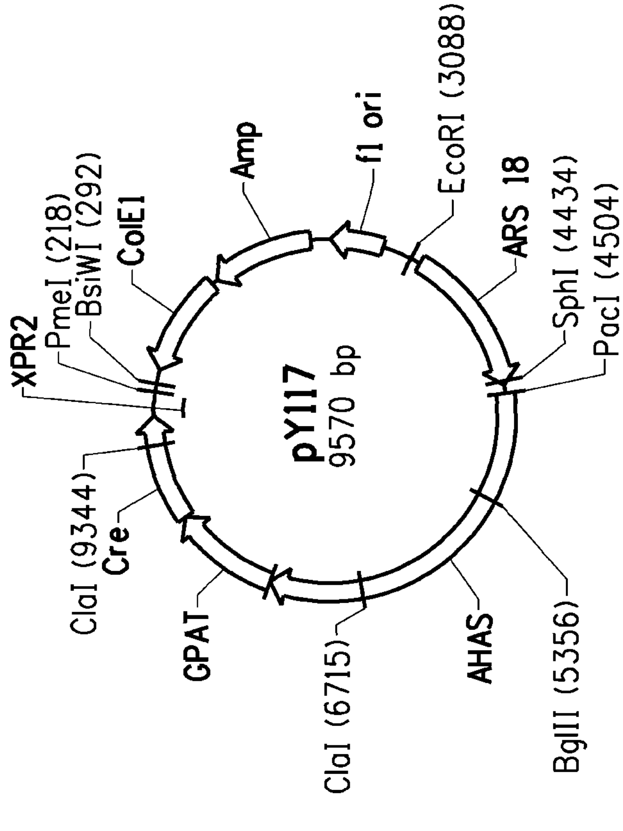

Strain Y4086U1 was created via temporary expression of the Cre recombinase enzyme in construct pY117 (FIG. 4A; SEQ ID NO:29; described in Table 20 of Int'l. App. Pub. No. WO 2008/073367, hereby incorporated herein by reference) within strain Y4086 to produce a Ura− phenotype. This released the LoxP sandwiched Ura3 gene from the genome. The mutated *Yarrowia* acetohydroxyacid synthase ["AHAS"; E.C. 4.1.3.18] enzyme (i.e., GenBank Accession No. XP_501277, comprising a W497L mutation as set forth in SEQ ID NO:27; see Int'l. App. Pub. No. WO 2006/052870) in plasmid pY117 conferred sulfonyl urea herbicide resistance ($SU^R$), which was used as a positive screening marker.

Plasmid pY117 was used to transform strain Y4086 according to the General Methods. Following transformation, the cells were plated onto MMU+SU (280 μg/mL sulfonylurea; also known as chlorimuron ethyl, E. I. duPont de Nemours & Co., Inc., Wilmington, Del.) plates and maintained at 30° C. for 2 to 3 days. The individual $SU^R$ colonies grown on MMU+SU plates were picked, and streaked into YPD liquid media at 30° C. and shaken at 250 rpm/min for 1 day to cure the pY117 plasmid. The grown cultures were streaked onto MMU plates. After two days at 30° C., the individual colonies were re-streaked onto MM and MMU plates. Those colonies that could grow on MMU, but not on MM plates were selected. Two of these strains with Ura− phenotypes were designated as Y4086U1 and Y4086U2.

Generation of Y4128 Strain to Produce about 37% EPA of Total Lipids

Construct pZP2-2988 (FIG. 4B; SEQ ID NO:30; described in Table 21 of Int'l. App. Pub. No. WO 2008/073367, hereby incorporated herein by reference) was generated to integrate one Δ12 desaturase gene (i.e., FmD12S, a codon-optimized Δ12 desaturase gene derived from *Fusarium moniliforme* [Int'l. App. Pub. No. WO 2005/047485]), two Δ8 desaturase genes (i.e., EgD8M) and one Δ9 elongase gene (i.e., EgD9eS) into the Pox2 loci (GenBank Accession No. AJ001300) of strain Y4086U1, to thereby enable higher level production of EPA. The pZP2-2988 plasmid was digested with AscI/SphI, and then used for transformation of strain Y4086U1 according to the General Methods. The transformant cells were plated onto MM plates and maintained at 30° C. for 2 to 3 days. Single colonies were re-streaked onto MM plates, and then inoculated into liquid MMLeuLys at 30° C. and shaken at 250 rpm/min for 2 days. The cells were collected by centrifugation, resuspended in HGM and then shaken at 250 rpm/min for 5 days. The cells were collected by centrifugation, lipids were extracted, and FAMEs were prepared by trans-esterification, and subsequently analyzed with a Hewlett-Packard 6890 GC.

GC analyses showed that most of the selected 96 strains produced 12-15.6% EPA of total lipids. There were 2 strains (i.e., #37 within Group I and #33 within Group II) that produced about 37.6% and 16.3% EPA of total lipids. These two strains were designated as Y4128 and Y4129, respectively.

The final genotype of strain Y4128 with respect to wildtype *Yarrowia lipolytica* ATCC #20362 was: YALI0F24167g−, Pex10−, unknown 1−, unknown 2−, GPD::FmD12::Pex20, YAT1::FmD12::OCT, GPM/FBAIN::FmD12S::OCT, YAT1::ME3S::Pex16, GPAT::EgD9e::Lip2, EXP1::EgD9eS::Lip1, FBAINm::EgD9eS::Lip2, FBA::EgD9eS::Pex20, FBAINm::EgD8M::Pex20, EXP1::EgD8M::Pex16, GPDIN::EgD8M::Lip1, YAT1::EgD8M::Aco, FBAIN::EgD5::Aco, EXP1::EgD5S::Pex20, YAT1::RD5S::OCT, YAT1::PaD17S::Lip1, EXP1::PaD17::Pex16, FBAINm::PaD17::Aco.

*Yarrowia lipolytica* strain Y4128 was deposited with the American Type Culture Collection on Aug. 23, 2007 and bears the designation ATCC PTA-8614.

Generation of Y4128U Strains with a Ura− Phenotype

Figure 5B:
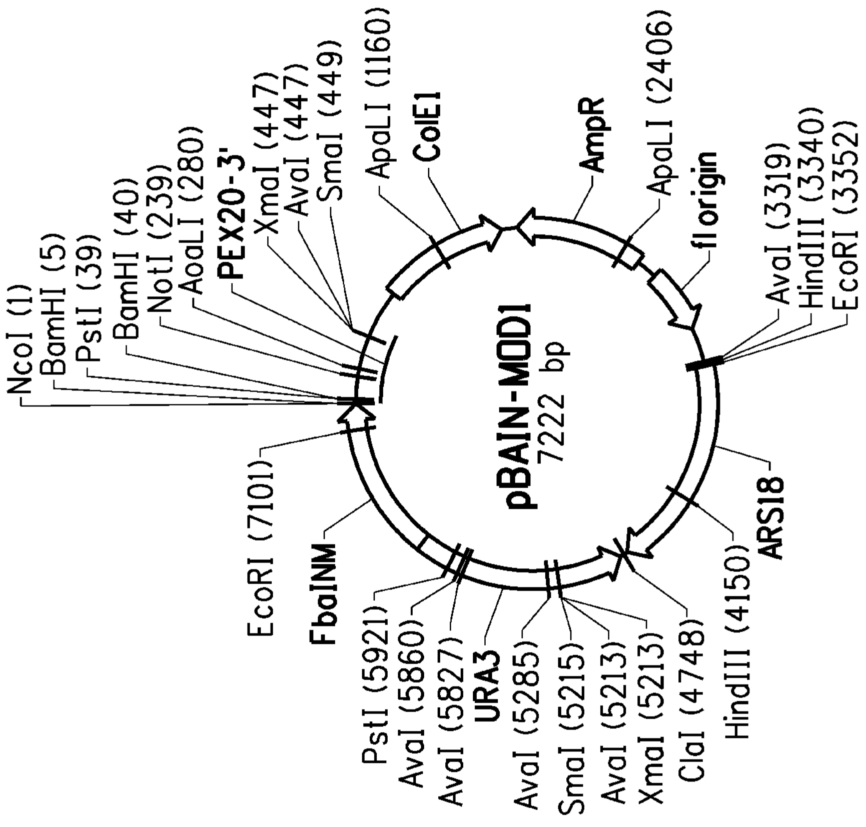
Figure 5A:
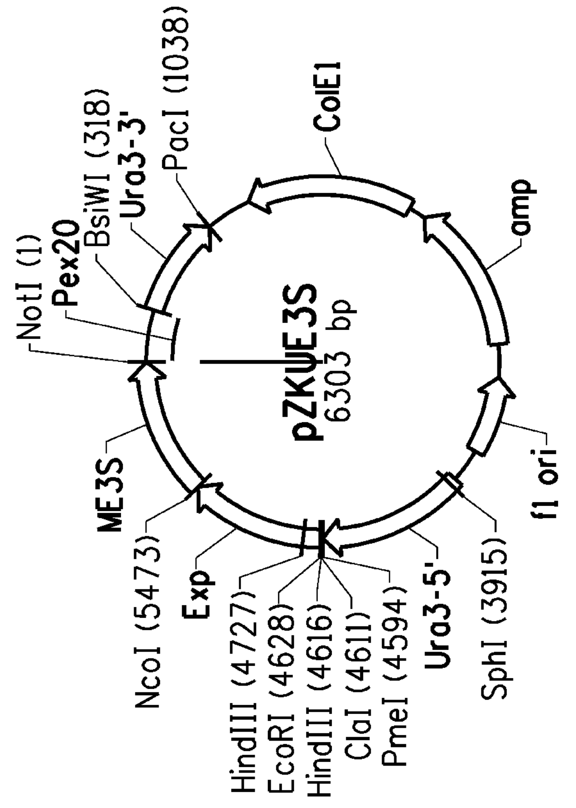

In order to disrupt the Ura3 gene in strain Y4128, construct pZKUE3S (FIG. 5A; SEQ ID NO:31; described in Table 22 of Int'l. App. Pub. No. WO 2008/073367, hereby incorporated herein by reference) was created to integrate a EXP1::ME3S::Pex20 chimeric gene into the Ura3 gene of strain Y4128. Plasmid pZKUE3S was digested with SphI/PacI, and then used to transform strain Y4128 according to the General Methods. Following transformation, cells were plated onto MM+5-FOA selection plates and maintained at 30'C for 2 to 3 days.

A total of 24 transformants grown on MM+5-FOA selection plates were picked and re-streaked onto fresh MM+5-FOA plates. The cells were stripped from the plates, lipids were extracted, and FAMEs were prepared by trans-esterification, and subsequently analyzed with a Hewlett-Packard 6890 GC.

GC analyses showed the presence of between 10-15% EPA in all of the transformants with pZKUE3S from plates. The strains identified as #3, #4, #10, #12, #19 and #21 that produced 12.9%, 14.4%, 15.2%, 15.4%, 14% and 10.9% EPA of total lipids were designated as Y4128U1, Y4128U2, Y4128U3, Y4128U4, Y4128U5 and Y4128U6, respectively (collectively, Y4128U).

The discrepancy in the % EPA quantified in Y4128 (37.6%) versus Y4128U (average 13.8%) is based on differing growth conditions. Specifically, the former culture was analyzed following two days of growth in liquid culture, while the latter culture was analyzed after growth on an agar plate. The Applicants have observed a 2-3 fold increase in % EPA, when comparing results from agar plates to those in liquid culture. Thus, although results are not directly comparable, both Y4128 and Y4128U strains demonstrate production of EPA.

Example 3

Determination of Total Lipid Content of *Yarrowia lipolytica* Strain Y4128

The total amount of lipid produced by strain Y4128 and the percentage of each fatty acid species in the lipid were measured by GC analysis. Specifically, total lipids were extracted, and FAMEs were prepared by trans-esterification, and subsequently analyzed with a Hewlett-Packard 6890 GC, as described in the General Methods.

Dry cell weight was determined by collecting cells from 10 mL of culture via centrifugation, washing the cells with water once to remove residual medium, drying the cells in a vacuum oven at 80° C. overnight, and weighing the dried cells. The total amount of FAMEs in a sample was determined by comparing the areas of all peaks in the GC profile with the peak area of an added known amount of internal standard C15:0 fatty acid.

Based on the above analyses, lipid content as a percentage of dry cell weight (DCW) and lipid composition was determined for strains Y4086 and Y4128. Strain Y4128 had decreased lipid content with respect to strain Y4086 (11.2 TFAs % DCW versus 28.6 TFAs % DCW). In contrast, strain Y4128 had elevated EPA concentrations among lipids with respect to strain Y4086, as shown below in Table 6. Fatty acids are identified as 18:0 (stearic acid), 18:1 (oleic acid), LA, ALA, EDA, DGLA, ETrA, ETA and EPA; fatty acid compositions were expressed as the weight percent (wt. %) of total fatty acids (TFAs).

TABLE 6

Lipid Composition In *Yarrowia lipolytica* Strains Y4086 And Y4128

| Sample | 18:0 | 18:1 | 18:2 [LA] | 18:3 (n-3) [ALA] | 20:2 [EDA] | 20:3 (n-6) [DGLA] | 20:3 (n-3) [ETrA] | 20:4 (n-3) [ETA] | 20:5 (n-3) [EPA] |
|---|---|---|---|---|---|---|---|---|---|
| Y4086 | 4.6 | 26.8 | 28.0 | 6.9 | 7.6 | 0.9 | 4.9 | 2.0 | 9.8 |
| Y4128 | 1.8 | 6.7 | 19.6 | 1.8 | 4.2 | 3.4 | 1.5 | 6.0 | 42.8 |

EPA content in the cell, expressed as mg EPA/g dry cell and calculated according to the following formula: (% of EPA/Lipid)*(% of Lipid/dry cell weight)*0.1, increased from 28 mg EPA/g DCW in strain Y4086 to 47.9 mg EPA/g DCW in strain Y4128.

Thus, the results in Table 6 showed that compared to the parent strain Y4086, strain Y4128 had a lower total lipid content (TFAs % DCW) (11.2% versus 28.6%), higher EPA % TFAs (42.8% versus 9.8%), and higher EPA % DCW (4.8% versus 2.8%). Additionally, strain Y4128 had a 3.3-fold increase in the amount of EPA relative to the total PUFAs (54% of the PUFAs [as a % TFAs] versus 16.3% of the PUFAs [as a % TFAs]) and a 1.7-fold increase in the amount of C20 PUFAs relative to the total PUFAs (73% of the PUFAs [as a % TFAs] versus 42% of the PUFAs [as a % TFAs]).

Example 4

Determination of the Integration Site of pZP2-2988 in *Yarrowia lipolytica* Strain Y4128 as a Pex10 Integration The genomic integration site of pZP2-2988 in strain Y4128 was determined by genome walking using the Universal GenomeWalker™ Kit from Clontech (Palo Alto, Calif.), following the manufacturer's recommended protocol. Based on the sequence of the plasmid, the following primers were designed for genome walking: pZP-GW-5-1 (SEQ ID NO:32), pZP-GW-5-2 (SEQ ID NO:33), pZP-GW-5-3 (SEQ ID NO:34), pZP-GW-5-4 (SEQ ID NO:35), pZP-GW-3-1 (SEQ ID NO:36), pZP-GW-3-2 (SEQ ID NO:37), pZP-GW-3-3 (SEQ ID NO:38) and pZP-GW-3-4 (SEQ ID NO:39).

Genomic DNA was prepared from strain Y4128 using the Qiagen Miniprep kit with a modified protocol. Cells were scraped off a YPD medium plate into a 1.5 mL microfuge tube. Cell pellet (100 μl) was resuspended with 250 μl of buffer P1 containing 0.125 M β-mercaptoethanol and 1 mg/mL zymolyase 20T (MP Biomedicals, Inc., Solon, Ohio). The cell suspension was incubated at 37° C. for 30 min. Buffer P2 (250 μl) was then added to the tube. After mixing by inverting the tube for several times, 350 μl of buffer N3 was added. The mixture was then centrifuged at 14,000 rpm for 5 min in a microfuge. Supernatant was poured into a Qiagen miniprep spin column, and centrifuged for 1 min. The column was washed once by adding 0.75 mL of buffer PE, followed by centrifugation at 14,000 rpm for 1 min. The column was dried by further centrifugation at 14,000 rpm for 1 min. Genomic DNA was eluted by adding 50 μl of buffer EB to the column, allowed to sit for 1 min and centrifuged at 14,000 rpm for 1 min.

Purified genomic DNA was used for genome walking. The DNA was digested with restriction enzymes DraI, EcoRV, PvuII and StuI separately, according to the protocol of the GenomeWalker kit. For each digestion, the reaction mixture contained 10 μl of 10× restriction buffer, 10 μl of the appropriate restriction enzyme and 8 μg of genomic DNA in a total volume of 100 μl. The reaction mixtures were incubated at 37° C. for 4 hrs. The digested DNA samples were then purified using Qiagen PCR purification kit following the manufacturer's protocol exactly. DNA samples were eluted in 16 μl water. Purified, digested genomic DNA samples were then ligated to the genome walker adaptor (infra). Each ligation mixture contained 1.9 μl of the genome walker adaptor, 1.6 μl of 10× ligation buffer, 0.5 μl T4 DNA ligase and 4 μl of the digested DNA. The reaction mixtures were incubated at 16° C. overnight. Then, 72 μl of 50 mM TrisHCl, 1 mM EDTA, pH 7.5 were added to each ligation mixture.

For 5'-end genome walking, four PCR reactions were carried out using 1 μl of each ligation mixture individually as template. In addition, each reaction mixture contained 1 μl of 10 μM primer pZP-GW-5-1 (SEQ ID NO:32), 1 μl of 10 μM kit-supplied Genome Walker adaptor, 41 μl water, 5 μl 10× cDNA PCR reaction buffer and 1 μl Advantage cDNA polymerase mix from Clontech. The sequence of the Genome Walker adaptor (SEQ ID NOs:40 [top strand] and 41 [bottom strand]), is shown below:

```
5'-GTAATACGACTCACTATAGGGCACGCGTGGTCG

                     ACGGCCCGGGCTGGT-3'

                     3'-H2N-CCCGACCA-5'
```

The PCR conditions were as follows: 95° C. for 1 min, followed by 30 cycles at 95° C. for 20 sec and 68° C. for 3 min, followed by a final extension at 68° C. for 7 min. The PCR products were each diluted 1:100 and 1 μl of the diluted PCR product used as template for a second round of PCR. The conditions were exactly the same except that pZP-GW-5-2 (SEQ ID NO:33) replaced pZP-GW-5-1 (SEQ ID NO:32).

For 3'-end genome walking, four PCR reactions were carried out as above, except primer pZP-GW-3-1 (SEQ ID NO:36) and nested adaptor primer (SEQ ID NO:42) were used. The PCR products were similarly diluted and used as template for a second round of PCR, using pZP-GW-3-2 (SEQ ID NO:37) to replace pZP-GW-3-1 (SEQ ID NO:36).

PCR products were analyzed by gel electrophoresis. One reaction product, using EcoRV digested genomic DNA as template and the primers pZP-GW-3-2 and nested adaptor primer, generated a ~1.6 kB fragment. This fragment was isolated, purified with a Qiagen gel purification kit and cloned into pCR2.1-TOPO. Sequence analysis showed that the fragment included both part of plasmid pZP2-2988 and the *Yarrowia* genomic DNA from chromosome C. The junction between them was at nucleotide position 139826 of chromosome C. This was inside the coding region of the Pex10 gene (GenBank Accession No. CAG81606; SEQ ID NO:10).

To determine the 5' end of the junction, PCR amplification was performed using genomic DNA from strain Y4128 as the template and primers Per10 F1 (SEQ ID NO:43) and ZPGW-5-5 (SEQ ID NO:44). The reaction mixture included 1 μl each of 20 μM primer, 1 μl genomic DNA, 22 μl water and 25 μl TaKaRa ExTaq 2× premix (TaKaRa Bio Inc., Otsu Shiga, Japan). The thermocycler conditions were: 94° C. for 1 min, followed by 30 cycles of 94° C. for 20 sec, 55° C. for 20 sec and 72° C. for 2 min, followed by a final extension at 72° C. for 7 min. A 1.6 kB DNA fragment was amplified and cloned into pCR2.1-TOPO. Sequence analysis showed that it was a chimeric fragment between *Yarrowia* genomic DNA from chromosome C and pZP2-2988. The junction was at nucleotide position 139817 of chromosome C. Thus, a 10 nucleotide segment of chromosome C was replaced by the AscI/SphI fragment from pZP2-2988 (FIG. 4B) in strain Y4128. As a result, Pex10 in strain Y4128 was lacking the last 32 amino acids of the encoded protein.

Based on the above conclusions, the Y4128U strains isolated in Example 2 (supra) are referred to subsequently as Δpex10 strains. For clarity, strain Y4128U1 is equivalent to strain Y4128U1 (Δpex10).

Example 5

Plasmid Expression of Pex10 in *Yarrowia lipolytica* Strain Y4128U1 (ΔPex10)

Three plasmids that carried the *Y. lipolytica* Pex10 gene were constructed: 1) pFBAIn-PEX10 allowed the expression of the Pex10 ORF under the control of the FBAINm promoter; and, 2) pPEX10-1 and pPEX10-2 allowed the expression of Pex10 under control of the native Pex10 promoter, although pPEX10-1 used a shorter version (~500 bp) while pPEX10-2 used a longer version (~900 bp) of the promoter. Following construction of these expression plasmids and transformation, the effect of Pex10 plasmid expression on total oil and on EPA level in the *Y. lipolytica* strain Y4128U1 (Δpex10) was determined. Deletion of Pex10 resulted in an increased amount of EPA as a percent of TFAs, but a reduced amount of total lipid, as a percent of DCW, in the cell.

Construction of pFBAIn-PEX10, pPEX10-1 and pPEX10-2

To construct pFBAIn-PEX10, the primers Per10 F1 (SEQ ID NO:43) and Per10 R (SEQ ID NO:45) were used to amplify the coding region of the Pex10 gene using *Y. lipolytica* genomic DNA as template. The PCR reaction mixture contained 1 μl each of 20 μM primers, 1 μl of *Y. lipolytica* genomic DNA (~100 ng), 25 μl ExTaq 2× premix and 22 μl water. The reaction was carried out as follows: 94° C. for 1 min, followed by 30 cycles of 94° C. for 20 sec, 55° C. for 20 sec and 72° C. for 90 sec, followed by a final extension of 72° C. for 7 min. The PCR product, a 1168 bp DNA fragment, was purified with a Qiagen PCR purification kit, digested with NcoI and NotI, and cloned into pFBAIn-MOD-1 (SEQ ID NO:46; FIG. 5B) digested with the same two restriction enzymes.

Figure 6B:
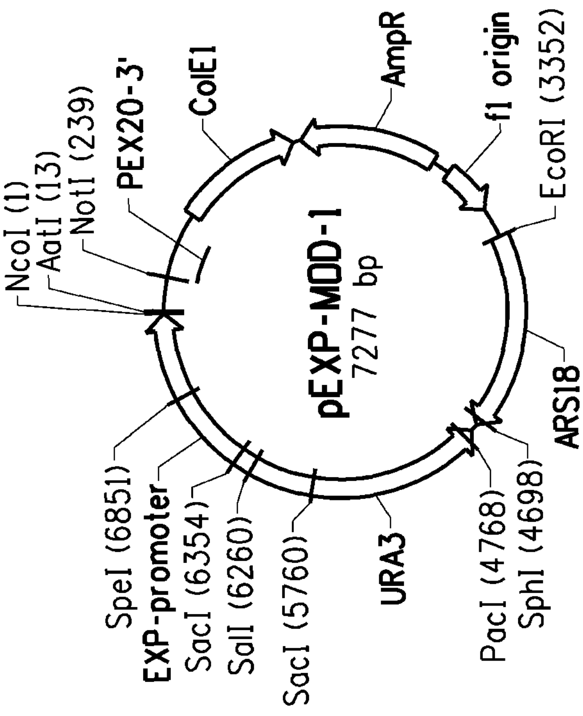
Figure 6A:
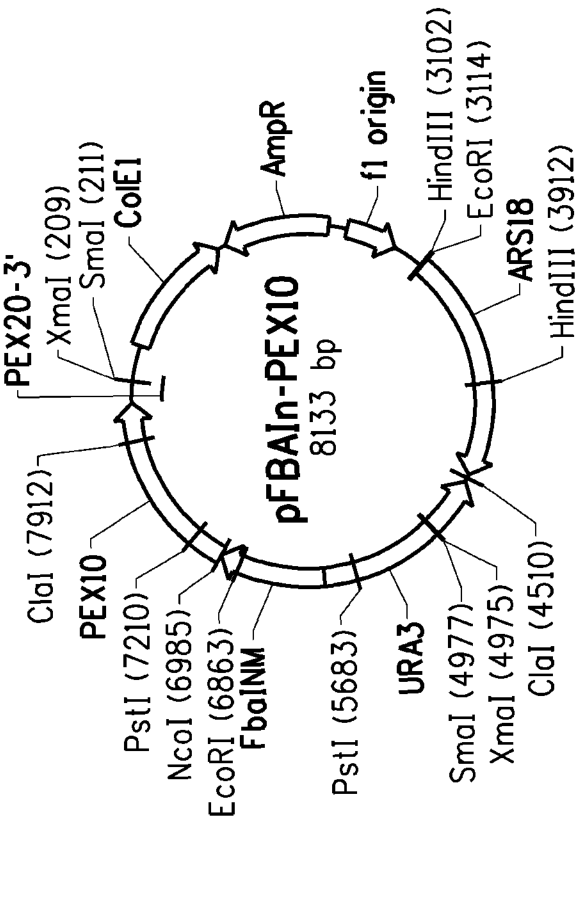

Of the 8 individual clones subjected to sequence analysis, 2 had the correct sequence of Pex10 with no errors. The components of pFBAIn-PEX10 (SEQ ID NO:47; FIG. 6A) are listed below in Table 7.

TABLE 7

Components Of Plasmid pFBAIn-PEX10 (SEQ ID NO: 47)

| RE Sites And Nucleotides Within SEQ ID NO: 47 | Description Of Fragment And Chimeric Gene Components |
|---|---|
| BglII-BsiWI (6040-318) | FBAINm::Pex10::Pex20, comprising: FBAINm: *Yarrowia lipolytica* FBAINm promoter (U.S. Pat. No. 7,202,356); Pex10: *Y. lipolytica* Pex10 ORF (GenBank Accession No. AB036770, nucleotides 1038-2171; SEQ ID NO: 21); Pex20: Pex20 terminator sequence from *Yarrowia* Pex20 gene (GenBank Accession No. AF054613) |
| PacI-BglII (4530-6040) | *Yarrowia* URA3 (GenBank Accession No. AJ306421) |
| (3123-4487) | *Yarrowia* autonomous replicating sequence 18 (ARS18; GenBank Accession No. A17608) |
| (2464-2864) | *E. coli* f1 origin of replication |
| (1424-2284) | Ampicillin-resistance gene ($Amp^R$) for selection in *E. coli* |
| (474-1354) | ColE1 plasmid origin of replication |

To construct pPEX10-1 and pPEX10-2, primers PEX10-R-BsiWI (SEQ ID NO:48), PEX10-F1-SalI (SEQ ID NO:49) and PEX10-F2-SalI (SEQ ID NO:50) were designed and synthesized. PCR amplification using genomic *Yarrowia lipolytica* DNA and primers PEX10-R-BsiWI and PEX10-F1-SalI generated a 1873 bp fragment containing the Pex10 ORF, 500 bp of the 5' upstream region and 215 bp of the 3' downstream region of the Pex10 gene, flanked by SalI and Bs/WI restriction sites at either end. This fragment was purified with the Qiagen PCR purification kit, digested with SalI and Bs/WI, and cloned into pEXP-MOD-1 (SEQ ID NO:51; FIG. 6B) digested with the same two enzymes to generate pPEX10-1 (SEQ ID NO:52; FIG. 7A). Plasmid pEXP-MOD1 is similar to pFBAIn-MOD-1 (SEQ ID NO:46; FIG. 5B) except that the FBAINm promoter in the latter was replaced with the EXP1 promoter. Table 8 lists the components of pPEX10-1.

TABLE 8

Components Of Plasmid pPEX10-1 (SEQ ID NO: 52)

| RE Sites And Nucleotides Within SEQ ID NO: 52 | Description Of Fragment And Chimeric Gene Components |
|---|---|
| SalI-BsiWI (5705-1) | Pex10-5'::Pex10::Pex10-3', comprising: Pex10-5': 500 bp of the 5' promoter region of *Yarrowia lipolytica* Pex10 gene; Pex10: *Yarrowia lipolytica* Pex10 ORF (GenBank Accession No. AB036770, nucleotides 1038-2171; SEQ ID NO: 21); Pex10-3': 215 bp of Pex10 terminator sequence from *Yarrowia* Pex10 gene (GenBank Accession No. AB036770) [Note the entire Pex10-5'::Pex10::Pex10-3' expression cassette is labeled collectively as "PEX10" in the Figure] |
| PacI-SalI (4216-5703) | *Yarrowia* URA3 gene (GenBank Accession No. AJ306421) |

TABLE 8-continued

| Components Of Plasmid pPEX10-1 (SEQ ID NO: 52) | |
|---|---|
| RE Sites And Nucleotides Within SEQ ID NO: 52 | Description Of Fragment And Chimeric Gene Components |
| (2806-4170) | *Yarrowia* autonomous replicating sequence 18 (ARS18; GenBank Accession No. A17608) |
| (2147-2547) | *E. coli* f1 origin of replication |
| (1107-1967) | Ampicillin-resistance gene ($Amp^R$) for selection in *E. coli* |
| (157-1037) | ColE1 plasmid origin of replication |

PCR amplification of *Yarrowia lipolytica* genomic DNA using PEX10-R-BsiWI (SEQ ID NO:48) and PEX10-F2-SalI (SEQ ID NO:50) generated a 2365 bp fragment containing the PEX10 ORF, 991 bp of the 5' upstream region and 215 bp of the 3' downstream region of the Pex10 gene, flanked by SalI and Bs/WI restriction sites at either end. This fragment was purified with a Qiagen PCR purification kit, digested with SalI and Bs/WI, and cloned into similarly digested pEXP-MOD-1. This resulted in synthesis of pPEX10-2 (SEQ ID NO:53), whose construction is analogous to that of plasmid pPEX10-1 (Table 8, supra), with the exception of the longer Pex10-5' promoter in the chimeric Pex10-5'::Pex10::Pex10-3' gene.

Expression of Pex10 in Strain Y4128U1 (ΔPex10)

Plasmids pFBAIN-MOD-1 (control; SEQ ID NO:46), pFBAIn-PEX10 (SEQ ID NO:47), pPEX10-1 (SEQ ID NO:52) and pPEX10-2 (SEQ ID NO:53) were transformed into Y4128U1 (Δpex10) according to the protocol in the General Methods. Transformants were plated on MM plates. The total lipid content and fatty acid composition of transformants carrying the above plasmids were analyzed as described in Example 3.

Lipid content as a percentage of dry cell weight (DCW) and lipid composition are shown below in Table 9. Specifically, fatty acids are identified as 18:0 (stearic acid), 18:1 (oleic acid), LA, ALA, EDA, DGLA, ETrA, ETA and EPA; fatty acid compositions were expressed as the weight percent (wt. %) of total fatty acids.

TABLE 9

Lipid Composition In *Yarrowia lipolytica* Strain Y4128U1 (Δpex10) Transformed With Various Pex10 Plasmids

| Plasmid | TFA % DCW | 18:0 | 18:1 | 18:2 [LA] | 18:3 (ω3) [ALA] | 20:2 [EDA] | 20:3 (ω6) [DGLA] | 20:3 (ω3) [ETrA] | 20:4 (ω3) [ETA] | 20:5 (ω3) [EPA] |
|---|---|---|---|---|---|---|---|---|---|---|
| pFBAIN-MOD-1 | 22.8 | 1.9 | 9.6 | 18.3 | 2.0 | 4.3 | 2.3 | 2.1 | 5.9 | 27.7 |
| pFBAIN-PEX10 | 29.2 | 4.0 | 24.9 | 25.1 | 7.6 | 6.6 | 1.0 | 5.3 | 3.6 | 10.8 |
| pPEX10-1 | 27.1 | 3.9 | 25.0 | 25.2 | 8.2 | 6.4 | 0.9 | 5.2 | 3.5 | 10.7 |
| pPEX10-2 | 28.5 | 4.3 | 25.4 | 24.5 | 7.6 | 6.4 | 1.0 | 5.3 | 3.4 | 10.8 |

The results in Table 9 showed that expression of Pex10 in Y4128U1 (Δpex10), either from the native *Y. lipolytica* Pex10 promoter or from the *Y. lipolytica* FBAINm promoter, reduced the percent of EPA back to the level of Y4086 while increasing the total lipid content (TFA % DCW) up to the level of Y4086 (see data of Table 6 for comparison). EPA content per gram of dry cell changed from 63.2 mg in the case of the control sample (i.e., cells carrying pFBAIn-MOD-1) to 31.5 mg in cells carrying pFBAIn-PEX10, 29 mg in cells carrying pPEX10-1 and 30.8 mg in cells carrying pPEX10-2. These results demonstrated that disruption of the ring-finger domain of Pex10 increased the amount of EPA but reduced the total lipid content in the cell.

Thus, the results in Table 9 showed that compared to Y4128U1 (Δpex10) transformant with control plasmid, all transformants with Pex10 expressing plasmids showed higher lipid content (TFAs % DCW) (>27% versus 22.8%), lower EPA % TFAs (ca. 10.8% versus 27.7%), and lower EPA % DCW (<3.1% versus 6.3%). Additionally, strain Y4128U1 (Δpex10) transformant with control plasmid, as compared to those transformants with Pex10 expressing plasmids, had a 2.5-fold increase in the amount of EPA relative to the total PUFAs (44% of the PUFAs [as a % TFAs] versus 17.5% (avg) of the PUFAs [as a % TFAs]) and a 1.5-fold increase in the amount of C20 PUFAs relative to the total PUFAs (67% of the PUFAs [as a % TFAs] versus 44% (avg) of the PUFAs [as a % TFAs]).

Example 6

Generation of Y4184U Strain to Produce EPA

*Y. lipolytica* strain Y4184U was used as the host in Example 7, infra. Strain Y4184U was derived from *Y. lipolytica* ATCC #20362, and is capable of producing EPA via expression of a Δ9 elongase/Δ8 desaturase pathway. The strain has a Ura− phenotype and its construction is described in Example 7 of Int'l. App. Pub. No. WO 2008/073367, hereby incorporated herein by reference.

Figure 8B:
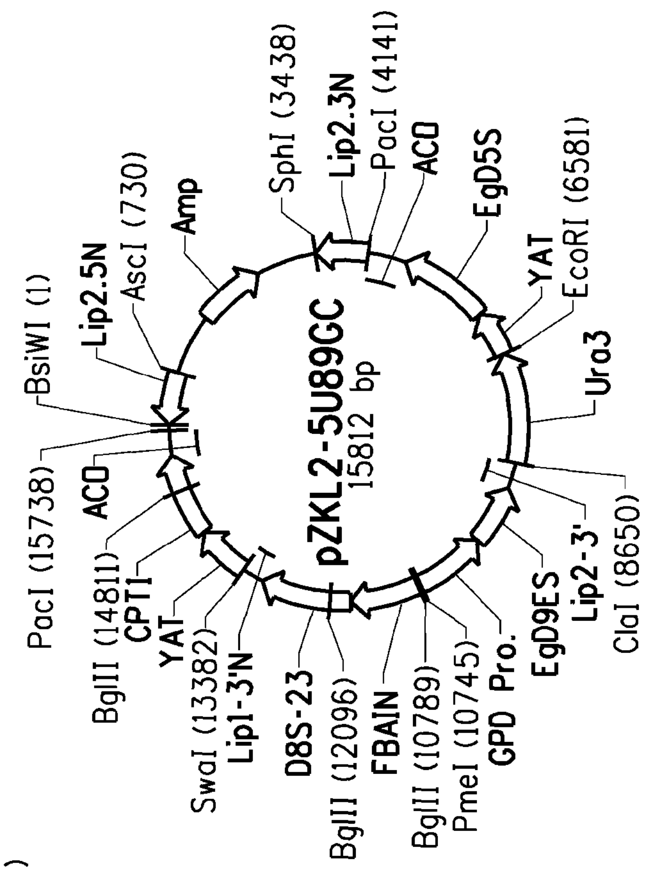
Figure 8A:
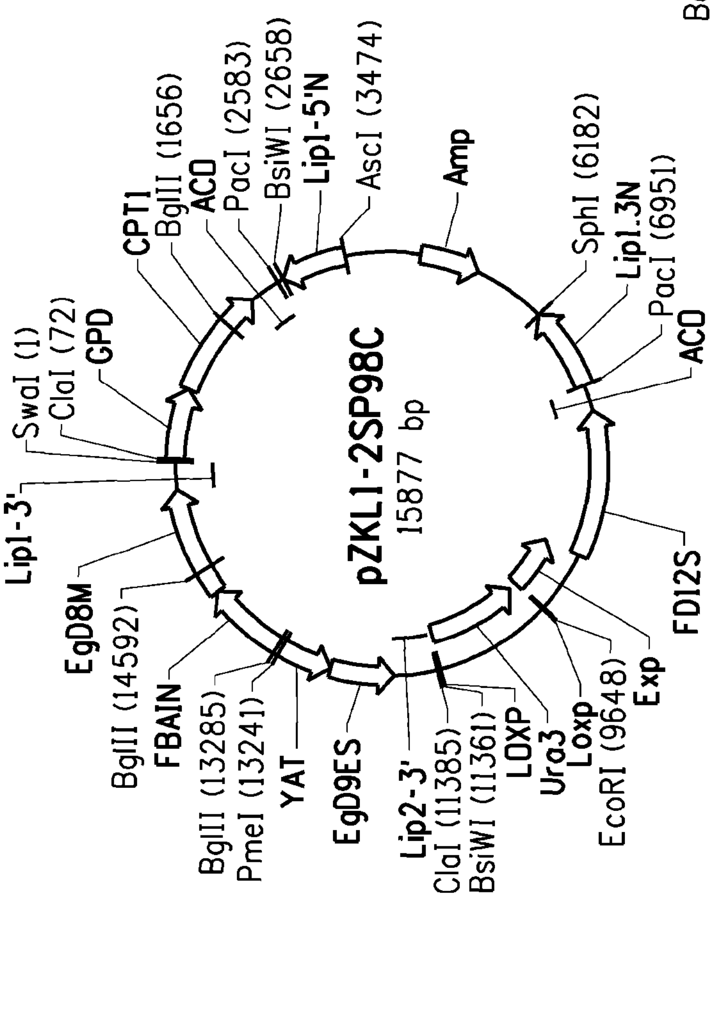

In summary, however, the development of strain Y4184U required the construction of strain Y2224, strain Y4001, strain Y4001U, strain Y4036, strain Y4036U and strain Y4069 (supra, Example 1). Further development of strain Y4184U (diagrammed in FIG. 7B) required generation of strain Y4084, strain Y4084U1, strain Y4127 (deposited with the American Type Culture Collection on Nov. 29, 2007, under accession number ATCC PTA-8802), strain Y4127U2, strain Y4158, strain Y4158U1 and strain Y4184. The plasmid construct pZKL1-2SP98C, used for transformation of strain Y4127U2, is diagrammed in FIG. 8A (SEQ ID NO:54; described in Table 23 of Int'l. App. Pub. No. WO 2008/073367, hereby incorporated herein by reference). Plasmid pZKL2-5U89GC, used for transformation of strain Y4158U1, is shown in FIG. 8B (SEQ ID NO:55; described in Table 24 of Int'l. App. Pub. No. WO 2008/073367, hereby incorporated herein by reference).

The final genotype of strain Y4184 (producing 31% EPA of total lipids) with respect to wildtype *Yarrowia lipolytica* ATCC #20362 was unknown 1−, unknown 2−, unknown 4−, unknown 5−, unknown 6−, unknown 7−, YAT1::ME3S::Pex16, EXP1::ME3S::Pex20 (2 copies), GPAT::EgD9e::Lip2, FBAINm::EgD9eS::Lip2, EXP1::EgD9eS::Lip1, FBA::EgD9eS::Pex20, YAT1::EgD9eS::Lip2, GPD::EgD9eS::Lip2, GPDIN::EgD8M::Lip1, YAT1::EgD8M::Aco, EXP1::EgD8M::Pex16, FBAINm::EgD8M::Pex20, FBAIN::EgD8M::Lip1 (2 copies), GPM/FBAIN::FmD12S::

Oct, EXP1::FmD12S::Aco, YAT1::FmD12::Oct, GPD::FmD12::Pex20, EXP1::EgD5S::Pex20, YAT1::EgD5S::Aco, YAT1::Rd5S::Oct, FBAIN::EgD5::Aco, FBAINm::PaD17::Aco, EXP1::PaD17::Pex16, YAT1::PaD17S::Lip1, YAT1::YlCPT1::Aco, GPD::YlCPT1::Aco (wherein FmD12 is a *Fusarium moniliforme* Δ12 desaturase gene [Int'l. App. Pub. No. WO 2005/047485]; FmD12S is a codon-optimized Δ12 desaturase gene, derived from *Fusarium moniliforme* [Int'l. App. Pub. No. WO 2005/047485]; ME3S is a codon-optimized $C_{16/18}$ elongase gene, derived from *Mortierella alpina* [Int'l. App. Pub. No. WO 2007/046817]; EgD9e is a *Euglena gracilis* Δ9 elongase gene [Int'l. App. Pub. No. WO 2007/061742]; EgD9eS is a codon-optimized Δ9 elongase gene, derived from *Euglena gracilis* [Int'l. App. Pub. No. WO 2007/061742]; EgD8M is a synthetic mutant Δ8 desaturase [Int'l. App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. US 2007-0292924-A1]; EgD5S is a codon-optimized Δ5 desaturase gene, derived from *Euglena gracilis* [U.S. Pat. App. Pub. No. 2007-0292924]; RD5S is a codon-optimized Δ5 desaturase, derived from *Peridinium* sp. CCMP626 [U.S. Pat. App. Pub. No. 2007-0271632]; PaD17 is a *Pythium aphanidermatum* Δ17 desaturase [Int'l. App. Pub. No. WO 2008/054565]; PaD17S is a codon-optimized Δ17 desaturase, derived from *Pythium aphanidermatum* [Int'l. App. Pub. No. WO 2008/054565]; and, YlCPT1 is a *Yarrowia lipolytica* diacylglycerol cholinephosphotransferase gene [Int'l. App. Pub. No. WO 2006/052870]).

In order to disrupt the Ura3 gene in strain Y4184, construct pZKUE3S (FIG. 5A; SEQ ID NO:31; described in Table 22 of Int'l. App. Pub. No. WO 2008/073367, hereby incorporated herein by reference) was used to integrate a EXP1::ME3S::Pex20 chimeric gene into the Ura3 gene of strain Y4184 to result in strains Y4184U1 (11.2% EPA of total lipids), Y4184U2 (10.6% EPA of total lipids) and Y4184U4 (15.5% EPA of total lipids), respectively (collectively, Y4184U).

Example 7

Chromosomal Deletion of Pex10 in *Yarrowia lipolytica* Strain Y4184U4 Increases Accumulation of EPA and Total Lipid Content Construct pYPS161 (FIG. 9A, SEQ ID NO:56) was used to knock out the chromosomal Pex10 gene from the EPA-producing *Yarrowia* strain Y4184U4 (Example 6). Transformation of *Y. lipolytica* strain Y4184U4 with the Pex10 knock out construct resulted in creation of strain Y4184 (pex10). The effect of the Pex10 knockout on total oil and on EPA level was determined and compared. Specifically, knockout of Pex10 resulted in an increased percentage of EPA (as % TFAs and % DCW) and an increased total lipid content in the cell.

Construct pYSP161

The construct pYPS161 contained the following components:

TABLE 10

Description of Plasmid pYPS161 (SEQ ID NO: 56)

| RE Sites And Nucleotides Within SEQ ID NO: 56 | Description Of Fragment And Chimeric Gene Components |
|---|---|
| AscI/BsiWI (1521-157) | 1364 bp Pex10 knockout fragment #1 of *Yarrowia* Pex10 gene (GenBank Accession No. AB036770) |
| PacI/SphI (5519-4229) | 1290 bp Pex10 knockout fragment #2 of *Yarrowia* Pex10 gene (GenBank Accession No. AB036770) |
| SalI/EcoRI (7170-5551) | *Yarrowia* URA3 gene (GenBank Accession No. AJ306421) |
| 2451-1571 | ColE1 plasmid origin of replication |
| 3369-2509 | ampicillin-resistance gene ($Amp^R$) for selection in *E. coli* |
| 3977-3577 | *E. coli* f1 origin of replication |

Generation of *Yarrowia lipolytica* Knockout Strain Y4184 (ΔPex10)

Standard protocols were used to transform *Yarrowia lipolytica* strain Y4184U4 (Example 6) with the purified 5.3 kB AscI/SphI fragment of Pex10 knockout construct pYPS161 (supra), and a cells alone control was also prepared. There were about 200 to 250 colonies present for each of the experimental transformations, while there were no colonies present on the cells alone plates (per expectations).

Colony PCR was used to screen for cells having the Pex10 deletion. Specifically, the PCR reaction was performed using MasterAmp Taq polymerase (Epicentre Technologies, Madison, Wis.) following standard protocols, using PCR primers Pex-10del1 3'.Forward (SEQ ID NO:57) and Pex-10del2 5'.Reverse (SEQ ID NO:58). The PCR reaction conditions were 94° C. for 5 min, followed by 30 cycles at 94° C. for 30 sec, 60° C. for 30 sec and 72° C. for 2 min, followed by a final extension at 72° C. for 6 min. The reaction was then held at 4° C. If the Pex10 knockout construct integrated within the Pex10 region, a single PCR product 2.8 kB in size was expected to be produced. In contrast, if the strain integrated the Pex10 knockout construct in a chromosomal region other than the Pex10 region, then two PCR fragments, i.e., 2.8 kB and 1.1 kB, would be generated. Of the 288 colonies screened, the majority had the Pex10 knockout construct integrated at a random site. Only one of the 288 colonies contained the Pex10 knockout. This strain was designated Y4184 (Δpex10).

Evaluation of *Yarrowia lipolytica* Strains Y4184 and Y4184 (ΔPex10) for Total Oil and EPA Production To evaluate the effect of the Pex10 knockout on the percent of PUFAs in the total lipid fraction and the total lipid content in the cells, strains Y4184 and Y4184 (Δpex10) were grown under comparable oleaginous conditions. Specifically, cultures were grown at a starting $OD_{600}$ of ~0.1 in 25 mL of either fermentation media (FM) or FM medium without Yeast Extract (FM without YE) in a 250 mL flask for 48 hrs. The cells were harvested by centrifugation for 10 min at 8000 rpm in a 50 mL conical tube. The supernatant was discarded and the cells were re-suspended in 25 mL of HGM and transferred to a new 250 mL flask. The cells were incubated with aeration for an additional 120 hrs at 30° C.

To determine the dry cell weight (DCW), the cells from 5 mL of the FM-grown cultures and 10 mL of the FM without YE-grown cultures were processed. The cultured cells were centrifuged for 10 min at 4300 rpm. The pellet was re-suspended using 10 mL of saline and was centrifuged under the same conditions for a second time. The pellet was then re-suspended using 1 mL of sterile $H_2O$ (three times) and was transferred to a pre-weighed aluminum pan. The cells were dried overnight in a vacuum oven at 80° C. The weight of the cells was determined.

The total lipid content and fatty acid composition of transformants carrying the above plasmids were analyzed as described in Example 3. DCW, total lipid content (TFAs % DCW), total EPA % TFAs, and EPA % DCW are shown below in Table 11.

TABLE 11

Lipid Composition In *Y. lipolytica* Strains Y4184 And Y4184 (ΔPex10)

| Media | Strain | DCW | TFAs % DCW | EPA % TFAs | EPA % DCW |
|---|---|---|---|---|---|
| FM | Y4184 | 11.5 | 11.8 | 20.6 | 2.4 |
| | Y4184 (ΔPex10) | 11.5 | 17.6 | 43.2 | 7.6 |
| FM | Y4184 | 4.6 | 8.8 | 23.2 | 2.0 |
| without YE | Y4184 (ΔPex10) | 4.0 | 13.2 | 46.1 | 6.1 |

The results in Table 11 showed that knockout of the chromosomal Pex10 gene in Y4184 (ΔPex10) increased the percent of EPA (as % TFAs and as % DCW) and increased the total oil content, as compared to the percent of EPA and total oil content in strain Y4184 whose native Pex10p had not been knocked out. More specifically, in FM media, there was about 109% increase in EPA (% TFAs), about 216% increase in EPA productivity (% DCW) and about 49% increase in total oil (TFAs % DCW). In FM without YE media, there was about 100% increase in EPA (% TFAs), about 205% increase in EPA productivity (% DCW) and about 50% increase in total oil (TFAs % DCW).

Thus, the results in Table 11 showed that in FM medium, compared to the parent strain Y4184, Y4184 (ΔPex10) strain had higher lipid content (TFAs % DCW) (17.6% versus 11.8%), higher EPA % TFAs (43.2% versus 20.6%), and higher EPA % DCW (7.6% versus 2.4%). Similarly, in FM medium without YE, compared to the parent strain Y4184, Y4184 (ΔPex10) strain had higher lipid content (TFAs % DCW) (13.2% versus 8.8%), higher EPA % TFAs (46.1% versus 23.2%), and higher EPA % DCW (6.1% versus 2.0%).

Example 8

Prophetic

Chromosomal Knockout of Alternate Pex Genes in PUFA-Producing Strains of *Yarrowia lipolytica*

The present Example describes various strains of *Yarrowia lipolytica* that have been engineered to produce ω-3/ω-6 PUFAs. It is contemplated that any of these *Y. lipolytica* host strains could be engineered to produce an increased amount of ω-3/ω-6 PUFAs in the total lipid fraction and in the oil fraction, if the chromosomal gene encoding Pex1p, Pex2p, Pex3p, Pex3Bp, Pex4p, Pex5p, Pex6p, Pex7p, Pex8p, Pex12p, Pex13p, Pex14p, Pex16p, Pex17p, Pex19p, Pex20p, Pex22p or Pex26p was disrupted using the methodology of Example 7, supra.

More specifically, a variety of *Yarrowia lipolytica* strains have been engineered by the Applicant's Assignee to produce high concentrations of various ω-3/ω-6 PUFAs via expression of a heterologous Δ6 desaturase/Δ6 elongase PUFA pathway or a heterologous Δ9 elongase/Δ8 desaturase PUFA pathway.

Summary of Representative *Yarrowia lipolytica* Strains Producing ω-3/ω-6 PUFAs

Although some representative strains are summarized in the Table below, the disclosure of *Yarrowia lipolytica* strains producing ω-3/ω-6 PUFAs is not limited in any way to the strains therein. Instead, all of the teachings provided in the present Application, in addition to the following commonly owned and co-pending applications, are useful for development of a suitable *Yarrowia lipolytica* strain engineered to produce ω-3/ω-6 PUFAs. These specifically include the following Applicants' Assignee's co-pending patents and applications: U.S. Pat. No. 7,125,672, U.S. Pat. No. 7,189,559, U.S. Pat. No. 7,192,762, U.S. Pat. No. 7,198,937, U.S. Pat. No. 7,202,356, U.S. Pat. No. 7,214,491, U.S. Pat. No. 7,238,482, U.S. Pat. No. 7,256,033, U.S. Pat. No. 7,259,255, U.S. Pat. No. 7,264,949, U.S. Pat. No. 7,267,976, U.S. Pat. No. 7,273,746, U.S. patent application Ser. No. 10/985,254 and No. 10/985,691 (filed Nov. 10, 2004), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/253,882 (filed Oct. 19, 2005), U.S. patent application Ser. No. 11/264,784 and No. 11/264,737 (filed Nov. 1, 2005), U.S. patent application Ser. No. 11/265,761 (filed Nov. 2, 2005), U.S. patent application Ser. No. 11/601,563 and No. 11/601,564 (filed Nov. 16, 2006), U.S. patent application Ser. No. 11/635,258 (filed Dec. 7, 2006), U.S. patent application Ser. No. 11/613,420 (filed Dec. 20, 2006), U.S. patent application Ser. No. 11/787,772 (filed Apr. 18, 2007), U.S. patent application Ser. No. 11/737,772 (filed Apr. 20, 2007), U.S. patent application Ser. No. 11/740,298 (filed Apr. 26, 2007), U.S. patent application Ser. No. 12/111,237 (filed Apr. 29, 2008), U.S. patent application Ser. No. 11/748,629 and No. 11/748,637 (filed May 15, 2007), U.S. patent application Ser. No. 11/779,915 (filed Jul. 19, 2007), U.S. Pat. App. No. 60/991,266 (filed Nov. 30, 2007), U.S. patent application Ser. No. 11/952,243 (filed Dec. 7, 2007), U.S. Pat. App. No. 61/041,716 (filed Apr. 2, 2008), U.S. patent application Ser. No. 12/061,738 (filed Apr. 3, 2008), U.S. patent application Ser. No. 12/099,811 (filed Apr. 9, 2008), U.S. patent application Ser. No. 12/102,879 (filed Apr. 15, 2008), U.S. patent application Ser. No. 12/111,237 (filed Apr. 29, 2008), U.S. Pat. App. No. 61/055,511 (filed May 23, 2008) and U.S. Pat. App. No. 61/093,007 (filed Aug. 29, 2008).

TABLE 12

Lipid Profile Of Representative *Yarrowia lipolytica* Strains Engineered To Produce ω-3/ω-6 PUFAs

| Strain | Reference | ATCC Deposit No. | Fatty Acid Content (As A Percent [%] of Total Fatty Acids) 16:0 | 16:1 | 18:0 | 18:1 | 18:2 | 18:3 (ALA) | GLA | 20:2 |
|---|---|---|---|---|---|---|---|---|---|---|
| Wildtype | US 2006-0035351-A1; WO2006/033723 | #76982 | 14 | 11 | 3.5 | 34.8 | 31 | — | 0 | — |
| pDMW208 | | — | 11.9 | 8.6 | 1.5 | 24.4 | 17.8 | — | 25.9 | — |
| pDMW208D62 | | — | 16.2 | 1.5 | 0.1 | 17.8 | 22.2 | — | 34 | — |
| M4 | US 2006-0115881-A1; WO2006/052870 | — | 15 | 4 | 2 | 5 | 27 | — | 35 | — |

TABLE 12-continued

Lipid Profile Of Representative *Yarrowia lipolytica* Strains Engineered To Produce ω-3/ω-6 PUFAs

| | | | | | | | | | | |
|---|---|---|---|---|---|---|---|---|---|---|
| Y2034 | US 2006-0094092- | — | 13.1 | 8.1 | 1.7 | 7.4 | 14.8 | — | 25.2 | — |
| Y2047 | A1;WO2006/055322 | PTA-7186 | 15.9 | 6.6 | 0.7 | 8.9 | 16.6 | — | 29.7 | — |
| Y2214 | | — | 7.9 | 15.3 | 0 | 13.7 | 37.5 | — | 0 | — |
| EU | US 2006-0115881- | — | 19 | 10.3 | 2.3 | 15.8 | 12 | — | 18.7 | — |
| Y2072 | A1; WO2006/052870 | — | 7.6 | 4.1 | 2.2 | 16.8 | 13.9 | — | 27.8 | — |
| Y2102 | | — | 9 | 3 | 3.5 | 5.6 | 18.6 | — | 29.6 | — |
| Y2088 | | — | 17 | 4.5 | 3 | 2.5 | 10 | — | 20 | — |
| Y2089 | | — | 7.9 | 3.4 | 2.5 | 9.9 | 14.3 | — | 37.5 | — |
| Y2095 | | — | 13 | 0 | 2.6 | 5.1 | 16 | — | 29.1 | — |
| Y2090 | | — | 6 | 1 | 6.1 | 7.7 | 12.6 | — | 26.4 | — |
| Y2096 | | PTA-7184 | 8.1 | 1 | 6.3 | 8.5 | 11.5 | — | 25 | — |
| Y2201 | | PTA-7185 | 11 | 16.1 | 0.7 | 18.4 | 27 | — | — | 3.3 |
| Y3000 | US 2006-0110806-<br>A1; WO2006/052871 | PTA-7187 | 5.9 | 1.2 | 5.5 | 7.7 | 11.7 | — | 30.1 | — |
| Y4001 | WO2008/073367 | — | 4.3 | 4.4 | 3.9 | 35.9 | 23 | 0 | — | 23.8 |
| Y4036 | | — | 7.7 | 3.6 | 1.1 | 14.2 | 32.6 | 0 | — | 15.6 |
| Y4070 | | — | 8 | 5.3 | 3.5 | 14.6 | 42.1 | 0 | — | 6.7 |
| Y4158 | | — | 3.2 | 1.2 | 2.7 | 14.5 | 30.4 | 5.3 | — | 6.2 |
| Y4184 | | — | 3.1 | 1.5 | 1.8 | 8.7 | 31.5 | 4.9 | — | 5.6 |

| | | ATCC Deposit | Fatty Acid Content (As A Percent [%] of Total Fatty Acids) | | | | | | Lipid % |
|---|---|---|---|---|---|---|---|---|---|
| Strain | Reference | No. | DGLA | ARA | ETA | EPA | DPA | DHA | dcw |
| Wildtype | US 2006-0035351- | #76982 | — | — | — | — | — | — | — |
| pDMW208 | A1; WO2006/033723 | — | — | — | — | — | — | — | — |
| pDMW208D62 | | — | — | — | — | — | — | — | — |
| M4 | US 2006-0115881-<br>A1; WO2006/052870 | — | 8 | 0 | 0 | 0 | — | — | — |
| Y2034 | US 2006-0094092- | — | 8.3 | 11.2 | — | — | — | — | — |
| Y2047 | A1; WO2006/055322 | PTA-7186 | 0 | 10.9 | — | — | — | — | — |
| Y2214 | | — | 7.9 | 14 | — | — | — | — | — |
| EU | US 2006-0115881- | — | 5.7 | 0.2 | 3 | 10.3 | — | — | 36 |
| Y2072 | A1; WO2006/052870 | — | 3.7 | 1.7 | 2.2 | 15 | — | — | — |
| Y2102 | | — | 3.8 | 2.8 | 2.3 | 18.4 | — | — | — |
| Y2088 | | — | 3 | 2.8 | 1.7 | 20 | — | — | — |
| Y2089 | | — | 2.5 | 1.8 | 1.6 | 17.6 | — | — | — |
| Y2095 | | — | 3.1 | 1.9 | 2.7 | 19.3 | — | — | — |
| Y2090 | | — | 6.7 | 2.4 | 3.6 | 26.6 | — | — | 22.9 |
| Y2096 | | PTA-7184 | 5.8 | 2.1 | 2.5 | 28.1 | — | — | 20.8 |
| Y2201 | | PTA-7185 | 3.3 | 1 | 3.8 | 9 | — | — | — |
| Y3000 | US 2006-0110806-<br>A1; WO2006/052871 | PTA-7187 | 2.6 | 1.2 | 1.2 | 4.7 | 18.3 | 5.6 | — |
| Y4001 | WO2008/073367 | — | 0 | 0 | 0 | — | — | — | |
| Y4036 | | — | 18.2 | 0 | 0 | — | — | — | |
| Y4070 | | — | 2.4 | 11.9 | — | — | — | — | |
| Y4158 | | — | 3.1 | 0.3 | 3.4 | 20.5 | — | — | 27.3 |
| Y4184 | | — | 2.9 | 0.6 | 2.4 | 28.9 | — | — | 23.9 |

Chromosomal Knockout of Pex Genes

Following selection of a preferred *Yarrowia lipolytica* strain producing the desired ω-3/ω-6 PUFA (or combination of PUFAs thereof), one of skill in the art could readily engineer a suitable knockout construct, similar to pYPS161 in Example 7, to result in knockout of a chromosomal Pex gene upon transformation into the parental *Y. lipolytica* strain. Preferred Pex genes would include: YlPex1p (GenBank Accession No. CAG82178; SEQ ID NO:1), YlPex2p (Gen Bank Accession No. CAG77647; SEQ ID NO:2), YlPex3p (Gen Bank Accession No. CAG78565; SEQ ID NO:3), YlPex3Bp (GenBank Accession No. CAG83356; SEQ ID NO:4), YlPex4p (GenBank Accession No. CAG79130; SEQ ID NO:5), YlPex5p (GenBank Accession No. CAG78803; SEQ ID NO:6), YlPex6p (GenBank Accession No. CAG82306; SEQ ID NO:7), YlPex7p (GenBank Accession No. CAG78389; SEQ ID NO:8), YlPex8p (Gen Bank Accession No. CAG80447; SEQ ID NO:9), YlPex12p (GenBank Accession No. CAG81532; SEQ ID NO:11), YlPex13p (GenBank Accession No. CAG81789; SEQ ID NO:12), YlPex14p (GenBank Accession No. CAG79323; SEQ ID NO:13), YlPex16p (GenBank Accession No. CAG79622; SEQ ID NO:14), YlPex17p (GenBank Accession No. CAG84025; SEQ ID NO:15), YlPex19p (GenBank Accession No. AAK84827; SEQ ID NO:16), YlPex20p (GenBank Accession No. CAG79226; SEQ ID NO:17), YlPex22p (GenBank Accession No. CAG77876; SEQ ID NO:18) and YlPex26p (GenBank Accession No. NC_006072, antisense translation of nucleotides 117230-118387; SEQ ID NO:19).

It would be expected that the chromosomal disruption of Pex would result in an increased amount of PUFAs in the total lipid fraction and in the oil fraction, as a percent of total fatty acids, as compared with a eukaryotic organism whose native peroxisome biogenesis factor protein has not been disrupted, wherein the amount of PUFAs can be: 1) the PUFA that is the desired end product of a functional PUFA biosynthetic pathway, as opposed to PUFA intermediates or by-products, 2) $C_{20}$ and $C_{22}$ PUFAs, and/or 3) total PUFAs. Preferred results not only achieve an increase in the amount of PUFAs as a percent of total fatty acids but also result in an increased amount of PUFAs as a percent of dry cell weight, as compared with a eukaryotic organism whose native peroxisome biogenesis factor protein has not been disrupted. Again, the amount of PUFAs can be: 1) the PUFA that is the desired end product of a functional PUFA biosynthetic pathway, as opposed to PUFA intermediates or by-products, 2) the $C_{20}$ and $C_{22}$ PUFAs, and/or 3) the total PUFAs. In some cases, the total lipid content also increases, relative to that of a eukaryotic organism whose native peroxisome biogenesis factor protein has not been disrupted.

Example 9

Figure 9A:
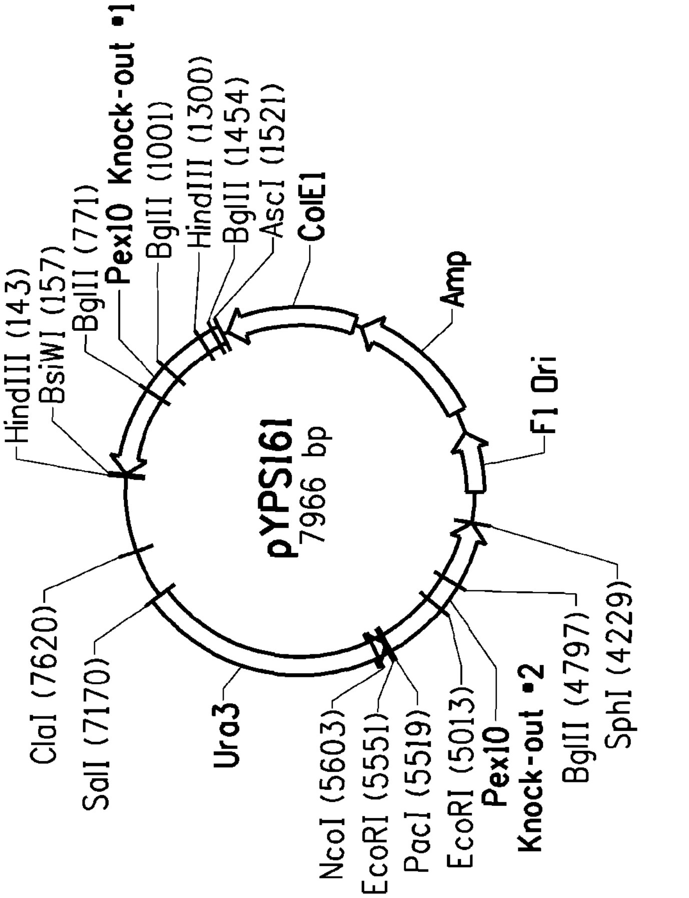
Figure 9B:
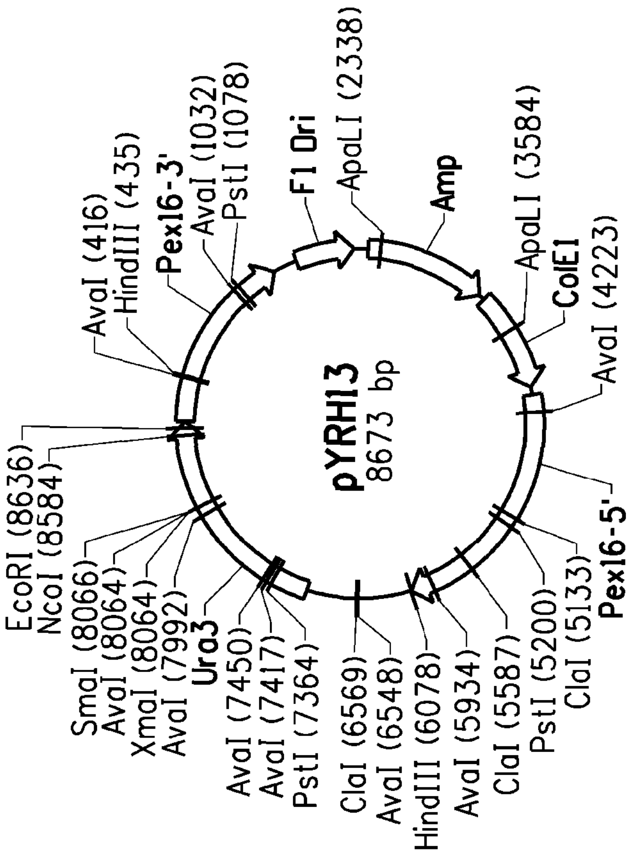

Chromosomal Deletion of Pex16 in *Yarrowia lipolytica* Strain Y4036U Increases Percent DGLA Accumulated The present Example describes use of construct pYRH13 (FIG. 9B; SEQ ID NO:59) to knock out the chromosomal Pex16 gene in the DGLA-producing *Yarrowia* strain Y4036U (Example 1). Transformation of *Y. lipolytica* strain Y4036U with the Pex16 knockout construct resulted in creation of strain Y4036U (Δpex16). The effect of the Pex16 knockout on DGLA level was determined and compared. Specifically, knockout of Pex16 resulted in an increased percentage of DGLA as a percent of total fatty acids in the cell.

Construct pYRH13

Plasmid pYRH13 was derived from plasmid pYPS161 (FIG. 9A, SEQ ID NO:56; Example 7). Specifically, a 1982 bp 5' promoter region of the *Yarrowia lipolytica* Pex16 gene (GenBank Accession No. CAG79622) replaced the AscI/BsiWI fragment of pYPS161 and a 448 bp 3' terminator region of the *Yarrowia lipolytica* Pex16 gene (GenBank Accession No. CAG79622) replaced the PacI/SphI fragment of pYPS161 to produce pYRH13 (SEQ ID NO:59; FIG. 9B).

Generation of *Yarrowia lipolytica* Knockout Strain Y4036 (ΔPex16)

Standard protocols were used to transform *Yarrowia lipolytica* strain Y4036U (Example 1) with the purified 6.0 kB AscI/SphI fragment of Pex16 knockout construct pYRH13.

To screen for cells having the Pex16 deletion, colony PCR was performed using Taq polymerase (Invitrogen; Carlsbad, Calif.) and the PCR primers PEX16Fii (SEQ ID NO:60) and PEX16Rii (SEQ ID NO:61). This set of primers was designed to amplify a 1.1 kB region of the intact Pex16 gene, and therefore the Pex16 deleted mutant (i.e., Δpex16) would not produce the band. A second set of primers was designed to produce a band only when the Pex16 gene was deleted. Specifically, one primer (i.e., 3UTR-URA3; SEQ ID NO:62) binds to a region in the vector sequences of the introduced 6.0 kB AscI/SphI disruption fragment, and the other primer (i.e., PEX16-conf; SEQ ID NO:63) binds to the Pex16 terminator sequences of chromosome outside of the homologous region of the disruption fragment.

More specifically, the colony PCR was performed using a reaction mixture that contained: 20 mM Tris-HCl (pH 8.4), 50 mM KCl, 1.5 mM $MgCl_2$, 400 μM each of dGTP, dCTP, dATP, and dTTP, 2 μM of each primer, 20 μl water and 2 U Taq polymerase. Amplification was carried out as follows: initial denaturation at 94° C. for 120 sec, followed by 35 cycles of denaturation at 94° C. for 60 sec, annealing at 55° C. for 60 sec, and elongation at 72° C. for 120 sec. A final elongation cycle at 72° C. for 5 min was carried out, followed by reaction termination at 4° C.

Of 205 colonies screened, 195 had the Pex16 knockout fragment integrated at a random site in the chromosome and thus were not Δpex16 mutants (however, the cells could grow on ura− plates, due to the presence of pYRH13). Three of these random integrants, designated as Y4036U-17, Y4036U-19 and Y4036U-33, were used as controls in lipid production experiments (infra).

The remaining 10 colonies screened (i.e., of the total 205) contained the Pex16 knockout. These ten Δpex16 mutants within the Y4036U strain background were designated RHY25 through RHY34.

Confirmation of *Yarrowia lipolytica* Knockout Strain Y4036U (ΔPex16) by Quantitative Real Time PCR Further confirmation of the Pex16 knockout in strains RHY25 through RHY34 was performed by quantitative real time PCR, with the *Yarrowia* translation elongation factor (tef-1) gene (GenBank Accession No. AF054510) used as the control.

First, real time PCR primers and TaqMan probes targeting the Pex16 gene and the tef-1 gene, respectively, were designed with Primer Express software v 2.0 (AppliedBiosystems, Foster City, Calif.). Specifically, real time PCR primers ef-324F (SEQ ID NO:64), ef-392R (SEQ ID NO:65), PEX16-741F (SEQ ID NO:66) and PEX16-802R (SEQ ID NO:67) were designed, as well as the TaqMan probes ef-345T (i.e., 5' 6-FAM™-TGCTGGTGGTGTTGGTGAGTT-TAMRAT™, wherein the nucleotide sequence is set forth as SEQ ID NO:68) and PEX16-760T (i.e., 5'-6FAM™-CTGTCCATTCTGCGACCCCTC-TAMRAT™, wherein the nucleotide sequence is set forth as SEQ ID NO:69). The 5' end of the TaqMan fluorogenic probes have the 6FAM™ fluorescent reporter dye bound, while the 3' end comprises the TAMRA™ quencher. All primers and probes were obtained from Sigma-Genosys (Woodlands, Tex.).

Knockout candidate DNA was prepared by suspending 1 colony in 50 μl of water. Reactions for tef-1 and PEX16 were run separately, in triplicate for each sample. Real time PCR reactions included 20 pmoles each of forward and reverse primers (i.e., ef-324F, ef-392R, PEX16-741F and PEX16-802R 5', supra), 5 pmoles TaqMan probe (i.e., ef-345T and PEX16-760T), 10 μl TaqMan Universal PCR Master Mix—No AmpErase® Uracil-N-Glycosylase (UNG) (Catalog No. PN 4326614, AppliedBiosystems), 1 μl colony suspension and 8.5 μl RNase/DNase free water for a total volume of 20 μl per reaction. Reactions were run on the ABI PRISM® 7900 Sequence Detection System under the following conditions: initial denaturation at 95° C. for 10 min, followed by 40 cycles of denaturation at 95° C. for 15 sec and annealing at 60° C. for 1 min. Real time data was collected automatically during each cycle by monitoring 6-FAM™ fluorescence. Data analysis was performed using tef-1 gene threshold cycle ($C_T$) values for data normalization as per the ABI PRISM® 7900 Sequence Detection System instruction manual.

Based on this analysis, it was concluded that all ten of the Y4036U (Δpex16) colonies (i.e., RHY25 through RHY34) were valid Pex16 knockouts, wherein the pYRH13 construct had integrated into the chromosomal YlPex16.

Evaluation of *Yarrowia lipolytica* Strains Y4036U and Y4036U (ΔPex16) for DGLA Production To evaluate the effect of the Pex16 knockout on the percent of PUFAs in the total lipid fraction and the total lipid content in the cells, the Y4036U and Y4036U (Δpex16) strains were grown under comparable oleaginous conditions. More specifically, strains Y4036U-17, Y4036U-19 and Y4036U-33 having the Pex16 knockout fragment integrated at a random site in the chromosome were considered as Pex16 wild type (i.e., Y4036U) and strains RHY25 through RHY34 were the Pex16 mutant strains (i.e., Y4036U (Δpex16)). Cultures of each strain were grown at a starting $OD_{600}$ of ~0.1 in 25 mL of MM containing 90 mg/L L-leucine in a 125 mL flask for 48 hrs. The cells were harvested by centrifugation for 5 min at 4300 rpm in a 50 mL conical tube. The supernatant was discarded and the cells were re-suspended in 25 mL of HGM and transferred to a new 125 mL flask. The cells were incubated with aeration for an additional 120 hrs at 30° C.

The fatty acid composition (i.e., LA (18:2), ALA, EDA and DGLA) for each of the strains is shown below in Table 13; fatty acid composition is expressed as the weight percent (wt. %) of total fatty acids. The average fatty acid composition of strains Y4036U and Y4036U (Δpex16) are highlighted in gray and indicated with "Ave". None of the strains tested provided sufficient cell mass in MM+L-leucine media, and thus total lipid content was not analyzed.

TABLE 13

Lipid Composition In *Y. lipolytica* Strains Y4036U And Y4036U (Δpex16)

| Strain | Sample | 18:2 | ALA | EDA | DGLA |
|---|---|---|---|---|---|
| Y4036U | Y4036U-17 | 26.1 | 2.4 | 9.9 | 24.9 |
| | Y4036U-19 | 29.4 | 1.6 | 9.9 | 18.1 |
| | Y4036U-33 | 20.7 | 3.1 | 11.2 | 27.3 |
| Y4036U | AVE | 25.4 | 2.4 | 10.3 | 23.4 |
| Y4036U | RHY25-1 | 14.9 | 5.1 | 5.5 | 44.1 |
| (Δpex16) | RHY25-2 | 14.3 | 5.0 | 5.4 | 42.6 |
| | RHY26-1 | 14.4 | 5.1 | 5.6 | 42.9 |
| | RHY26-2 | 13.8 | 4.9 | 5.9 | 44.6 |
| | RHY27-1 | 14.4 | 5.0 | 5.4 | 42.6 |
| | RHY27-2 | 15.1 | 4.9 | 5.6 | 44.2 |
| | RHY28 | 15.3 | 4.6 | 5.7 | 42.6 |
| | RHY29 | 15.4 | 4.8 | 5.5 | 43.9 |
| | RHY30 | 15.5 | 4.5 | 5.9 | 43.6 |
| | RHY31 | 15.5 | 4.7 | 5.8 | 43.9 |
| | RHY32 | 15.5 | 4.9 | 5.9 | 44.4 |
| | RHY33 | 15.9 | 4.7 | 5.9 | 41.8 |
| | RHY34 | 15.9 | 4.9 | 6.2 | 43.5 |
| Y4036U (Δpex16) | AVE | 15.1 | 4.9 | 5.7 | 43.4 |

The results in Table 13 showed that knockout of the chromosomal Pex16 gene in Y4036U (Δpex16) increased the DGLA % TFAs approximately 85%, as compared to the DGLA % TFAs in strain Y4036U whose native Pex16p had not been knocked out. However, Y4036U (Δpex16) also had a ~40% decrease in the LA (18:2) accumulation.

Thus, the results in Table 13 showed that compared to the parent strain Y4036, Y4036 (ΔPex16) strain had higher average DGLA % TFAs (43.4% versus 23.4%). Additionally, strain Y4036U (Δpex16) had a 1.65-fold increase in the amount of DGLA relative to the total PUFAs (62.8% of the PUFAs [as a % TFAs] versus 38.1% of the PUFAs [as a % TFAs]) and a 1.3-fold increase in the amount of C20 PUFAs relative to the total PUFAs (71% of the PUFAs [as a % TFAs] versus 54.8% of the PUFAs [as a % TFAs]).

Example 10

Generation of Y4305 Strain to Produce about 53.2% EPA of Total Lipids

*Y. lipolytica* strain Y4305U, having a Ura− phenotype, was used as the host in Example 11, infra. Strain Y4305 (a Ura+ strain that was parent to Y4305U) was derived from *Y. lipolytica* ATCC #20362, and is capable of producing about 53.2% EPA relative to the total lipids via expression of a Δ9 elongase/Δ8 desaturase pathway.

The development of strain Y4305U required the construction of strain Y2224, strain Y4001, strain Y4001U, strain Y4036, strain Y4036U, strain Y4070 and strain Y4086 (supra, Example 1). Further development of strain Y4305U required construction of strain Y4086U1, strain Y4128 and strain Y4128U3 (supra, Example 2). Subsequently, development of strain Y4305U (diagrammed in FIG. 10) required construction of strain Y4217 (producing 42% EPA), strain Y4217U2 (Ura−), strain Y4259 (producing 46.5% EPA), strain Y4259U2 (Ura−) and strain Y4305 (producing 53.2% EPA).

Although the details concerning transformation and selection of the EPA-producing strains developed after strain Y4128U3 are not elaborated herein, the methodology used for isolation of strain Y4217, strain Y4217U2, strain Y4259, strain Y4259U2, strain Y4305 and strain Y4305U was as described in Examples 1 and 2.

Briefly, construct pZKL2-5U89GC (FIG. 8B; SEQ ID NO:55; described in Table 24 of Int'l. App. Pub. No. WO 2008/073367, hereby incorporated herein by reference) was generated to integrate one Δ9 elongase gene (i.e., EgD9eS), one Δ8 desaturase gene (i.e., EgD8M), one Δ5 desaturase gene (i.e., EgD5S), and one *Yarrowia lipolytica* diacylglycerol cholinephosphotransferase (CPT1) gene into the Lip2 loci (GenBank Accession No. AJ012632) of strain Y4128U3 to thereby enable higher level production of EPA. Six strains, designated as Y4215, Y4216, Y4217, Y4218, Y4219 and Y4220, produced about 41.1%, 41.8%, 41.7%, 41.1%, 41% and 41.1% EPA of total lipids, respectively.

Strain Y4217U1 and Y4217U2 were created by disrupting the Ura3 gene in strain Y4217 via construct pZKUE3S (FIG. 5A; SEQ ID NO:31; described in Table 22 of Int'l. App. Pub. No. WO 2008/073367, hereby incorporated herein by reference), comprising a chimeric EXP1::ME3S::Pex20 gene targeted for the Ura3 gene. Construct pZKL1-2SP98C (FIG. 8A; SEQ ID NO:54; described in Table 23 of Int'l. App. Pub. No. WO 2008/073367, hereby incorporated herein by reference) was utilized to integrate one Δ9 elongase gene (i.e., EgD9eS), one Δ8 desaturase gene (i.e., EgD8M), one Δ12 desaturase gene (i.e., FmD12S), and one *Yarrowia lipolytica* CPT1 gene into the Lip1 loci (GenBank Accession No. Z50020) of strain Y4217U2, thereby resulting in isolation of strains Y4259, Y4260, Y4261, Y4262, Y4263 and Y4264, producing about 46.5%, 44.5%, 44.5%, 44.8%, 44.5% and 44.3% EPA of total lipids, respectively.

Figure 11A:
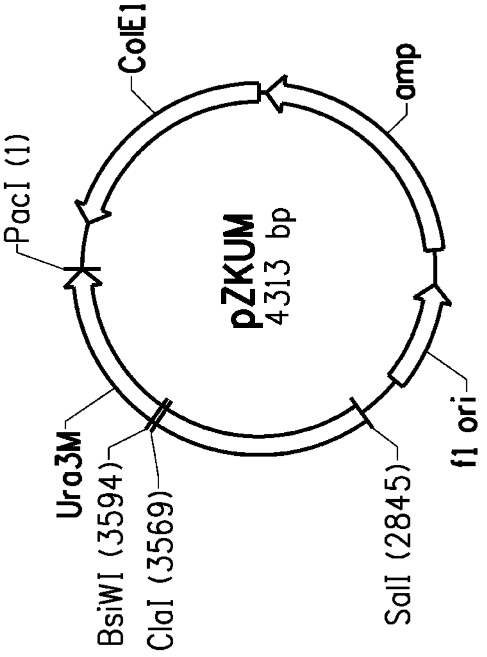

A Ura− derivative (i.e., strain Y4259U2) was then created, via transformation with construct pZKUM (FIG. 11A; SEQ ID NO:70; described in Table 33 of Int'l. App. Pub. No. WO 2008/073367, hereby incorporated herein by reference), which integrated a Ura3 mutant gene into the Ura3 gene of strain Y4259, thereby resulting in isolation of strains Y4259U1, Y4259U2 and Y4259U3, respectively (collectively, Y4259U) (producing 31.4%, 31% and 31.3% EPA of total lipids, respectively).

Figure 11B:
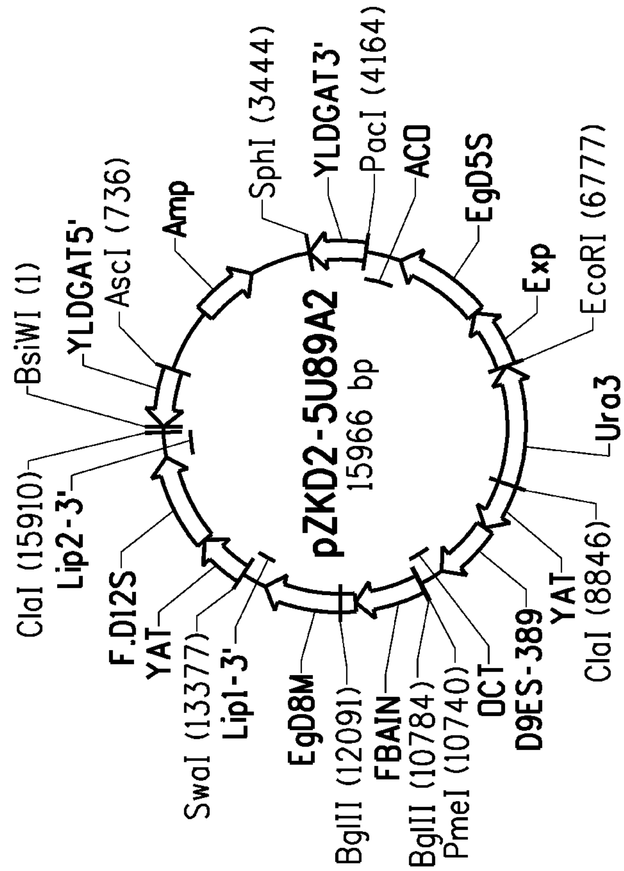

Finally, construct pZKD2-5U89A2 (FIG. 11B; SEQ ID NO:71) was generated to integrate one Δ9 elongase gene, one Δ5 desaturase gene, one Δ8 desaturase gene, and one Δ12 desaturase gene into the diacylglycerol acyltransferase (DGAT2) loci of strain Y4259U2, to thereby enable increased production of EPA. The pZKD2-5U89A2 plasmid contained the following components:

TABLE 14

Description of Plasmid pZKD2-5U89A2 (SEQ ID NO: 71)

| RE Sites And Nucleotides Within SEQ ID NO: 71 | Description Of Fragment And Chimeric Gene Components |
|---|---|
| AscI/BsiWI (1-736) | 728 bp 5' portion of *Yarrowia* DGAT2 gene (SEQ ID NO: 72) (labeled as "YLDGAT5'" in Figure; U.S. Pat. No. 7,267,976) |

TABLE 14-continued

| Description of Plasmid pZKD2-5U89A2 (SEQ ID NO: 71) | |
|---|---|
| RE Sites And Nucleotides Within SEQ ID NO: 71 | Description Of Fragment And Chimeric Gene Components |
| PacI/SphI (4164-3444) | 714 bp 3' portion of *Yarrowia* DGAT2 gene (SEQ ID NO: 72) (labeled as "YLDGAT3'" in Figure; U.S. Pat. No. 7,267,976) |
| SwaI/BsiWI (13377-1) | YAT1::FmD12S::Lip2, comprising:<br>YAT1: *Yarrowia lipolytica* YAT1 promoter (labeled as "YAT" in Figure; Pat. Appl. Pub. No. US 2006/0094102-A1);<br>FmD12S: codon-optimized Δ12 elongase (SEQ ID NO: 74), derived from *Fusarium moniliforme* (labeled as "F.D12S" in Figure; Int'l. App. Pub. No. WO 2005/047485);<br>Lip2: Lip2 terminator sequence from *Yarrowia* Lip2 gene (GenBank Accession No. AJ012632) |
| PmeI/SwaI (10740-13377) | FBAIN::EgD8M::Lip1 comprising:<br>FBAIN: *Yarrowia lipolytica* FBAIN promoter (U.S. Pat. No. 7,202,356);<br>EgD8M: Synthetic mutant Δ8 desaturase (SEQ ID NO: 76; Pat. Appl. Pub. No. US 2008-0138868 A1), derived from *Euglena gracilis* ("EgD8S"; U.S. Pat. No. 7,256,033);<br>Lip1: Lip1 terminator sequence from *Yarrowia* Lip1 gene (GenBank Accession No. Z50020) |
| ClaI/PmeI (8846-10740) | YAT1::E389D9eS::OCT, comprising:<br>YAT1: *Yarrowia lipolytica* YAT1 promoter (labeled as "YAT" in Figure; Pat. Appl. Pub. No. US 2006/0094102-A1);<br>E389D9eS: codon-optimized Δ9 elongase (SEQ ID NO: 78), derived from *Eutreptiella* sp. CCMP389 (labeled as "D9ES-389" in Figure; Int'l. App. Pub. No. WO 2007/061742);<br>OCT: OCT terminator sequence from *Yarrowia* OCT gene (GenBank Accession No. X69988) |
| ClaI/EcoRI (8846-6777) | *Yarrowia* Ura3 gene (GenBank Accession No. AJ306421) |
| EcoRI/PacI (6777-4164) | EXP1::EgD5S::ACO, comprising:<br>EXP1: *Yarrowia lipolytica* export protein (EXP1) promoter (labeled as "Exp" in Figure; Int'l. App. Pub. No. WO 2006/052870);<br>EgD5S: codon-optimized Δ5 desaturase (SEQ ID NO: 80), derived from *Euglena gracilis* (Pat. Appl. Pub. No. US 2007-0292924-A1);<br>Aco: Aco terminator sequence from *Yarrowia* Aco gene (GenBank Accession No. AJ001300) |

The pZKD2-5U89A2 plasmid was digested with AscI/SphI and then used for transformation of strain Y4259U2 according to the General Methods. The transformed cells were plated onto MM plates, and plates were maintained at 30° C. for 3 to 4 days. Single colonies were re-streaked onto MM plates, and the resulting colonies were used to inoculate liquid MM. Liquid cultures were shaken at 250 rpm/min for 2 days at 30° C. The cells were collected by centrifugation, resuspended in HGM, and then shaken at 250 rpm/min for 5 days. The cells were collected by centrifugation, and lipids were extracted. FAMEs were prepared by trans-esterification and subsequently analyzed with a Hewlett-Packard 6890 GC.

GC analyses showed that most of the selected 96 strains produced 40-46% EPA of total lipids. Four strains, designated as Y4305, Y4306, Y4307 and Y4308, produced about 53.2%, 46.4%, 46.8% and 47.8% EPA of total lipids, respectively. The complete lipid profile of Y4305 is as follows: 16:0 (2.8%), 16:1 (0.7%), 18:0 (1.3%), 18:1 (4.9%), 18:2 (17.6%), ALA (2.3%), EDA (3.4%), DGLA (2.0%), ARA (0.6%), ETA (1.7%) and EPA (53.2%). The total lipid % dry cell weight was 27.5.

The final genotype of strain Y4305 with respect to wild type *Yarrowia lipolytica* ATCC #20362 was SCP2− (YALI0E01298g), YALI0C18711g−, Pex10−, YALI0F24167g−, unknown 1−, unknown 3−, unknown 8−, GPD::FmD12::Pex20, YAT1::FmD12::OCT, GPM/FBAIN::FmD12S::OCT, EXP1::FmD12S::Aco, YAT1::FmD12S::Lip2, YAT1::ME3S::Pex16, EXP1::ME3S::Pex20 (3 copies), GPAT::EgD9e::Lip2, EXP1::EgD9eS::Lip1, FBAINm::EgD9eS::Lip2, FBA::EgD9eS::Pex20, GPD::EgD9eS::Lip2, YAT1::EgD9eS::Lip2, YAT1::E389D9eS::OCT, FBAINm::EgD8M::Pex20, FBAIN::EgD8M::Lip1 (2 copies), EXP1::EgD8M::Pex16, GPDIN::EgD8M::Lip1, YAT1::EgD8M::Aco, FBAIN::EgD5::Aco, EXP1::EgD5S::Pex20, YAT1::EgD5S::Aco, EXP1::EgD5S::ACO, YAT1::RD5S::OCT, YAT1::PaD17S::Lip1, EXP1::PaD17::Pex16, FBAINm::PaD17::Aco, YAT1::YICPT1::ACO, GPD::YICPT1::ACO.

In order to disrupt the Ura3 gene in strain Y4305, construct pZKUM (FIG. 11A; SEQ ID NO:70; described in Table 33 of Int'l. App. Pub. No. WO 2008/073367, hereby incorporated herein by reference) was used to integrate a Ura3 mutant gene into the Ura3 gene of strain Y4305. A total of 8 transformants grown on MM+5-FOA plates were picked and re-streaked onto MM plates and MM+5-FOA plates, separately. All 8 strains had a Ura− phenotype (i.e., cells could grow on MM+5-FOA plates, but not on MM plates). The cells were scraped from the MM+5-FOA plates, and lipids were extracted. FAMEs were prepared by trans-esterification and subsequently analyzed with a Hewlett-Packard 6890 GC.

GC analyses showed the presence of 37.6%, 37.3% and 36.5% EPA of total lipids in pZKUM transformants #1, #6 and #7 grown on MM+5-FOA plates. These three strains were designated as strains Y4305U1, Y4305U2 and Y4305U3, respectively (collectively, Y4305U). For clarity in Example 11, strain Y4305U is referred to as strain Y4305U (Δpex10).

Example 11

Chromosomal Deletion of Pex16 in *Yarrowia lipolytica* Strain Y4305U (ΔPex10) Further Increased Percent EPA Accumulated

The Double Pex10-Pex16 Knockout

The present Example describes use of construct pYRH13 (FIG. 9B; SEQ ID NO:59) to knock out the chromosomal Pex16 in *Yarrowia* strain Y4305U (Δpex10) (Example 10), to thereby result in a Pex10-Pex16 double mutant. The effect of the Pex10-Pex16 double knockout on total oil and EPA level was determined and compared. Specifically, the effect of the Pex10-Pex16 double mutation in strain Y4305U (Δpex10) (Δpex16) resulted in an increased amount of EPA in the cell (EPA % TFAs and EPA % DCW), as compared to the single mutant (i.e., strain Y4305U (Δpex10)).

Generation of *Yarrowia lipolytica* Knockout Strain Y4305U (ΔPex10) (Δpex16)

Standard protocols were used to transform *Yarrowia lipolytica* strain Y4305U (Δpex10) (Example 10) with the purified 6.0 kB AscI/SphI fragment of Pex16 knockout construct pYRH13 (Example 9; SEQ ID NO:59). Screening and identification of cells having the Pex16 deletion was conducted by colony PCR, as described in Example 9.

Of 93 colonies screened, 88 had the Pex16 knockout fragment integrated at a random site in the chromosome and thus were not Δpex16 mutants (however, the cells could grow on Ura− plates, due to the presence of pYRH13). Two of these random integrants, designated as Y4305U-22 and Y4305U-25, were used as controls in lipid production experiments (infra).

The remaining 5 colonies screened (i.e., of the total 93) contained the Pex16 knockout. These five Δpex16 mutants within the Y4305U strain background were designated RHY20, RHY21, RHY22, RHY23 and RHY24. Further confirmation of the YlPex16 knockout was performed by quantitative real time PCR, as described in Example 9.

Evaluation of *Yarrowia lipolytica* Strains Y4305U (ΔPex10) and Y4305U (ΔPex10) (Δpex16) for EPA Production To evaluate the effect of mutation in multiple Pex genes on the percent of PUFAs in the total lipid fraction and the total lipid content in the cells, Y4305U (Δpex10) and Y4305U (Δpex10) (Δpex16) strains were grown under comparable oleaginous conditions. More specifically, strains Y4305U-22 and Y4305U-25 having the Pex16 knockout fragment integrated at a random site in the chromosome were considered as Pex16 wild type, Pex10 knockouts (i.e., Y4305U (Δpex10)).

The cell suspension was dried overnight in a vacuum oven at 80° C. The weight of the cells was determined.

To determine the total lipid content, 1 mL of HGM cultured cells were collected by centrifugation for 1 min at 13,000 rpm, total lipids were extracted, and FAMEs were prepared by trans-esterification, and subsequently analyzed with a Hewlett-Packard 6890 GC (General Methods).

The fatty acid composition (i.e., 16:0 (palmitate), 16:1 (palmitoleic acid), 18:0, 18:1 (oleic acid), 18:2 (LA), 18:3 (ALA), EDA, DGLA, ARA, ETrA, ETA and EPA) for each of the strains is shown below in Table 15 (expressed as the weight percent (wt. %) of total fatty acids (TFA)), as well as the DCW (g/L) and total lipid content (TFAs % DCW). The average fatty acid composition of strains Y4305U (Δpex10) and Y4305U (Δpex10) (Δpex16) are highlighted in gray and indicated with “Ave”.

TABLE 15

Lipid Composition In *Y. lipolytica* Strains Y4305U (ΔPex10) And Y4305U (ΔPex10) (ΔPex16)

| Strain | Sample | DCW (g/L) | TFAs % DCW | 16:0 | 16:1 | 18:0 | 18:1 | 18:2 | 18:3 | EDA | DGLA | ARA | ETrA | ETA | EPA |
|---|---|---|---|---|---|---|---|---|---|---|---|---|---|---|---|
| Y4305U (Δpex10) | Y4305U-22 #1 | 3.50 | 29 | 3.1 | 0.7 | 2.1 | 6.4 | 18.7 | 2.6 | 4.2 | 1.8 | 0.5 | 1.8 | 2.0 | 45.4 |
| | Y4305U-22 #2 | 3.94 | 29 | 3.0 | 0.7 | 2.1 | 6.2 | 18.5 | 2.5 | 4.5 | 1.8 | 0.5 | 1.8 | 2.0 | 45.6 |
| | Y4305U-25 #1 | 4.14 | 31 | 3.6 | 1.1 | 1.8 | 6.1 | 18.8 | 2.4 | 4.5 | 1.9 | 0.6 | 1.6 | 2.0 | 43.9 |
| | Y4305U-25 #2 | 4.12 | 30 | 3.6 | 1.1 | 1.8 | 6.1 | 18.7 | 2.4 | 4.6 | 1.9 | 0.6 | 1.6 | 2.0 | 44.0 |
| Y43050 (Δpex10) | AVE | 3.93 | 30 | 3.3 | 0.9 | 2.0 | 6.2 | 18.7 | 2.5 | 4.5 | 1.9 | 0.6 | 1.7 | 2.0 | 44.7 |
| Y4305U (Δpex10) (Δpex16) | RHY22 #1 | 4.04 | 29 | 2.7 | 0.7 | 1.5 | 5.4 | 18.5 | 2.7 | 3.4 | 1.9 | 0.5 | 1.4 | 2.0 | 48.5 |
| | RHY22 #2 | 3.82 | 32 | 2.7 | 0.6 | 1.5 | 5.5 | 18.4 | 3.0 | 3.0 | 2.0 | 0.5 | 1.5 | 2.0 | 48.8 |
| | RHY23 #1 | 4.66 | 30 | 2.7 | 0.7 | 1.5 | 5.4 | 18.6 | 2.7 | 3.5 | 2.0 | 0.6 | 1.4 | 2.0 | 48.2 |
| | RHY23 #2 | 4.18 | 30 | 2.7 | 0.7 | 1.5 | 5.4 | 18.4 | 2.6 | 3.5 | 1.9 | 0.6 | 1.4 | 2.0 | 48.5 |
| | RHY24 #1 | 4.34 | 30 | 2.8 | 0.8 | 1.5 | 5.5 | 18.6 | 2.6 | 3.6 | 1.9 | 0.6 | 1.4 | 2.0 | 47.9 |
| | RHY24 #2 | 4.58 | 30 | 2.7 | 0.7 | 1.5 | 5.6 | 18.8 | 2.6 | 3.6 | 2.0 | 0.6 | 1.4 | 2.0 | 47.8 |
| Y4305U (Δpex10) (Δpex16) | AVE | 4.27 | 30 | 2.7 | 0.7 | 1.5 | 5.5 | 18.6 | 2.7 | 3.4 | 2.0 | 0.6 | 1.4 | 2.0 | 48.3 |

Strains RHY22, RHY23 and RHY24 were the double knockout mutant strains (i.e., Y4305U (Δpex10) (Δpex16)). Cultures of each strain were grown in duplicate under comparable oleaginous conditions.

Specifically, cultures were grown at a starting $OD_{600}$ of ~0.1 in 25 mL of synthetic dextrose media (SD) in a 125 mL flask for 48 hrs. The cells were harvested by centrifugation for 5 min at 4300 rpm in a 50 mL conical tube. The supernatant was discarded and the cells were re-suspended in 25 mL of HGM and transferred to a new 125 mL flask. The cells were incubated with aeration for an additional 120 hrs at 30° C.

To determine the dry cell weight (DCW), the cells from 5 mL of the HGM-grown cultures were processed. The cultured cells were centrifuged for 5 min at 4300 rpm. The pellet was re-suspended using 10 mL of sterile water and was centrifuged under the same conditions for a second time. The pellet was then re-suspended using 1 mL of sterile $H_2O$ (three times) and was transferred to a pre-weighed aluminum pan.

The results in Table 15 showed that knockout of the chromosomal Pex16 gene in Y4305U (Δpex10) (Δpex16) increased the EPA % TFAs approximately 8%, as compared to the EPA % TFAs in strain Y4305U (Δpex10) whose native Pex16p had not been knocked out. Additionally, the EPA % DCW was also increased in the double mutant as compared to in the single mutant strain, while the TFAs % DCW remained the same.

Thus, the results in Table 15 showed that compared to the control Y4305 (ΔPex10) strains, Y4305 (ΔPex10, ΔPex16) strains on average had higher EPA % TFAs (48.3% versus 44.7%) and higher EPA % DCW (14.57% versus 13.23%). Strain Y4305 (ΔPex10, ΔPex16) had only a 1.05-fold increase in the amount of EPA relative to the total PUFAs (61% of the PUFAs [as a % TFAs] versus 58.3% of the PUFAs [as a % TFAs]) relative to strain Y4305 (ΔPex10), while the increase in the amount of C20 PUFAs relative to the total PUFAs was effectively identical (73% of the PUFAs [as a % TFAs] versus 72% of the PUFAs [as a % TFAs]).

Example 12

Figure 12B:
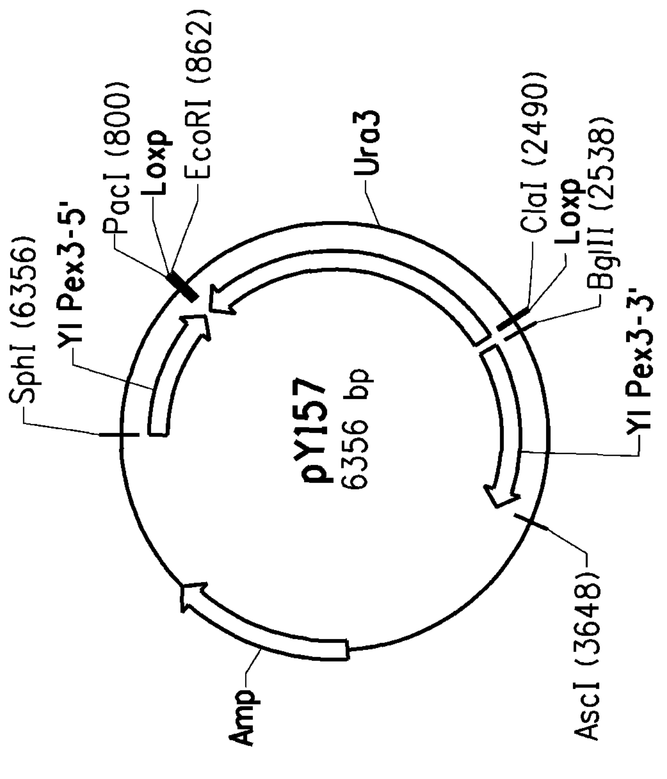

Chromosomal Deletion of Pex3 in *Yarrowia lipolytica* Strain Y4036U Increases Percent DGLA Accumulated The present Example describes use of construct pY157 (FIG. 12B; SEQ ID NO:82) to knock out the chromosomal Pex3 gene (SEQ ID NO:3) in the Ura−, DGLA-producing *Yarrowia* strain Y4036U (Example 1). Transformation of *Y. lipolytica* strain Y4036U with the Pex3 knockout construct resulted in creation of strain Y4036 (Δpex3). The effect of the Pex3 knockout on DGLA level was determined and compared to the control strain Y4036 (a Ura+ strain that was parent to strain Y4036U). Specifically, knockout of Pex3 increased DGLA as a percentage of total fatty acids and improved ca. 3-fold DGLA % DCW, compared to the control.

Construct pY157

Plasmid pY87 (FIG. 12A) contained a cassette to knock out the *Yarrowia lipolytica* diacylglycerol acyltransferase (DGAT2) gene, as described below in Table 16:

TABLE 16

Description of Plasmid pY87 (SEQ ID NO: 83)

| RE Sites And Nucleotides Within SEQ ID NO: 83 | Description Of Fragment And Chimeric Gene Components |
|---|---|
| SphI/PacI (1-721) | 5' portion of *Yarrowia* DGAT2 gene (bases 1-720 of SEQ ID NO: 72) (U.S. Pat. No. 7,267,976) |
| PacI/BglII (721-2459) | LoxP::Ura3::LoxP, comprising: LoxP sequence (SEQ ID NO: 84); *Yarrowia* Ura3 gene (GenBank Accession No. AJ306421); LoxP sequence (SEQ ID NO: 84) |
| BglII/AscI (2459-3203) | 3' portion of *Yarrowia* DGAT2 gene (bases 2468-3202 of SEQ ID NO: 72) (U.S. Pat. No. 7,267,976) |
| AscI/SphI (3203-5910) | Vector backbone including: ColE1 plasmid origin of replication; ampicillin-resistance gene ($Amp^R$) for selection in *E. coli* (4191-5051); *E. coli* f1 origin of replication |

Plasmid pY157 was derived from plasmid pY87. Specifically, a 704 bp 5' promoter region of the *Yarrowia lipolytica* Pex3 gene replaced the SphI/PacI fragment of pY87 and a 448 bp 3' terminator region of the *Yarrowia lipolytica* Pex3 gene replaced the BglII/AscI fragment of pY87 to produce pY157 (SEQ ID NO:82; FIG. 12B).

Generation of *Yarrowia lipolytica* Knockout Strain Y4036 (ΔPex3)

Standard protocols were used to transform *Yarrowia lipolytica* strain Y4036U (Example 1) with the purified 3648 bp AscI/SphI fragment of Pex3 knockout construct pY157 (supra).

To screen for cells having the Pex3 deletion, colony PCR was performed using Taq polymerase (Invitrogen; Carlsbad, Calif.) and the PCR primers UP 768 (SEQ ID NO:85) and LP 769 (SEQ ID NO:86). This set of primers was designed to amplify a 2039 bp wild type band of the intact Pex3 gene and 3719 bp knockout-specific band when the Pex3 gene was disrupted by targeted knockout.

More specifically, the colony PCR was performed using a MasterAmp Taq kit (Epicentre Technologies, Madison, Wis.; Catalog No. 82250) and the manufacturer's instructions in a 25 μl reaction comprising: 2.5 μl of 10× MasterAmp Taq buffer, 2.0 μl of 25 mM $MgCl_2$, 7.5 μl of 10× MasterAmp Enhancer, 2.5 μl of 2.5 mM dNTPs (TaKaRa Bio Inc., Otsu Shiga, Japan), 1.0 μl of 10 μM Upper primer, 1.0 μl of 10 μM Lower primer, 0.25 μl of MasterAmp Taq DNA polymerase and 19.75 μl of water. Amplification was carried out as follows: initial denaturation at 95° C. for 5 min, followed by 40 cycles of denaturation at 95° C. for 30 sec, annealing at 56° C. for 60 sec, and elongation at 72° C. for 4 min. A final elongation cycle at 72° C. for 10 min was carried out, followed by reaction termination at 4° C.

Of 48 colonies screened, 46 had the 2039 bp band expected from the wild type (i.e., undisrupted) Pex3 gene thus were not Δpex3 mutants. The remaining 2 colonies showed only a faint band of 2039 bp, suggesting that they were Δpex3 mutants with some contaminating untransformed cells present in the background. This was confirmed by streaking the 2 putative knockout colonies on selection plates to isolate single colonies. Then, genomic DNA was isolated from 3 single colonies from each putative knockout strain and screened by the same primer pair. i.e., UP 768 and LP 769 (SEQ ID NOs:85 and 86). This method was considered more sensitive than colony PCR. All three single colonies from both primary transformants lacked the 2039 bp wild type band and instead possessed the 3719 bp knockout-specific band. The two Δpex3 mutants within the Y4036U strain background were designated L134 and L135.

Evaluation of *Yarrowia lipolytica* Strains Y4036 and Y4036 (ΔPex3) for DGLA Production To evaluate the effect of the Pex3 knockout on the percent of PUFAs in the total lipid fraction and the total lipid content in the cells, the Y4036 and Y4036 (Δpex3) strains were grown under comparable oleaginous conditions. Strains Y4036, L134 (i.e., Y4036 (Δpex3)) and L135 (i.e., Y4036 (Δpex3)) were inoculated into 25 mL of CSM-Ura and grown at 30° C. overnight in a shaker. The preculture was aliquoted into fresh 25 mL CSM-Ura flasks at a final $OD_{600}$ of 0.4. Cultures were grown at 30° C. in shaker. After 48 hrs, the cells (which barely grew) were spun down and resuspended in fresh 25 mL CSM-Ura and continued to grow for 72 hrs. Cells were spun down, re-suspended in 25 mL of HGM, and continued to grow as above for 72 hrs. Cells were harvested by centrifugation, washed once in distilled water and resuspended in 25 mL water to give a final volume of 20.5 mL. An aliquot (1.5 mL) was used for lipid content, following extraction of the total lipids, preparation of FAMEs by base trans-esterification, and analysis by a Hewlett-Packard 6890 GC (General Methods). The remaining aliquot was dried down to measure dry cell weight (DCW), as described in Example 11.

The fatty acid composition (i.e., 16:0 (palmitate), 16:1 (palmitoleic acid), 18:0, 18:1 (oleic acid), 18:2 (LA), EDA and DGLA) for each of the strains is shown below in Table 17 (expressed as the weight percent (wt. %) of total fatty acids (TFA)), as well as the total lipid content (TFA % DCW). The conversion efficiency ("CE") was measured according to the following formula: ([product]/[substrate+product])*100, where 'product' includes the immediate product and all products in the pathway derived from it. Thus, the Δ12 desaturase conversion efficiency (Δ12% CE) was calculated as: ([LA+EDA+DGLA]/[18:1+LA+EDA+DGLA])*100; the Δ9 elongase conversion efficiency (Δ9 elo % CE) was calculated as:

([EDA+DGLA]/[LA+EDA+DGLA])*100;

and, the Δ8 desaturase conversion efficiency (Δ8% CE) was calculated as: ([DGLA]/[EDA+DGLA])*100. The average fatty acid composition of strains Y4036, L134 and L135 are highlighted in gray and indicated with "Ave", while "S.D." indicates the Standard Deviation. As expected, the Δpex3 strains did not grow on plates with oleate as a sole source of carbon.

TABLE 17

Lipid Content And Composition In *Y. lipolytica* Strains Y4036 And Y4036 (ΔPex3)

| Strain | Sample | TFA % DCW | 16:0 | 16:1 | 18:0 | 18:1 | 18:2 | EDA | DGLA | Δ12 % CE | Δ9 elo % CE | Δ8 % CE |
|---|---|---|---|---|---|---|---|---|---|---|---|---|
| Y4036 | Y4036-1 | 6.1 | 10 | 7 | 1 | 14 | 29 | 9 | 19 | 80 | 49 | 69 |
| | Y4036-2 | 3.7 | 11 | 6 | 1 | 14 | 30 | 8 | 20 | 81 | 48 | 70 |
| | Y4036-3 | 4.1 | 11 | 5 | 1 | 15 | 31 | 8 | 19 | 80 | 47 | 70 |
| | Avg. | 4.7 | 10 | 6 | 1 | 14 | 30 | 8 | 19 | 80 | 48 | 70 |
| | S.D. | 1.3 | 0.3 | 0.9 | 0.1 | 0.3 | 0.7 | 0.3 | 0.2 | 0.3 | 0.9 | 0.8 |
| Y4036 (Δpex3) | L134-1 | 6.2 | 7 | 5 | 1 | 8 | 12 | 10 | 45 | 89 | 83 | 81 |
| | L134-2 | 5.4 | 7 | 5 | 1 | 8 | 11 | 10 | 47 | 90 | 83 | 82 |
| | L134-3 | 6.7 | 6 | 5 | 1 | 8 | 12 | 11 | 46 | 90 | 83 | 82 |
| | Avg. | 6.1 | 7 | 5 | 1 | 8 | 12 | 10 | 46 | 90 | 83 | 82 |
| | S.D. | 0.6 | 0.5 | 0.1 | 0.1 | 0.3 | 0.1 | 0.1 | 1.0 | 0.5 | 0.4 | 0.3 |
| Y4036 (Δpex3) | L135-1 | 4.2 | 7 | 5 | 1 | 8 | 12 | 11 | 45 | 89 | 82 | 81 |
| | L135-2 | 6.5 | 6 | 5 | 1 | 8 | 12 | 10 | 47 | 90 | 83 | 82 |
| | L135-3 | 7.1 | 7 | 5 | 1 | 8 | 12 | 10 | 46 | 90 | 83 | 82 |
| | Avg. | 5.9 | 7 | 5 | 1 | 8 | 12 | 10 | 46 | 90 | 83 | 81 |
| | S.D. | 1.6 | 0.6 | 0.1 | 0.1 | 0.3 | 0.1 | 0.1 | 1.1 | 0.5 | 0.4 | 0.5 |

The results in Table 17 showed that knockout of the chromosomal Pex3 gene in Y4036 (Δpex3) increased the DGLA % TFAs approximately 142%, as compared to the DGLA % TFAs in strain Y4036 whose native Pex3p had not been knocked out. Specifically, the Pex3 knockout increased DGLA levels from ca. 19% in Y4036 to 46% in Y4036 (Δpex3) strains, L134 and L135. Additionally, the Δ9 elongase percent conversion efficiency increased from ca. 48% in Y4036 to 83% in Y4036 (Δpex3) strains, L134 and L135; and, TFA % DCW increased from 4.7% to 6% in the strains L134 and L135. The LA % TFAs decreased from 30% to 12%. Pex3 deletion indeed increases the flux of fatty acids and thus the substrate availability for Δ9 elongation.

Thus, the results in Table 17 showed that compared to the parent strain Y4036, Y4036 (ΔPex3) strain had on average higher lipid content (TFAs % DCW) (ca. 6.0% versus 4.7%), higher DGLA % TFAs (46% versus 19%), and higher DGLA % DCW (ca. 2.8% versus 0.9%). Additionally, strain Y4036 (ΔPex3) had a 2-fold increase in the amount of DGLA relative to the total PUFAs (67.7% of the PUFAs [as a % TFAs] versus 33.3% of the PUFAs [as a % TFAs]) and a 1.7-fold increase in the amount of C20 PUFAs relative to the total PUFAs (82% of the PUFAs [as a % TFAs] versus 47% of the PUFAs [as a % TFAs]).

It is hypothesized that the improved DGLA productivity would also result in improved EPA productivity in *Yarrowia lipolytica* strains engineered for EPA production (e.g., *Y. lipolytica* strain Y4305U, as described in Example 10, and derivatives therefrom).

What is claimed is:

1. A method of increasing the weight percent of at least one polyunsaturated fatty acid in the total fatty acids of an oleaginous *Yarrowia*, comprising:

a) providing an oleaginous *Yarrowia* comprising:

1) genes encoding a functional polyunsaturated fatty acid biosynthetic pathway, said genes comprising at least one gene encoding an enzyme selected from the group consisting of delta-15 desaturase, delta-6 desaturase, and delta-9 elongase; and 2) a disruption in a native gene encoding a peroxisome biogenesis factor 3 protein, wherein the disruption comprises a gene knockout comprising a nucleotide sequence having at least 95% identity with sequence 1-862 of SEQ ID NO:82; and b) growing said *Yarrowia* under conditions as to increase the weight percent of at least one polyunsaturated fatty acid in the total fatty acids of said *Yarrowia*, wherein said increase is with respect to the weight percent of the at least one polyunsaturated fatty acid in the total fatty acids of the *Yarrowia* in which no native gene encoding a PEX protein has been disrupted.

2. The method of claim 1, wherein the polyunsaturated fatty acid is selected from the group consisting of: gamma-linolenic acid, dihomo-gamma-linolenic acid, arachidonic acid, docosatetraenoic acid, omega-6 docosapentaenoic acid, alpha-linolenic acid, stearidonic acid, eicosatetraenoic acid, eicosapentaenoic acid, omega-3 docosapentaenoic acid, eicosadienoic acid, eicosatrienoic acid, docosahexaenoic acid, hydroxylated or epoxy fatty acids of these, $C_{18}$ polyunsaturated fatty acids, $C_{20}$ polyunsaturated fatty acids, and $C_{22}$ polyunsaturated fatty acids.

3. The method of claim 2, wherein the polyunsaturated fatty acid is selected from the group consisting of gamma-linolenic acid, dihomo-gamma-linolenic acid, eicosatetraenoic acid and eicosapentaenoic acid.

4. The method of claim 1, wherein the weight percent of linoleic acid in the total fatty acids of the *Yarrowia* is decreased with respect to the weight percent of linoleic acid in the total fatty acids of the *Yarrowia* in which no native gene encoding a PEX protein has been disrupted.

5. The method of claim 1, wherein the genes encoding the polyunsaturated fatty acid biosynthetic pathway further comprise a gene encoding an enzyme selected from the group consisting of: delta-9 desaturase, delta-12 desaturase, delta-5 desaturase, delta-17 desaturase, delta-8 desaturase, delta-4 desaturase, $C_{14/16}$ elongase, $C_{16/18}$ elongase, $C_{18/20}$ elongase, and $C_{20/22}$ elongase.

6. The method of claim 1, wherein the site of the gene knockout comprises sequence 1-862 of SEQ ID NO:82.

7. A method of increasing the weight percent of at least one polyunsaturated fatty acid relative to the dry cell weight of an oleaginous *Yarrowia*, comprising:

a) providing an oleaginous *Yarrowia* comprising:

i) genes encoding a functional polyunsaturated fatty acid biosynthetic pathway, said genes comprising at least one gene encoding an enzyme selected from the group consisting of delta-15 desaturase, delta-6 desaturase, and delta-9 elongase; and ii) a disruption in a native gene encoding a peroxisome biogenesis factor 3 protein, wherein the disruption comprises a gene knockout comprising a nucleotide sequence having at least 95% identity with sequence 1-862 of SEQ ID NO:82; and b) growing said *Yarrowia* under conditions as to increase the weight percent of at least one polyunsaturated fatty acid relative to the dry cell weight of the *Yarrowia*, wherein said increase is with respect to the weight percent of the at least one polyunsaturated fatty acid relative to the dry cell weight of the *Yarrowia* in which no native gene encoding a PEX protein has been disrupted.

8. The method of claim 7, wherein the polyunsaturated fatty acid is selected from the group consisting of: gamma-linolenic acid, dihomo-gamma-linolenic acid, arachidonic acid, docosatetraenoic acid, omega-6 docosapentaenoic acid, alpha-linolenic acid, stearidonic acid, eicosatetraenoic acid, eicosapentaenoic acid, omega-3 docosapentaenoic acid, eicosadienoic acid, eicosatrienoic acid, docosahexaenoic acid, hydroxylated or epoxy fatty acids of these, $C_{18}$ polyunsaturated fatty acids, $C_{20}$ polyunsaturated fatty acids, and $C_{22}$ polyunsaturated fatty acids.

9. The method of claim 7, wherein the weight percent of linoleic acid in the total fatty acids of the *Yarrowia* is decreased with respect to the weight percent of linoleic acid in the total fatty acids of the *Yarrowia* in which no native gene encoding a PEX protein has been disrupted.

10. The method of claim 7, wherein the site of the gene knockout comprises sequence 1-862 of SEQ ID NO:82.

11. A method of increasing the weight percent of at least one polyunsaturated fatty acid in the total fatty acids of an oleaginous *Yarrowia*, comprising:

a) providing an oleaginous *Yarrowia* comprising:

1) genes encoding a functional polyunsaturated fatty acid biosynthetic pathway; and 2) a disruption in a native gene encoding a peroxisome biogenesis factor 3 protein, wherein the disruption comprises a gene knockout comprising a nucleotide sequence having at least 95% identity with sequence 1-862 of SEQ ID NO:82; and b) growing said *Yarrowia* under conditions as to increase the weight percent of at least one polyunsaturated fatty acid in the total fatty acids of said *Yarrowia*, wherein said increase is with respect to the weight percent of the at least one polyunsaturated fatty acid in the total fatty acids of the *Yarrowia* in which no native gene encoding a PEX protein has been disrupted.

12. The method of claim 11, wherein the polyunsaturated fatty acid is selected from the group consisting of: gamma-linolenic acid, dihomo-gamma-linolenic acid, arachidonic acid, docosatetraenoic acid, omega-6 docosapentaenoic acid, alpha-linolenic acid, stearidonic acid, eicosatetraenoic acid, eicosapentaenoic acid, omega-3 docosapentaenoic acid, eicosadienoic acid, eicosatrienoic acid, and docosahexaenoic acid.

13. The method of claim 12, wherein the polyunsaturated fatty acid is selected from the group consisting of gamma-linolenic acid, dihomo-gamma-linolenic acid, eicosatetraenoic acid and eicosapentaenoic acid.

14. The method of claim 11, wherein the site of the gene knockout comprises sequence 1-862 of SEQ ID NO:82.

* * * * *

SEQUENCE LISTING

```
<160> NUMBER OF SEQ ID NOS: 86

<210> SEQ ID NO 1
<211> LENGTH: 1024
<212> TYPE: PRT
<213> ORGANISM: Yarrowia lipolytica
<220> FEATURE:
<221> NAME/KEY: MISC_FEATURE
<222> LOCATION: (1)..(1024)
<223> OTHER INFORMATION: YlPex1p; GenBank Accession No. CAG82178

<400> SEQUENCE: 1

Met Thr Ser Lys Ser Asp Tyr Ser Gly Lys Asp Lys Ile Glu Leu Asp
1               5                   10                  15

Pro Val Phe Ala Lys Ser Ile Asp Leu Leu Pro Asn Thr Gln Val Val
            20                  25                  30

Ile Asp Ile Gln Leu Asn Pro Lys Ile Ala His Thr Ile His Leu Glu
        35                  40                  45

Pro Val Thr Val Ala Asp Trp Glu Ile Val Glu Leu His Ala Ala Tyr
    50                  55                  60

Leu Glu Ser Arg Met Ile Asn Gln Val Arg Ala Val Ser Pro Asn Gln
65                  70                  75                  80

Pro Val Thr Val Tyr Pro Ser Ser Thr Thr Ser Ala Thr Leu Lys Val
                85                  90                  95

Ile Arg Ile Glu Pro Asp Leu Gly Ala Ala Gly Phe Ala Lys Leu Ser
            100                 105                 110
```

```
Pro Asp Ser Glu Val Val Val Ala Pro Lys Gln Arg Lys Lys Glu Glu
        115                 120                 125

Lys Gln Val Lys Lys Arg Ser Gly Ser Ala Arg Ser Thr Gly Ser Gln
    130                 135                 140

Lys Arg Lys Gly Gly Arg Gly Pro His Ala Leu Arg Arg Ala Ile Ser
145                 150                 155                 160

Glu Asp Phe Asp Gly His Leu Arg Leu Glu Val Ser Leu Asp Val Ser
                165                 170                 175

Gln Leu Pro Pro Glu Phe His Gln Leu Lys Asn Val Ser Ile Lys Val
            180                 185                 190

Ile Thr Pro Pro Asn Leu Ala Ser Pro Gln Gln Ala Ala Ser Ile Ala
        195                 200                 205

Val Glu Glu Lys Ser Glu Glu Ser Leu Ser Gln Asn Lys Pro Pro Ser
    210                 215                 220

Ser Glu Pro Lys Val Glu Val Pro Pro Asp Ile Ile Asn Pro Ala Ser
225                 230                 235                 240

Glu Ile Val Ala Thr Leu Val Asn Asp Thr Thr Ser Pro Thr Gly His
                245                 250                 255

Ala Lys Leu Ser Tyr Ala Leu Ala Asp Ala Leu Gly Ile Pro Ser Ser
            260                 265                 270

Val Gly His Val Ile Arg Phe Glu Ser Ala Ser Lys Pro Leu Ser Gln
        275                 280                 285

Lys Pro Gly Ala Leu Val Ile His Arg Phe Ile Thr Lys Thr Val Gly
    290                 295                 300

Ala Ala Glu Gln Lys Ser Leu Arg Leu Lys Gly Glu Lys Asn Ala Asp
305                 310                 315                 320

Asp Gly Val Ser Ala Asp Asp Gln Phe Ser Leu Leu Glu Glu Leu Lys
                325                 330                 335

Lys Leu Gln Met Leu Glu Gly Pro Ile Thr Asn Phe Gln Arg Leu Pro
            340                 345                 350

Pro Ile Pro Glu Leu Leu Pro Leu Gly Gly Val Ile Gly Leu Gln Asn
        355                 360                 365

Ser Glu Gly Trp Ile Gln Gly Gly Tyr Leu Gly Glu Glu Pro Ile Pro
    370                 375                 380

Phe Val Ser Gly Ser Glu Ile Leu Arg Ser Glu Ser Ser Leu Ser Pro
385                 390                 395                 400

Ser Asn Ile Glu Ser Glu Asp Lys Arg Val Val Gly Leu Asp Asn Met
                405                 410                 415

Leu Asn Lys Ile Asn Glu Val Leu Ser Arg Asp Ser Ile Gly Cys Leu
            420                 425                 430

Val Tyr Gly Ser Arg Gly Ser Gly Lys Ser Ala Val Leu Asn His Ile
        435                 440                 445

Lys Lys Glu Cys Lys Val Ser His Thr His Thr Val Ser Ile Ala Cys
    450                 455                 460

Gly Leu Ile Ala Gln Asp Arg Val Gln Ala Val Arg Glu Ile Leu Thr
465                 470                 475                 480

Lys Ala Phe Leu Glu Ala Ser Trp Phe Ser Pro Ser Val Leu Phe Leu
                485                 490                 495

Asp Asp Ile Asp Ala Leu Met Pro Ala Glu Val Glu His Ala Asp Ser
            500                 505                 510

Ser Arg Thr Arg Gln Leu Thr Gln Leu Phe Leu Glu Leu Ala Leu Pro
        515                 520                 525
```

```
Ile Met Lys Ser Arg His Val Ser Val Val Ala Ser Ala Gln Ala Lys
    530                 535                 540

Glu Ser Leu His Met Asn Leu Val Thr Gly His Val Phe Glu Glu Leu
545                 550                 555                 560

Phe His Leu Lys Ser Pro Asp Lys Glu Ala Arg Leu Ala Ile Leu Ser
                565                 570                 575

Glu Ala Val Lys Leu Met Asp Gln Asn Val Ser Phe Ser Gln Asn Asp
            580                 585                 590

Val Leu Glu Ile Ala Ser Gln Val Asp Gly Tyr Leu Pro Gly Asp Leu
        595                 600                 605

Trp Thr Leu Ser Glu Arg Ala Gln His Glu Met Ala Leu Arg Gln Ile
    610                 615                 620

Glu Ile Gly Leu Glu Asn Pro Ser Ile Gln Leu Ala Asp Phe Met Lys
625                 630                 635                 640

Ala Leu Glu Asp Phe Val Pro Ser Ser Leu Arg Gly Val Lys Leu Gln
                645                 650                 655

Lys Ser Asn Val Lys Trp Asn Asp Ile Gly Gly Leu Lys Glu Thr Lys
            660                 665                 670

Ala Val Leu Leu Glu Thr Leu Glu Trp Pro Thr Lys Tyr Ala Pro Ile
        675                 680                 685

Phe Ala Ser Cys Pro Leu Arg Leu Arg Ser Gly Leu Leu Leu Tyr Gly
    690                 695                 700

Tyr Pro Gly Cys Gly Lys Thr Tyr Leu Ala Ser Ala Val Ala Ala Gln
705                 710                 715                 720

Cys Gly Leu Asn Phe Ile Ser Ile Lys Gly Pro Glu Ile Leu Asn Lys
                725                 730                 735

Tyr Ile Gly Ala Ser Glu Gln Ser Val Arg Glu Leu Phe Glu Arg Ala
            740                 745                 750

Gln Ala Ala Lys Pro Cys Ile Leu Phe Phe Asp Glu Phe Asp Ser Ile
        755                 760                 765

Ala Pro Lys Arg Gly His Asp Ser Thr Gly Val Thr Asp Arg Val Val
    770                 775                 780

Asn Gln Met Leu Thr Gln Met Asp Gly Ala Glu Gly Leu Asp Gly Val
785                 790                 795                 800

Tyr Val Leu Ala Ala Thr Ser Arg Pro Asp Leu Ile Asp Pro Ala Leu
                805                 810                 815

Leu Arg Pro Gly Arg Leu Asp Lys Met Leu Ile Cys Asp Leu Pro Ser
            820                 825                 830

Tyr Glu Asp Arg Leu Asp Ile Leu Arg Ala Ile Val Asp Gly Lys Met
        835                 840                 845

His Leu Asp Gly Glu Val Glu Leu Glu Tyr Val Ala Ser Arg Thr Asp
    850                 855                 860

Gly Phe Ser Gly Ala Asp Leu Gln Ala Val Met Phe Asn Ala Tyr Leu
865                 870                 875                 880

Glu Ala Ile His Glu Val Val Asp Val Ala Asp Asp Thr Ala Ala Asp
                885                 890                 895

Thr Pro Ala Leu Glu Asp Lys Arg Leu Glu Phe Phe Gln Thr Thr Leu
            900                 905                 910

Gly Asp Ala Lys Lys Asp Pro Ala Ala Val Gln Asn Glu Val Met Asn
        915                 920                 925

Ala Arg Ala Ala Val Ala Glu Lys Ala Arg Val Thr Ala Lys Leu Glu
    930                 935                 940

Ala Leu Phe Lys Gly Met Ser Val Gly Val Asp Asn Asp Asp Asp Lys
```

-continued

```
945                 950                 955                 960

Pro Arg Lys Lys Ala Val Val Val Ile Lys Pro Gln His Met Asn Lys
                965                 970                 975

Ser Leu Asp Glu Thr Ser Pro Ser Ile Ser Lys Lys Glu Leu Leu Lys
            980                 985                 990

Leu Lys Gly Ile Tyr Ser Gln Phe  Val Ser Gly Arg Ser  Gly Asp Met
        995                 1000                 1005

Pro Pro  Gly Thr Ala Ser Thr  Asp Val Gly Gly Arg  Ala Thr Leu
    1010                 1015                 1020

Ala


<210> SEQ ID NO 2
<211> LENGTH: 381
<212> TYPE: PRT
<213> ORGANISM: Yarrowia lipolytica
<220> FEATURE:
<221> NAME/KEY: MISC_FEATURE
<222> LOCATION: (1)..(381)
<223> OTHER INFORMATION: YlPex2p; GenBank Accession No. CAG77647

<400> SEQUENCE: 2

Met Ser Ser Val Leu Arg Leu Phe Lys Ile Gly Ala Pro Val Pro Asn
1               5                   10                  15

Val Arg Val His Gln Leu Asp Ala Ser Leu Leu Asp Ala Glu Leu Val
            20                  25                  30

Asp Leu Leu Lys Asn Gln Leu Phe Lys Gly Phe Thr Asn Phe His Pro
        35                  40                  45

Glu Phe Arg Asp Lys Tyr Glu Ser Glu Leu Val Leu Ala Leu Lys Leu
    50                  55                  60

Ile Leu Phe Lys Leu Thr Val Trp Asp His Ala Ile Thr Tyr Gly Gly
65                  70                  75                  80

Lys Leu Gln Asn Leu Lys Phe Ile Asp Ser Arg His Ser Ser Lys Leu
                85                  90                  95

Gln Ile Gln Pro Ser Val Ile Gln Lys Leu Gly Tyr Gly Ile Leu Val
            100                 105                 110

Val Gly Gly Gly Tyr Leu Trp Ser Lys Ile Glu Gly Tyr Leu Leu Ala
        115                 120                 125

Arg Ser Glu Asp Asp Val Ala Thr Asp Gly Thr Ser Val Arg Gly Ala
    130                 135                 140

Ser Ala Ala Arg Gly Ala Leu Lys Val Ala Asn Phe Ala Ser Leu Leu
145                 150                 155                 160

Tyr Ser Ala Ala Thr Leu Gly Asn Phe Val Ala Phe Leu Tyr Thr Gly
                165                 170                 175

Arg Tyr Ala Thr Val Ile Met Arg Leu Leu Arg Ile Arg Leu Val Pro
            180                 185                 190

Ser Gln Arg Thr Ser Ser Arg Gln Val Ser Tyr Glu Phe Gln Asn Arg
        195                 200                 205

Gln Leu Val Trp Asn Ala Phe Thr Glu Phe Leu Ile Phe Ile Leu Pro
    210                 215                 220

Leu Leu Gln Leu Pro Lys Leu Lys Arg Arg Ile Glu Arg Lys Leu Gln
225                 230                 235                 240

Ser Leu Asn Val Thr Arg Val Gly Asn Val Glu Glu Ala Ser Glu Gly
                245                 250                 255

Glu Leu Ala His Leu Pro Gln Lys Thr Cys Ala Ile Cys Phe Arg Asp
            260                 265                 270
```

```
Glu Glu Glu Gln Glu Gly Gly Gly Gly Ala Ser His Tyr Ser Thr Asp
        275                 280                 285

Val Thr Asn Pro Tyr Gln Ala Asp Cys Gly His Val Tyr Cys Tyr Val
    290                 295                 300

Cys Leu Val Thr Lys Leu Ala Gln Gly Asp Gly Asp Gly Trp Asn Cys
305                 310                 315                 320

Tyr Arg Cys Ala Lys Gln Val Gln Lys Met Lys Pro Trp Val Asp Val
                325                 330                 335

Asp Glu Ala Ala Val Val Gly Ala Ala Glu Met His Glu Lys Val Asp
            340                 345                 350

Val Ile Glu His Ala Glu Asp Asn Glu Gln Glu Glu Glu Glu Phe Asp
        355                 360                 365

Asp Asp Asp Glu Asp Ser Asn Phe Gln Leu Met Lys Asp
    370                 375                 380


<210> SEQ ID NO 3
<211> LENGTH: 431
<212> TYPE: PRT
<213> ORGANISM: Yarrowia lipolytica
<220> FEATURE:
<221> NAME/KEY: MISC_FEATURE
<222> LOCATION: (1)..(431)
<223> OTHER INFORMATION: YlPex3p; GenBank Accession No. CAG78565

<400> SEQUENCE: 3

Met Asp Phe Phe Arg Arg His Gln Lys Lys Val Leu Ala Leu Val Gly
1               5                   10                  15

Val Ala Leu Ser Ser Tyr Leu Phe Ile Asp Tyr Val Lys Lys Lys Phe
            20                  25                  30

Phe Glu Ile Gln Gly Arg Leu Ser Ser Glu Arg Thr Ala Lys Gln Asn
        35                  40                  45

Leu Arg Arg Arg Phe Glu Gln Asn Gln Gln Asp Ala Asp Phe Thr Ile
    50                  55                  60

Met Ala Leu Leu Ser Ser Leu Thr Thr Pro Val Met Glu Arg Tyr Pro
65                  70                  75                  80

Val Asp Gln Ile Lys Ala Glu Leu Gln Ser Lys Arg Arg Pro Thr Asp
                85                  90                  95

Arg Val Leu Ala Leu Glu Ser Ser Thr Ser Ser Ser Ala Thr Ala Gln
            100                 105                 110

Thr Val Pro Thr Met Thr Ser Gly Ala Thr Glu Glu Gly Glu Lys Ser
        115                 120                 125

Lys Thr Gln Leu Trp Gln Asp Leu Lys Arg Thr Thr Ile Ser Arg Ala
    130                 135                 140

Phe Ser Leu Val Tyr Ala Asp Ala Leu Leu Ile Phe Phe Thr Arg Leu
145                 150                 155                 160

Gln Leu Asn Ile Leu Gly Arg Arg Asn Tyr Val Asn Ser Val Val Ala
                165                 170                 175

Leu Ala Gln Gln Gly Arg Glu Gly Asn Ala Glu Gly Arg Val Ala Pro
            180                 185                 190

Ser Phe Gly Asp Leu Ala Asp Met Gly Tyr Phe Gly Asp Leu Ser Gly
        195                 200                 205

Ser Ser Ser Phe Gly Glu Thr Ile Val Asp Pro Asp Leu Asp Glu Gln
    210                 215                 220

Tyr Leu Thr Phe Ser Trp Trp Leu Leu Asn Glu Gly Trp Val Ser Leu
225                 230                 235                 240

Ser Glu Arg Val Glu Glu Ala Val Arg Arg Val Trp Asp Pro Val Ser
```

```
                245                 250                 255

Pro Lys Ala Glu Leu Gly Phe Asp Glu Leu Ser Glu Leu Ile Gly Arg
            260                 265                 270

Thr Gln Met Leu Ile Asp Arg Pro Leu Asn Pro Ser Ser Pro Leu Asn
        275                 280                 285

Phe Leu Ser Gln Leu Leu Pro Pro Arg Glu Gln Glu Glu Tyr Val Leu
    290                 295                 300

Ala Gln Asn Pro Ser Asp Thr Ala Ala Pro Ile Val Gly Pro Thr Leu
305                 310                 315                 320

Arg Arg Leu Leu Asp Glu Thr Ala Asp Phe Ile Glu Ser Pro Asn Ala
                325                 330                 335

Ala Glu Val Ile Glu Arg Leu Val His Ser Gly Leu Ser Val Phe Met
            340                 345                 350

Asp Lys Leu Ala Val Thr Phe Gly Ala Thr Pro Ala Asp Ser Gly Ser
        355                 360                 365

Pro Tyr Pro Val Val Leu Pro Thr Ala Lys Val Lys Leu Pro Ser Ile
    370                 375                 380

Leu Ala Asn Met Ala Arg Gln Ala Gly Gly Met Ala Gln Gly Ser Pro
385                 390                 395                 400

Gly Val Glu Asn Glu Tyr Ile Asp Val Met Asn Gln Val Gln Glu Leu
                405                 410                 415

Thr Ser Phe Ser Ala Val Val Tyr Ser Ser Phe Asp Trp Ala Leu
            420                 425                 430


<210> SEQ ID NO 4
<211> LENGTH: 395
<212> TYPE: PRT
<213> ORGANISM: Yarrowia lipolytica
<220> FEATURE:
<221> NAME/KEY: MISC_FEATURE
<222> LOCATION: (1)..(395)
<223> OTHER INFORMATION: YlPex3Bp; GenBank Accession No. CAG83356

<400> SEQUENCE: 4

Met Leu Gln Ser Leu Asn Arg Asn Lys Lys Arg Leu Ala Val Ser Thr
1               5                   10                  15

Gly Leu Ile Ala Val Ala Tyr Val Val Ile Ser Tyr Thr Thr Lys Arg
            20                  25                  30

Leu Ile Glu Lys Gln Glu Gln Lys Leu Glu Glu Glu Arg Ala Lys Glu
        35                  40                  45

Arg Leu Lys Gln Leu Phe Ala Gln Thr Gln Asn Glu Ala Ala Phe His
    50                  55                  60

Thr Ala Ser Val Leu Pro Gln Leu Cys Glu Gln Ile Met Glu Phe Val
65                  70                  75                  80

Ala Val Glu Lys Ile Ala Glu Gln Leu Gln Asn Met Arg Ala Glu Lys
                85                  90                  95

Arg Lys Lys Gln Asn Met Asp Asp Asp Lys His Ser Val Leu Ser Leu
            100                 105                 110

Gly Thr Glu Thr Thr Ala Ser Met Ala Asp Gly Gln Lys Met Ser Lys
        115                 120                 125

Ile Gln Leu Trp Asp Glu Leu Lys Ile Glu Ser Leu Thr Arg Ile Val
    130                 135                 140

Thr Leu Ile Tyr Cys Val Ser Leu Leu Asn Tyr Leu Ile Arg Leu Gln
145                 150                 155                 160

Thr Asn Ile Val Gly Arg Lys Arg Tyr Gln Asn Glu Ala Gly Pro Ala
                165                 170                 175
```

```
Gly Ala Thr Tyr Asp Met Ser Leu Glu Gln Cys Tyr Thr Trp Leu Leu
            180                 185                 190

Thr Arg Gly Trp Lys Ser Val Val Asp Asn Val Arg Arg Ser Val Gln
        195                 200                 205

Gln Val Phe Thr Gly Val Asn Pro Arg Gln Asn Leu Ser Leu Asp Glu
    210                 215                 220

Phe Ala Thr Leu Leu Lys Arg Val Gln Thr Leu Val Asn Ser Pro Pro
225                 230                 235                 240

Tyr Ser Thr Thr Pro Asn Thr Phe Leu Thr Ser Leu Leu Pro Pro Arg
                245                 250                 255

Glu Leu Glu Gln Leu Arg Leu Glu Lys Glu Lys Gln Ser Leu Ser Pro
            260                 265                 270

Asn Tyr Thr Tyr Gly Ser Pro Leu Lys Asp Leu Val Phe Glu Ser Ala
        275                 280                 285

Gln His Ile Gln Ser Pro Gln Gly Met Ser Ser Phe Arg Ala Ile Ile
    290                 295                 300

Asp Gln Ser Phe Lys Val Phe Leu Glu Lys Val Asn Glu Ser Gln Tyr
305                 310                 315                 320

Val Asn Pro Pro Ser Thr Gly Gly Lys Arg Ile Ala Val Gly Ala Leu
                325                 330                 335

Gln Pro Pro Ile Ile Ser Gly Gly Pro Lys Lys Val Lys Leu Ala Ser
            340                 345                 350

Leu Leu Ser Val Ala Thr Arg Gln Ser Ser Val Ile Ser His Ala Gln
        355                 360                 365

Pro Asn Pro Tyr Val Asp Ala Ile Asn Ser Val Ala Glu Tyr Asn Gly
    370                 375                 380

Leu Cys Ala Val Ile Tyr Ser Ser Phe Glu Gln
385                 390                 395


<210> SEQ ID NO 5
<211> LENGTH: 153
<212> TYPE: PRT
<213> ORGANISM: Yarrowia lipolytica
<220> FEATURE:
<221> NAME/KEY: MISC_FEATURE
<222> LOCATION: (1)..(153)
<223> OTHER INFORMATION: YlPex4p; GenBank Accession No. CAG79130

<400> SEQUENCE: 5

Met Ala Ser Gln Lys Arg Leu Ile Lys Glu Leu Ala Ala Tyr Lys Lys
1               5                   10                  15

Asp Pro Asn Pro Cys Leu Ala Ser Leu Thr Ala Asp Gly Asp Ser Leu
            20                  25                  30

Tyr Lys Trp Thr Ala Val Met Arg Gly Thr Glu Gly Thr Ala Tyr Glu
        35                  40                  45

Asn Gly Leu Trp Gln Val Glu Ile Asn Ile Pro Glu Asn Tyr Pro Leu
    50                  55                  60

Gln Pro Pro Thr Met Phe Phe Arg Thr Lys Ile Cys His Pro Asn Ile
65                  70                  75                  80

His Phe Glu Thr Gly Glu Val Cys Ile Asp Val Leu Lys Thr Gln Trp
                85                  90                  95

Ser Pro Ala Trp Thr Ile Ser Ser Ala Cys Thr Ala Val Ser Ala Met
            100                 105                 110

Leu Ser Leu Pro Glu Pro Asp Ser Pro Leu Asn Ile Asp Ala Ala Asn
        115                 120                 125
```

```
Leu Val Arg Cys Gly Asp Glu Ser Ala Met Glu Gly Leu Val Arg Tyr
    130                 135                 140

Tyr Val Asn Lys Tyr Ala Ser Gly Asn
145                 150


<210> SEQ ID NO 6
<211> LENGTH: 598
<212> TYPE: PRT
<213> ORGANISM: Yarrowia lipolytica
<220> FEATURE:
<221> NAME/KEY: MISC_FEATURE
<222> LOCATION: (1)..(598)
<223> OTHER INFORMATION: YlPex5p; GenBank Accession No. CAG78803

<400> SEQUENCE: 6

Met Ser Phe Met Arg Gly Gly Ser Glu Cys Ser Thr Gly Arg Asn Pro
1               5                   10                  15

Leu Ser Gln Phe Thr Lys His Thr Ala Glu Asp Arg Ser Leu Gln His
            20                  25                  30

Asp Arg Val Ala Gly Pro Ser Gly Gly Arg Val Gly Gly Met Arg Ser
        35                  40                  45

Asn Thr Gly Glu Met Ser Gln Gln Asp Arg Glu Met Met Ala Arg Phe
    50                  55                  60

Gly Ala Ala Gly Pro Glu Gln Ser Ser Phe Asn Tyr Glu Gln Met Arg
65                  70                  75                  80

His Glu Leu His Asn Met Gly Ala Gln Gly Gly Gln Ile Pro Gln Val
                85                  90                  95

Pro Ser Gln Gln Gly Ala Ala Asn Gly Gly Gln Trp Ala Arg Asp Phe
            100                 105                 110

Gly Gly Gln Gln Thr Ala Pro Gly Ala Ala Pro Gln Asp Ala Lys Asn
        115                 120                 125

Trp Asn Ala Glu Phe Gln Arg Gly Gly Ser Pro Ala Glu Ala Met Gln
    130                 135                 140

Gln Gln Gly Pro Gly Pro Met Gln Gly Gly Met Gly Met Gly Gly Met
145                 150                 155                 160

Pro Met Tyr Gly Met Ala Arg Pro Met Tyr Ser Gly Met Ser Ala Asn
                165                 170                 175

Met Ala Pro Gln Phe Gln Pro Gln Gln Ala Asn Ala Arg Val Val Glu
            180                 185                 190

Leu Asp Glu Gln Asn Trp Glu Glu Gln Phe Lys Gln Met Asp Ser Ala
        195                 200                 205

Val Gly Lys Gly Lys Glu Val Glu Glu Gln Thr Ala Glu Thr Ala Thr
    210                 215                 220

Ala Thr Glu Thr Val Thr Glu Thr Glu Thr Thr Thr Glu Asp Lys Pro
225                 230                 235                 240

Met Asp Ile Lys Asn Met Asp Phe Glu Asn Ile Trp Lys Asn Leu Gln
                245                 250                 255

Val Asn Val Leu Asp Asn Met Asp Glu Trp Leu Glu Glu Thr Asn Ser
            260                 265                 270

Pro Ala Trp Glu Arg Asp Phe His Glu Tyr Thr His Asn Arg Pro Glu
        275                 280                 285

Phe Ala Asp Tyr Gln Phe Glu Glu Asn Asn Gln Phe Met Glu His Pro
    290                 295                 300

Asp Pro Phe Lys Ile Gly Val Glu Leu Met Glu Thr Gly Gly Arg Leu
305                 310                 315                 320

Ser Glu Ala Ala Leu Ala Phe Glu Ala Ala Val Gln Lys Asn Thr Glu
```

```
                325                 330                 335

His Ala Glu Ala Trp Gly Arg Leu Gly Ala Cys Gln Ala Gln Asn Glu
            340                 345                 350

Lys Glu Asp Pro Ala Ile Arg Ala Leu Glu Arg Cys Ile Lys Leu Glu
        355                 360                 365

Pro Gly Asn Leu Ser Ala Leu Met Asn Leu Ser Val Ser Tyr Thr Asn
    370                 375                 380

Glu Gly Tyr Glu Asn Ala Ala Tyr Ala Thr Leu Glu Arg Trp Leu Ala
385                 390                 395                 400

Thr Lys Tyr Pro Glu Val Val Asp Gln Ala Arg Asn Gln Glu Pro Arg
                405                 410                 415

Leu Gly Asn Glu Asp Lys Phe Gln Leu His Ser Arg Val Thr Glu Leu
            420                 425                 430

Phe Ile Arg Ala Ala Gln Leu Ser Pro Asp Gly Ala Asn Ile Asp Ala
        435                 440                 445

Asp Val Gln Val Gly Leu Gly Val Leu Phe Tyr Gly Asn Glu Glu Tyr
    450                 455                 460

Asp Lys Ala Ile Asp Cys Phe Asn Ala Ala Ile Ala Val Arg Pro Asp
465                 470                 475                 480

Asp Ala Leu Leu Trp Asn Arg Leu Gly Ala Thr Leu Ala Asn Ser His
                485                 490                 495

Arg Ser Glu Glu Ala Ile Asp Ala Tyr Tyr Lys Ala Leu Glu Leu Arg
            500                 505                 510

Pro Ser Phe Val Arg Ala Arg Tyr Asn Leu Gly Val Ser Cys Ile Asn
        515                 520                 525

Ile Gly Cys Tyr Lys Glu Ala Ala Gln Tyr Leu Leu Gly Ala Leu Ser
    530                 535                 540

Met His Lys Val Glu Gly Val Gln Asp Asp Val Leu Ala Asn Gln Ser
545                 550                 555                 560

Thr Asn Leu Tyr Asp Thr Leu Lys Arg Val Phe Leu Gly Met Asp Arg
                565                 570                 575

Arg Asp Leu Val Ala Lys Val Gly Asn Gly Met Asp Val Asn Gln Phe
            580                 585                 590

Arg Asn Glu Phe Glu Phe
        595


<210> SEQ ID NO 7
<211> LENGTH: 1024
<212> TYPE: PRT
<213> ORGANISM: Yarrowia lipolytica
<220> FEATURE:
<221> NAME/KEY: MISC_FEATURE
<222> LOCATION: (1)..(1024)
<223> OTHER INFORMATION: YlPex6p; GenBank Accession No. CAG82306

<400> SEQUENCE: 7

Met Pro Ser Ile Ser His Lys Pro Ile Thr Ala Lys Leu Val Ala Ala
1               5                   10                  15

Pro Asp Ala Thr Lys Leu Glu Leu Ser Ser Tyr Leu Tyr Gln Gln Leu
            20                  25                  30

Phe Ser Asp Lys Pro Ala Glu Pro Tyr Val Ala Phe Glu Ala Pro Gly
        35                  40                  45

Ile Lys Trp Ala Leu Tyr Pro Ala Ser Glu Asp Arg Ser Leu Pro Gln
    50                  55                  60

Tyr Thr Cys Lys Ala Asp Ile Arg His Val Ala Gly Ser Leu Lys Lys
65                  70                  75                  80
```

```
Phe Met Pro Val Val Leu Lys Arg Val Asn Pro Val Thr Ile Glu His
                85                  90                  95

Ala Ile Val Thr Val Pro Ala Ser Gln Tyr Glu Thr Leu Asn Thr Pro
            100                 105                 110

Glu Gln Val Leu Lys Ala Leu Glu Pro Gln Leu Asp Lys Asp Arg Pro
        115                 120                 125

Val Ile Arg Gln Gly Asp Val Leu Leu Asn Gly Cys Arg Val Arg Leu
    130                 135                 140

Cys Glu Pro Val Asn Gln Gly Lys Val Val Lys Gly Thr Thr Lys Leu
145                 150                 155                 160

Thr Val Ala Lys Glu Gln Glu Thr Ile Gln Pro Ala Asp Glu Ala Ala
                165                 170                 175

Asp Val Ala Phe Asp Ile Ala Glu Phe Leu Asp Phe Asp Thr Ser Val
            180                 185                 190

Ala Lys Thr Arg Glu Ser Thr Asn Leu Gln Val Ala Pro Leu Glu Gly
        195                 200                 205

Ala Ile Pro Thr Pro Leu Ser Asp Arg Phe Asp Asp Cys Glu Ser Arg
    210                 215                 220

Gly Phe Val Lys Ser Glu Thr Met Ser Lys Leu Gly Val Phe Ser Gly
225                 230                 235                 240

Asp Ile Val Ser Ile Lys Thr Lys Asn Gly Ala Glu Arg Val Leu Arg
                245                 250                 255

Leu Phe Ala Tyr Pro Glu Pro Asn Thr Val Lys Tyr Asp Val Val Tyr
            260                 265                 270

Val Ser Pro Ile Leu Tyr His Asn Ile Gly Asp Lys Glu Ile Glu Val
        275                 280                 285

Thr Pro Asn Gly Glu Thr His Lys Ser Val Gly Glu Ala Leu Asp Ser
    290                 295                 300

Val Leu Glu Ala Ala Glu Glu Val Lys Leu Ala Arg Val Leu Gly Pro
305                 310                 315                 320

Thr Thr Thr Asp Arg Thr Phe Gln Thr Ala Tyr His Ala Gly Leu Gln
                325                 330                 335

Ala Tyr Phe Lys Pro Val Lys Arg Ala Val Arg Val Gly Asp Leu Ile
            340                 345                 350

Pro Ile Pro Phe Asp Ser Ile Leu Ala Arg Thr Ile Gly Glu Asp Pro
        355                 360                 365

Glu Met Ser His Ile Pro Leu Glu Ala Leu Ala Val Lys Pro Asp Ser
    370                 375                 380

Val Ala Trp Phe Gln Val Thr Ser Leu Asn Gly Ser Glu Asp Pro Ala
385                 390                 395                 400

Ser Lys Gln Tyr Leu Val Asp Ser Ser Gln Thr Lys Leu Ile Glu Gly
                405                 410                 415

Gly Thr Thr Ser Ser Ala Val Ile Pro Thr Ser Val Pro Trp Arg Glu
            420                 425                 430

Tyr Leu Gly Leu Asp Thr Leu Pro Lys Phe Gly Ser Glu Phe Ala Tyr
        435                 440                 445

Ala Asp Lys Ile Arg Asn Leu Val Gln Ile Ser Thr Ser Ala Leu Ser
    450                 455                 460

His Ala Lys Leu Asn Thr Ser Val Leu Leu His Ser Ala Lys Arg Gly
465                 470                 475                 480

Val Gly Lys Ser Thr Val Leu Arg Ser Val Ala Ala Gln Cys Gly Ile
                485                 490                 495
```

```
Ser Val Phe Glu Ile Ser Cys Phe Gly Leu Ile Gly Asp Asn Glu Ala
            500                 505                 510

Gln Thr Leu Gly Thr Leu Arg Ala Lys Leu Asp Arg Ala Tyr Gly Cys
        515                 520                 525

Ser Pro Cys Val Val Val Leu Gln His Leu Glu Ser Ile Ala Lys Lys
    530                 535                 540

Ser Asp Gln Asp Gly Lys Asp Glu Gly Ile Val Ser Lys Leu Val Asp
545                 550                 555                 560

Val Leu Ala Asp Tyr Ser Gly His Gly Val Leu Leu Ala Ala Thr Ser
                565                 570                 575

Asn Asp Pro Asp Lys Ile Ser Glu Ala Ile Arg Ser Arg Phe Gln Phe
            580                 585                 590

Glu Ile Glu Ile Gly Val Pro Ser Glu Pro Gln Arg Arg Gln Ile Phe
        595                 600                 605

Ser His Leu Thr Lys Ser Gly Pro Gly Gly Asp Ser Ile Arg Asn Ala
    610                 615                 620

Pro Ile Ser Leu Arg Ser Asp Val Ser Val Glu Asn Leu Ala Leu Gln
625                 630                 635                 640

Ser Ala Gly Leu Thr Pro Pro Asp Leu Thr Ala Ile Val Gln Thr Thr
                645                 650                 655

Arg Leu Arg Ala Ile Asp Arg Leu Asn Lys Leu Thr Lys Asp Ser Asp
            660                 665                 670

Thr Thr Leu Asp Asp Leu Leu Thr Leu Ser His Gly Thr Leu Gln Leu
        675                 680                 685

Thr Pro Ser Asp Phe Asp Asp Ala Ile Ala Asp Ala Arg Gln Lys Tyr
    690                 695                 700

Ser Asp Ser Ile Gly Ala Pro Arg Ile Pro Asn Val Gly Trp Asp Asp
705                 710                 715                 720

Val Gly Gly Met Glu Gly Val Lys Lys Asp Ile Leu Asp Thr Ile Glu
                725                 730                 735

Thr Pro Leu Lys Tyr Pro His Trp Phe Ser Asp Gly Val Lys Lys Arg
            740                 745                 750

Ser Gly Ile Leu Phe Tyr Gly Pro Pro Gly Thr Gly Lys Thr Leu Leu
        755                 760                 765

Ala Lys Ala Ile Ala Thr Thr Phe Ser Leu Asn Phe Phe Ser Val Lys
    770                 775                 780

Gly Pro Glu Leu Leu Asn Met Tyr Ile Gly Glu Ser Glu Ala Asn Val
785                 790                 795                 800

Arg Arg Val Phe Gln Lys Ala Arg Asp Ala Lys Pro Cys Val Val Phe
                805                 810                 815

Phe Asp Glu Leu Asp Ser Val Ala Pro Gln Arg Gly Asn Gln Gly Asp
            820                 825                 830

Ser Gly Gly Val Met Asp Arg Ile Val Ser Gln Leu Leu Ala Glu Leu
        835                 840                 845

Asp Gly Met Ser Thr Ala Gly Gly Glu Gly Val Phe Val Val Gly Ala
    850                 855                 860

Thr Asn Arg Pro Asp Leu Leu Asp Glu Ala Leu Leu Arg Pro Gly Arg
865                 870                 875                 880

Phe Asp Lys Met Leu Tyr Leu Gly Ile Ser Asp Thr His Glu Lys Gln
                885                 890                 895

Gln Thr Ile Met Glu Ala Leu Thr Arg Lys Phe Arg Leu Ala Ala Asp
            900                 905                 910

Val Ser Leu Glu Ala Ile Ser Lys Arg Cys Pro Phe Thr Phe Thr Gly
```

```
        915                 920                 925

Ala Asp Phe Tyr Ala Leu Cys Ser Asp Ala Met Leu Asn Ala Met Thr
    930                 935                 940

Arg Thr Ala Asn Glu Val Asp Ala Lys Ile Lys Leu Leu Asn Lys Asn
945                 950                 955                 960

Arg Glu Glu Ala Gly Glu Glu Pro Val Ser Ile Arg Trp Trp Phe Asp
                965                 970                 975

His Glu Ala Thr Lys Ser Asp Ile Glu Val Glu Val Ala Gln Gln Asp
            980                 985                 990

Phe Glu Lys Ala Lys Asp Glu Leu  Ser Pro Ser Val Ser  Ala Glu Glu
        995                 1000                1005

Leu Gln  His Tyr Leu Lys Leu  Arg Gln Gln Phe Glu  Gly Gly Lys
    1010                 1015                1020

Lys


<210> SEQ ID NO 8
<211> LENGTH: 356
<212> TYPE: PRT
<213> ORGANISM: Yarrowia lipolytica
<220> FEATURE:
<221> NAME/KEY: MISC_FEATURE
<222> LOCATION: (1)..(356)
<223> OTHER INFORMATION: YlPex7p; GenBank Accession No. CAG78389

<400> SEQUENCE: 8

Met Leu Gly Phe Lys Thr Gln Gly Phe Asn Gly Tyr Ala Ala Asn Tyr
1               5                   10                  15

Ser Pro Phe Phe Asn Asp Lys Ile Ala Val Gly Thr Ala Ala Asn Tyr
            20                  25                  30

Gly Leu Val Gly Asn Gly Lys Leu Phe Ile Leu Gly Ile Ser Pro Glu
        35                  40                  45

Gly Arg Met Val Cys Glu Gly Gln Phe Asp Thr Gln Asp Gly Ile Phe
    50                  55                  60

Asp Val Ala Trp Ser Glu Gln His Glu Asn His Val Ala Thr Ala Cys
65                  70                  75                  80

Gly Asp Gly Ser Val Lys Leu Phe Asp Ile Lys Ala Gly Ala Phe Pro
                85                  90                  95

Leu Val Ser Phe Lys Glu His Thr Arg Glu Val Phe Ser Val Asn Trp
            100                 105                 110

Asn Met Ala Asn Lys Ala Leu Phe Cys Thr Ser Ser Trp Asp Ser Thr
        115                 120                 125

Ile Lys Ile Trp Thr Pro Glu Arg Thr Asn Ser Ile Met Thr Leu Gly
    130                 135                 140

Gln Pro Ala Pro Ala Gln Gly Thr Asn Ala Ser Ala His Ile Gly Arg
145                 150                 155                 160

Gln Thr Ala Pro Asn Gln Ala Ala Ala Gln Glu Cys Ile Tyr Ser Ala
                165                 170                 175

Lys Phe Ser Pro His Thr Asp Ser Ile Ile Ala Ser Ala His Ser Thr
            180                 185                 190

Gly Met Val Lys Val Trp Asp Thr Arg Ala Pro Gln Pro Leu Gln Gln
        195                 200                 205

Gln Phe Ser Thr Gln Gln Thr Glu Ser Gly Gly Pro Pro Glu Val Leu
    210                 215                 220

Ser Leu Asp Trp Asn Lys Tyr Arg Pro Thr Val Ile Ala Thr Gly Gly
225                 230                 235                 240
```

```
Val Asp Arg Ser Val Gln Val Tyr Asp Ile Arg Met Thr Gln Pro Ala
                245                 250                 255

Ala Asn Gln Pro Val Gln Pro Leu Ser Leu Ile Leu Gly His Arg Leu
            260                 265                 270

Pro Val Arg Gly Val Ser Trp Ser Pro His His Ala Asp Leu Leu Leu
        275                 280                 285

Ser Cys Ser Tyr Asp Met Thr Ala Arg Val Trp Arg Asp Ala Ser Thr
    290                 295                 300

Gly Gly Asn Tyr Leu Ala Arg Gln Arg Gly Gly Thr Glu Val Lys Cys
305                 310                 315                 320

Met Asp Arg His Thr Glu Phe Val Ile Gly Gly Asp Trp Ser Leu Trp
                325                 330                 335

Gly Asp Pro Gly Trp Ile Thr Thr Val Gly Trp Asp Gln Met Val Tyr
            340                 345                 350

Val Trp His Ala
        355


<210> SEQ ID NO 9
<211> LENGTH: 671
<212> TYPE: PRT
<213> ORGANISM: Yarrowia lipolytica
<220> FEATURE:
<221> NAME/KEY: MISC_FEATURE
<222> LOCATION: (1)..(671)
<223> OTHER INFORMATION: YlPex8p; GenBank Accession No. CAG80447

<400> SEQUENCE: 9

Met Asn Lys Tyr Leu Val Pro Pro Pro Gln Ala Asn Arg Thr Val Thr
1               5                   10                  15

Asn Leu Asp Leu Leu Ile Asn Asn Leu Arg Gly Ser Ser Thr Pro Gly
            20                  25                  30

Ala Ala Glu Val Asp Thr Arg Asp Ile Leu Gln Arg Ile Val Phe Ile
        35                  40                  45

Leu Pro Thr Ile Lys Asn Pro Leu Asn Leu Asp Leu Val Ile Lys Glu
    50                  55                  60

Ile Ile Asn Ser Pro Arg Leu Leu Pro Pro Leu Ile Asp Leu His Asp
65                  70                  75                  80

Tyr Gln Gln Leu Thr Asp Ala Phe Arg Ala Thr Ile Lys Arg Lys Ala
                85                  90                  95

Leu Val Thr Asp Pro Thr Ile Ser Phe Glu Ala Trp Leu Glu Thr Cys
            100                 105                 110

Phe Gln Val Ile Thr Arg Phe Ala Gly Pro Gly Trp Lys Lys Leu Pro
        115                 120                 125

Leu Leu Ala Gly Leu Ile Leu Ala Asp Tyr Asp Ile Ser Ala Asp Gly
    130                 135                 140

Pro Thr Leu Glu Arg Lys Pro Gly Phe Pro Ser Lys Leu Lys His Leu
145                 150                 155                 160

Leu Lys Arg Glu Phe Val Thr Thr Phe Asp Gln Cys Leu Ser Ile Asp
                165                 170                 175

Thr Arg Asn Arg Ser Asp Ala Thr Lys Trp Val Pro Val Leu Ala Cys
            180                 185                 190

Ile Ser Ile Ala Gln Val Tyr Ser Leu Leu Gly Asp Val Ala Ile Asn
        195                 200                 205

Tyr Arg Arg Phe Leu Gln Val Gly Leu Asp Leu Ile Phe Ser Asn Tyr
    210                 215                 220

Gly Leu Glu Met Gly Thr Ala Leu Ala Arg Leu His Ala Glu Ser Gly
```

-continued

```
225                 230                 235                 240

Gly Asp Ala Thr Thr Ala Gly Gly Leu Ile Gly Lys Lys Leu Lys Glu
                245                 250                 255

Pro Val Val Ala Leu Leu Asn Thr Phe Ala His Ile Ala Ser Ser Cys
            260                 265                 270

Ile Val His Val Asp Ile Asp Tyr Ile Asp Arg Ile Gln Asn Lys Ile
        275                 280                 285

Ile Leu Val Cys Glu Asn Gln Ala Glu Thr Trp Arg Ile Leu Thr Ile
    290                 295                 300

Glu Ser Pro Thr Val Met His His Gln Glu Ser Val Gln Tyr Leu Lys
305                 310                 315                 320

Trp Glu Leu Phe Thr Leu Cys Ile Ile Met Gln Gly Ile Ala Asn Met
                325                 330                 335

Leu Leu Thr Gln Lys Met Asn Gln Phe Met Tyr Leu Gln Leu Ala Tyr
            340                 345                 350

Lys Gln Leu Gln Ala Leu His Ser Ile Tyr Phe Ile Val Asp Gln Met
        355                 360                 365

Gly Ser Gln Phe Ala Ala Tyr Asp Tyr Val Phe Phe Ser Ala Ile Asp
    370                 375                 380

Val Leu Leu Ser Glu Tyr Ala Pro Tyr Ile Lys Asn Arg Gly Thr Ile
385                 390                 395                 400

Pro Pro Asn Lys Glu Phe Val Ala Glu Arg Leu Ala Ala Asn Leu Ala
                405                 410                 415

Gly Thr Ser Asn Val Gly Ser His Leu Pro Ile Asp Arg Ser Arg Val
            420                 425                 430

Leu Phe Ala Leu Asn Tyr Tyr Glu Gln Leu Val Thr Val Cys His Asp
        435                 440                 445

Ser Cys Val Glu Thr Ile Ile Tyr Pro Met Ala Arg Ser Phe Leu Tyr
    450                 455                 460

Pro Thr Ser Asp Ile Gln Gln Leu Lys Pro Leu Val Glu Ala Ala His
465                 470                 475                 480

Ser Val Ile Leu Ala Gly Leu Ala Val Pro Thr Asn Ala Val Val Asn
                485                 490                 495

Ala Lys Leu Ile Pro Glu Tyr Met Gly Gly Val Leu Pro Leu Phe Pro
            500                 505                 510

Gly Val Phe Ser Trp Asn Gln Phe Val Leu Ala Ile Gln Ser Ile Val
        515                 520                 525

Asn Thr Val Ser Pro Pro Ser Glu Val Phe Lys Thr Asn Gln Lys Leu
    530                 535                 540

Phe Arg Leu Val Leu Asp Ser Leu Met Lys Lys Cys Arg Asp Thr Pro
545                 550                 555                 560

Val Gly Ile Pro Val Pro His Ser Val Thr Val Ser Gln Glu Gln Glu
                565                 570                 575

Asp Ile Pro Pro Thr Gln Arg Ala Val Val Met Leu Ala Leu Ile Asn
            580                 585                 590

Ser Leu Pro Tyr Val Asp Ile Arg Ser Phe Glu Leu Trp Leu Gln Glu
        595                 600                 605

Thr Trp Asn Met Ile Glu Ala Thr Pro Met Leu Ala Glu Asn Ala Pro
    610                 615                 620

Asn Lys Glu Leu Ala His Ala Glu His Glu Phe Leu Val Leu Glu Met
625                 630                 635                 640

Trp Lys Met Ile Ser Gly Asn Ile Asp Gln Arg Leu Asn Asp Val Ala
                645                 650                 655
```

```
Ile Arg Trp Trp Tyr Lys Lys Asn Ala Arg Val His Gly Thr Leu
            660                 665                 670


<210> SEQ ID NO 10
<211> LENGTH: 377
<212> TYPE: PRT
<213> ORGANISM: Yarrowia lipolytica
<220> FEATURE:
<221> NAME/KEY: MISC_FEATURE
<222> LOCATION: (1)..(377)
<223> OTHER INFORMATION: YlPex10p; GenBank Accession No. CAG81606

<400> SEQUENCE: 10

Met Trp Gly Ser Ser His Ala Phe Ala Gly Glu Ser Asp Leu Thr Leu
1               5                   10                  15

Gln Leu His Thr Arg Ser Asn Met Ser Asp Asn Thr Thr Ile Lys Lys
            20                  25                  30

Pro Ile Arg Pro Lys Pro Ile Arg Thr Glu Arg Leu Pro Tyr Ala Gly
        35                  40                  45

Ala Ala Glu Ile Ile Arg Ala Asn Gln Lys Asp His Tyr Phe Glu Ser
    50                  55                  60

Val Leu Glu Gln His Leu Val Thr Phe Leu Gln Lys Trp Lys Gly Val
65                  70                  75                  80

Arg Phe Ile His Gln Tyr Lys Glu Glu Leu Glu Thr Ala Ser Lys Phe
                85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175

Pro Glu Thr Trp Lys Glu Arg Val Ile Lys Thr Phe Val Asn Lys Phe
            180                 185                 190

Asp Lys Phe Thr Ala Leu Glu Gly Phe Thr Ala Ile His Leu Ala Ile
        195                 200                 205

Phe Tyr Val Tyr Gly Ser Tyr Tyr Gln Leu Ser Lys Arg Ile Trp Gly
    210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
                245                 250                 255

Phe Val Gln Thr Gly Arg Glu Tyr Leu Gly Ala Leu Leu Glu Lys Ser
            260                 265                 270

Val Glu Lys Glu Ala Gly Glu Lys Glu Asp Glu Lys Glu Ala Val Val
        275                 280                 285

Pro Lys Lys Lys Ser Ser Ile Pro Phe Ile Glu Asp Thr Glu Gly Glu
    290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
                325                 330                 335
```

```
Pro Ala Cys Thr Pro Cys Gly His Phe Phe Cys Trp Asp Cys Ile Ser
            340                 345                 350

Glu Trp Val Arg Glu Lys Pro Glu Cys Pro Leu Cys Arg Gln Gly Val
        355                 360                 365

Arg Glu Gln Asn Leu Leu Pro Ile Arg
    370                 375


<210> SEQ ID NO 11
<211> LENGTH: 408
<212> TYPE: PRT
<213> ORGANISM: Yarrowia lipolytica
<220> FEATURE:
<221> NAME/KEY: MISC_FEATURE
<222> LOCATION: (1)..(408)
<223> OTHER INFORMATION: YlPex12p; GenBank Accession No. CAG81532

<400> SEQUENCE: 11

Met Asp Tyr Phe Ser Ser Leu Asn Ala Ser Gln Leu Asp Pro Asp Val
1               5                   10                  15

Pro Thr Leu Phe Glu Leu Leu Ser Ala Lys Gln Leu Glu Gly Leu Ile
            20                  25                  30

Ala Pro Ser Val Arg Tyr Ile Leu Ala Phe Tyr Ala Gln Arg His Pro
        35                  40                  45

Arg Tyr Leu Leu Arg Ile Val Asn Arg Tyr Asp Glu Leu Tyr Ala Leu
    50                  55                  60

Phe Met Gly Leu Val Glu Tyr Tyr Asn Leu Lys Thr Trp Asn Ala Ser
65                  70                  75                  80

Phe Thr Glu Lys Phe Tyr Gly Leu Lys Arg Thr Gln Ile Leu Thr Asn
                85                  90                  95

Pro Ala Leu Arg Thr Arg Gln Ala Val Pro Asp Leu Val Glu Ala Glu
            100                 105                 110

Lys Arg Leu Ser Lys Lys Lys Ile Trp Gly Ser Leu Phe Phe Leu Ile
        115                 120                 125

Val Val Pro Tyr Val Lys Glu Lys Leu Asp Ala Arg Tyr Glu Arg Leu
    130                 135                 140

Lys Gly Arg Tyr Leu Ala Arg Asp Ile Asn Glu Glu Arg Ile Glu Ile
145                 150                 155                 160

Lys Arg Thr Gly Thr Ala Gln Gln Ile Ala Val Phe Glu Phe Asp Tyr
                165                 170                 175

Trp Leu Leu Lys Leu Tyr Pro Ile Val Thr Met Gly Cys Thr Thr Ala
            180                 185                 190

Thr Leu Ala Phe His Met Leu Phe Leu Phe Ser Val Thr Arg Ala Tyr
        195                 200                 205

Ser Ile Asp Asp Phe Leu Leu Asn Ile Gln Phe Ser Arg Met Thr Arg
    210                 215                 220

Tyr Asp Tyr Gln Met Glu Thr Gln Arg Asp Ser Arg Asn Ala Ala Asn
225                 230                 235                 240

Val Ala His Thr Met Lys Ser Ile Ser Glu Tyr Pro Val Ala Glu Arg
                245                 250                 255

Val Met Leu Leu Leu Thr Thr Lys Ala Gly Ala Asn Ala Met Arg Ser
            260                 265                 270

Ala Ala Leu Ser Gly Leu Ser Tyr Val Leu Pro Thr Ser Ile Phe Ala
        275                 280                 285

Leu Lys Phe Leu Glu Trp Trp Tyr Ala Ser Asp Phe Ala Arg Gln Leu
    290                 295                 300

Asn Gln Lys Arg Arg Gly Asp Leu Glu Asp Asn Leu Pro Val Pro Asp
```

305 310 315 320

Lys Val Lys Gly Ala Asp Lys Leu Ala Glu Ser Val Ala Lys Trp Lys
325 330 335

Glu Asp Thr Ser Lys Cys Pro Leu Cys Ser Lys Glu Leu Val Asn Pro
340 345 350

Thr Val Ile Glu Ser Gly Tyr Val Phe Cys Tyr Thr Cys Ile Tyr Arg
355 360 365

His Leu Glu Asp Gly Asp Glu Glu Thr Gly Gly Arg Cys Pro Val Thr
370 375 380

Gly Gln Lys Leu Leu Gly Cys Arg Trp Gln Asp Asp Val Trp Gln Val
385 390 395 400

Thr Gly Leu Arg Arg Leu Met Val
405

<210> SEQ ID NO 12
<211> LENGTH: 412
<212> TYPE: PRT
<213> ORGANISM: Yarrowia lipolytica
<220> FEATURE:
<221> NAME/KEY: MISC_FEATURE
<222> LOCATION: (1)..(412)
<223> OTHER INFORMATION: YlPex13p; GenBank Accession No. CAG81789

<400> SEQUENCE: 12

Met Ser Val Pro Arg Pro Lys Pro Trp Glu Gly Ala Ser Gly Ser Ser
1 5 10 15

Ala Ala Thr Ala Thr Pro Ala Ala Thr Ala Thr Pro Ala Ser Thr Asp
20 25 30

Ala Val Ser Ser Ser Ala Gly Ser Ala Thr Gly Ala Pro Glu Leu Pro
35 40 45

Ser Arg Pro Ser Ala Met Gly Ser Thr Ser Asn Ala Leu Ser Ser Pro
50 55 60

Met Gly Ser Ser Met Asn Ser Gly Tyr Gly Gly Met Asn Ser Gly Tyr
65 70 75 80

Gly Gly Met Gly Ser Ser Tyr Gly Ser Gly Tyr Gly Ser Ser Tyr Gly
85 90 95

Met Gly Ser Ser Tyr Gly Ser Gly Tyr Gly Ser Gly Leu Gly Gly Tyr
100 105 110

Gly Ser Tyr Gly Gly Met Gly Gly Met Gly Gly Met Tyr Gly Ser Arg
115 120 125

Tyr Gly Gly Tyr Gly Ser Tyr Gly Gly Met Gly Gly Tyr Gly Gly Tyr
130 135 140

Gly Gly Met Gly Gly Gly Pro Met Gly Gln Asn Gly Leu Ala Gly Gly
145 150 155 160

Thr Gln Ala Thr Phe Gln Leu Ile Glu Ser Ile Val Gly Ala Val Gly
165 170 175

Gly Phe Ala Gln Met Leu Glu Ser Thr Tyr Met Ala Thr Gln Ser Ser
180 185 190

Phe Phe Ala Met Val Ser Val Ala Glu Gln Phe Gly Asn Leu Lys Asn
195 200 205

Thr Leu Gly Ser Leu Leu Gly Ile Tyr Ala Ile Met Arg Trp Ala Arg
210 215 220

Arg Leu Val Ala Lys Leu Ser Gly Gln Pro Val Thr Gly Ala Asn Gly
225 230 235 240

Ile Thr Pro Ala Gly Phe Ala Lys Phe Glu Ala Thr Gly Gly Ala Ala
245 250 255

```
Gly Pro Gly Arg Gly Pro Arg Pro Ser Tyr Lys Pro Leu Leu Phe Phe
            260                 265                 270

Leu Thr Ala Val Phe Gly Leu Pro Tyr Leu Leu Gly Arg Leu Ile Lys
        275                 280                 285

Ala Leu Ala Ala Lys Gln Glu Gly Met Tyr Asp Glu His Gly Asn Leu
    290                 295                 300

Leu Pro Gly Ala Gln Met Gly Met Gly Gly Pro Gly Met Glu Gly Gly
305                 310                 315                 320

Ala Glu Ile Asp Pro Ser Lys Leu Glu Phe Cys Arg Ala Asn Phe Asp
                325                 330                 335

Phe Val Pro Glu Asn Pro Gln Leu Glu Leu Glu Leu Arg Lys Gly Asp
            340                 345                 350

Leu Val Ala Val Leu Ala Lys Thr Asp Pro Met Gly Asn Pro Ser Gln
        355                 360                 365

Trp Trp Arg Val Arg Thr Arg Asp Gly Arg Ser Gly Tyr Val Pro Ala
    370                 375                 380

Asn Tyr Leu Glu Val Ile Pro Arg Pro Ala Val Glu Ala Pro Lys Lys
385                 390                 395                 400

Val Glu Glu Ile Gly Ala Ser Ala Val Pro Val Asn
                405                 410


<210> SEQ ID NO 13
<211> LENGTH: 380
<212> TYPE: PRT
<213> ORGANISM: Yarrowia lipolytica
<220> FEATURE:
<221> NAME/KEY: MISC_FEATURE
<222> LOCATION: (1)..(380)
<223> OTHER INFORMATION: YlPex14p; GenBank Accession No. CAG79323

<400> SEQUENCE: 13

Met Ile Pro Ser Cys Leu Ser Thr Gln His Met Ala Pro Arg Glu Asp
1               5                   10                  15

Leu Val Gln Ser Ala Val Ala Phe Leu Asn Asp Pro Gln Ala Ala Thr
            20                  25                  30

Ala Pro Leu Ala Lys Arg Ile Glu Phe Leu Glu Ser Lys Asp Met Thr
        35                  40                  45

Pro Glu Glu Ile Glu Glu Ala Leu Lys Arg Ala Gly Ser Gly Ser Ala
    50                  55                  60

Gln Ser His Pro Gly Ser Val Val Ser His Gly Gly Ala Ala Pro Thr
65                  70                  75                  80

Val Pro Ala Ser Tyr Ala Phe Gln Ser Ala Pro Pro Leu Pro Glu Arg
                85                  90                  95

Asp Trp Lys Asp Val Phe Ile Met Ala Thr Val Thr Val Gly Val Gly
            100                 105                 110

Phe Gly Leu Tyr Thr Val Ala Lys Arg Tyr Leu Met Pro Leu Ile Leu
        115                 120                 125

Pro Pro Thr Pro Pro Ser Leu Glu Ala Asp Lys Glu Ala Leu Glu Ala
    130                 135                 140

Glu Phe Ala Arg Val Gln Gly Leu Leu Asp Gln Val Gln Gln Asp Thr
145                 150                 155                 160

Glu Glu Val Lys Asn Ser Gln Val Glu Val Ala Lys Arg Val Thr Asp
                165                 170                 175

Ala Leu Lys Gly Val Glu Glu Thr Ile Asp Gln Leu Lys Ser Gln Thr
            180                 185                 190
```

```
Lys Lys Arg Asp Asp Glu Met Lys Leu Val Thr Ala Glu Val Glu Arg
        195                 200                 205

Ile Arg Asp Arg Leu Pro Lys Asn Ile Asp Lys Leu Lys Asp Ser Gln
    210                 215                 220

Glu Gln Gly Leu Ala Asp Ile Gln Ser Glu Leu Lys Ser Leu Lys Gln
225                 230                 235                 240

Leu Leu Ser Thr Arg Thr Ala Ala Ser Ser Gly Pro Lys Leu Pro Pro
                245                 250                 255

Ile Pro Pro Pro Ser Ser Tyr Leu Thr Arg Lys Ala Ser Pro Ala Val
            260                 265                 270

Pro Ala Ala Ala Pro Ala Pro Val Thr Pro Gly Ser Pro Val His Asn
        275                 280                 285

Val Ser Ser Ser Ser Thr Val Pro Ala Asp Arg Asp Asp Phe Ile Pro
    290                 295                 300

Thr Pro Ala Gly Ala Val Pro Met Ile Pro Gln Pro Ala Ser Met Ser
305                 310                 315                 320

Ser Ser Ser Thr Ser Thr Val Pro Asn Ser Ala Ile Ser Ser Ala Pro
                325                 330                 335

Ser Pro Ile Gln Glu Pro Glu Pro Phe Val Pro Glu Pro Gly Asn Ser
            340                 345                 350

Ala Val Lys Lys Pro Ala Pro Lys Ala Ser Ile Pro Ala Trp Gln Leu
        355                 360                 365

Ala Ala Leu Glu Lys Glu Lys Glu Lys Glu Lys Glu
    370                 375                 380


<210> SEQ ID NO 14
<211> LENGTH: 391
<212> TYPE: PRT
<213> ORGANISM: Yarrowia lipolytica
<220> FEATURE:
<221> NAME/KEY: MISC_FEATURE
<222> LOCATION: (1)..(391)
<223> OTHER INFORMATION: YlPex16p; GenBank Accession No. CAG79622

<400> SEQUENCE: 14

Met Thr Asp Lys Leu Val Lys Val Met Gln Lys Lys Lys Ser Ala Pro
1               5                   10                  15

Gln Thr Trp Leu Asp Ser Tyr Asp Lys Phe Leu Val Arg Asn Ala Ala
            20                  25                  30

Ser Ile Gly Ser Ile Glu Ser Thr Leu Arg Thr Val Ser Tyr Val Leu
        35                  40                  45

Pro Gly Arg Phe Asn Asp Val Glu Ile Ala Thr Glu Thr Leu Tyr Ala
    50                  55                  60

Val Leu Asn Val Leu Gly Leu Tyr His Asp Thr Ile Ile Ala Arg Ala
65                  70                  75                  80

Val Ala Ala Ser Pro Asn Ala Ala Ala Val Tyr Arg Pro Ser Pro His
                85                  90                  95

Asn Arg Tyr Thr Asp Trp Phe Ile Lys Asn Arg Lys Gly Tyr Lys Tyr
            100                 105                 110

Ala Ser Arg Ala Val Thr Phe Val Lys Phe Gly Glu Leu Val Ala Glu
        115                 120                 125

Met Val Ala Lys Lys Asn Gly Gly Glu Met Ala Arg Trp Lys Cys Ile
    130                 135                 140

Ile Gly Ile Glu Gly Ile Lys Ala Gly Leu Arg Ile Tyr Met Leu Gly
145                 150                 155                 160

Ser Thr Leu Tyr Gln Pro Leu Cys Thr Thr Pro Tyr Pro Asp Arg Glu
```

```
                165                 170                 175

Val Thr Gly Glu Leu Leu Glu Thr Ile Cys Arg Asp Glu Gly Glu Leu
            180                 185                 190

Asp Ile Glu Lys Gly Leu Met Asp Pro Gln Trp Lys Met Pro Arg Thr
        195                 200                 205

Gly Arg Thr Ile Pro Glu Ile Ala Pro Thr Asn Val Glu Gly Tyr Leu
    210                 215                 220

Leu Thr Lys Val Leu Arg Ser Glu Asp Val Asp Arg Pro Tyr Asn Leu
225                 230                 235                 240

Leu Ser Arg Leu Asp Asn Trp Gly Val Val Ala Glu Leu Leu Ser Ile
                245                 250                 255

Leu Arg Pro Leu Ile Tyr Ala Cys Leu Leu Phe Arg Gln His Val Asn
            260                 265                 270

Lys Thr Val Pro Ala Ser Thr Lys Ser Lys Phe Pro Phe Leu Asn Ser
        275                 280                 285

Pro Trp Ala Pro Trp Ile Ile Gly Leu Val Ile Glu Ala Leu Ser Arg
    290                 295                 300

Lys Met Met Gly Ser Trp Leu Leu Arg Gln Arg Gln Ser Gly Lys Thr
305                 310                 315                 320

Pro Thr Ala Leu Asp Gln Met Glu Val Lys Gly Arg Thr Asn Leu Leu
                325                 330                 335

Gly Trp Trp Leu Phe Arg Gly Glu Phe Tyr Gln Ala Tyr Thr Arg Pro
            340                 345                 350

Leu Leu Tyr Ser Ile Val Ala Arg Leu Glu Lys Ile Pro Gly Leu Gly
        355                 360                 365

Leu Phe Gly Ala Leu Ile Ser Asp Tyr Leu Tyr Leu Phe Asp Arg Tyr
    370                 375                 380

Tyr Phe Thr Ala Ser Thr Leu
385                 390


<210> SEQ ID NO 15
<211> LENGTH: 225
<212> TYPE: PRT
<213> ORGANISM: Yarrowia lipolytica
<220> FEATURE:
<221> NAME/KEY: MISC_FEATURE
<222> LOCATION: (1)..(225)
<223> OTHER INFORMATION: YlPex17p; GenBank Accession No. CAG84025

<400> SEQUENCE: 15

Met Ser Ala Phe Pro Glu Pro Ser Ser Phe Glu Ile Glu Phe Ala Lys
1               5                   10                  15

Gln Met Asn Arg Pro Arg Thr Val Gln Phe Lys Gln Leu Val Ala Val
            20                  25                  30

Leu Tyr Ile Phe Gly Gly Thr Ser Ala Leu Ile Tyr Ile Ile Ser Lys
        35                  40                  45

Thr Ile Leu Asn Pro Leu Phe Glu Glu Leu Thr Phe Ala Arg Ser Glu
    50                  55                  60

Tyr Ala Ile His Ala Arg Arg Leu Met Glu Gln Leu Asn Ala Lys Leu
65                  70                  75                  80

Ser Ser Met Ala Ser Tyr Ile Pro Pro Val Arg Ala Leu Gln Gly Gln
                85                  90                  95

Arg Phe Val Asp Ala Gln Thr Gln Thr Glu Asp Glu Glu Gly Glu Asp
            100                 105                 110

Ile Pro Asn Pro Ser Leu Gly Lys Ser Ser His Val Ser Phe Gly Glu
        115                 120                 125
```

```
Ser Pro Met Gln Leu Lys Leu Ala Glu Lys Glu Lys Gln Gln Lys Leu
    130                 135                 140

Ile Asp Asp Ser Val Asp Asn Leu Glu Arg Leu Ala Asp Ser Leu Lys
145                 150                 155                 160

His Ala Gly Glu Val Ser Asp Leu Ser Ala Leu Ser Gly Phe Lys Tyr
                165                 170                 175

Gln Val Glu Glu Leu Thr Asn Tyr Ser Asp Gln Leu Ala Met Ser Gly
            180                 185                 190

Tyr Ser Met Met Lys Ser Gly Leu Pro Gly His Glu Thr Ala Met Ser
        195                 200                 205

Glu Thr Lys Lys Glu Ile Arg Ser Leu Lys Gly Ser Val Leu Ser Val
    210                 215                 220

Arg
225


<210> SEQ ID NO 16
<211> LENGTH: 324
<212> TYPE: PRT
<213> ORGANISM: Yarrowia lipolytica
<220> FEATURE:
<221> NAME/KEY: MISC_FEATURE
<222> LOCATION: (1)..(324)
<223> OTHER INFORMATION: YlPex19p; GenBank Accession No. AAK84827

<400> SEQUENCE: 16

Met Ser His Glu Glu Asp Leu Asp Asp Leu Asp Asp Phe Leu Asp Glu
1               5                   10                  15

Phe Asp Glu Gln Val Leu Ser Lys Pro Pro Gly Ala Gln Lys Asp Ala
            20                  25                  30

Thr Pro Thr Thr Ser Thr Ala Pro Thr Thr Ala Glu Ala Lys Pro Asp
        35                  40                  45

Ala Thr Lys Lys Ser Thr Glu Thr Ser Gly Thr Asp Ser Lys Thr Glu
    50                  55                  60

Gly Ala Asp Thr Ala Asp Lys Asn Ala Ala Thr Asp Ser Ala Glu Ala
65                  70                  75                  80

Gly Ala Glu Lys Val Ser Leu Pro Asn Leu Glu Asp Gln Leu Ala Gly
                85                  90                  95

Leu Lys Met Asp Asp Phe Leu Lys Asp Ile Glu Ala Asp Pro Glu Ser
            100                 105                 110

Lys Ala Gln Phe Glu Ser Leu Leu Lys Glu Ile Asn Asn Val Thr Ser
        115                 120                 125

Ala Thr Ala Ser Glu Lys Ala Gln Gln Pro Lys Ser Phe Lys Glu Thr
    130                 135                 140

Ile Ser Ala Thr Ala Asp Arg Leu Asn Gln Ser Asn Gln Glu Met Gly
145                 150                 155                 160

Asp Met Pro Leu Gly Asp Asp Met Leu Ala Gly Leu Met Glu Gln Leu
                165                 170                 175

Ser Gly Ala Gly Gly Phe Gly Glu Gly Gly Glu Gly Asp Phe Gly Asp
            180                 185                 190

Met Leu Gly Gly Ile Met Arg Gln Leu Ala Ser Lys Glu Val Leu Tyr
        195                 200                 205

Gln Pro Leu Lys Glu Met His Asp Asn Tyr Pro Lys Trp Trp Asp Glu
    210                 215                 220

His Gly Ser Lys Val Thr Glu Glu Lys Glu Arg Asp Arg Leu Lys Leu
225                 230                 235                 240
```

Gln Gln Asp Ile Val Gly Lys Ile Cys Ala Lys Phe Glu Asp Pro Ser
245 250 255

Tyr Ser Asp Asp Ser Glu Ala Asp Arg Ala Val Ile Thr Gln Leu Met
260 265 270

Asp Glu Met Gln Glu Thr Gly Ala Pro Pro Asp Glu Ile Met Ser Asn
275 280 285

Val Ala Asp Gly Ser Ile Pro Gly Gly Leu Asp Gly Leu Gly Leu Gly
290 295 300

Gly Leu Gly Gly Gly Lys Met Pro Glu Met Pro Glu Asn Met Pro Glu
305 310 315 320

Cys Asn Gln Gln

<210> SEQ ID NO 17
<211> LENGTH: 417
<212> TYPE: PRT
<213> ORGANISM: Yarrowia lipolytica
<220> FEATURE:
<221> NAME/KEY: MISC_FEATURE
<222> LOCATION: (1)..(417)
<223> OTHER INFORMATION: YlPex20p; GenBank Accession No. CAG79226

<400> SEQUENCE: 17

Met Ala Ser Cys Gly Pro Ser Asn Ala Leu Gln Asn Leu Ser Lys His
1 5 10 15

Ala Ser Ala Asp Arg Ser Leu Gln His Asp Arg Met Ala Pro Gly Gly
20 25 30

Ala Pro Gly Ala Gln Arg Gln Gln Phe Arg Ser Gln Thr Gln Gly Gly
35 40 45

Gln Leu Asn Asn Glu Phe Gln Gln Phe Ala Gln Ala Gly Pro Ala His
50 55 60

Asn Ser Phe Glu Gln Ser Gln Met Gly Pro His Phe Gly Gln Gln His
65 70 75 80

Phe Gly Gln Pro His Gln Pro Gln Met Gly Gln His Ala Pro Met Ala
85 90 95

His Gly Gln Gln Ser Asp Trp Ala Gln Ser Phe Ser Gln Leu Asn Leu
100 105 110

Gly Pro Gln Thr Gly Pro Gln His Thr Gln Gln Ser Asn Trp Gly Gln
115 120 125

Asp Phe Met Arg Gln Ser Pro Gln Ser His Gln Val Gln Pro Gln Met
130 135 140

Ala Asn Gly Val Met Gly Ser Met Ser Gly Met Ser Ser Phe Gly Pro
145 150 155 160

Met Tyr Ser Asn Ser Gln Leu Met Asn Ser Thr Tyr Gly Leu Gln Thr
165 170 175

Glu His Gln Gln Thr His Lys Thr Glu Thr Lys Ser Ser Gln Asp Ala
180 185 190

Ala Phe Glu Ala Ala Phe Gly Ala Val Glu Glu Ser Ile Thr Lys Thr
195 200 205

Ser Asp Lys Gly Lys Glu Val Glu Lys Asp Pro Met Glu Gln Thr Tyr
210 215 220

Arg Tyr Asp Gln Ala Asp Ala Leu Asn Arg Gln Ala Glu His Ile Ser
225 230 235 240

Asp Asn Ile Ser Arg Glu Glu Val Asp Ile Lys Thr Asp Glu Asn Gly
245 250 255

Glu Phe Ala Ser Ile Ala Arg Gln Ile Ala Ser Ser Leu Glu Glu Ala
260 265 270

```
Asp Lys Ser Lys Phe Glu Lys Ser Thr Phe Met Asn Leu Met Arg Arg
        275                 280                 285

Ile Gly Asn His Glu Val Thr Leu Asp Gly Asp Lys Leu Val Asn Lys
    290                 295                 300

Glu Gly Glu Asp Ile Arg Glu Glu Val Arg Asp Glu Leu Leu Arg Glu
305                 310                 315                 320

Gly Ala Ser Gln Glu Asn Gly Phe Gln Ser Glu Ala Gln Gln Thr Ala
                325                 330                 335

Pro Leu Pro Val His His Glu Ala Pro Pro Pro Glu Gln Ile His Pro
            340                 345                 350

His Thr Glu Thr Gly Asp Lys Gln Leu Glu Asp Pro Met Val Tyr Ile
        355                 360                 365

Glu Gln Glu Ala Ala Arg Arg Ala Ala Glu Ser Gly Arg Thr Val Glu
    370                 375                 380

Glu Glu Lys Leu Asn Phe Tyr Ser Pro Phe Glu Tyr Ala Gln Lys Leu
385                 390                 395                 400

Gly Pro Gln Gly Val Ala Lys Gln Ser Asn Trp Glu Glu Asp Tyr Asp
                405                 410                 415

Phe


<210> SEQ ID NO 18
<211> LENGTH: 195
<212> TYPE: PRT
<213> ORGANISM: Yarrowia lipolytica
<220> FEATURE:
<221> NAME/KEY: MISC_FEATURE
<222> LOCATION: (1)..(195)
<223> OTHER INFORMATION: YlPex22p; GenBank Accession No. CAG77876

<400> SEQUENCE: 18

Val Pro Arg Cys Thr Ser His Pro Cys Asn Leu Thr Leu His Leu Pro
1               5                   10                  15

Val Thr Thr Met Ala Pro Arg Lys Thr Arg Leu Pro Ala Val Ile Gly
            20                  25                  30

Ala Ala Ala Ala Ala Ala Ala Val Ala Tyr Leu Val Tyr Ser Phe Val
        35                  40                  45

Ala Lys Ser Asn Ser Asp Gln Asp Thr Phe Asp Ser Ser Val Gln Ser
    50                  55                  60

Ser Ser Lys Ser Ser Thr Lys Ser Pro Lys Ser Thr Ala Thr Asn Ser
65                  70                  75                  80

Lys Ile Thr Val Val Val Ser Gln Glu Leu Val Gln Ser Gln Leu Val
                85                  90                  95

Asp Phe Lys His Leu Met Ser Val His Pro Asn Leu Val Val Ile Val
            100                 105                 110

Pro Pro Met Val Ala Asn Lys Phe His Arg Ala Leu Lys Ser Ser Val
        115                 120                 125

Gly His Asp His Gly Val Lys Val Ile Arg Cys Asp Thr Asp Val Gly
    130                 135                 140

Val Ile His Val Ile Lys His Ile Arg Pro Asp Leu Ala Leu Ile Ala
145                 150                 155                 160

Asp Gly Val Gly Asp Asn Ile Gln Gly Glu Ile Lys Arg Phe Val Gly
                165                 170                 175

Ser Ser Glu Ala Leu Ser Gly Asp Val Asn Leu Ala Ala Glu Arg Leu
            180                 185                 190

Thr Gly Leu
```

195

<210> SEQ ID NO 19
<211> LENGTH: 386
<212> TYPE: PRT
<213> ORGANISM: Yarrowia lipolytica
<220> FEATURE:
<221> NAME/KEY: MISC_FEATURE
<222> LOCATION: (1)..(386)
<223> OTHER INFORMATION: YlPex26p

<400> SEQUENCE: 19

```
Met Pro Pro Ala Met Pro Gln Met Thr Thr Ser Thr Leu Leu Thr Asp
1               5                   10                  15

Ser Val Thr Ser Ala Val Asn Gln Ala Ala Thr Pro Lys Val Asp Gln
            20                  25                  30

Met Tyr Gln Thr Phe Gly Glu Ser Ala Arg Glu Phe Val Asn Lys Asn
        35                  40                  45

Phe Tyr Asn Ser Tyr Glu Leu Ile Arg Pro Phe Phe Asp Glu Ile Thr
    50                  55                  60

Ala Lys Gly Ala Gln Gln Asn Gly Ser Thr Val Leu Asp Ala Glu Asn
65                  70                  75                  80

Pro His Asn Ile Pro Leu Ser Leu Trp Ile Lys Val Trp Ser Leu Tyr
                85                  90                  95

Leu Ala Ile Leu Asp Ala Ser Cys Lys Gln Ala Gly Glu Ala Leu Leu
            100                 105                 110

Asn Ser Thr Gly Asp Leu Ser Gly Ser Asp Ser Gly Glu Trp Asn Gln
        115                 120                 125

Thr Arg Lys Leu Leu Ala Arg Lys Leu Thr Ser Gly Ser Val Trp Asp
    130                 135                 140

Glu Leu Val Thr Ala Ser Gly Gly Thr Gly Asn Ile His Pro Thr Ile
145                 150                 155                 160

Leu Ala Leu Leu Ala Ser Leu Ser Ile Arg His Asp Thr Asp Ala Lys
                165                 170                 175

Leu Met Ala Asp Asn Leu Glu Lys Phe Ile Val Thr Tyr Asn Asp Asn
            180                 185                 190

Gly Ser Asp Asp Val Lys Thr Lys Thr Ala Phe Tyr Lys Val Leu Asp
        195                 200                 205

Leu Tyr Leu Leu Arg Val Leu Pro Asp Leu Gly Gln Trp Asp Val Ala
    210                 215                 220

His Ser Phe Val Asn Asn Thr Asn Leu Phe Ser His Glu Gln Lys Lys
225                 230                 235                 240

Glu Met Thr His Lys Leu Asp Gln Ser Gln Lys His Ala Glu Gln Glu
                245                 250                 255

His Lys Arg Leu Leu Glu Glu Ala Gln Glu Lys Glu Lys Ser Asp Ala
            260                 265                 270

Lys Glu Lys Glu Arg Glu Glu Arg Val Ser Arg Asp Thr Gln Ser Arg
        275                 280                 285

Glu Ile Lys Ser Pro Ile Val Asp Ser Ser Thr Ser Ser Arg Asp Val
    290                 295                 300

Thr Arg Asp Thr Thr Arg Glu Leu Ser Lys Ser Ser Arg Gln Pro Arg
305                 310                 315                 320

Thr Leu Ser Gln Ile Ile Ser Thr Ser Leu Lys Ser Gln Phe Asp Gly
                325                 330                 335

Asn Ala Ile Phe Arg Thr Leu Ala Leu Ile Val Ile Val Ser Leu Ser
            340                 345                 350
```

```
Ala Ala Asn Pro Leu Ile Arg Lys Arg Val Val Asp Thr Leu Lys Met
        355                 360                 365

Leu Trp Ile Lys Ile Leu Gln Thr Leu Ser Met Gly Phe Lys Val Ser
    370                 375                 380

Tyr Leu
385


<210> SEQ ID NO 20
<211> LENGTH: 3387
<212> TYPE: DNA
<213> ORGANISM: Yarrowia lipolytica
<220> FEATURE:
<221> NAME/KEY: misc_feature
<222> LOCATION: (1)..(3387)
<223> OTHER INFORMATION: GenBank Accession No. AB036770

<400> SEQUENCE: 20

ggtaccatca agggtaaaat caaggctatc atcaagggcc atatatcgca agtttggggg     60

aagataatat gttcatagtg aatcgggttg tggatttcct catctaacgg cattataact    120

agtcctggag ggtctttttt atggataacc tccatgtacg atgtatccaa gatctccacg    180

tactgtgttc tgtttcctaa gtaataccca acaacctctc caacaaacac ttgggaagat    240

gcacttgtgc tgagatgtca agatgttaga gagtagagac agtagcaagc gtaaaaggcg    300

gccgaggcca ccgagagaac agcgtagcag ggcgcgtagt caccacaggg gacgcagaac    360

caaacaaatg acgaagaaga accacaagga gacgttttca aaggcaatgc aaacgaagag    420

ggcaatggaa ggattgagat tagagaactg gagactggag tggcgttttc ccgatgaacg    480

aacaaacacg cgaagctatg tggaccaaca tacaacacgg actgaaccag gttttttat     540

gatttttttta ctggaaatag gtacgtgcca agttggacca tgacactaaa cgtgtttaat    600

tagtaatatt cgtgtaagcg tacattcatt tcaaaggtta ttctttcacg gcaaagttat    660

aattaaatga atgtatatgc agaaaaaaaa aaaaaaagta ctgtactgga tggagagaat    720

attaataaat aattgttacc caactacatc ttgtcgattg aaagagaccc ctaagacaga    780

taggatatct gcaacccgag gaatgaaccc cccagcaccg gcaccctttc tattaacaaa    840

atgccaactg aaatttgaaa agttcaacta aacttatttg acccacaaaa actcgtcaaa    900

agtggcggcg aaagctggca aatgatgaca tcccccttgga accatgatat cctctcggaa    960

tcttcgtccc catttgccac atctacttgc aacgccacat ctgcttacta agcaacccaa   1020

atctgcctcg gctcaaaatg tggggaagtt cacatgcatt cgctggtgaa tctgatctga   1080

cactacaact acacaccagg tccaacatga gcgacaatac gacaatcaaa aagccgatcc   1140

gacccaaacc gatccggacg gaacgcctgc cttacgctgg ggccgcagaa atcatccgag   1200

ccaaccagaa agaccactac tttgagtccg tgcttgaaca gcatctcgtc acgtttctgc   1260

agaaatggaa gggagtacga tttatccacc agtacaagga ggagctggag acggcgtcca   1320

agtttgcata tctcggtttg tgtacgcttg tgggctccaa gactctcgga gaagagtaca   1380

ccaatctcat gtacactatc agagaccgaa cagctctacc gggggtggtg agacggtttg   1440

gctacgtgct ttccaacact ctgtttccat acctgtttgt gcgctacatg ggcaagttgc   1500

gcgccaaact gatgcgcgag tatccccatc tggtggagta cgacgaagat gagcctgtgc   1560

ccagcccgga aacatggaag gagcgggtca tcaagacgtt tgtgaacaag tttgacaagt   1620

tcacggcgct ggaggggttt accgcgatcc acttggcgat tttctacgtc tacggctcgt   1680

actaccagct cagtaagcgg atctggggca tgcgttatgt atttggacac cgactggaca   1740
```

agaatgagcc tcgaatcggt tacgagatgc tcggtctgct gattttcgcc cggtttgcca 1800
cgtcatttgt gcagacggga agagagtacc tcggagcgct gctggaaaag agcgtggaga 1860
aagaggcagg ggagaaggaa gatgaaaagg aagcggttgt gccgaaaaag aagtcgtcaa 1920
ttccgttcat tgaggataca gaaggggaga cggaagacaa gatcgatctg gaggaccctc 1980
gacagctcaa gttcattcct gaggcgtcca gagcgtgcac tctgtgtctg tcatacatta 2040
gtgcgccggc atgtacgcca tgtggacact ttttctgttg ggactgtatt tccgaatggg 2100
tgagagagaa gcccgagtgt cccttgtgtc ggcagggtgt gagagagcag aacttgttgc 2160
ctatcagata atgacgaggt ctggatggaa ggactagtca gcgagacaca gagcatcagg 2220
gaccagacac gaccaattca atcgacaaca ctgtgctgca tagcagtgca cagaggtcct 2280
gggcatgaat atattttagc attggagata tgagtggtag agcgtataca gtattaattg 2340
tggaggtatc tcgtcgcatt gatagagcaa tacagttact gctgaaggga atgataccga 2400
gtatttcggc ccgattcagt tcttgatatc gtcattttgt ctctattgtc tacttttcag 2460
ataacctcaa caaatcttca acaaatctcc cagtaaacag tcagagatca tatccgagat 2520
catatcagat atgtcacgat ccgagtacaa taatggatat taatctgctt gatttgaat 2580 tctgttgcga ttatgatttc tttgatttcg atatgaacac atacggcgac tcccagacct 2640
ttagaagctc cagtttggat tcttagcaat ggttacactc aactatatcc caagtaatac 2700
ttggtaacaa tatgccaagt tagtcattca ttcgttatag gagttagcaa gtgtttgtca 2760
gctaaaaatg gttagtcggt cgattaccac ttagatcttt tcagcgtgga acttgatggt 2820
acgcttgaac cgacacttgg agtagtcggg gctgttgatg acgtagatga cgtttcgctc 2880
agggtgagga gtgcaatagt agtactcctt ggggccgtct ctcagctcaa aggttccatc 2940
ggcggcaatg tcaaagaccg agccctggag cttgtagccg tagtcgccgg tccagaacaa 3000
agcctgcagc tccagatagg cgatgggcat gtcgttaaca gagaaggtgt tgccctcgcc 3060
ctcggtgatg gtgatgggtt cgccgtcggt ggaggcggtg atcaggtcat cttggtaggt 3120
gacgggcaga gattcgaccg attgggcgtc tgatctggta taggtcagct tgtacttgtc 3180
tccgacagcc gccagagcgg tggtagcgac ggtgatgagg gagatgagtt tcatattggc 3240
ggcaagttta gcaaaagatg gcagtgggat tgagggacaa gagtgtttat atagatatag 3300
atacaacaca acgagtctga atgagacaac cgagacaacc actcccgaag cctcactaat 3360
agttactaac ggcatatttc aggtacc 3387

<210> SEQ ID NO 21
<211> LENGTH: 1134
<212> TYPE: DNA
<213> ORGANISM: Yarrowia lipolytica
<220> FEATURE:
<221> NAME/KEY: CDS
<222> LOCATION: (1)..(1134)
<223> OTHER INFORMATION: Pex10

<400> SEQUENCE: 21

```
atg tgg gga agt tca cat gca ttc gct ggt gaa tct gat ctg aca cta       48
Met Trp Gly Ser Ser His Ala Phe Ala Gly Glu Ser Asp Leu Thr Leu
1               5                   10                  15

caa cta cac acc agg tcc aac atg agc gac aat acg aca atc aaa aag       96
Gln Leu His Thr Arg Ser Asn Met Ser Asp Asn Thr Thr Ile Lys Lys
            20                  25                  30

ccg atc cga ccc aaa ccg atc cgg acg gaa cgc ctg cct tac gct ggg      144
Pro Ile Arg Pro Lys Pro Ile Arg Thr Glu Arg Leu Pro Tyr Ala Gly
```

```
        35                  40                  45

gcc gca gaa atc atc cga gcc aac cag aaa gac cac tac ttt gag tcc      192
Ala Ala Glu Ile Ile Arg Ala Asn Gln Lys Asp His Tyr Phe Glu Ser
    50                  55                  60

gtg ctt gaa cag cat ctc gtc acg ttt ctg cag aaa tgg aag gga gta      240
Val Leu Glu Gln His Leu Val Thr Phe Leu Gln Lys Trp Lys Gly Val
65                  70                  75                  80

cga ttt atc cac cag tac aag gag gag ctg gag acg gcg tcc aag ttt      288
Arg Phe Ile His Gln Tyr Lys Glu Glu Leu Glu Thr Ala Ser Lys Phe
                85                  90                  95

gca tat ctc ggt ttg tgt acg ctt gtg ggc tcc aag act ctc gga gaa      336
Ala Tyr Leu Gly Leu Cys Thr Leu Val Gly Ser Lys Thr Leu Gly Glu
            100                 105                 110

gag tac acc aat ctc atg tac act atc aga gac cga aca gct cta ccg      384
Glu Tyr Thr Asn Leu Met Tyr Thr Ile Arg Asp Arg Thr Ala Leu Pro
        115                 120                 125

ggg gtg gtg aga cgg ttt ggc tac gtg ctt tcc aac act ctg ttt cca      432
Gly Val Val Arg Arg Phe Gly Tyr Val Leu Ser Asn Thr Leu Phe Pro
    130                 135                 140

tac ctg ttt gtg cgc tac atg ggc aag ttg cgc gcc aaa ctg atg cgc      480
Tyr Leu Phe Val Arg Tyr Met Gly Lys Leu Arg Ala Lys Leu Met Arg
145                 150                 155                 160

gag tat ccc cat ctg gtg gag tac gac gaa gat gag cct gtg ccc agc      528
Glu Tyr Pro His Leu Val Glu Tyr Asp Glu Asp Glu Pro Val Pro Ser
                165                 170                 175

ccg gaa aca tgg aag gag cgg gtc atc aag acg ttt gtg aac aag ttt      576
Pro Glu Thr Trp Lys Glu Arg Val Ile Lys Thr Phe Val Asn Lys Phe
            180                 185                 190

gac aag ttc acg gcg ctg gag ggg ttt acc gcg atc cac ttg gcg att      624
Asp Lys Phe Thr Ala Leu Glu Gly Phe Thr Ala Ile His Leu Ala Ile
        195                 200                 205

ttc tac gtc tac ggc tcg tac tac cag ctc agt aag cgg atc tgg ggc      672
Phe Tyr Val Tyr Gly Ser Tyr Tyr Gln Leu Ser Lys Arg Ile Trp Gly
    210                 215                 220

atg cgt tat gta ttt gga cac cga ctg gac aag aat gag cct cga atc      720
Met Arg Tyr Val Phe Gly His Arg Leu Asp Lys Asn Glu Pro Arg Ile
225                 230                 235                 240

ggt tac gag atg ctc ggt ctg ctg att ttc gcc cgg ttt gcc acg tca      768
Gly Tyr Glu Met Leu Gly Leu Leu Ile Phe Ala Arg Phe Ala Thr Ser
                245                 250                 255

ttt gtg cag acg gga aga gag tac ctc gga gcg ctg ctg gaa aag agc      816
Phe Val Gln Thr Gly Arg Glu Tyr Leu Gly Ala Leu Leu Glu Lys Ser
            260                 265                 270

gtg gag aaa gag gca ggg gag aag gaa gat gaa aag gaa gcg gtt gtg      864
Val Glu Lys Glu Ala Gly Glu Lys Glu Asp Glu Lys Glu Ala Val Val
        275                 280                 285

ccg aaa aag aag tcg tca att ccg ttc att gag gat aca gaa ggg gag      912
Pro Lys Lys Lys Ser Ser Ile Pro Phe Ile Glu Asp Thr Glu Gly Glu
    290                 295                 300

acg gaa gac aag atc gat ctg gag gac cct cga cag ctc aag ttc att      960
Thr Glu Asp Lys Ile Asp Leu Glu Asp Pro Arg Gln Leu Lys Phe Ile
305                 310                 315                 320

cct gag gcg tcc aga gcg tgc act ctg tgt ctg tca tac att agt gcg     1008
Pro Glu Ala Ser Arg Ala Cys Thr Leu Cys Leu Ser Tyr Ile Ser Ala
                325                 330                 335

ccg gca tgt acg cca tgt gga cac ttt ttc tgt tgg gac tgt att tcc     1056
Pro Ala Cys Thr Pro Cys Gly His Phe Phe Cys Trp Asp Cys Ile Ser
            340                 345                 350

gaa tgg gtg aga gag aag ccc gag tgt ccc ttg tgt cgg cag ggt gtg     1104
```

```
Glu Trp Val Arg Glu Lys Pro Glu Cys Pro Leu Cys Arg Gln Gly Val
        355                 360                 365

aga gag cag aac ttg ttg cct atc aga taa                          1134
Arg Glu Gln Asn Leu Leu Pro Ile Arg
    370                 375


<210> SEQ ID NO 22
<211> LENGTH: 377
<212> TYPE: PRT
<213> ORGANISM: Yarrowia lipolytica

<400> SEQUENCE: 22

Met Trp Gly Ser Ser His Ala Phe Ala Gly Glu Ser Asp Leu Thr Leu
1               5                   10                  15

Gln Leu His Thr Arg Ser Asn Met Ser Asp Asn Thr Thr Ile Lys Lys
            20                  25                  30

Pro Ile Arg Pro Lys Pro Ile Arg Thr Glu Arg Leu Pro Tyr Ala Gly
        35                  40                  45

Ala Ala Glu Ile Ile Arg Ala Asn Gln Lys Asp His Tyr Phe Glu Ser
    50                  55                  60

Val Leu Glu Gln His Leu Val Thr Phe Leu Gln Lys Trp Lys Gly Val
65                  70                  75                  80

Arg Phe Ile His Gln Tyr Lys Glu Glu Leu Glu Thr Ala Ser Lys Phe
                85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175

Pro Glu Thr Trp Lys Glu Arg Val Ile Lys Thr Phe Val Asn Lys Phe
            180                 185                 190

Asp Lys Phe Thr Ala Leu Glu Gly Phe Thr Ala Ile His Leu Ala Ile
        195                 200                 205

Phe Tyr Val Tyr Gly Ser Tyr Tyr Gln Leu Ser Lys Arg Ile Trp Gly
    210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
                245                 250                 255

Phe Val Gln Thr Gly Arg Glu Tyr Leu Gly Ala Leu Leu Glu Lys Ser
            260                 265                 270

Val Glu Lys Glu Ala Gly Glu Lys Glu Asp Glu Lys Glu Ala Val Val
        275                 280                 285

Pro Lys Lys Lys Ser Ser Ile Pro Phe Ile Glu Asp Thr Glu Gly Glu
    290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
                325                 330                 335

Pro Ala Cys Thr Pro Cys Gly His Phe Phe Cys Trp Asp Cys Ile Ser
```

```
            340                 345                 350

Glu Trp Val Arg Glu Lys Pro Glu Cys Pro Leu Cys Arg Gln Gly Val
        355                 360                 365

Arg Glu Gln Asn Leu Leu Pro Ile Arg
    370                 375


<210> SEQ ID NO 23
<211> LENGTH: 1065
<212> TYPE: DNA
<213> ORGANISM: Yarrowia lipolytica
<220> FEATURE:
<221> NAME/KEY: CDS
<222> LOCATION: (1)..(1065)
<223> OTHER INFORMATION: YlPEX10

<400> SEQUENCE: 23

atg agc gac aat acg aca atc aaa aag ccg atc cga ccc aaa ccg atc       48
Met Ser Asp Asn Thr Thr Ile Lys Lys Pro Ile Arg Pro Lys Pro Ile
1               5                   10                  15

cgg acg gaa cgc ctg cct tac gct ggg gcc gca gaa atc atc cga gcc       96
Arg Thr Glu Arg Leu Pro Tyr Ala Gly Ala Ala Glu Ile Ile Arg Ala
            20                  25                  30

aac cag aaa gac cac tac ttt gag tcc gtg ctt gaa cag cat ctc gtc      144
Asn Gln Lys Asp His Tyr Phe Glu Ser Val Leu Glu Gln His Leu Val
        35                  40                  45

acg ttt ctg cag aaa tgg aag gga gta cga ttt atc cac cag tac aag      192
Thr Phe Leu Gln Lys Trp Lys Gly Val Arg Phe Ile His Gln Tyr Lys
    50                  55                  60

gag gag ctg gag acg gcg tcc aag ttt gca tat ctc ggt ttg tgt acg      240
Glu Glu Leu Glu Thr Ala Ser Lys Phe Ala Tyr Leu Gly Leu Cys Thr
65                  70                  75                  80

ctt gtg ggc tcc aag act ctc gga gaa gag tac acc aat ctc atg tac      288
Leu Val Gly Ser Lys Thr Leu Gly Glu Glu Tyr Thr Asn Leu Met Tyr
                85                  90                  95

act atc aga gac cga aca gct cta ccg ggg gtg gtg aga cgg ttt ggc      336
Thr Ile Arg Asp Arg Thr Ala Leu Pro Gly Val Val Arg Arg Phe Gly
            100                 105                 110

tac gtg ctt tcc aac act ctg ttt cca tac ctg ttt gtg cgc tac atg      384
Tyr Val Leu Ser Asn Thr Leu Phe Pro Tyr Leu Phe Val Arg Tyr Met
        115                 120                 125

ggc aag ttg cgc gcc aaa ctg atg cgc gag tat ccc cat ctg gtg gag      432
Gly Lys Leu Arg Ala Lys Leu Met Arg Glu Tyr Pro His Leu Val Glu
    130                 135                 140

tac gac gaa gat gag cct gtg ccc agc ccg gaa aca tgg aag gag cgg      480
Tyr Asp Glu Asp Glu Pro Val Pro Ser Pro Glu Thr Trp Lys Glu Arg
145                 150                 155                 160

gtc atc aag acg ttt gtg aac aag ttt gac aag ttc acg gcg ctg gag      528
Val Ile Lys Thr Phe Val Asn Lys Phe Asp Lys Phe Thr Ala Leu Glu
                165                 170                 175

ggg ttt acc gcg atc cac ttg gcg att ttc tac gtc tac ggc tcg tac      576
Gly Phe Thr Ala Ile His Leu Ala Ile Phe Tyr Val Tyr Gly Ser Tyr
            180                 185                 190

tac cag ctc agt aag cgg atc tgg ggc atg cgt tat gta ttt gga cac      624
Tyr Gln Leu Ser Lys Arg Ile Trp Gly Met Arg Tyr Val Phe Gly His
        195                 200                 205

cga ctg gac aag aat gag cct cga atc ggt tac gag atg ctc ggt ctg      672
Arg Leu Asp Lys Asn Glu Pro Arg Ile Gly Tyr Glu Met Leu Gly Leu
    210                 215                 220

ctg att ttc gcc cgg ttt gcc acg tca ttt gtg cag acg gga aga gag      720
Leu Ile Phe Ala Arg Phe Ala Thr Ser Phe Val Gln Thr Gly Arg Glu
225                 230                 235                 240
```

```
tac ctc gga gcg ctg ctg gaa aag agc gtg gag aaa gag gca ggg gag      768
Tyr Leu Gly Ala Leu Leu Glu Lys Ser Val Glu Lys Glu Ala Gly Glu
                245                 250                 255

aag gaa gat gaa aag gaa gcg gtt gtg ccg aaa aag aag tcg tca att      816
Lys Glu Asp Glu Lys Glu Ala Val Val Pro Lys Lys Lys Ser Ser Ile
            260                 265                 270

ccg ttc att gag gat aca gaa ggg gag acg gaa gac aag atc gat ctg      864
Pro Phe Ile Glu Asp Thr Glu Gly Glu Thr Glu Asp Lys Ile Asp Leu
        275                 280                 285

gag gac cct cga cag ctc aag ttc att cct gag gcg tcc aga gcg tgc      912
Glu Asp Pro Arg Gln Leu Lys Phe Ile Pro Glu Ala Ser Arg Ala Cys
    290                 295                 300

act ctg tgt ctg tca tac att agt gcg ccg gca tgt acg cca tgt gga      960
Thr Leu Cys Leu Ser Tyr Ile Ser Ala Pro Ala Cys Thr Pro Cys Gly
305                 310                 315                 320

cac ttt ttc tgt tgg gac tgt att tcc gaa tgg gtg aga gag aag ccc     1008
His Phe Phe Cys Trp Asp Cys Ile Ser Glu Trp Val Arg Glu Lys Pro
                325                 330                 335

gag tgt ccc ttg tgt cgg cag ggt gtg aga gag cag aac ttg ttg cct     1056
Glu Cys Pro Leu Cys Arg Gln Gly Val Arg Glu Gln Asn Leu Leu Pro
            340                 345                 350

atc aga taa                                                         1065
Ile Arg


<210> SEQ ID NO 24
<211> LENGTH: 354
<212> TYPE: PRT
<213> ORGANISM: Yarrowia lipolytica

<400> SEQUENCE: 24

Met Ser Asp Asn Thr Thr Ile Lys Lys Pro Ile Arg Pro Lys Pro Ile
1               5                   10                  15

Arg Thr Glu Arg Leu Pro Tyr Ala Gly Ala Ala Glu Ile Ile Arg Ala
            20                  25                  30

Asn Gln Lys Asp His Tyr Phe Glu Ser Val Leu Glu Gln His Leu Val
        35                  40                  45

Thr Phe Leu Gln Lys Trp Lys Gly Val Arg Phe Ile His Gln Tyr Lys
    50                  55                  60

Glu Glu Leu Glu Thr Ala Ser Lys Phe Ala Tyr Leu Gly Leu Cys Thr
65                  70                  75                  80

Leu Val Gly Ser Lys Thr Leu Gly Glu Glu Tyr Thr Asn Leu Met Tyr
                85                  90                  95

Thr Ile Arg Asp Arg Thr Ala Leu Pro Gly Val Val Arg Arg Phe Gly
            100                 105                 110

Tyr Val Leu Ser Asn Thr Leu Phe Pro Tyr Leu Phe Val Arg Tyr Met
        115                 120                 125

Gly Lys Leu Arg Ala Lys Leu Met Arg Glu Tyr Pro His Leu Val Glu
    130                 135                 140

Tyr Asp Glu Asp Glu Pro Val Pro Ser Pro Glu Thr Trp Lys Glu Arg
145                 150                 155                 160

Val Ile Lys Thr Phe Val Asn Lys Phe Asp Lys Phe Thr Ala Leu Glu
                165                 170                 175

Gly Phe Thr Ala Ile His Leu Ala Ile Phe Tyr Val Tyr Gly Ser Tyr
            180                 185                 190

Tyr Gln Leu Ser Lys Arg Ile Trp Gly Met Arg Tyr Val Phe Gly His
        195                 200                 205
```

```
Arg Leu Asp Lys Asn Glu Pro Arg Ile Gly Tyr Glu Met Leu Gly Leu
    210                 215                 220

Leu Ile Phe Ala Arg Phe Ala Thr Ser Phe Val Gln Thr Gly Arg Glu
225                 230                 235                 240

Tyr Leu Gly Ala Leu Leu Glu Lys Ser Val Glu Lys Glu Ala Gly Glu
                245                 250                 255

Lys Glu Asp Glu Lys Glu Ala Val Val Pro Lys Lys Lys Ser Ser Ile
            260                 265                 270

Pro Phe Ile Glu Asp Thr Glu Gly Glu Thr Glu Asp Lys Ile Asp Leu
        275                 280                 285

Glu Asp Pro Arg Gln Leu Lys Phe Ile Pro Glu Ala Ser Arg Ala Cys
    290                 295                 300

Thr Leu Cys Leu Ser Tyr Ile Ser Ala Pro Ala Cys Thr Pro Cys Gly
305                 310                 315                 320

His Phe Phe Cys Trp Asp Cys Ile Ser Glu Trp Val Arg Glu Lys Pro
                325                 330                 335

Glu Cys Pro Leu Cys Arg Gln Gly Val Arg Glu Gln Asn Leu Leu Pro
            340                 345                 350

Ile Arg


<210> SEQ ID NO 25
<211> LENGTH: 38
<212> TYPE: PRT
<213> ORGANISM: Yarrowia lipolytica
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid

<400> SEQUENCE: 25

Cys Xaa Xaa Cys Xaa Xaa Xaa Xaa Xaa Xaa Xaa Xaa Xaa Xaa Xaa Cys
1               5                   10                  15

Xaa His Xaa Xaa Cys Xaa Xaa Cys Xaa Xaa Xaa Xaa Xaa Xaa Xaa Xaa
            20                  25                  30

Xaa Xaa Cys Xaa Xaa Cys
        35


<210> SEQ ID NO 26
<211> LENGTH: 345
<212> TYPE: PRT
<213> ORGANISM: Yarrowia lipolytica
```

<400> SEQUENCE: 26

```
Met Trp Gly Ser Ser His Ala Phe Ala Gly Glu Ser Asp Leu Thr Leu
1               5                   10                  15

Gln Leu His Thr Arg Ser Asn Met Ser Asp Asn Thr Thr Ile Lys Lys
            20                  25                  30

Pro Ile Arg Pro Lys Pro Ile Arg Thr Glu Arg Leu Pro Tyr Ala Gly
        35                  40                  45

Ala Ala Glu Ile Ile Arg Ala Asn Gln Lys Asp His Tyr Phe Glu Ser
    50                  55                  60

Val Leu Glu Gln His Leu Val Thr Phe Leu Gln Lys Trp Lys Gly Val
65                  70                  75                  80

Arg Phe Ile His Gln Tyr Lys Glu Glu Leu Glu Thr Ala Ser Lys Phe
                85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175

Pro Glu Thr Trp Lys Glu Arg Val Ile Lys Thr Phe Val Asn Lys Phe
            180                 185                 190

Asp Lys Phe Thr Ala Leu Glu Gly Phe Thr Ala Ile His Leu Ala Ile
        195                 200                 205

Phe Tyr Val Tyr Gly Ser Tyr Tyr Gln Leu Ser Lys Arg Ile Trp Gly
    210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
                245                 250                 255

Phe Val Gln Thr Gly Arg Glu Tyr Leu Gly Ala Leu Leu Glu Lys Ser
            260                 265                 270

Val Glu Lys Glu Ala Gly Glu Lys Glu Asp Glu Lys Glu Ala Val Val
        275                 280                 285

Pro Lys Lys Lys Ser Ser Ile Pro Phe Ile Glu Asp Thr Glu Gly Glu
    290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
                325                 330                 335

Pro Ala Cys Thr Pro Cys Gly His Phe
            340                 345
```

<210> SEQ ID NO 27
<211> LENGTH: 2987
<212> TYPE: DNA
<213> ORGANISM: Yarrowia lipolytica
<220> FEATURE:
<221> NAME/KEY: misc_feature
<223> OTHER INFORMATION: acetohydroxyacid synthase (AHAS) with W497L mutation
<300> PUBLICATION INFORMATION:

-continued

```
<302> TITLE: HIGH EICOSAPENTAENOIC ACID PRODUCING STRAINS OF YARROWIA
      LIPOLYTICA
<310> PATENT DOCUMENT NUMBER: US 2006-0115881-A1
<311> PATENT FILING DATE: 2005-11-02
<312> PUBLICATION DATE: 2006-06-01
<313> RELEVANT RESIDUES IN SEQ ID NO: (1)..(2987)
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(2987)

<400> SEQUENCE: 27

ttccctagtc ccagtgtaca cccgccgata tcgcttaccc tgcagccgga ttaaggttgg     60

caatttttca cgtccttgtc tccgcaatta ctcaccgggt ggtttataag attgcaagcg    120

tcttgatttg tctctgtata ctaacatgca atcgcgactc gcccgacggg ccactaacct    180

ggccagaatc tccagatcca agtattctct tggtctgcga tatgtttcca acacaaaagc    240

ccctgctgcc cagccggcaa ctgctgagtg agtattcctt gccataaacg acccagaacc    300

actgtatagt gtttggaagc actagtcaga agaccagcga aaacaggtgg aaaaaactga    360

gacgaaaagc aacgaccaga aatgtaatgt gtggaaaagc gacacacaca gagcagataa    420

agaggtgaca aataacgaca aatgaaatat cagtatcttc ccacaatcac tacctctcag    480

ctgtctgaag gtgcggctga tatatccatc ccacgtctaa cgtatggagt gtgatagaat    540

atgacgacac aagcatgaga actcgctctc tatccaacca ccgaaacact gtcactacag    600

ccgttcttgt tgctccattc gcttttgtga ttccatgcct tctctggtga ctgacaacat    660

tccttccttt tctccagccc tgttgttatc tgctcatgac ctacggccac tctctatcgc    720

atactaacat agacgatccc agcccgctcc ccacttccag ggcaccgttg gcaagcctcc    780

tatcctcaag aaggctgagg ctgccaacgc tgacatggac gagtccttca tcggaatgtc    840

tggaggagag atcttccacg agatgatgct gcgacacaac gtcgacactg tcttcggtta    900

ccccggtgga gccattctcc ccgtctttga cgccattcac aactctgagt acttcaactt    960

tgtgctccct cgacacgagc agggtgccgg ccacatggcc gagggctacg ctcgagcctc   1020

tggtaagccc ggtgtcgttc tcgtcacctc tggccccggt gccaccaacg tcatcacccc   1080

catgcaggac gctctttccg atggtacccc catggttgtc ttcaccggtc aggtcctgac   1140

ctccgttatc ggcactgacg ccttccagga ggccgatgtt gtcggcatct cccgatcttg   1200

caccaagtgg aacgtcatgg tcaagaacgt tgctgagctc ccccgacgaa tcaacgaggc   1260

ctttgagatt gctacttccg gccgacccgg tcccgttctc gtcgatctgc ccaaggatgt   1320

tactgctgcc atcctgcgag agcccatccc caccaagtcc accattccct cgcattctct   1380

gaccaacctc acctctgccg ccgccaccga gttccagaag caggctatcc agcgagccgc   1440

caacctcatc aaccagtcca agaagcccgt cctttacgtc ggacagggta tccttggctc   1500

cgaggagggt cctaagctgc ttaaggagct ggctgagaag gccgagattc ccgtcaccac   1560

tactctgcag ggtcttggtg cctttgacga gcgagacccc aagtctctgc acatgctcgg   1620

tatgcacggt tccggctacg ccaacatggc catgcagaac gctgactgta tcattgctct   1680

cggcgcccga tttgatgacc gagttaccgg ctccatcccc aagtttgccc ccgaggctcg   1740

agccgctgcc cttgagggtc gaggtggtat tgttcacttt gagatccagg ccaagaacat   1800

caacaaggtt gttcaggcca ccgaagccgt tgagggagac gttaccgagt ctgtccgaca   1860

gctcatcccc ctcatcaaca aggtctctgc cgctgagcga gctccctgga ctgagactat   1920
```

ccagtcctgg aagcagcagt tccccttcct cttcgaggct gaaggtgagg atggtgttat 1980
caagccccag tccgtcattg ctctgctctc tgacctgaca gagaacaaca aggacaagac 2040
catcatcacc accggtgttg gtcagcatca gatgtggact gcccagcatt tccgatggcg 2100
acaccctcga accatgatca cttctggtgg tcttggaact atgggttacg gcctgcccgc 2160
cgctatcggc gccaaggttg cccgacctga ctgcgacgtc attgacatcg atggtgacgc 2220
ttctttcaac atgactctga ccgagctgtc caccgccgtt cagttcaaca ttggcgtcaa 2280
ggctattgtc ctcaacaacg aggaacaggg tatggtcacc cagctgcagt ctctcttcta 2340
cgagaaccga tactgccaca ctcatcagaa gaaccccgac ttcatgaagc tggccgagtc 2400
catgggcatg aagggtatcc gaatcactca cattgaccag ctggaggccg gtctcaagga 2460
gatgctcgca tacaagggcc ctgtgctcgt tgaggttgtt gtcgacaaga agatccccgt 2520
tcttcccatg gttcccgctg gtaaggcttt gcatgagttc cttgtctacg acgctgacgc 2580
cgaggctgct tctcgacccg atcgactgaa gaatgccccc gcccctcacg tccaccagac 2640
cacctttgag aactaagtgg aaaggaacac aagcaatccg aaccaaaaat aattggggtc 2700
ccgtgcccac agagtctagt gcagacctaa aatgaccaca gtaaattata gctgttatta 2760
aacatgagat tttgaccaac aagagcgtag gaatgttatt agctactact tgtacataca 2820
cagcatttgt tttaaataat gttgcctcca ggggcagtga gatcaggacc cagatccgtg 2880
gccagctctc tgacttcaga ccgcttgtac ttaagcagct cgcaacactg ttgtcgagga 2940
ttgaacttgc catattcgat tttgtggtca tgaatccagc acacctc 2987

<210> SEQ ID NO 28
<211> LENGTH: 13066
<212> TYPE: DNA
<213> ORGANISM: Artificial Sequence
<220> FEATURE:
<223> OTHER INFORMATION: Plasmid pZP3-Pa777U

<400> SEQUENCE: 28
tctcggtcta ttcttttgat ttataaggga ttttgccgat ttcggcctat tggttaaaaa 60
atgagctgat ttaacaaaaa tttaacgcga attttaacaa aatattaacg cttacaattt 120
cctgatgcgg tattttctcc ttacgcatct gtgcggtatt tcacaccgca tcaggtggca 180
cttttcgggg aaatgtgcgc ggaaccccta tttgtttatt tttctaaata cattcaaata 240
tgtatccgct catgagacaa taaccctgat aaatgcttca ataatattga aaaaggaaga 300
gtatgagtat tcaacatttc cgtgtcgccc ttattccctt ttttgcggca ttttgccttc 360
ctgtttttgc tcacccagaa acgctggtga aagtaaaaga tgctgaagat cagttgggtg 420
cacgagtggg ttacatcgaa ctggatctca acagcggtaa gatccttgag agttttcgcc 480
ccgaagaacg ttttccaatg atgagcactt ttaaagttct gctatgtggc gcggtattat 540
cccgtattga cgccgggcaa gagcaactcg gtcgccgcat acactattct cagaatgact 600
tggttgagta ctcaccagtc acagaaaagc atcttacgga tggcatgaca gtaagagaat 660
tatgcagtgc tgccataacc atgagtgata acactgcggc caacttactt ctgacaacga 720
tcggaggacc gaaggagcta accgcttttt tgcacaacat gggggatcat gtaactcgcc 780
ttgatcgttg ggaaccggag ctgaatgaag ccataccaaa cgacgagcgt gacaccacga 840
tgcctgtagc aatggcaaca acgttgcgca aactattaac tggcgaacta cttactctag 900
cttcccggca acaattaata gactggatgg aggcggataa agttgcagga ccacttctgc 960

-continued

```
gctcggccct tccggctggc tggtttattg ctgataaatc tggagccggt gagcgtgggt   1020
ctcgcggtat cattgcagca ctggggccag atggtaagcc ctcccgtatc gtagttatct   1080
acacgacggg gagtcaggca actatggatg aacgaaatag acagatcgct gagataggtg   1140
cctcactgat taagcattgg taactgtcag accaagttta ctcatatata ctttagattg   1200
atttaaaact tcatttttaa tttaaaagga tctaggtgaa gatccttttt gataatctca   1260
tgaccaaaat cccttaacgt gagttttcgt tccactgagc gtcagacccc gtagaaaaga   1320
tcaaaggatc ttcttgagat cctttttttc tgcgcgtaat ctgctgcttg caaacaaaaa   1380
aaccaccgct accagcggtg gtttgtttgc cggatcaaga gctaccaact ctttttccga   1440
aggtaactgg cttcagcaga gcgcagatac caaatactgt tcttctagtg tagccgtagt   1500
taggccacca cttcaagaac tctgtagcac cgcctacata cctcgctctg ctaatcctgt   1560
taccagtggc tgctgccagt ggcgataagt cgtgtcttac cgggttggac tcaagacgat   1620
agttaccgga taaggcgcag cggtcgggct gaacgggggg ttcgtgcaca cagcccagct   1680
tggagcgaac gacctacacc gaactgagat acctacagcg tgagctatga gaaagcgcca   1740
cgcttcccga agggagaaag gcggacaggt atccggtaag cggcagggtc ggaacaggag   1800
agcgcacgag ggagcttcca gggggaaacg cctggtatct ttatagtcct gtcgggtttc   1860
gccacctctg acttgagcgt cgatttttgt gatgctcgtc aggggggcgg agcctatgga   1920
aaaacgccag caacgcggcc tttttacggt tcctggcctt ttgctggcct tttgctcaca   1980
tgttctttcc tgcgttatcc cctgattctg tggataaccg tattaccgcc tttgagtgag   2040
ctgataccgc tcgccgcagc cgaacgaccg agcgcagcga gtcagtgagc gaggaagcgg   2100
aagagcgccc aatacgcaaa ccgcctctcc ccgcgcgttg gccgattcat taatgcagct   2160
ggcgcgccac caatcacaat tctgaaaagc acatcttgat ctcctcattg cggggagtcc   2220
aacggtggtc ttattccccc gaatttcccg ctcaatctcg ttccagaccg acccggacac   2280
agtgcttaac gccgttccga aactctaccg cagatatgct ccaacggact gggctgcata   2340
gatgtgatcc tcggcttgga gaaatggata aaagccggcc aaaaaaaaag cggaaaaaag   2400
cggaaaaaaa gagaaaaaaa atcgcaaaat ttgaaaaata gggggaaaag acgcaaaaac   2460
gcaaggaggg gggagtatat gacactgata agcaagctca caacggttcc tcttattttt   2520
ttcctcatct tctgcctagg ttcccaaaat cccagatgct tctctccagt gccaaaagta   2580
agtaccccac aggttttcgg ccgaaaattc cacgtgcagc aacgtcgtgt ggggtgttaa   2640
aatgtggggg gggggaacca ggacaagagg ctcttgtggg agccgaatga gagcacaaag   2700
cgggcgggtg tgataagggc atttttgccc attttccctt ctcctgtctc tccgacggtg   2760
atggcgttgt gcgtcctcta tttcttttta tttctttttg ttttatttct ctgactaccg   2820
atttggtttg atttcctcaa ccccacacaa ataagctcgg gccgaggaat atatatatac   2880
acggacacag tcgccctgtg gacaacacgt cactacctct acgatacaca ccgtacgttg   2940
tgtggaagct tgtgagcgga taacaatttc acacaggaaa cagctatgac catgattacg   3000
ccaagctcga aattaaccct cactaaaggg aacaaaagct ggagctccac cgcggacaca   3060
atatctggtc aaatttcagt ttcgttacat ttaaattcct tcacttcaag ttcattcttc   3120
atctgcttct gttttacttt gacaggcaaa tgaagacatg gtacgacttg atggaggcca   3180
agaacgccat ttcaccccga gacaccgaag tgcctgaaat cctggctgcc cccattgata   3240
acatcggaaa ctacggtatt ccggaaagtg tatatagaac ctttccccag cttgtgtctg   3300
tggatatgga tggtgtaatc ccctttgagt actcgtcttg gcttctctcc gagcagtatg   3360
```

-continued

```
aggctctcta atctagcgca tttaatatct caatgtattt atatatttat cttctcatgc   3420
ggccgcttag ttggctttgg tcttggcagc cttggcctcc ttgagggtaa acatcttggc   3480
atccttgtcg accacgccgt acttggcgta cataagacca attcggatga aggtgggaat   3540
gatgggagaa gccgactttc gcaccagttc gggaaaggcc tgagcgaagg cagcagtggc   3600
ctcgttgagc ttgtagtgag gaatgatggg aaacagatgg tggatctgat gtgtaccaat   3660
gttgtgggac aggttgtcga tgagggctcc gtagcttcgg tccacagagg acaagttgcc   3720
cttgacatag gtccactccg aatcggcgta ccagggagtt tcctcgtcgt tgtgatggag   3780
gaaggtagtg acaaccagca tggtggcgaa tccaaagaga ggtgcgaagt aatacagagc   3840
catggtcttg aggccgtaga cgtaggtaag gtaggcgtac agaccagcaa aggccacgag   3900
agagccgagg gaaatgatga cggcagacat tcttcgcagg tagagaggct cccagggatt   3960
gaagtggttg acctttcggg gaggaaatcc agcaacgagg taggcaaacc aagccgaacc   4020
aagggagatg accatgtgtc gggacagggg atgagagtcg gcttctcgct gagggtagaa   4080
gatctcatcc ttgtcgatgt tgccggtgtt cttgtgatgg tgtcgatggc tgatcttcca   4140
cgactcgtag ggagtcagaa tgatggagtg aatgagtgtg ccaacagaga agttgagcag   4200
gtgggatcgc gagaaggcac catgtccaca gtcgtgaccg atggtaaaga atccccagaa   4260
cacgataccc tggagcagaa tgtagccagt gcaaaggacg gcatcgagca gtgcaaactc   4320
ctgcacgata gcaagggctc gagcatagta cagtccgaga gcaagggaac cggcaatgcc   4380
cagagctcgc acggtatagt agagggacca gggaacagag gcttcgaagc agtgggcagg   4440
cagggatcgc ttgatctcgg tgagagtagg gaactcgtag ggagcggcaa cggtagagga   4500
agccatggtt gtgaattagg gtggtgagaa tggttggttg tagggaagaa tcaaaggccg   4560
gtctcgggat ccgtgggtat atatatatat atatatatat acgatccttc gttacctccc   4620
tgttctcaaa actgtggttt ttcgtttttc gtttttttgct tttttgatt tttttagggc   4680
caactaagct tccagatttc gctaatcacc tttgtactaa ttacaagaaa ggaagaagct   4740
gattagagtt gggcttttta tgcaactgtg ctactcctta tctctgatat gaaagtgtag   4800
acccaatcac atcatgtcat ttagagttgg taatactggg aggatagata aggcacgaaa   4860
acgagccata gcagacatgc tgggtgtagc caagcagaag aaagtagatg ggagccaatt   4920
gacgagcgag ggagctacgc caatccgaca tacgacacgc tgagatcgtc ttggccgggg   4980
ggtacctaca gatgtccaag ggtaagtgct tgactgtaat tgtatgtctg aggacaaata   5040
tgtagtcagc cgtataaagt cataccaggc accagtgcca tcatcgaacc actaactctc   5100
tatgatacat gcctccggta ttattgtacc atgcgtcgct ttgttacata cgtatcttgc   5160
ctttttctct cagaaactcc agactttggc tattggtcga gataagcccg gaccatagtg   5220
agtctttcac actctacatt tctcccttgc tccaactatc gattgttgtc tactaactat   5280
cgtacgataa cttcgtatag catacattat acgaagttat cgcgtcgacg agtatctgtc   5340
tgactcgtca ttgccgcctt tggagtacga ctccaactat gagtgtgctt ggatcacttt   5400
gacgatacat tcttcgttgg aggctgtggg tctgacagct gcgttttcgg cgcggttggc   5460
cgacaacaat atcagctgca acgtcattgc tggctttcat catgatcaca tttttgtcgg   5520
caaaggcgac gcccagagag ccattgacgt tctttctaat ttggaccgat agccgtatag   5580
tccagtctat ctataagttc aactaactcg taactattac cataacatat acttcactgc   5640
cccagataag gttccgataa aaagttctgc agactaaatt tatttcagtc tcctcttcac   5700
```

-continued

```
caccaaaatg ccctcctacg aagctcgagc taacgtccac aagtccgcct ttgccgctcg   5760
agtgctcaag ctcgtggcag ccaagaaaac caacctgtgt gcttctctgg atgttaccac   5820
caccaaggag ctcattgagc ttgccgataa ggtcggacct tatgtgtgca tgatcaaaac   5880
ccatatcgac atcattgacg acttcaccta cgccggcact gtgctccccc tcaaggaact   5940
tgctcttaag cacggtttct tcctgttcga ggacagaaag ttcgcagata ttggcaacac   6000
tgtcaagcac cagtaccggt gtcaccgaat cgccgagtgg tccgatatca ccaacgccca   6060
cggtgtaccc ggaaccggaa tcattgctgg cctgcgagct ggtgccgagg aaactgtctc   6120
tgaacagaag aaggaggacg tctctgacta cgagaactcc cagtacaagg agttcctagt   6180
cccctctccc aacgagaagc tggccagagg tctgctcatg ctggccgagc tgtcttgcaa   6240
gggctctctg gccactggcg agtactccaa gcagaccatt gagcttgccc gatccgaccc   6300
cgagtttgtg gttggcttca ttgcccagaa ccgacctaag ggcgactctg aggactggct   6360
tattctgacc cccggggtgg gtcttgacga caagggagac gctctcggac agcagtaccg   6420
aactgttgag gatgtcatgt ctaccggaac ggatatcata attgtcggcc gaggtctgta   6480
cggccagaac cgagatccta ttgaggaggc caagcgatac cagaaggctg gctgggaggc   6540
ttaccagaag attaactgtt agaggttaga ctatggatat gtaatttaac tgtgtatata   6600
gagagcgtgc aagtatggag cgcttgttca gcttgtatga tggtcagacg acctgtctga   6660
tcgagtatgt atgatactgc acaacctgtg tatccgcatg atctgtccaa tggggcatgt   6720
tgttgtgttt ctcgatacgg agatgctggg tacagtgcta atacgttgaa ctacttatac   6780
ttatatgagg ctcgaagaaa gctgacttgt gtatgactta ttctcaacta catccccagt   6840
cacaatacca ccactgcact accactacac caaaaccatg atcaaaccac ccatggactt   6900
cctggaggca gaagaacttg ttatggaaaa gctcaagaga gagatcataa cttcgtatag   6960
catacattat acgaagttat cctgcaggta aaggaattca tgctgttcat cgtggttaat   7020
gctgctgtgt gctgtgtgtg tgtgttgttt ggcgctcatt gttgcgttat gcagcgtaca   7080
ccacaatatt ggaagcttat tagcctttct atttttttcgt ttgcaaggct taacaacatt   7140
gctgtggaga gggatgggga tatggaggcc gctggaggga gtcggagagg cgtttggag    7200
cggcttggcc tggcgcccag ctcgcgaaac gcacctagga ccctttggca cgccgaaatg   7260
tgccactttt cagtctagta acgccttacc tacgtcattc catgcgtgca tgtttgcgcc   7320
tttttccct tgcccttgat cgccacacag tacagtgcac tgtacagtgg aggttttggg    7380
ggggtcttag atgggagcta aaagcggcct agcggtacac tagtgggatt gtatggagtg   7440
gcatggagcc taggtggagc ctgacaggac gcacgaccgg ctagcccgtg acagacgatg   7500
ggtggctcct gttgtccacc gcgtacaaat gtttgggcca aagtcttgtc agccttgctt   7560
gcgaacctaa ttcccaattt tgtcacttcg cacccccatt gatcgagccc taacccctgc   7620
ccatcaggca atccaattaa gctcgcattg tctgccttgt ttagtttggc tcctgcccgt   7680
ttcggcgtcc acttgcacaa acacaaacaa gcattatata taaggctcgt ctctccctcc   7740
caaccacact cactttttg cccgtcttcc cttgctaaca caaaagtcaa gaacacaaac    7800
aaccacccca accccttac acacaagaca tatctacagc aatggccatg gcttcttcca    7860
ctgttgctgc gccgtacgag ttcccgacgc tgacggagat caagcgctcg ctgccagcgc   7920
actgctttga ggcctcggtc ccgtggtcgc tctactacac cgtgcgcgcg ctgggcatcg   7980
ccggctcgct cgcgctcggc ctctactacg cgcgcgcgct cgcgatcgtg caggagtttg   8040
ccctgctgga tgcggtgctc tgcacggggt acattctgct gcagggcatc gtattctggg   8100
```

-continued

```
ggttcttcac catcggccat gactgcggcc acggcgcgtt ctcgcgttcg cacctgctca   8160
acttcagcgt cggcacgctc attcactcga tcatcctcac gccgtacgag tcatggaaga   8220
tctcgcaccg ccaccaccac aagaacacgg gcaacatcga caaggacgag attttctacc   8280
cgcagcgcga ggccgactcg cacccactgt cccgacacat ggtgatctcg ctcggctcgg   8340
cctggttcgc gtacctcgtt gcgggcttcc ctcctcgcaa ggtgaaccac ttcaaccctt   8400
gggaaccgtt gtacctgcgc cgcatgtctg ccgtcatcat ctcactcggc tcgctcgtgg   8460
cgttcgcggg cttgtatgcg tatctcacct acgtctatgg ccttaagacc atggcgctgt   8520
actacttcgc ccctctcttt gggttcgcca cgatgctcgt ggtcactacc tttttgcacc   8580
acaatgacga ggaaacgcca tggtacgccg actcggagtg gacgtacgtc aagggcaacc   8640
tctcgtccgt ggaccgctcg tacggcgcgc tcatcgacaa cctgagccac aacatcggca   8700
cgcaccagat ccaccacctg tttccgatca tcccgcacta caagctgaac gaggcgacgg   8760
cagcgttcgc gcaggcgttc ccggagctcg tgcgcaagag cgcgtcgccg atcatcccga   8820
cgttcatccg catcgggctc atgtacgcca agtacggcgt cgtggacaag gacgccaaga   8880
tgtttacgct caaggaggcc aaggccgcca agaccaaggc caactaggcg gccgcattga   8940
tgattggaaa cacacacatg ggttatatct aggtgagagt tagttggaca gttatatatt   9000
aaatcagcta tgccaacggt aacttcattc atgtcaacga ggaaccagtg actgcaagta   9060
atatagaatt tgaccacctt gccattctct tgcactcctt tactatatct catttatttc   9120
ttatatacaa atcacttctt cttcccagca tcgagctcgg aaacctcatg agcaataaca   9180
tcgtggatct cgtcaataga gggctttttg gactccttgc tgttggccac cttgtccttg   9240
ctgtttaaac agtgtacgca gatctactat agaggaacat ttaaattgcc ccggagaaga   9300
cggccaggcc gcctagatga caaattcaac aactcacagc tgactttctg ccattgccac   9360
taggggggggg cctttttata tggccaagcc aagctctcca cgtcggttgg gctgcaccca   9420
acaataaatg ggtagggttg caccaacaaa gggatgggat ggggggtaga agatacgagg   9480
ataacggggc tcaatggcac aaataagaac gaatactgcc attaagactc gtgatccagc   9540
gactgacacc attgcatcat ctaagggcct caaaactacc tcggaactgc tgcgctgatc   9600
tggacaccac agaggttccg agcactttag gttgcaccaa atgtcccacc aggtgcaggc   9660
agaaaacgct ggaacagcgt gtacagtttg tcttaacaaa aagtgagggc gctgaggtcg   9720
agcagggtgg tgtgacttgt tatagccttt agagctgcga aagcgcgtat ggatttggct   9780
catcaggcca gattgagggt ctgtggacac atgtcatgtt agtgtacttc aatcgccccc   9840
tggatatagc cccgacaata ggccgtggcc tcattttttt gccttccgca catttccatt   9900
gctcggtacc cacaccttgc ttctcctgca cttgccaacc ttaatactgg tttacattga   9960
ccaacatctt acaagcgggg ggcttgtcta gggtatatat aaacagtggc tctcccaatc  10020
ggttgccagt ctcttttttc ctttctttcc ccacagattc gaaatctaaa ctacacatca  10080
cagaattccg agccgtgagt atccacgaca agatcagtgt cgagacgacg cgttttgtgt  10140
aatgacacaa tccgaaagtc gctagcaaca cacactctct acacaaacta acccagctct  10200
ggtaccatgg cttcttccac tgttgctgcg ccgtacgagt tcccgacgct gacggagatc  10260
aagcgctcgc tgccagcgca ctgctttgag gcctcggtcc cgtggtcgct ctactacacc  10320
gtgcgcgcgc tgggcatcgc cggctcgctc gcgctcggcc tctactacgc gcgcgcgctc  10380
gcgatcgtgc aggagtttgc cctgctggat gcggtgctct gcacggggta cattctgctg  10440
```

-continued

```
cagggcatcg tattctgggg gttcttcacc atcggccatg actgcggcca cggcgcgttc  10500
tcgcgttcgc acctgctcaa cttcagcgtc ggcacgctca ttcactcgat catcctcacg  10560
ccgtacgagt catggaagat ctcgcaccgc caccaccaca agaacacggg caacatcgac  10620
aaggacgaga ttttctaccc gcagcgcgag gccgactcgc acccactgtc ccgacacatg  10680
gtgatctcgc tcggctcggc ctggttcgcg tacctcgttg cgggcttccc tcctcgcaag  10740
gtgaaccact tcaacccttg ggaaccgttg tacctgcgcc gcatgtctgc cgtcatcatc  10800
tcactcggct cgctcgtggc gttcgcgggc ttgtatgcgt atctcaccta cgtctatggc  10860
cttaagacca tggcgctgta ctacttcgcc cctctctttg ggttcgccac gatgctcgtg  10920
gtcactacct ttttgcacca caatgacgag gaaacgccat ggtacgccga ctcggagtgg  10980
acgtacgtca agggcaacct ctcgtccgtg gaccgctcgt acggcgcgct catcgacaac  11040
ctgagccaca acatcggcac gcaccagatc caccacctgt ttccgatcat cccgcactac  11100
aagctgaacg aggcgacggc agcgttcgcg caggcgttcc cggagctcgt gcgcaagagc  11160
gcgtcgccga tcatcccgac gttcatccgc atcgggctca tgtacgccaa gtacggcgtc  11220
gtggacaagg acgccaagat gtttacgctc aaggaggcca aggccgccaa gaccaaggcc  11280
aactaggcgg ccgcatggag cgtgtgttct gagtcgatgt ttctatgga gttgtgagtg  11340
ttagtagaca tgatgggttt atatatgatg aatgaataga tgtgattttg atttgcacga  11400
tggaattgag aactttgtaa acgtacatgg gaatgtatga atgtgggggt tttgtgactg  11460
gataactgac ggtcagtgga cgccgttgtt caaatatcca agagatgcga gaaactttgg  11520
gtcaagtgaa catgtcctct ctgttcaagt aaaccatcaa ctatgggtag tatatttagt  11580
aaggacaaga gttgagattc tttggagtcc tagaaacgta ttttcgcgtt ccaagatcaa  11640
attagtagag taatacgggc acgggaatcc attcatagtc tcaatcctgc aggtgagtta  11700
attaagatga cgacatttgc gagctggacg aggaatagat ggagcgtgtg ttctgagtcg  11760
atgttttcta tggagttgtg agtgttagta gacatgatgg gtttatatat gatgaatgaa  11820
tagatgtgat tttgatttgc acgatggaat tgagaacttt gtaaacgtac atgggaatgt  11880
atgaatgtgg gggttttgtg actggataac tgacggtcag tggacgccgt tgttcaaata  11940
tccaagagat gcgagaaact ttgggtcaag tgaacatgtc ctctctgttc aagtaaacca  12000
tcaactatgg gtagtatatt tagtaaggac aagagttgag attctttgga gtcctagaaa  12060
cgtattttcg cgttccaaga tcaaattagt agagtaatac gggcacggga atccattcat  12120
agtctcaatt ttcccatagg tgtgctacaa ggtgttgaga tgtggtacag taccaccatg  12180
attcgaggta aagagcccag aagtcattga tgaggtcaag aaatacacag atctacagct  12240
caatacaatg aatatcttct ttcatattct tcaggtgaca ccaagggtgt ctattttccc  12300
cagaaatgcg tgaaaaggcg cgtgtgtagc gtggagtatg ggttcggttg gcgtatcctt  12360
catatatcga cgaaatagta gggcaagaga tgacaaaaag tatctatatg tagacagcgt  12420
agaatatgga tttgattggt ataaattcat ttattgcgtg tctcacaaat actctcgata  12480
agttggggtt aaactggaga tggaacaatg tcgatatctc gacgcatgcg acgtcgggcc  12540
caattcgccc tatagtgagt cgtattacaa ttcactggcc gtcgttttac aacgtcgtga  12600
ctgggaaaac cctggcgtta cccaacttaa tcgccttgca gcacatcccc ctttcgccag  12660
ctggcgtaat agcgaagagg cccgcaccga tcgcccttcc caacagttgc gcagcctgaa  12720
tggcgaatgg acgcgccctg tagcggcgca ttaagcgcgg cgggtgtggt ggttacgcgc  12780
agcgtgaccg ctacacttgc cagcgcccta gcgcccgctc ctttcgcttt cttcccttcc  12840
```

```
tttctcgcca cgttcgccgg ctttccccgt caagctctaa atcgggggct ccctttaggg  12900

ttccgattta gtgctttacg gcacctcgac cccaaaaaac ttgattaggg tgatggttca  12960

cgtagtgggc catcgccctg atagacggtt tttcgccctt tgacgttgga gtccacgttc  13020

tttaatagtg gactcttgtt ccaaactgga acaacactca acccta                 13066


<210> SEQ ID NO 29
<211> LENGTH: 9570
<212> TYPE: DNA
<213> ORGANISM: Artificial Sequence
<220> FEATURE:
<223> OTHER INFORMATION: Plasmid pY117

<400> SEQUENCE: 29

ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggtttaaa cgagcttggc gtaatcatgg    240

tcatagctgt ttcctgtgtg aaattgttat ccgctcacaa ttccacacaa cgtacgagcc    300

ggaagcataa agtgtaaagc ctggggtgcc taatgagtga gctaactcac attaattgcg    360

ttgcgctcac tgcccgcttt ccagtcggga aacctgtcgt gccagctgca ttaatgaatc    420

ggccaacgcg cggggagagg cggtttgcgt attgggcgct cttccgcttc ctcgctcact    480

gactcgctgc gctcggtcgt tcggctgcgg cgagcggtat cagctcactc aaaggcggta    540

atacggttat ccacagaatc aggggataac gcaggaaaga acatgtgagc aaaaggccag    600

caaaaggcca ggaaccgtaa aaaggccgcg ttgctggcgt ttttccatag gctccgcccc    660

cctgacgagc atcacaaaaa tcgacgctca agtcagaggt ggcgaaaccc gacaggacta    720

taaagatacc aggcgtttcc ccctggaagc tccctcgtgc gctctcctgt tccgaccctg    780

ccgcttaccg gatacctgtc cgcctttctc ccttcgggaa gcgtggcgct ttctcatagc    840

tcacgctgta ggtatctcag ttcggtgtag gtcgttcgct ccaagctggg ctgtgtgcac    900

gaaccccccg ttcagcccga ccgctgcgcc ttatccggta actatcgtct tgagtccaac    960

ccggtaagac acgacttatc gccactggca gcagccactg gtaacaggat tagcagagcg   1020

aggtatgtag gcggtgctac agagttcttg aagtggtggc ctaactacgg ctacactaga   1080

aggacagtat ttggtatctg cgctctgctg aagccagtta ccttcggaaa aagagttggt   1140

agctcttgat ccggcaaaca aaccaccgct ggtagcggtg gtttttttgt ttgcaagcag   1200

cagattacgc gcagaaaaaa aggatctcaa gaagatcctt tgatcttttc tacggggtct   1260

gacgctcagt ggaacgaaaa ctcacgttaa gggattttgg tcatgagatt atcaaaaagg   1320

atcttcacct agatcctttt aaattaaaaa tgaagtttta aatcaatcta aagtatatat   1380

gagtaaactt ggtctgacag ttaccaatgc ttaatcagtg aggcacctat ctcagcgatc   1440

tgtctatttc gttcatccat agttgcctga ctccccgtcg tgtagataac tacgatacgg   1500

gagggcttac catctggccc cagtgctgca atgataccgc gagacccacg ctcaccggct   1560

ccagatttat cagcaataaa ccagccagcc ggaagggccg agcgcagaag tggtcctgca   1620

actttatccg cctccatcca gtctattaat tgttgccggg aagctagagt aagtagttcg   1680

ccagttaata gtttgcgcaa cgttgttgcc attgctacag gcatcgtggt gtcacgctcg   1740

tcgtttggta tggcttcatt cagctccggt tcccaacgat caaggcgagt tacatgatcc   1800
```

-continued cccatgttgt gcaaaaaagc ggttagctcc ttcggtcctc cgatcgttgt cagaagtaag 1860
ttggccgcag tgttatcact catggttatg gcagcactgc ataattctct tactgtcatg 1920
ccatccgtaa gatgcttttc tgtgactggt gagtactcaa ccaagtcatt ctgagaatag 1980
tgtatgcggc gaccgagttg ctcttgcccg gcgtcaatac gggataatac cgcgccacat 2040
agcagaactt taaaagtgct catcattgga aaacgttctt cggggcgaaa actctcaagg 2100
atcttaccgc tgttgagatc cagttcgatg taacccactc gtgcacccaa ctgatcttca 2160
gcatctttta ctttcaccag cgtttctggg tgagcaaaaa caggaaggca aaatgccgca 2220
aaaaagggaa taagggcgac acggaaatgt tgaatactca tactcttcct ttttcaatat 2280
tattgaagca tttatcaggg ttattgtctc atgagcggat acatatttga atgtatttag 2340
aaaaataaac aaataggggt tccgcgcaca tttccccgaa aagtgccacc tgacgcgccc 2400
tgtagcggcg cattaagcgc ggcgggtgtg gtggttacgc gcagcgtgac cgctacactt 2460
gccagcgccc tagcgcccgc tcctttcgct ttcttccctt cctttctcgc cacgttcgcc 2520
ggctttcccc gtcaagctct aaatcggggg ctccctttag ggttccgatt tagtgcttta 2580
cggcacctcg accccaaaaa acttgattag ggtgatggtt cacgtagtgg gccatcgccc 2640
tgatagacgg tttttcgccc tttgacgttg gagtccacgt tctttaatag tggactcttg 2700
ttccaaactg gaacaacact caaccctatc tcggtctatt cttttgattt ataagggatt 2760
ttgccgattt cggcctattg gttaaaaaat gagctgattt aacaaaaatt taacgcgaat 2820
tttaacaaaa tattaacgct tacaatttcc attcgccatt caggctgcgc aactgttggg 2880
aagggcgatc ggtgcgggcc tcttcgctat tacgccagct ggcgaaaggg ggatgtgctg 2940
caaggcgatt aagttgggta acgccagggt tttcccagtc acgacgttgt aaaacgacgg 3000
ccagtgaatt gtaatacgac tcactatagg gcgaattggg taccgggccc cccctcgagg 3060
tcgatggtgt cgataagctt gatatcgaat tcatgtcaca caaaccgatc ttcgcctcaa 3120
ggaaacctaa ttctacatcc gagagactgc cgagatccag tctacactga ttaattttcg 3180
ggccaataat ttaaaaaaat cgtgttatat aatattatat gtattatata tatacatcat 3240
gatgatactg acagtcatgt cccattgcta aatagacaga ctccatctgc cgcctccaac 3300
tgatgttctc aatatttaag ggtcatctc gcattgttta ataataaaca gactccatct 3360
accgcctcca aatgatgttc tcaaaatata ttgtatgaac ttattttat tacttagtat 3420
tattagacaa cttacttgct ttatgaaaaa cacttcctat ttaggaaaca atttataatg 3480
gcagttcgtt catttaacaa tttatgtaga ataaatgtta taaatgcgta tgggaaatct 3540
taaatatgga tagcataaat gatatctgca ttgcctaatt cgaaatcaac agcaacgaaa 3600
aaaatccctt gtacaacata aatagtcatc gagaaatatc aactatcaaa gaacagctat 3660
tcacacgtta ctattgagat tattattgga cgagaatcac acactcaact gtctttctct 3720
cttctagaaa tacaggtaca agtatgtact attctcattg ttcatacttc tagtcatttc 3780
atcccacata ttccttggat ttctctccaa tgaatgacat tctatcttgc aaattcaaca 3840
attataataa gatataccaa agtagcggta tagtggcaat caaaaagctt ctctggtgtg 3900
cttctcgtat ttatttttat tctaatgatc cattaaaggt atatatttat ttcttgttat 3960
ataatccttt tgtttattac atgggctgga tacataaagg tattttgatt taatttttg 4020
cttaaattca atcccccctc gttcagtgtc aactgtaatg gtaggaaatt accatacttt 4080
tgaagaagca aaaaaaatga aagaaaaaaa aaatcgtatt tccaggttag acgttccgca 4140
gaatctagaa tgcggtatgc ggtacattgt tcttcgaacg taaaagttgc gctccctgag 4200

```
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaattcc ctagtcccag tgtacacccg ccgatatcgc ttaccctgca gccggattaa   4560
ggttggcaat ttttcacgtc cttgtctccg caattactca ccgggtggtt tataagattg   4620
caagcgtctt gatttgtctc tgtatactaa catgcaatcg cgactcgccc gacgggccac   4680
taacctggcc agaatctcca gatccaagta ttctcttggt ctgcgatatg tttccaacac   4740
aaaagcccct gctgcccagc cggcaactgc tgagtgagta ttccttgcca taaacgaccc   4800
agaaccactg tatagtgttt ggaagcacta gtcagaagac cagcgaaaac aggtggaaaa   4860
aactgagacg aaaagcaacg accagaaatg taatgtgtgg aaaagcgaca cacacagagc   4920
agataaagag gtgacaaata acgacaaatg aaatatcagt atcttcccac aatcactacc   4980
tctcagctgt ctgaaggtgc ggctgatata tccatcccac gtctaacgta tggagtgtga   5040
tagaatatga cgacacaagc atgagaactc gctctctatc caaccaccga aacactgtca   5100
ctacagccgt tcttgttgct ccattcgctt ttgtgattcc atgccttctc tggtgactga   5160
caacattcct tccttttctc cagccctgtt gttatctgct catgacctac ggccactctc   5220
tatcgcatac taacatagac gatcccagcc cgctccccac ttccagggca ccgttggcaa   5280
gcctcctatc ctcaagaagg ctgaggctgc caacgctgac atggacgagt ccttcatcgg   5340
aatgtctgga ggagagatct tccacgagat gatgctgcga cacaacgtcg acactgtctt   5400
cggttacccc ggtggagcca ttctccccgt ctttgacgcc attcacaact ctgagtactt   5460
caactttgtg ctccctcgac acgagcaggg tgccggccac atggccgagg gctacgctcg   5520
agcctctggt aagcccggtg tcgttctcgt cacctctggc cccggtgcca ccaacgtcat   5580
cacccccatg caggacgctc tttccgatgg taccccccatg gttgtcttca ccggtcaggt   5640
cctgacctcc gttatcggca ctgacgcctt ccaggaggcc gatgttgtcg gcatctcccg   5700
atcttgcacc aagtggaacg tcatggtcaa gaacgttgct gagctccccc gacgaatcaa   5760
cgaggccttt gagattgcta cttccggccg acccggtccc gttctcgtcg atctgcccaa   5820
ggatgttact gctgccatcc tgcgagagcc catccccacc aagtccacca ttccctcgca   5880
ttctctgacc aacctcacct ctgccgccgc caccgagttc cagaagcagg ctatccagcg   5940
agccgccaac ctcatcaacc agtccaagaa gcccgtcctt tacgtcggac agggtatcct   6000
tggctccgag gagggtccta agctgcttaa ggagctggct gagaaggccg agattcccgt   6060
caccactact ctgcagggtc ttggtgcctt tgacgagcga gaccccaagt ctctgcacat   6120
gctcggtatg cacggttccg gctacgccaa catggccatg cagaacgctg actgtatcat   6180
tgctctcggc gcccgatttg atgaccgagt taccggctcc atccccaagt ttgcccccga   6240
ggctcgagcc gctgcccttg agggtcgagg tggtattgtt cactttgaga tccaggccaa   6300
gaacatcaac aaggttgttc aggccaccga agccgttgag ggagacgtta ccgagtctgt   6360
ccgacagctc atccccctca tcaacaaggt ctctgccgct gagcgagctc cctggactga   6420
gactatccag tcctggaagc agcagttccc cttcctcttc gaggctgaag gtgaggatgg   6480
tgttatcaag ccccagtccg tcattgctct gctctctgac ctgacagaga acaacaagga   6540
```

-continued

```
caagaccatc atcaccaccg gtgttggtca gcatcagatg tggactgccc agcatttccg   6600
atggcgacac cctcgaacca tgatcacttc tggtggtctt ggaactatgg gttacggcct   6660
gcccgccgct atcggcgcca aggttgcccg acctgactgc gacgtcattg acatcgatgg   6720
tgacgcttct ttcaacatga ctctgaccga gctgtccacc gccgttcagt tcaacattgg   6780
cgtcaaggct attgtcctca acaacgagga acagggtatg gtcacccagc tgcagtctct   6840
cttctacgag aaccgatact gccacactca tcagaagaac cccgacttca tgaagctggc   6900
cgagtccatg ggcatgaagg gtatccgaat cactcacatt gaccagctgg aggccggtct   6960
caaggagatg ctcgcataca agggccctgt gctcgttgag gttgttgtcg acaagaagat   7020
ccccgttctt cccatggttc ccgctggtaa ggctttgcat gagttccttg tctacgacgc   7080
tgacgccgag gctgcttctc gacccgatcg actgaagaat gccccccgccc ctcacgtcca   7140
ccagaccacc tttgagaact aagtggaaag gaacacaagc aatccgaacc aaaaataatt   7200
ggggtcccgt gcccacagag tctagtgcag acctaaaatg accacagtaa attatagctg   7260
ttattaaaca tgagattttg accaacaaga gcgtaggaat gttattagct actacttgta   7320
catacacagc atttgtttta aataatgttg cctccagggg cagtgagatc aggacccaga   7380
tccgtggcca gctctctgac ttcagaccgc ttgtacttaa gcagctcgca acactgttgt   7440
cgaggattga acttgccata ttcgattttg tggtcatgaa tccagcacac ctcatttaaa   7500
tgtagctaac ggtagcaggc gaactactgg tacatacctc cccggaata tgtacaggca   7560
taatgcgtat ctgtgggaca tgtggtcgtt gcgccattat gtaagcagcg tgtactcctc   7620
tgactgtcca tatggtttgc tccatctcac cctcatcgtt ttcattgttc acaggcggcc   7680
acaaaaaaac tgtcttctct ccttctctct tcgccttagt ctactcggac cagttttagt   7740
ttagcttggc gccactggat aaatgagacc tcaggccttg tgatgaggag gtcacttatg   7800
aagcatgtta ggaggtgctt gtatggatag agaagcaccc aaaataataa gaataataat   7860
aaaacagggg gcgttgtcat ttcatatcgt gttttcacca tcaatacacc tccaaacaat   7920
gcccttcatg tggccagccc caatattgtc ctgtagttca actctatgca gctcgtatct   7980
tattgagcaa gtaaaactct gtcagccgat attgcccgac ccgcgacaag ggtcaacaag   8040
gtggtgtaag gccttcgcag aagtcaaaac tgtgccaaac aaacatctag agtctctttg   8100
gtgtttctcg catatatttw atcggctgtc ttacgtattt gcgcctcggt accggactaa   8160
tttcggatca tccccaatac gctttttctt cgcagctgtc aacagtgtcc atgatctatc   8220
cacctaaatg ggtcatatga ggcgtataat ttcgtggtgc tgataataat tcccatatat   8280
ttgacacaaa acttcccccc ctagacatac atctcacaat ctcacttctt gtgcttctgt   8340
cacacatctc ctccagctga cttcaactca cacctctgcc ccagttggtc tacagcggta   8400
taaggtttct ccgcatagag gtgcaccact cctcccgata cttgtttgtg tgacttgtgg   8460
gtcacgacat atatatctac acacattgcg ccaccctttg gttcttccag cacaacaaaa   8520
acacgacacg ctaaccatgg ccaatttact gaccgtacac caaaatttgc ctgcattacc   8580
ggtcgatgca acgagtgatg aggttcgcaa gaacctgatg gacatgttca gggatcgcca   8640
ggcgttttct gagcatacct ggaaaatgct tctgtccgtt tgccggtcgt gggcggcatg   8700
gtgcaagttg aataaccgga aatggtttcc cgcagaacct gaagatgttc gcgattatct   8760
tctatatctt caggcgcgcg gtctggcagt aaaaactatc cagcaacatt tgggccagct   8820
aaacatgctt catcgtcggt ccgggctgcc acgaccaagt gacagcaatg ctgtttcact   8880
ggttatgcgg cggatccgaa aagaaaacgt tgatgccggt gaacgtgcaa aacaggctct   8940
```

agcgttcgaa cgcactgatt tcgaccaggt tcgttcactc atggaaaata gcgatcgctg 9000
ccaggatata cgtaatctgg catttctggg gattgcttat aacaccctgt tacgtatagc 9060
cgaaattgcc aggatcaggg ttaaagatat ctcacgtact gacggtggga gaatgttaat 9120
ccatattggc agaacgaaaa cgctggttag caccgcaggt gtagagaagg cacttagcct 9180
gggggtaact aaactggtcg agcgatggat ttccgtctct ggtgtagctg atgatccgaa 9240
taactacctg ttttgccggg tcagaaaaaa tggtgttgcc gcgccatctg ccaccagcca 9300
gctatcaact cgcgccctgg aagggatttt tgaagcaact catcgattga tttacggcgc 9360
taaggatgac tctggtcaga gatacctggc ctggtctgga cacagtgccc gtgtcggagc 9420
cgcgcgagat atggcccgcg ctggagtttc aataccggag atcatgcaag ctggtggctg 9480
gaccaatgta aatattgtca tgaactatat ccgtaacctg gatagtgaaa caggggcaat 9540
ggtgcgcctg ctggaagatg gcgattaagc 9570

<210> SEQ ID NO 30
<211> LENGTH: 15743
<212> TYPE: DNA
<213> ORGANISM: Artificial Sequence
<220> FEATURE:
<223> OTHER INFORMATION: Plasmid pZP2-2988

<400> SEQUENCE: 30
ggccgcatgt acatacaaga ttatttatag aaatgaatcg cgatcgaaca aagagtacga 60
gtgtacgagt aggggatgat gataaaagtg gaagaagttc cgcatctttg gatttatcaa 120
cgtgtaggac gatacttcct gtaaaaatgc aatgtcttta ccataggttc tgctgtagat 180
gttattaact accattaaca tgtctacttg tacagttgca gaccagttgg agtatagaat 240
ggtacactta ccaaaaagtg ttgatggttg taactacgat atataaaact gttgacggga 300
tctgtatatt cggtaagata tattttgtgg ggttttagtg gtgtttaaac agtgtacgca 360
gtactataga ggaacaattg ccccggagaa gacggccagg ccgcctagat gacaaattca 420
acaactcaca gctgactttc tgccattgcc actagggggg ggccttttta tatggccaag 480
ccaagctctc cacgtcggtt gggctgcacc caacaataaa tgggtagggt tgcaccaaca 540
aagggatggg atgggggta gaagatacga ggataacggg gctcaatggc acaaataaga 600
acgaatactg ccattaagac tcgtgatcca gcgactgaca ccattgcatc atctaagggc 660
ctcaaaacta cctcggaact gctgcgctga tctggacacc acagaggttc cgagcacttt 720
aggttgcacc aaatgtccca ccaggtgcag gcagaaaacg ctggaacagc gtgtacagtt 780
tgtcttaaca aaaagtgagg gcgctgaggt cgagcagggt ggtgtgactt gttatagcct 840
ttagagctgc gaaagcgcgt atggatttgg ctcatcaggc cagattgagg gtctgtggac 900
acatgtcatg ttagtgtact tcaatcgccc cctggatata gccccgacaa taggccgtgg 960
cctcattttt ttgccttccg cacatttcca ttgctcggta cccacacctt gcttctcctg 1020
cacttgccaa ccttaatact ggtttacatt gaccaacatc ttacaagcgg ggggcttgtc 1080
tagggtatat ataaacagtg gctctcccaa tcggttgcca gtctcttttt tcctttcttt 1140
ccccacagat tcgaaatcta aactacacat cacaccatgg aggtcgtgaa cgaaatcgtc 1200
tccattggcc aggaggttct tcccaaggtc gactatgctc agctctggtc tgatgcctcg 1260
cactgcgagg tgctgtacct ctccatcgcc ttcgtcatcc tgaagttcac ccttggtcct 1320
ctcggaccca agggtcagtc tcgaatgaag tttgtgttca ccaactacaa cctgctcatg 1380

-continued

```
tccatctact cgctgggctc cttcctctct atggcctacg ccatgtacac cattggtgtc   1440
atgtccgaca actgcgagaa ggctttcgac aacaatgtct tccgaatcac cactcagctg   1500
ttctacctca gcaagttcct cgagtacatt gactccttct atctgcccct catgggcaag   1560
cctctgacct ggttgcagtt ctttcaccat ctcggagctc ctatggacat gtggctgttc   1620
tacaactacc gaaacgaagc cgtttggatc tttgtgctgc tcaacggctt cattcactgg   1680
atcatgtacg gctactattg gacccgactg atcaagctca agttccctat gcccaagtcc   1740
ctgattactt ctatgcagat cattcagttc aacgttggct tctacatcgt ctggaagtac   1800
cggaacattc cctgctaccg acaagatgga atgagaatgt ttggctggtt tttcaactac   1860
ttctacgttg gtactgtcct gtgtctgttc ctcaacttct acgtgcagac ctacatcgtc   1920
cgaaagcaca agggagccaa aaagattcag tgagcggccg caagtgtgga tggggaagtg   1980
agtgcccggt tctgtgtgca caattggcaa tccaagatgg atggattcaa cacagggata   2040
tagcgagcta cgtggtggtg cgaggatata gcaacggata tttatgtttg acacttgaga   2100
atgtacgata caagcactgt ccaagtacaa tactaaacat actgtacata ctcatactcg   2160
tacccgggca acggtttcac ttgagtgcag tggctagtgc tcttactcgt acagtgtgca   2220
atactgcgta tcatagtctt tgatgtatat cgtattcatt catgttagtt gcgtacgggc   2280
gtcgttgctt gtgtgatttt tgaggaccca tccctttggt atataagtat actctggggt   2340
taaggttgcc cgtgtagtct aggttatagt tttcatgtga aataccgaga gccgagggag   2400
aataaacggg ggtatttgga cttgtttttt tcgcggaaaa gcgtcgaatc aaccctgcgg   2460
gccttgcacc atgtccacga cgtgtttctc gccccaattc gccccttgca cgtcaaaatt   2520
aggcctccat ctagacccct ccataacatg tgactgtggg gaaaagtata agggaaacca   2580
tgcaaccata gacgacgtga aagacgggga ggaaccaatg gaggccaaag aaatggggta   2640
gcaacagtcc aggagacaga caaggagaca aggagagggc gcccgaaaga tcggaaaaac   2700
aaacatgtcc aattggggca gtgacggaaa cgacacggac acttcagtac aatggaccga   2760
ccatctccaa gccagggtta ttccggtatc accttggccg taacctcccg ctggtacctg   2820
atattgtaca cgttcacatt caatatactt tcagctacaa taagagaggc tgtttgtcgg   2880
gcatgtgtgt ccgtcgtatg ggtgatgtc cgagggcgaa attcgctaca agcttaactc   2940
tggcgcttgt ccagtatgaa tagacaagtc aagaccagtg gtgccatgat tgacagggag   3000
gtacaagact tcgatactcg agcattactc ggacttgtgg cgattgaaca gacgggcgat   3060
cgcttctccc ccgtattgcc ggcgcgccag ctgcattaat gaatcggcca acgcgcgggg   3120
agaggcggtt tgcgtattgg gcgctcttcc gcttcctcgc tcactgactc gctgcgctcg   3180
gtcgttcggc tgcggcgagc ggtatcagct cactcaaagg cggtaatacg gttatccaca   3240
gaatcagggg ataacgcagg aaagaacatg tgagcaaaag gccagcaaaa ggccaggaac   3300
cgtaaaaagg ccgcgttgct ggcgtttttc cataggctcc gcccccctga cgagcatcac   3360
aaaaatcgac gctcaagtca gaggtggcga aacccgacag gactataaag ataccaggcg   3420
tttccccctg gaagctccct cgtgcgctct cctgttccga ccctgccgct taccggatac   3480
ctgtccgcct ttctcccttc gggaagcgtg gcgctttctc atagctcacg ctgtaggtat   3540
ctcagttcgg tgtaggtcgt tcgctccaag ctgggctgtg tgcacgaacc ccccgttcag   3600
cccgaccgct gcgccttatc cggtaactat cgtcttgagt ccaacccggt aagacacgac   3660
ttatcgccac tggcagcagc cactggtaac aggattagca gagcgaggta tgtaggcggt   3720
gctacagagt tcttgaagtg gtggcctaac tacggctaca ctagaagaac agtatttggt   3780
```

atctgcgctc tgctgaagcc agttaccttc ggaaaaagag ttggtagctc ttgatccggc 3840
aaacaaacca ccgctggtag cggtggtttt tttgtttgca agcagcagat tacgcgcaga 3900
aaaaaaggat ctcaagaaga tcctttgatc ttttctacgg ggtctgacgc tcagtggaac 3960
gaaaactcac gttaagggat tttggtcatg agattatcaa aaaggatctt cacctagatc 4020
cttttaaatt aaaaatgaag ttttaaatca atctaaagta tatatgagta aacttggtct 4080
gacagttacc aatgcttaat cagtgaggca cctatctcag cgatctgtct atttcgttca 4140
tccatagttg cctgactccc cgtcgtgtag ataactacga tacgggaggg cttaccatct 4200
ggccccagtg ctgcaatgat accgcgagac ccacgctcac cggctccaga tttatcagca 4260
ataaaccagc cagccggaag ggccgagcgc agaagtggtc ctgcaacttt atccgcctcc 4320
atccagtcta ttaattgttg ccgggaagct agagtaagta gttcgccagt taatagtttg 4380
cgcaacgttg ttgccattgc tacaggcatc gtggtgtcac gctcgtcgtt tggtatggct 4440
tcattcagct ccggttccca acgatcaagg cgagttacat gatcccccat gttgtgcaaa 4500
aaagcggtta gctccttcgg tcctccgatc gttgtcagaa gtaagttggc cgcagtgtta 4560
tcactcatgg ttatggcagc actgcataat tctcttactg tcatgccatc cgtaagatgc 4620
ttttctgtga ctggtgagta ctcaaccaag tcattctgag aatagtgtat gcggcgaccg 4680
agttgctctt gcccggcgtc aatacgggat aataccgcgc cacatagcag aactttaaaa 4740
gtgctcatca ttggaaaacg ttcttcgggg cgaaaactct caaggatctt accgctgttg 4800
agatccagtt cgatgtaacc cactcgtgca cccaactgat cttcagcatc ttttactttc 4860
accagcgttt ctgggtgagc aaaaacagga aggcaaaatg ccgcaaaaaa gggaataagg 4920
gcgacacgga aatgttgaat actcatactc ttcctttttc aatattattg aagcatttat 4980
cagggttatt gtctcatgag cggatacata tttgaatgta tttagaaaaa taaacaaata 5040
ggggttccgc gcacatttcc ccgaaaagtg ccacctgatg cggtgtgaaa taccgcacag 5100
atgcgtaagg agaaaatacc gcatcaggaa attgtaagcg ttaatatttt gttaaaattc 5160
gcgttaaatt tttgttaaat cagctcattt tttaaccaat aggccgaaat cggcaaaatc 5220
ccttataaat caaaagaata gaccgagata gggttgagtg ttgttccagt ttggaacaag 5280
agtccactat taaagaacgt ggactccaac gtcaaagggc gaaaaaccgt ctatcagggc 5340
gatggcccac tacgtgaacc atcaccctaa tcaagttttt tggggtcgag gtgccgtaaa 5400
gcactaaatc ggaaccctaa agggagcccc cgatttagag cttgacgggg aaagccggcg 5460
aacgtggcga gaaaggaagg gaagaaagcg aaaggagcgg gcgctagggc gctggcaagt 5520
gtagcggtca cgctgcgcgt aaccaccaca cccgccgcgc ttaatgcgcc gctacagggc 5580
gcgtccattc gccattcagg ctgcgcaact gttgggaagg gcgatcggtg cgggcctctt 5640
cgctattacg ccagctggcg aaagggggat gtgctgcaag gcgattaagt tgggtaacgc 5700
cagggttttc ccagtcacga cgttgtaaaa cgacggccag tgaattgtaa tacgactcac 5760
tatagggcga attgggcccg acgtcgcatg cgctgatgac actttggtct gaaagagatg 5820
cattttgaat cccaaacttg cagtgcccaa gtgacataca tctccgcgtt ttggaaaatg 5880
ttcagaaaca gttgattgtg ttggaatggg gaatggggaa tggaaaaatg actcaagtat 5940
caattccaaa aacttctctg gctggcagta cctactgtcc atactactgc attttctcca 6000
gtcaggccac tctatactcg acgacacagt agtaaaaccc agataatttc gacataaaca 6060
agaaaacaga cccaataata tttatatata gtcagccgtt tgtccagttc agactgtaat 6120

-continued agccgaaaaa aaatccaaag tttctattct aggaaaatat attccaatat ttttaattct 6180
taatctcatt tattttattc tagcgaaata catttcagct acttgagaca tgtgataccc 6240
acaaatcgga ttcggactcg gttgttcaga agagcatatg gcattcgtgc tcgcttgttc 6300
acgtattctt cctgttccat ctcttggccg acaatcacac aaaaatgggg ttttttttt 6360
aattctaatg attcattaca gcaaaattga gatatagcag accacgtatt ccataatcac 6420
caaggaagtt cttgggcgtc ttaattaact cacctgcagg attgagacta tgaatggatt 6480
cccgtgcccg tattactcta ctaatttgat cttggaacgc gaaaatacgt ttctaggact 6540
ccaaagaatc tcaactcttg tccttactaa atatactacc catagttgat ggtttacttg 6600
aacagagagg acatgttcac ttgacccaaa gtttctcgca tctcttggat atttgaacaa 6660
cggcgtccac tgaccgtcag ttatccagtc acaaaacccc cacattcata cattcccatg 6720
tacgtttaca aagttctcaa ttccatcgtg caaatcaaaa tcacatctat tcattcatca 6780
tatataaacc catcatgtct actaacactc acaactccat agaaaacatc gactcagaac 6840
acacgctcca tgcggccgct tactgagcct tggcaccggg ctgcttctcg gccattcgag 6900
cgaactggga caggtatcgg agcaggatga cgagaccttc atggggcaga gggtttcggt 6960
aggggaggtt gtgcttctgg cacagctgtt ccacctggta ggaaacggca gtgaggttgt 7020
gtcgaggcag ggtgggccag agatggtgct cgatctggta gttcaggcct ccaaagaacc 7080
agtcagtaat gatgcctcgt cgaatgttca tggtctcatg gatctgaccc acagagaagc 7140
catgtccgtc ccagacggaa tcaccgatct tctccagagg gtagtggttc atgaagacca 7200
cgatggcaat tccgaagcca ccgacgagct cggaaacaaa gaacaccagc atcgaggtca 7260
ggatggaggg cataaagaag aggtggaaca gggtcttgag agtccagtgc agagcgagtc 7320
caatggcctc tttcttgtac tgagatcggt agaactggtt gtctcggtcc ttgagggatc 7380
gaacggtcag cacagactgg aaacaccaga tgaatcgcag gagaatacag atgaccagga 7440
aatagtactg ttggaactga atgagctttc gggagatggg agaagctcga gtgacatcgt 7500
cctcggacca ggcgagcaga ggcaggttat caatgtcggg atcgtgaccc tgaacgttgg 7560
tagcagaatg atgggcgttg tgtctgtcct tccaccaggt cacggagaag ccctggagtc 7620
cgttgccaaa gaccagaccc aggacgttat tccagtttcg gttcttgaag gtctggtggt 7680
ggcagatgtc atgagacagc catcccattt gctggtagtg cataccgagc acgagagcac 7740
caatgaagta caggtggtac tggaccagca tgaagaaggc aagcacgcca agacccaggg 7800
tggtcaagat cttgtacgag taccagaggg gagaggcgtc aaacatgcca gtggcgatca 7860
gctcttctcg gagctttcgg aaatcctcct gagcttcgtt gacggcagcc tggggaggca 7920
gctcggaagc ctggttgatc ttgggcattc gcttgagctt gtcgaaggct tcctgagagt 7980
gcataaccat gaaggcgtca gtagcatctc gtccctggta gttctcaatg atttcagctc 8040
caccagggtg gaagttcacc caagcggaga cgtcgtacac ctttccgtcg atgacgaggg 8100
gcagagcctg tcgagaagcc ttcaccatgg ttgtgaatta gggtggtgag aatggttggt 8160
tgtagggaag aatcaaaggc cggtctcggg atccgtgggt atatatatat atatatatat 8220
atacgatcct tcgttacctc cctgttctca aaactgtggt ttttcgtttt tcgtttttg 8280
cttttttga ttttttagg gccaactaag cttccagatt tcgctaatca cctttgtact 8340
aattacaaga aaggaagaag ctgattagag ttgggctttt tatgcaactg tgctactcct 8400
tatctctgat atgaaagtgt agacccaatc acatcatgtc atttagagtt ggtaatactg 8460
ggaggataga taaggcacga aaacgagcca tagcagacat gctgggtgta gccaagcaga 8520

```
agaaagtaga tgggagccaa ttgacgagcg agggagctac gccaatccga catacgacac    8580
gctgagatcg tcttggccgg ggggtaccta cagatgtcca agggtaagtg cttgactgta    8640
attgtatgtc tgaggacaaa tatgtagtca gccgtataaa gtcataccag gcaccagtgc    8700
catcatcgaa ccactaactc tctatgatac atgcctccgg tattattgta ccatgcgtcg    8760
ctttgttaca tacgtatctt gcctttttct ctcagaaact ccagactttg gctattggtc    8820
gagataagcc cggaccatag tgagtctttc acactctaca tttctccctt gctccaacta    8880
tttaaattcc ttcacttcaa gttcattctt catctgcttc tgttttactt tgacaggcaa    8940
atgaagacat ggtacgactt gatggaggcc aagaacgcca tttcaccccg agacaccgaa    9000
gtgcctgaaa tcctggctgc ccccattgat aacatcggaa actacggtat tccggaaagt    9060
gtatatagaa cctttcccca gcttgtgtct gtggatatgg atggtgtaat ccccttttgag    9120
tactcgtctt ggcttctctc cgagcagtat gaggctctct aatctagcgc atttaatatc    9180
tcaatgtatt tatatattta tcttctcatg cggccgctta ctgagccttg gcaccgggct    9240
gcttctcggc cattcgagcg aactgggaca ggtatcggag caggatgacg agaccttcat    9300
ggggcagagg gtttcggtag gggaggttgt gcttctggca cagctgttcc acctggtagg    9360
aaacggcagt gaggttgtgt cgaggcaggg tgggccagag atggtgctcg atctggtagt    9420
tcaggcctcc aaagaaccag tcagtaatga tgcctcgtcg aatgttcatg gtctcatgga    9480
tctgacccac agagaagcca tgtccgtccc agacggaatc accgatcttc tccagagggt    9540
agtggttcat gaagaccacg atggcaattc cgaagccacc gacgagctcg gaaacaaaga    9600
acaccagcat cgaggtcagg atggagggca taaagaagag gtggaacagg gtcttgagag    9660
tccagtgcag agcgagtcca atggcctctt tcttgtactg agatcggtag aactggttgt    9720
ctcggtcctt gagggatcga acggtcagca cagactggaa acaccagatg aatcgcagga    9780
gaatacagat gaccaggaaa tagtactgtt ggaactgaat gagctttcgg gagatgggag    9840
aagctcgagt gacatcgtcc tcggaccagg cgagcagagg caggttatca atgtcgggat    9900
cgtgaccctg aacgttggta gcagaatgat gggcgttgtg tctgtccttc caccaggtca    9960
cggagaagcc ctggagtccg ttgccaaaga ccagacccag gacgttattc cagtttcggt   10020
tcttgaaggt ctggtggtgg cagatgtcat gagacagcca tcccatttgc tggtagtgca   10080
taccgagcac gagagcacca atgaagtaca ggtggtactg gaccagcatg aagaaggcaa   10140
gcacgccaag acccagggtg gtcaagatct tgtacgagta ccagagggga gaggcgtcaa   10200
acatgccagt ggcgatcagc tcttctcgga gctttcggaa atcctcctga gcttcgttga   10260
cggcagcctg gggaggcagc tcggaagcct ggttgatctt gggcattcgc ttgagcttgt   10320
cgaaggcttc ctgagagtgc ataaccatga aggcgtcagt agcatctcgt ccctggtagt   10380
tctcaatgat ttcagctcca ccagggtgga agttcaccca agcggagacg tcgtacacct   10440
ttccgtcgat gacgaggggc agagcctgtc gagaagcctt caccatgggc aggacctgtg   10500
ttagtacatt gtcggggagt catcaattgg ttcgacaggt tgtcgactgt tagtatgagc   10560
tcaattgggc tctggtgggt cgatgacact tgtcatctgt ttctgttggg tcatgtttcc   10620
atcaccttct atggtactca caattcgtcc gattcgcccg aatccgttaa taccgacttt   10680
gatggccatg ttgatgtgtg tttaattcaa gaatgaatat agagaagaga agaagaaaaa   10740
agattcaatt gagccggcga tgcagaccct tatataaatg ttgccttgga cagacggagc   10800
aagcccgccc aaacctacgt tcggtataat atgttaagct ttttaacaca aaggtttggc   10860
```

ttggggtaac ctgatgtggt gcaaaagacc gggcgttggc gagccattgc gcgggcgaat 10920
ggggccgtga ctcgtctcaa attcgagggc gtgcctcaat tcgtgccccc gtggcttttt 10980
cccgccgttt ccgccccgtt tgcaccactg cagccgcttc tttggttcgg acaccttgct 11040
gcgagctagg tgccttgtgc tacttaaaaa gtggcctccc aacaccaaca tgacatgagt 11100
gcgtgggcca agacacgttg gcggggtcgc agtcggctca atggcccgga aaaaacgctg 11160
ctggagctgg ttcggacgca gtccgccgcg gcgtatggat atccgcaagg ttccatagcg 11220
ccattgccct ccgtcggcgt ctatcccgca acctctaaat agagcgggaa tataacccaa 11280
gcttcttttt tttcctttaa cacgcacacc cccaactatc atgttgctgc tgctgtttga 11340
ctctactctg tggaggggtg ctcccaccca acccaaccta caggtggatc cggcgctgtg 11400
attggctgat aagtctccta tccggactaa ttctgaccaa tgggacatgc gcgcaggacc 11460
caaatgccgc aattacgtaa ccccaacgaa atgcctaccc ctctttggag cccagcggcc 11520
ccaaatcccc ccaagcagcc cggttctacc ggcttccatc tccaagcaca agcagcccgg 11580
aattccttta cctgcaggat aacttcgtat aatgtatgct atacgaagtt atgatctctc 11640
tcttgagctt ttccataaca agttcttctg cctccaggaa gtccatgggt ggtttgatca 11700
tggttttggt gtagtggtag tgcagtggtg gtattgtgac tggggatgta gttgagaata 11760
agtcatacac aagtcagctt tcttcgagcc tcatataagt ataagtagtt caacgtatta 11820
gcactgtacc cagcatctcc gtatcgagaa acacaacaac atgccccatt ggacagatca 11880
tgcggataca caggttgtgc agtatcatac atactcgatc agacaggtcg tctgaccatc 11940
atacaagctg aacaagcgct ccatacttgc acgctctcta tatacacagt taaattacat 12000
atccatagtc taacctctaa cagttaatct tctggtaagc ctcccagcca gccttctggt 12060
atcgcttggc ctcctcaata ggatctcggt tctggccgta cagacctcgg ccgacaatta 12120
tgatatccgt tccggtagac atgacatcct caacagttcg gtactgctgt ccgagagcgt 12180 ctccccttgtc gtcaagaccc accccggggg tcagaataag ccagtcctca gagtcgccct 12240
taggtcggtt ctgggcaatg aagccaacca caaactcggg gtcggatcgg gcaagctcaa 12300
tggtctgctt ggagtactcg ccagtggcca gagagccctt gcaagacagc tcggccagca 12360
tgagcagacc tctggccagc ttctcgttgg gagaggggac taggaactcc ttgtactggg 12420
agttctcgta gtcagagacg tcctccttct tctgttcaga gacagtttcc tcggcaccag 12480
ctcgcaggcc agcaatgatt ccggttccgg gtacaccgtg ggcgttggtg atatcggacc 12540
actcggcgat tcggtgacac cggtactggt gcttgacagt gttgccaata tctgcgaact 12600
ttctgtcctc gaacaggaag aaaccgtgct taagagcaag ttccttgagg gggagcacag 12660
tgccggcgta ggtgaagtcg tcaatgatgt cgatatgggt tttgatcatg cacacataag 12720
gtccgacctt atcggcaagc tcaatgagct ccttggtggt ggtaacatcc agagaagcac 12780
acaggttggt tttcttggct gccacgagct tgagcactcg agcggcaaag gcggacttgt 12840
ggacgttagc tcgagcttcg taggagggca ttttggtggt gaagaggaga ctgaaataaa 12900
tttagtctgc agaacttttt atcggaacct tatctggggc agtgaagtat atgttatggt 12960
aatagttacg agttagttga acttatagat agactggact atacggctat cggtccaaat 13020
tagaaagaac gtcaatggct ctctgggcgt cgcctttgcc gacaaaaatg tgatcatgat 13080
gaaagccagc aatgacgttg cagctgatat tgttgtcggc caaccgcgcc gaaaacgcag 13140
ctgtcagacc cacagcctcc aacgaagaat gtatcgtcaa agtgatccaa gcacactcat 13200
agttggagtc gtactccaaa ggcggcaatg acgagtcaga cagatactcg tcgacgcgat 13260
aacttcgtat aatgtatgct atacgaagtt atcgtacgat agttagtaga caacaatcga 13320
taacgtctcg taccaaccac agattacgac ccattcgcag tcacagttca ctagggtttg 13380
ggttgcatcc gttgagagcg gtttgttttt aaccttctcc atgtgctcac tcaggttttg 13440
ggttcagatc aaatcaaggc gtgaaccact ttgtttgagg acaaatgtga cacaaccaac 13500
cagtgtcagg ggcaagtccg tgacaaaggg gaagatacaa tgcaattact gacagttaca 13560
gactgcctcg atgccctaac cttgccccaa aataagacaa ctgtcctcgt ttaagcgcaa 13620
ccctattcag cgtcacgtca taatagcgtt tggatagcac tagtctatga ggagcgtttt 13680
atgttgcggt gagggcgatt ggtgctcata tgggttcaat tgaggtggcg gaacgagctt 13740
agtcttcaat tgaggtgcga gcgacacaat tgggtgtcac gtggcctaat tgacctcggg 13800
tcgtggagtc cccagttata cagcaaccac gaggtgcatg ggtaggagac gtcaccagac 13860
aatagggttt tttttggact ggagagggtt gggcaaaagc gctcaacggg ctgtttgggg 13920
agctgtgggg gaggaattgg cgatatttgt gaggttaacg gctccgattt gcgtgttttg 13980
tcgctcctgc atctccccat acccatatct tccctcccca cctctttcca cgataatttt 14040
acggatcagc aataaggttc cttctcctag tttccacgtc catatatatc tatgctgcgt 14100
cgtccttttc gtgacatcac caaaacacat acaacaatgg ctgttactga cgtccttaag 14160
cgaaagtccg gtgtcatcgt cggcgacgat gtccgagccg tgagtatcca cgacaagatc 14220
agtgtcgaga cgacgcgttt tgtgtaatga cacaatccga aagtcgctag caacacacac 14280
tctctacaca aactaaccca gctctccatg gcctccacct cggctctgcc caagcagaac 14340
cctgccctcc gacgaaccgt cacttccacc actgtgaccg actcggagtc tgctgccgtc 14400
tctccctccg attctcccag acactcggcc tcctctacat cgctgtcttc catgtccgag 14460
gtggacattg ccaagcccaa gtccgagtac ggtgtcatgc tggataccta cggcaaccag 14520
ttcgaagttc ccgacttcac catcaaggac atctacaacg ctattcccaa gcactgcttc 14580
aagcgatctg ctctcaaggg atacggctac attcttcgag acattgtcct cctgactacc 14640
actttcagca tctggtacaa ctttgtgaca cccgagtaca ttccctccac tcctgctcga 14700
gccggtctgt gggctgtgta caccgttctt cagggactct tcggtactgg actgtgggtc 14760
attgcccacg agtgtggaca tggtgctttc tccgattccc gaatcatcaa cgacattact 14820
ggctgggtgc ttcactcttc cctgcttgtt ccctacttca gctggcaaat ctcccaccgg 14880
aagcatcaca aggccactgg aaacatggag cgagacatgg tcttcgttcc tcgaacccga 14940
gagcagcaag ctactcgact cggcaagatg acccacgaac tcgcccatct taccgaggaa 15000
actcctgctt tcaccctgct catgcttgtg cttcagcaac tggtcggttg gcccaactat 15060
ctcattacca acgttactgg acacaactac catgagcggc agcgagaggg tcgaggcaag 15120
ggaaagcaca acggtcttgg cggtggagtt aaccatttcg atccccgatc tcctctgtac 15180
gagaacagcg acgccaagct catcgtgctc tccgacattg gcattggtct tatggccacc 15240
gctctgtact ttctcgttca gaagttcgga ttctacaaca tggccatctg gtacttcgtt 15300
ccctacttgt gggttaacca ctggctcgtc gccattacct ttctgcagca cacagatcct 15360
actcttcccc actacaccaa cgacgagtgg aactttgtgc gaggtgccgc tgcaaccatc 15420
gaccgagaga tgggcttcat tggacgtcat ctgctccacg gcattatcga gactcacgtc 15480
ctgcatcact acgtctcttc cattcccttc tacaatgcgg acgaagctac cgaggccatc 15540
aaacctatca tgggcaagca ctatcgagct gatgtccagg acggtcctcg aggattcatt 15600
cgagccatgt accgatctgc acgaatgtgc cagtgggttg aaccctccgc tggtgccgag 15660
ggagctggca agggtgtcct gttctttcga aaccgaaaca atgtgggcac tcctcccgct 15720
gtcatcaagc ccgttgccta agc 15743

<210> SEQ ID NO 31
<211> LENGTH: 6303
<212> TYPE: DNA
<213> ORGANISM: Artificial Sequence
<220> FEATURE:
<223> OTHER INFORMATION: Plasmid pZKUE3S

<400> SEQUENCE: 31
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgaggaaact gtctctgaac agaagaagga ggacgtctct 360
gactacgaga actcccagta caaggagttc ctagtcccct ctcccaacga gaagctggcc 420
agaggtctgc tcatgctggc cgagctgtct tgcaagggct ctctggccac tggcgagtac 480
tccaagcaga ccattgagct tgcccgatcc gaccccgagt ttgtggttgg cttcattgcc 540
cagaaccgac ctaagggcga ctctgaggac tggcttattc tgacccccgg ggtgggtctt 600
gacgacaagg gagacgctct cggacagcag taccgaactg ttgaggatgt catgtctacc 660
ggaacggata tcataattgt cggccgaggt ctgtacggcc agaaccgaga tcctattgag 720
gaggccaagc gataccagaa ggctggctgg gaggcttacc agaagattaa ctgttagagg 780
ttagactatg gatatgtaat ttaactgtgt atatagagag cgtgcaagta tggagcgctt 840
gttcagcttg tatgatggtc agacgacctg tctgatcgag tatgtatgat actgcacaac 900
ctgtgtatcc gcatgatctg tccaatgggg catgttgttg tgtttctcga tacggagatg 960
ctgggtacag tgctaatacg ttgaactact tatacttata tgaggctcga agaaagctga 1020
cttgtgtatg acttaattaa tcgagcttgg cgtaatcatg gtcatagctg tttcctgtgt 1080
gaaattgtta tccgctcaca attccacaca acatacgagc cggaagcata aagtgtaaag 1140
cctggggtgc ctaatgagtg agctaactca cattaattgc gttgcgctca ctgcccgctt 1200
tccagtcggg aaacctgtcg tgccagctgc attaatgaat cggccaacgc gcggggagag 1260
gcggtttgcg tattgggcgc tcttccgctt cctcgctcac tgactcgctg cgctcggtcg 1320
ttcggctgcg gcgagcggta tcagctcact caaaggcggt aatacggtta tccacagaat 1380
caggggataa cgcaggaaag aacatgtgag caaaaggcca gcaaaaggcc aggaaccgta 1440
aaaaggccgc gttgctggcg tttttccata ggctccgccc ccctgacgag catcacaaaa 1500
atcgacgctc aagtcagagg tggcgaaacc cgacaggact ataaagatac caggcgtttc 1560
cccctggaag ctccctcgtg cgctctcctg ttccgaccct gccgcttacc ggatacctgt 1620
ccgcctttct cccttcggga agcgtggcgc tttctcatag ctcacgctgt aggtatctca 1680
gttcggtgta ggtcgttcgc tccaagctgg gctgtgtgca cgaacccccc gttcagcccg 1740
accgctgcgc cttatccggt aactatcgtc ttgagtccaa cccggtaaga cacgacttat 1800
cgccactggc agcagccact ggtaacagga ttagcagagc gaggtatgta ggcggtgcta 1860
cagagttctt gaagtggtgg cctaactacg gctacactag aaggacagta tttggtatct 1920
gcgctctgct gaagccagtt accttcggaa aaagagttgg tagctcttga tccggcaaac 1980
aaaccaccgc tggtagcggt ggtttttttg tttgcaagca gcagattacg cgcagaaaaa 2040
aaggatctca agaagatcct ttgatctttt ctacggggtc tgacgctcag tggaacgaaa 2100
actcacgtta agggattttg gtcatgagat tatcaaaaag gatcttcacc tagatccttt 2160
taaattaaaa atgaagtttt aaatcaatct aaagtatata tgagtaaact tggtctgaca 2220
gttaccaatg cttaatcagt gaggcaccta tctcagcgat ctgtctattt cgttcatcca 2280
tagttgcctg actccccgtc gtgtagataa ctacgatacg ggagggctta ccatctggcc 2340
ccagtgctgc aatgataccg cgagacccac gctcaccggc tccagattta tcagcaataa 2400
accagccagc cggaagggcc gagcgcagaa gtggtcctgc aactttatcc gcctccatcc 2460
agtctattaa ttgttgccgg gaagctagag taagtagttc gccagttaat agtttgcgca 2520
acgttgttgc cattgctaca ggcatcgtgg tgtcacgctc gtcgtttggt atggcttcat 2580
tcagctccgg ttcccaacga tcaaggcgag ttacatgatc ccccatgttg tgcaaaaaag 2640
cggttagctc cttcggtcct ccgatcgttg tcagaagtaa gttggccgca gtgttatcac 2700
tcatggttat ggcagcactg cataattctc ttactgtcat gccatccgta agatgctttt 2760
ctgtgactgg tgagtactca accaagtcat tctgagaata gtgtatgcgg cgaccgagtt 2820
gctcttgccc ggcgtcaata cgggataata ccgcgccaca tagcagaact ttaaaagtgc 2880
tcatcattgg aaaacgttct tcggggcgaa aactctcaag gatcttaccg ctgttgagat 2940
ccagttcgat gtaacccact cgtgcaccca actgatcttc agcatctttt actttcacca 3000
gcgtttctgg gtgagcaaaa acaggaaggc aaaatgccgc aaaaaaggga ataagggcga 3060
cacggaaatg ttgaatactc atactcttcc tttttcaata ttattgaagc atttatcagg 3120
gttattgtct catgagcgga tacatatttg aatgtattta gaaaaataaa caaatagggg 3180
ttccgcgcac atttccccga aaagtgccac ctgacgcgcc ctgtagcggc gcattaagcg 3240
cggcgggtgt ggtggttacg cgcagcgtga ccgctacact tgccagcgcc ctagcgcccg 3300
ctcctttcgc tttcttccct tcctttctcg ccacgttcgc cggctttccc cgtcaagctc 3360
taaatcgggg gctcccttta gggttccgat ttagtgcttt acggcacctc gaccccaaaa 3420
aacttgatta gggtgatggt tcacgtagtg ggccatcgcc ctgatagacg gtttttcgcc 3480
ctttgacgtt ggagtccacg ttctttaata gtggactctt gttccaaact ggaacaacac 3540
tcaaccctat ctcggtctat tcttttgatt tataagggat tttgccgatt tcggcctatt 3600
ggttaaaaaa tgagctgatt taacaaaaat ttaacgcgaa ttttaacaaa atattaacgc 3660
ttacaatttc cattcgccat tcaggctgcg caactgttgg gaagggcgat cggtgcgggc 3720
ctcttcgcta ttacgccagc tggcgaaagg gggatgtgct gcaaggcgat taagttgggt 3780
aacgccaggg ttttcccagt cacgacgttg taaaacgacg gccagtgaat tgtaatacga 3840
ctcactatag ggcgaattgg gtaccgggcc ccccctcgag gtcgacgagt atctgtctga 3900
ctcgtcattg catgcctttg gagtacgact ccaactatga gtgtgcttgg atcactttga 3960
cgatacattc ttcgttggag gctgtgggtc tgacagctgc gttttcggcg cggttggccg 4020
acaacaatat cagctgcaac gtcattgctg gctttcatca tgatcacatt tttgtcggca 4080
aaggcgacgc ccagagagcc attgacgttc tttctaattt ggaccgatag ccgtatagtc 4140
cagtctatct ataagttcaa ctaactcgta actattacca taacatatac ttcactgccc 4200
cagataaggt tccgataaaa agttctgcag actaaattta tttcagtctc ctcttcacca 4260
ccaaaatgcc ctcctacgaa gctcgagtgc tcaagctcgt ggcagccaag aaaaccaacc 4320
tgtgtgcttc tctggatgtt accaccacca aggagctcat tgagcttgcc gataaggtcg 4380
gaccttatgt gtgcatgatc aaaacccata tcgacatcat tgacgacttc acctacgccg 4440
gcactgtgct ccccctcaag gaacttgctc ttaagcacgg tttcttcctg ttcgaggaca 4500
gaaagttcgc agatattggc aacactgtca agcaccagta ccggtgtcac cgaatcgccg 4560
agtggtccga tatcaccaac gcccacggtg tttaaacccg gaaccggaat cgataagctt 4620
gatatcgaat tcatgctgtt catcgtggtt aatgctgctg tgtgctgtgt gtgtgtgttg 4680
tttggcgctc attgttgcgt tatgcagcgt acaccacaat attggaagct tattagcctt 4740
tctatttttt cgtttgcaag gcttaacaac attgctgtgg agagggatgg ggatatggag 4800
gccgctggag ggagtcggag aggcgttttg gagcggcttg gcctggcgcc cagctcgcga 4860
aacgcaccta ggaccctttg gcacgccgaa atgtgccact tttcagtcta gtaacgcctt 4920
acctacgtca ttccatgcgt gcatgtttgc gcctttttc ccttgccctt gatcgccaca 4980
cagtacagtg cactgtacag tggaggtttt gggggggtct tagatgggag ctaaaagcgg 5040
cctagcggta cactagtggg attgtatgga gtggcatgga gcctaggtgg agcctgacag 5100
gacgcacgac cggctagccc gtgacagacg atgggtggct cctgttgtcc accgcgtaca 5160
aatgtttggg ccaaagtctt gtcagccttg cttgcgaacc taattcccaa ttttgtcact 5220
tcgcaccccc attgatcgag ccctaacccc tgcccatcag gcaatccaat taagctcgca 5280
ttgtctgcct tgtttagttt ggctcctgcc cgtttcggcg tccacttgca caaacacaaa 5340
caagcattat atataaggct cgtctctccc tcccaaccac actcactttt ttgcccgtct 5400
tcccttgcta acacaaaagt caagaacaca aacaaccacc ccaacccct tacacacaag 5460 acatatctac accatggagt ctggacccat gcctgctggc attcccttcc ctgagtacta 5520
tgacttcttt atggactgga agactcccct ggccatcgct gccacctaca ctgctgccgt 5580
cggtctcttc aaccccaagg ttggcaaggt ctcccgagtg gttgccaagt cggctaacgc 5640
aaagcctgcc gagcgaaccc agtccggagc tgccatgact gccttcgtct ttgtgcacaa 5700
cctcattctg tgtgtctact ctggcatcac cttctactac atgtttcctg ctatggtcaa 5760
gaacttccga acccacacac tgcacgaagc ctactgcgac acggatcagt ccctctggaa 5820
caacgcactt ggctactggg gttacctctt ctacctgtcc aagttctacg aggtcattga 5880
caccatcatc atcatcctga agggacgacg gtcctcgctg cttcagacct accaccatgc 5940
tggagccatg attaccatgt ggtctggcat caactaccaa gccactccca tttggatctt 6000
tgtggtcttc aactccttca ttcacaccat catgtactgt tactatgcct tcacctctat 6060
cggattccat cctcctggca aaaagtacct gacttcgatg cagattactc agtttctggt 6120
cggtatcacc attgccgtgt cctacctctt cgttcctggc tgcatccgaa cacccggtgc 6180
tcagatggct gtctggatca acgtcggcta cctgtttccc ttgacctatc tgttcgtgga 6240
ctttgccaag cgaacctact ccaagcgatc tgccattgcc gctcagaaaa aggctcagta 6300
agc 6303

<210> SEQ ID NO 32
<211> LENGTH: 21
<212> TYPE: DNA
<213> ORGANISM: Artificial Sequence
<220> FEATURE:
<223> OTHER INFORMATION: Primer pZP-GW-5-1

<400> SEQUENCE: 32
cgacaagatg gaatgagaat g 21

<210> SEQ ID NO 33
<211> LENGTH: 22
<212> TYPE: DNA
<213> ORGANISM: Artificial Sequence
<220> FEATURE:
<223> OTHER INFORMATION: Primer pZP-GW-5-2

<400> SEQUENCE: 33
ctggtttttc aactacttct ac 22

<210> SEQ ID NO 34
<211> LENGTH: 21
<212> TYPE: DNA
<213> ORGANISM: Artificial Sequence
<220> FEATURE:
<223> OTHER INFORMATION: Primer pZP-GW-5-3

<400> SEQUENCE: 34
gtactgtcct gtgtctgttc c 21

<210> SEQ ID NO 35
<211> LENGTH: 22
<212> TYPE: DNA
<213> ORGANISM: Artificial Sequence
<220> FEATURE:
<223> OTHER INFORMATION: Primer pZP-GW-5-4

<400> SEQUENCE: 35
ctacatcgtc cgaaagcaca ag 22

<210> SEQ ID NO 36
<211> LENGTH: 24
<212> TYPE: DNA
<213> ORGANISM: Artificial Sequence
<220> FEATURE:
<223> OTHER INFORMATION: Primer pZP-GW-3-1

<400> SEQUENCE: 36
ctaccagatc gagcaccatc tctg 24

<210> SEQ ID NO 37
<211> LENGTH: 21
<212> TYPE: DNA
<213> ORGANISM: Artificial Sequence
<220> FEATURE:
<223> OTHER INFORMATION: Primer pZP-GW-3-2

<400> SEQUENCE: 37
ctaccaggtg gaacagctgt g 21

<210> SEQ ID NO 38
<211> LENGTH: 22
<212> TYPE: DNA
<213> ORGANISM: Artificial Sequence
<220> FEATURE:
<223> OTHER INFORMATION: Primer pZP-GW-3-3

<400> SEQUENCE: 38
tctgccccat gaaggtctcg tc 22

<210> SEQ ID NO 39
<211> LENGTH: 22
<212> TYPE: DNA

<213> ORGANISM: Artificial Sequence
<220> FEATURE:
<223> OTHER INFORMATION: Primer pZP-GW-3-4

<400> SEQUENCE: 39
cctgtcccag ttcgctcgaa tg 22

<210> SEQ ID NO 40
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 40
gtaatacgac tatagggcac gcgtggtcga cggcccgggc tggt 44

<210> SEQ ID NO 41
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 41 accagccc 8

<210> SEQ ID NO 42
<211> LENGTH: 22
<212> TYPE: DNA
<213> ORGANISM: Artificial Sequence
<220> FEATURE:
<223> OTHER INFORMATION: Nested adaptor primer

<400> SEQUENCE: 42
gtaatacgac tcactatagg gc 22

<210> SEQ ID NO 43
<211> LENGTH: 36
<212> TYPE: DNA
<213> ORGANISM: Artificial Sequence
<220> FEATURE:
<223> OTHER INFORMATION: Primer Per10F1

<400> SEQUENCE: 43
gatcaaccat gggggaagt tcacatgcat tcgctg 36

<210> SEQ ID NO 44
<211> LENGTH: 29
<212> TYPE: DNA
<213> ORGANISM: Artificial Sequence
<220> FEATURE:
<223> OTHER INFORMATION: Primer ZPGW-5-5

<400> SEQUENCE: 44
gttatagttt tcatgtgaaa taccgagag 29

<210> SEQ ID NO 45
<211> LENGTH: 37

<212> TYPE: DNA
<213> ORGANISM: Artificial Sequence
<220> FEATURE:
<223> OTHER INFORMATION: Primer Per10R

<400> SEQUENCE: 45
gatcaagcgg ccgccagacc tcgtcattat ctgatag 37

<210> SEQ ID NO 46
<211> LENGTH: 7222
<212> TYPE: DNA
<213> ORGANISM: Artificial Sequence
<220> FEATURE:
<223> OTHER INFORMATION: Plasmid pFBAIn-MOD-1

<400> SEQUENCE: 46
catggatcca ggcctgttaa cggccattac ggcctgcagg atccgaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatcttatc atgtctgcgg 240
ccgcaagtgt ggatggggaa gtgagtgccc ggttctgtgt gcacaattgg caatccaaga 300
tggatggatt caacacaggg atatagcgag ctacgtggtg gtgcgaggat atagcaacgg 360
atatttatgt ttgacacttg agaatgtacg atacaagcac tgtccaagta caatactaaa 420
catactgtac atactcatac tcgtacccgg gcaacggttt cacttgagtg cagtggctag 480
tgctcttact cgtacagtgt gcaatactgc gtatcatagt ctttgatgta tatcgtattc 540
attcatgtta gttgcgtacg agccggaagc ataaagtgta aagcctgggg tgcctaatga 600
gtgagctaac tcacattaat tgcgttgcgc tcactgcccg ctttccagtc gggaaacctg 660
tcgtgccagc tgcattaatg aatcggccaa cgcgcgggga gaggcggttt gcgtattggg 720
cgctcttccg cttcctcgct cactgactcg ctgcgctcgg tcgttcggct gcggcgagcg 780
gtatcagctc actcaaaggc ggtaatacgg ttatccacag aatcagggga taacgcagga 840
aagaacatgt gagcaaaagg ccagcaaaag gccaggaacc gtaaaaaggc cgcgttgctg 900
gcgtttttcc ataggctccg cccccctgac gagcatcaca aaaatcgacg ctcaagtcag 960
aggtggcgaa acccgacagg actataaaga taccaggcgt ttccccctgg aagctccctc 1020
gtgcgctctc ctgttccgac cctgccgctt accggatacc tgtccgcctt tctcccttcg 1080
ggaagcgtgg cgctttctca tagctcacgc tgtaggtatc tcagttcggt gtaggtcgtt 1140
cgctccaagc tgggctgtgt gcacgaaccc cccgttcagc ccgaccgctg cgccttatcc 1200
ggtaactatc gtcttgagtc caacccggta agacacgact tatcgccact ggcagcagcc 1260
actggtaaca ggattagcag agcgaggtat gtaggcggtg ctacagagtt cttgaagtgg 1320
tggcctaact acggctacac tagaaggaca gtatttggta tctgcgctct gctgaagcca 1380
gttaccttcg gaaaaagagt tggtagctct tgatccggca aacaaaccac cgctggtagc 1440
ggtggttttt ttgtttgcaa gcagcagatt acgcgcagaa aaaaaggatc tcaagaagat 1500
cctttgatct tttctacggg gtctgacgct cagtggaacg aaaactcacg ttaagggatt 1560
ttggtcatga gattatcaaa aaggatcttc acctagatcc ttttaaatta aaaatgaagt 1620
tttaaatcaa tctaaagtat atatgagtaa acttggtctg acagttacca atgcttaatc 1680
agtgaggcac ctatctcagc gatctgtcta tttcgttcat ccatagttgc ctgactcccc 1740
gtcgtgtaga taactacgat acgggagggc ttaccatctg gccccagtgc tgcaatgata 1800

-continued

```
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata ataccgcgcc acatagcaga actttaaaag tgctcatcat tggaaaacgt   2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct tcctttttca atattattga agcatttatc agggttattg tctcatgagc   2580
ggatacatat ttgaatgtat ttagaaaaat aaacaaatag gggttccgcg cacatttccc   2640
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
ccttcctttc tcgccacgtt cgccggcttt ccccgtcaag ctctaaatcg ggggctccct   2820
ttagggttcc gatttagtgc tttacggcac ctcgacccca aaaaacttga ttagggtgat   2880
ggttcacgta gtgggccatc gccctgatag acggtttttc gccctttgac gttggagtcc   2940
acgttcttta atagtggact cttgttccaa actggaacaa cactcaaccc tatctcggtc   3000
tattcttttg atttataagg gattttgccg atttcggcct attggttaaa aaatgagctg   3060
atttaacaaa aatttaacgc gaattttaac aaaatattaa cgcttacaat ttccattcgc   3120
cattcaggct gcgcaactgt tgggaagggc gatcggtgcg ggcctcttcg ctattacgcc   3180
agctggcgaa agggggatgt gctgcaaggc gattaagttg ggtaacgcca gggttttccc   3240
agtcacgacg ttgtaaaacg acggccagtg aattgtaata cgactcacta tagggcgaat   3300
tgggtaccgg gccccccctc gaggtcgatg gtgtcgataa gcttgatatc gaattcatgt   3360
cacacaaacc gatcttcgcc tcaaggaaac ctaattctac atccgagaga ctgccgagat   3420
ccagtctaca ctgattaatt ttcgggccaa taatttaaaa aaatcgtgtt atataatatt   3480
atatgtatta tatatataca tcatgatgat actgacagtc atgtcccatt gctaaataga   3540
cagactccat ctgccgcctc caactgatgt tctcaatatt taaggggtca tctcgcattg   3600
tttaataata aacagactcc atctaccgcc tccaaatgat gttctcaaaa tatattgtat   3660
gaacttattt ttattactta gtattattag acaacttact tgctttatga aaaacacttc   3720
ctatttagga aacaatttat aatggcagtt cgttcattta acaatttatg tagaataaat   3780
gttataaatg cgtatgggaa atcttaaata tggatagcat aaatgatatc tgcattgcct   3840
aattcgaaat caacagcaac gaaaaaaatc ccttgtacaa cataaatagt catcgagaaa   3900
tatcaactat caaagaacag ctattcacac gttactattg agattattat tggacgagaa   3960
tcacacactc aactgtcttt ctctcttcta gaaatacagg tacaagtatg tactattctc   4020
attgttcata cttctagtca tttcatccca catattcctt ggatttctct ccaatgaatg   4080
acattctatc ttgcaaattc aacaattata ataagatata ccaaagtagc ggtatagtgg   4140
caatcaaaaa gcttctctgg tgtgcttctc gtatttattt ttattctaat gatccattaa   4200
```

```
aggtatatat ttatttcttg ttatataatc cttttgttta ttacatgggc tggatacata   4260
aaggtatttt gatttaattt tttgcttaaa ttcaatcccc cctcgttcag tgtcaactgt   4320
aatggtagga aattaccata cttttgaaga agcaaaaaaa atgaaagaaa aaaaaaatcg   4380
tatttccagg ttagacgttc cgcagaatct agaatgcggt atgcggtaca ttgttcttcg   4440
aacgtaaaag ttgcgctccc tgagatattg tacatttttg cttttacaag tacaagtaca   4500
tcgtacaact atgtactact gttgatgcat ccacaacagt ttgttttgtt tttttttgtt   4560
tttttttttt ctaatgattc attaccgcta tgtataccta cttgtacttg tagtaagccg   4620
ggttattggc gttcaattaa tcatagactt atgaatctgc acggtgtgcg ctgcgagtta   4680
cttttagctt atgcatgcta cttgggtgta atattgggat ctgttcggaa atcaacggat   4740
gctcaatcga tttcgacagt aattaattaa gtcatacaca agtcagcttt cttcgagcct   4800
catataagta taagtagttc aacgtattag cactgtaccc agcatctccg tatcgagaaa   4860
cacaacaaca tgccccattg gacagatcat gcggatacac aggttgtgca gtatcataca   4920
tactcgatca gacaggtcgt ctgaccatca tacaagctga acaagcgctc catacttgca   4980
cgctctctat atacacagtt aaattacata tccatagtct aacctctaac agttaatctt   5040
ctggtaagcc tcccagccag ccttctggta tcgcttggcc tcctcaatag gatctcggtt   5100
ctggccgtac agacctcggc cgacaattat gatatccgtt ccggtagaca tgacatcctc   5160
aacagttcgg tactgctgtc cgagagcgtc tcccttgtcg tcaagaccca ccccgggggt   5220
cagaataagc cagtcctcag agtcgccctt aggtcggttc tgggcaatga agccaaccac   5280
aaactcgggg tcggatcggg caagctcaat ggtctgcttg gagtactcgc cagtggccag   5340
agagcccttg caagacagct cggccagcat gagcagacct ctggccagct tctcgttggg   5400
agaggggact aggaactcct tgtactggga gttctcgtag tcagagacgt cctccttctt   5460
ctgttcagag acagtttcct cggcaccagc tcgcaggcca gcaatgattc cggttccggg   5520
tacaccgtgg gcgttggtga tatcggacca ctcggcgatt cggtgacacc ggtactggtg   5580
cttgacagtg ttgccaatat ctgcgaactt tctgtcctcg aacaggaaga aaccgtgctt   5640
aagagcaagt tccttgaggg ggagcacagt gccggcgtag gtgaagtcgt caatgatgtc   5700
gatatgggtt ttgatcatgc acacataagg tccgacctta tcggcaagct caatgagctc   5760
cttggtggtg gtaacatcca gagaagcaca caggttggtt ttcttggctg ccacgagctt   5820
gagcactcga gcggcaaagg cggacttgtg gacgttagct cgagcttcgt aggagggcat   5880
tttggtggtg aagaggagac tgaaataaat ttagtctgca gaacttttta tcggaacctt   5940
atctggggca gtgaagtata tgttatggta atagttacga gttagttgaa cttatagata   6000
gactggacta tacggctatc ggtccaaatt agaaagaacg tcaatggctc tctgggcgtc   6060
gcctttgccg acaaaaatgt gatcatgatg aaagccagca atgacgttgc agctgatatt   6120
gttgtcggcc aaccgcgccg aaaacgcagc tgtcagaccc acagcctcca acgaagaatg   6180
tatcgtcaaa gtgatccaag cacactcata gttggagtcg tactccaaag gcggcaatga   6240
cgagtcagac agatactcgt cgaaaacagt gtacgcagat ctactataga ggaacattta   6300
aattgccccg gagaagacgg ccaggccgcc tagatgacaa attcaacaac tcacagctga   6360
ctttctgcca ttgccactag gggggggcct ttttatatgg ccaagccaag ctctccacgt   6420
cggttgggct gcacccaaca ataaatgggt agggttgcac caacaaaggg atgggatggg   6480
gggtagaaga tacgaggata acggggctca atggcacaaa taagaacgaa tactgccatt   6540
```

aagactcgtg atccagcgac tgacaccatt gcatcatcta agggcctcaa aactacctcg 6600
gaactgctgc gctgatctgg acaccacaga ggttccgagc actttaggtt gcaccaaatg 6660
tcccaccagg tgcaggcaga aaacgctgga acagcgtgta cagtttgtct taacaaaaag 6720
tgagggcgct gaggtcgagc agggtggtgt gacttgttat agcctttaga gctgcgaaag 6780
cgcgtatgga tttggctcat caggccagat tgagggtctg tggacacatg tcatgttagt 6840
gtacttcaat cgccccctgg atatagcccc gacaataggc cgtggcctca tttttttgcc 6900
ttccgcacat ttccattgct cggtacccac accttgcttc tcctgcactt gccaacctta 6960
atactggttt acattgacca acatcttaca agcggggggc ttgtctaggg tatatataaa 7020
cagtggctct cccaatcggt tgccagtctc ttttttcctt tctttcccca cagattcgaa 7080
atctaaacta cacatcacag aattccgagc cgtgagtatc cacgacaaga tcagtgtcga 7140
gacgacgcgt tttgtgtaat gacacaatcc gaaagtcgct agcaacacac actctctaca 7200
caaactaacc cagctctggt ac 7222

<210> SEQ ID NO 47
<211> LENGTH: 8133
<212> TYPE: DNA
<213> ORGANISM: Artificial Sequence
<220> FEATURE:
<223> OTHER INFORMATION: Plasmid pFBAIN-Pex10

<400> SEQUENCE: 47
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380

-continued

```
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
```

-continued

```
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgaaaaca gtgtacgcag atctactata gaggaacatt   6060
taaattgccc cggagaagac ggccaggccg cctagatgac aaattcaaca actcacagct   6120
```

gactttctgc cattgccact aggggggggc ctttttatat ggccaagcca agctctccac 6180
gtcggttggg ctgcacccaa caataaatgg gtagggttgc accaacaaag ggatgggatg 6240
gggggtagaa gatacgagga taacggggct caatggcaca aataagaacg aatactgcca 6300
ttaagactcg tgatccagcg actgacacca ttgcatcatc taagggcctc aaaactacct 6360
cggaactgct gcgctgatct ggacaccaca gaggttccga gcactttagg ttgcaccaaa 6420
tgtcccacca ggtgcaggca gaaaacgctg gaacagcgtg tacagtttgt cttaacaaaa 6480
agtgagggcg ctgaggtcga gcagggtggt gtgacttgtt atagccttta gagctgcgaa 6540
agcgcgtatg gatttggctc atcaggccag attgagggtc tgtggacaca tgtcatgtta 6600
gtgtacttca atcgcccccct ggatatagcc ccgacaatag gccgtggcct cattttttttg 6660 ccttccgcac atttccattg ctcggtaccc acaccttgct tctcctgcac ttgccaacct 6720
taatactggt ttacattgac caacatctta caagcggggg gcttgtctag ggtatatata 6780
aacagtggct ctcccaatcg gttgccagtc tcttttttcc tttctttccc cacagattcg 6840
aaatctaaac tacacatcac agaattccga gccgtgagta tccacgacaa gatcagtgtc 6900
gagacgacgc gttttgtgta atgacacaat ccgaaagtcg ctagcaacac acactctcta 6960
cacaaactaa cccagctctg gtaccatggg gggaagttca catgcattcg ctggtgaatc 7020
tgatctgaca ctacaactac acaccaggtc caacatgagc gacaatacga caatcaaaaa 7080
gccgatccga cccaaaccga tccggacgga acgcctgcct tacgctgggg ccgcagaaat 7140
catccgagcc aaccagaaag accactactt tgagtccgtg cttgaacagc atctcgtcac 7200
gtttctgcag aaatggaagg gagtacgatt tatccaccag tacaaggagg agctggagac 7260
ggcgtccaag tttgcatatc tcggtttgtg tacgcttgtg ggctccaaga ctctcggaga 7320
agagtacacc aatctcatgt acactatcag agaccgaaca gctctaccgg gggtggtgag 7380
acggtttggc tacgtgcttt ccaacactct gtttccatac ctgtttgtgc gctacatggg 7440
caagttgcgc gccaaactga tgcgcgagta tccccatctg gtggagtacg acgaagatga 7500
gcctgtgccc agcccggaaa catggaagga gcgggtcatc aagacgtttg tgaacaagtt 7560
tgacaagttc acggcgctgg aggggtttac cgcgatccac ttggcgattt tctacgtcta 7620
cggctcgtac taccagctca gtaagcggat ctggggcatg cgttatgtat ttggacaccg 7680
actggacaag aatgagcctc gaatcggtta cgagatgctc ggtctgctga ttttcgcccg 7740
gtttgccacg tcatttgtgc agacgggaag agagtacctc ggagcgctgc tggaaaagag 7800
cgtggagaaa gaggcagggg agaaggaaga tgaaaaggaa gcggttgtgc cgaaaaagaa 7860
gtcgtcaatt ccgttcattg aggatacaga aggggagacg gaagacaaga tcgatctgga 7920
ggaccctcga cagctcaagt tcattcctga ggcgtccaga gcgtgcactc tgtgtctgtc 7980
atacattagt gcgccggcat gtacgccatg tggacacttt ttctgttggg actgtatttc 8040
cgaatgggtg agagagaagc ccgagtgtcc cttgtgtcgg cagggtgtga gagagcagaa 8100
cttgttgcct atcagataat gacgaggtct ggc 8133

<210> SEQ ID NO 48
<211> LENGTH: 35
<212> TYPE: DNA
<213> ORGANISM: Artificial Sequence
<220> FEATURE:
<223> OTHER INFORMATION: Primer PEX10-R-BsiWI

<400> SEQUENCE: 48

-continued gatcaacgta cgcttcagca gtaactgtat tgctc 35

<210> SEQ ID NO 49
<211> LENGTH: 35
<212> TYPE: DNA
<213> ORGANISM: Artificial Sequence
<220> FEATURE:
<223> OTHER INFORMATION: Primer PEX10-F1-SalI

<400> SEQUENCE: 49
gatcaagtcg acattgtaac tagtcctgga gggtc 35

<210> SEQ ID NO 50
<211> LENGTH: 36
<212> TYPE: DNA
<213> ORGANISM: Artificial Sequence
<220> FEATURE:
<223> OTHER INFORMATION: Primer PEX10-F2-SalI

<400> SEQUENCE: 50
gatcaagtcg acgtcttagc gtcatgtatt ctcaag 36

<210> SEQ ID NO 51
<211> LENGTH: 7277
<212> TYPE: DNA
<213> ORGANISM: Artificial Sequence
<220> FEATURE:
<223> OTHER INFORMATION: Plasmid pEXP-MOD1

<400> SEQUENCE: 51
catggatcca ggcctgttaa cggccattac ggcctgcagg atccgaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatcttatc atgtctgcgg 240
ccgcaagtgt ggatggggaa gtgagtgccc ggttctgtgt gcacaattgg caatccaaga 300
tggatggatt caacacaggg atatagcgag ctacgtggtg gtgcgaggat atagcaacgg 360
atatttatgt ttgacacttg agaatgtacg atacaagcac tgtccaagta caatactaaa 420
catactgtac atactcatac tcgtacccgg gcaacggttt cacttgagtg cagtggctag 480
tgctcttact cgtacagtgt gcaatactgc gtatcatagt ctttgatgta tatcgtattc 540
attcatgtta gttgcgtacg agccggaagc ataaagtgta aagcctgggg tgcctaatga 600
gtgagctaac tcacattaat tgcgttgcgc tcactgcccg ctttccagtc gggaaacctg 660
tcgtgccagc tgcattaatg aatcggccaa cgcgcgggga gaggcggttt gcgtattggg 720
cgctcttccg cttcctcgct cactgactcg ctgcgctcgg tcgttcggct gcggcgagcg 780
gtatcagctc actcaaaggc ggtaatacgg ttatccacag aatcagggga taacgcagga 840
aagaacatgt gagcaaaagg ccagcaaaag gccaggaacc gtaaaaaggc cgcgttgctg 900
gcgtttttcc ataggctccg cccccctgac gagcatcaca aaaatcgacg ctcaagtcag 960
aggtggcgaa acccgacagg actataaaga taccaggcgt ttccccctgg aagctccctc 1020
gtgcgctctc ctgttccgac cctgccgctt accggatacc tgtccgcctt tctcccttcg 1080
ggaagcgtgg cgctttctca tagctcacgc tgtaggtatc tcagttcggt gtaggtcgtt 1140
cgctccaagc tgggctgtgt gcacgaaccc cccgttcagc ccgaccgctg cgccttatcc 1200
ggtaactatc gtcttgagtc caacccggta agacacgact tatcgccact ggcagcagcc 1260
actggtaaca ggattagcag agcgaggtat gtaggcggtg ctacagagtt cttgaagtgg 1320

-continued

```
tggcctaact acggctacac tagaaggaca gtatttggta tctgcgctct gctgaagcca   1380
gttaccttcg gaaaaagagt tggtagctct tgatccggca aacaaaccac cgctggtagc   1440
ggtggttttt ttgtttgcaa gcagcagatt acgcgcagaa aaaaaggatc tcaagaagat   1500
cctttgatct tttctacggg gtctgacgct cagtggaacg aaaactcacg ttaagggatt   1560
ttggtcatga gattatcaaa aaggatcttc acctagatcc ttttaaatta aaaatgaagt   1620
tttaaatcaa tctaaagtat atatgagtaa acttggtctg acagttacca atgcttaatc   1680
agtgaggcac ctatctcagc gatctgtcta tttcgttcat ccatagttgc ctgactcccc   1740
gtcgtgtaga taactacgat acgggagggc ttaccatctg gccccagtgc tgcaatgata   1800
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata ataccgcgcc acatagcaga actttaaaag tgctcatcat tggaaaacgt   2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct tcctttttca atattattga agcatttatc agggttattg tctcatgagc   2580
ggatacatat ttgaatgtat ttagaaaaat aaacaaatag gggttccgcg cacatttccc   2640
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
ccttcctttc tcgccacgtt cgccggcttt ccccgtcaag ctctaaatcg ggggctccct   2820
ttagggttcc gatttagtgc tttacggcac ctcgacccca aaaaacttga ttagggtgat   2880
ggttcacgta gtgggccatc gccctgatag acggtttttc gccctttgac gttggagtcc   2940
acgttcttta atagtggact cttgttccaa actggaacaa cactcaaccc tatctcggtc   3000
tattcttttg atttataagg gattttgccg atttcggcct attggttaaa aaatgagctg   3060
atttaacaaa aatttaacgc gaattttaac aaaatattaa cgcttacaat ttccattcgc   3120
cattcaggct gcgcaactgt tgggaagggc gatcggtgcg ggcctcttcg ctattacgcc   3180
agctggcgaa agggggatgt gctgcaaggc gattaagttg ggtaacgcca gggttttccc   3240
agtcacgacg ttgtaaaacg acggccagtg aattgtaata cgactcacta tagggcgaat   3300
tgggtaccgg gccccccctc gaggtcgatg gtgtcgataa gcttgatatc gaattcatgt   3360
cacacaaacc gatcttcgcc tcaaggaaac ctaattctac atccgagaga ctgccgagat   3420
ccagtctaca ctgattaatt ttcgggccaa taatttaaaa aaatcgtgtt atataatatt   3480
atatgtatta tatatataca tcatgatgat actgacagtc atgtcccatt gctaaataga   3540
cagactccat ctgccgcctc caactgatgt tctcaatatt taaggggtca tctcgcattg   3600
tttaataata aacagactcc atctaccgcc tccaaatgat gttctcaaaa tatattgtat   3660
```

gaacttattt ttattactta gtattattag acaacttact tgctttatga aaaacacttc 3720
ctatttagga aacaatttat aatggcagtt cgttcattta acaatttatg tagaataaat 3780
gttataaatg cgtatgggaa atcttaaata tggatagcat aaatgatatc tgcattgcct 3840
aattcgaaat caacagcaac gaaaaaaatc ccttgtacaa cataaatagt catcgagaaa 3900
tatcaactat caaagaacag ctattcacac gttactattg agattattat tggacgagaa 3960
tcacacactc aactgtcttt ctctcttcta gaaatacagg tacaagtatg tactattctc 4020
attgttcata cttctagtca tttcatccca catattcctt ggatttctct ccaatgaatg 4080
acattctatc ttgcaaattc aacaattata ataagatata ccaaagtagc ggtatagtgg 4140
caatcaaaaa gcttctctgg tgtgcttctc gtatttattt ttattctaat gatccattaa 4200
aggtatatat ttatttcttg ttatataatc cttttgttta ttacatgggc tggatacata 4260
aaggtatttt gatttaattt tttgcttaaa ttcaatcccc cctcgttcag tgtcaactgt 4320
aatggtagga aattaccata cttttgaaga agcaaaaaaa atgaaagaaa aaaaaaatcg 4380
tatttccagg ttagacgttc cgcagaatct agaatgcggt atgcggtaca ttgttcttcg 4440
aacgtaaaag ttgcgctccc tgagatattg tacatttttg cttttacaag tacaagtaca 4500
tcgtacaact atgtactact gttgatgcat ccacaacagt ttgttttgtt ttttttttgtt 4560 ttttttttt ctaatgattc attaccgcta tgtataccta cttgtacttg tagtaagccg 4620
ggttattggc gttcaattaa tcatagactt atgaatctgc acggtgtgcg ctgcgagtta 4680
cttttagctt atgcatgcta cttgggtgta atattgggat ctgttcggaa atcaacggat 4740
gctcaatcga tttcgacagt aattaattaa gtcatacaca agtcagcttt cttcgagcct 4800
catataagta taagtagttc aacgtattag cactgtaccc agcatctccg tatcgagaaa 4860
cacaacaaca tgccccattg gacagatcat gcggatacac aggttgtgca gtatcataca 4920
tactcgatca gacaggtcgt ctgaccatca tacaagctga acaagcgctc catacttgca 4980
cgctctctat atacacagtt aaattacata tccatagtct aacctctaac agttaatctt 5040
ctggtaagcc tcccagccag ccttctggta tcgcttggcc tcctcaatag gatctcggtt 5100
ctggccgtac agacctcggc cgacaattat gatatccgtt ccggtagaca tgacatcctc 5160
aacagttcgg tactgctgtc cgagagcgtc tcccttgtcg tcaagaccca ccccgggggt 5220
cagaataagc cagtcctcag agtcgccctt aggtcggttc tgggcaatga agccaaccac 5280
aaactcgggg tcggatcggg caagctcaat ggtctgcttg gagtactcgc cagtggccag 5340
agagcccttg caagacagct cggccagcat gagcagacct ctggccagct tctcgttggg 5400
agaggggact aggaactcct tgtactggga gttctcgtag tcagagacgt cctccttctt 5460
ctgttcagag acagtttcct cggcaccagc tcgcaggcca gcaatgattc cggttccggg 5520
tacaccgtgg gcgttggtga tatcggacca ctcggcgatt cggtgacacc ggtactggtg 5580
cttgacagtg ttgccaatat ctgcgaactt tctgtcctcg aacaggaaga aaccgtgctt 5640
aagagcaagt tccttgaggg ggagcacagt gccggcgtag gtgaagtcgt caatgatgtc 5700
gatatgggtt ttgatcatgc acacataagg tccgacctta tcggcaagct caatgagctc 5760
cttggtggtg gtaacatcca gagaagcaca caggttggtt ttcttggctg ccacgagctt 5820
gagcactcga gcggcaaagg cggacttgtg gacgttagct cgagcttcgt aggagggcat 5880
tttggtggtg aagaggagac tgaaataaat ttagtctgca gaacttttta tcggaacctt 5940
atctggggca gtgaagtata tgttatggta atagttacga gttagttgaa cttatagata 6000
gactggacta tacggctatc ggtccaaatt agaaagaacg tcaatggctc tctgggcgtc 6060

-continued

```
gcctttgccg acaaaaatgt gatcatgatg aaagccagca atgacgttgc agctgatatt   6120

gttgtcggcc aaccgcgccg aaaacgcagc tgtcagaccc acagcctcca acgaagaatg   6180

tatcgtcaaa gtgatccaag cacactcata gttggagtcg tactccaaag gcggcaatga   6240

cgagtcagac agatactcgt cgaccgtacg ggagtttgg cgcccgtttt ttcgagcccc   6300

acacgtttcg gtgagtatga gcggcggcag attcgagcgt ttccggtttc cgcggctgga   6360

cgagagccca tgatgggggc tcccaccacc agcaatcagg gccctgatta cacacccacc   6420

tgtaatgtca tgctgttcat cgatggttaa tgctgctgtg tgctgtgtgt gtgtgttgtt   6480

tggcgctcat tgttgcgtta tgcagcgtac accacaatat tggaagctta ttagcctttc   6540

tattttttcg tttgcaaggc ttaacaacat tgctgtggag agggatgggg atatggaggc   6600

cgctggaggg agtcggagag gcgttttgga gcggcttggc ctggcgccca gctcgcgaaa   6660

cgcacctagg accctttggc acgccgaaat gtgccacttt tcagtctagt aacgccttac   6720

ctacgtcatt ccatgcgtgc atgtttgcgc cttttttccc ttgcccttga tcgccacaca   6780

gtacagtgca ctgtacagtg gaggttttgg gggggtctta gatgggagct aaaagcggcc   6840

tagcggtaca ctagtgggat tgtatggagt ggcatggagc ctaggtggag cctgacagga   6900

cgcacgaccg gctagcccgt gacagacgat gggtggctcc tgttgtccac cgcgtacaaa   6960

tgtttgggcc aaagtcttgt cagccttgct tgcgaaccta attcccaatt ttgtcacttc   7020

gcacccccat tgatcgagcc ctaacccctg cccatcaggc aatccaatta agctcgcatt   7080

gtctgccttg tttagtttgg ctcctgcccg tttcggcgtc cacttgcaca aacacaaaca   7140

agcattatat ataaggctcg tctctccctc ccaaccacac tcactttttt gcccgtcttc   7200

ccttgctaac acaaaagtca agaacacaaa caaccacccc aaccccctta cacacaagac   7260

atatctacag caatggc                                                  7277
```

<210> SEQ ID NO 52
<211> LENGTH: 7559
<212> TYPE: DNA
<213> ORGANISM: Artificial Sequence
<220> FEATURE:
<223> OTHER INFORMATION: Plasmid pPEX10-1

<400> SEQUENCE: 52

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480

ccgaccctgc cgcttaccgg atacctgtcc gcctttctcc cttcgggaag cgtggcgctt    540

tctcatagct cacgctgtag gtatctcagt tcggtgtagg tcgttcgctc caagctgggc    600

tgtgtgcacg aaccccccgt tcagcccgac cgctgcgcct tatccggtaa ctatcgtctt    660

gagtccaacc cggtaagaca cgacttatcg ccactggcag cagccactgg taacaggatt    720

agcagagcga ggtatgtagg cggtgctaca gagttcttga agtggtggcc taactacggc    780
```

-continued

```
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
```

```
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgtttttttt ttgtttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg ggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
```

```
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgaca ttgtaactag tcctggaggg tctttttat ggataacctc catgtacgat   5760
gtatccaaga tctccacgta ctgtgttctg tttcctaagt aatacccaac aacctctcca   5820
acaaacactt gggaagatgc acttgtgctg agatgtcaag atgttagtac tgtactggat   5880
ggagagaata ttaataaata attgttaccc aactacatct tgtcgattga aagagatacc   5940
cctaagacag ataggatatc tgcaacccga ggaatgaacc ccccagcacc ggcacccttt   6000
ctattaacaa aatgccaact gaaatttgaa aagttcaact aaacttattt gacccacaaa   6060
aactcgtcaa aagtggcggc gaaagctggc aaatgatgac atccccttgg aactatgata   6120
tcccctcgga atcttcgtcc ccatttgcca catctacttg caacgccacg tctgcttact   6180
aagcaaccca aatctgcctc ggctcaaaat gtggggaagt tcacatgcat tcgctggtga   6240
atctgatctg acactacaac tacacaccag gtccaacatg agcgacaata cgacaatcaa   6300
aaagccgatc cgacccaaac cgatccggac ggaacgcctg ccttacgctg gggccgcaga   6360
aatcatccga gccaaccaga aagaccacta ctttgagtcc gtgcttgaac agcatctcgt   6420
cacgtttctg cagaaatgga agggagtacg atttatccac cagtacaagg aggagctgga   6480
gacggcgtcc aagtttgcat atctcggttt gtgtacgctt gtgggctcca agactctcgg   6540
agaagagtac accaatctca tgtacactat cagagaccga acagctctac cgggggtggt   6600
gagacggttt ggctacgtgc tttccaacac tctgtttcca tacctgtttg tgcgctacat   6660
gggcaagttg cgcgccaaac tgatgcgcga gtatccccat ctggtggagt acgacgaaga   6720
tgagcctgtg cccagcccgg aaacatggaa ggagcgggtc atcaagacgt ttgtgaacaa   6780
gtttgacaag ttcacggcgc tggaggggtt taccgcgatc cacttggcga ttttctacgt   6840
ctacggctcg tactaccagc tcagtaagcg gatctggggc atgcgttatg tatttggaca   6900
ccgactggac aagaatgagc ctcgaatcgg ttacgagatg ctcggtctgc tgattttcgc   6960
ccggtttgcc acgtcatttg tgcagacggg aagagagtac ctcggagcgc tgctggaaaa   7020
gagcgtggag aaagaggcag gggagaagga agatgaaaag gaagcggttg tgccgaaaaa   7080
gaagtcgtca attccgttca ttgaggatac agaaggggag acggaagaca agatcgatct   7140
ggaggaccct cgacagctca agttcattcc tgaggcgtcc agagcgtgca ctctgtgtct   7200
gtcatacatt agtgcgccgg catgtacgcc atgtggacac tttttctgtt gggactgtat   7260
ttccgaatgg gtgagagaga agcccgagtg tcccttgtgt cggcagggtg tgagagagca   7320
gaacttgttg cctatcagat aatgacgagg tctggatgga aggactagtc agcgagacac   7380
agagcatcag ggaccagaca cgaccaattc aatcgacaac actgtgctgc atagcagtgc   7440
acagaggtcc tgggcatgaa tatattttag cattggagat atgagtggta gagcgtatac   7500
agtattaatt gtggaggtat ctcgtcgcat tgatagagca atacagttac tgctgaagc    7559
```

<210> SEQ ID NO 53
<211> LENGTH: 8051
<212> TYPE: DNA
<213> ORGANISM: Artificial Sequence
<220> FEATURE:
<223> OTHER INFORMATION: Plasmid pPEX10-2

<400> SEQUENCE: 53

```
gtacgagccg gaagcataaa gtgtaaagcc tggggtgcct aatgagtgag ctaactcaca     60
```

-continued

```
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
```

-continued

```
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
```

-continued

```
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgacg tcttagcgtc atgtattctc aagcttagtc agagagaagg actatggagg   5760
agaaggggag aattgagaag ggtatttgaa gggactttga aggtcgcgtg gaagaggtac   5820
ttgaagaggt atttgaaggt cacgtggaag aggtatttga agatcacgtg gaagaagtac   5880
ttgttttaca gagaatatcg gggtgatttt gacagtggga ttgtctccca agtcctaatc   5940
gtttgacatg ggagcagtga aaagtcgggc taaaaaaggg aatatcggaa atcggaaaga   6000
cggaaagaat tactggactc atgtttagta gatctgagca cttcaaattt gaaaatatct   6060
cttcaaacag cagatcggtt ggtcgtggag gtaccatcaa gggtaaaatc aaggctatca   6120
tcaagggcca tatatcgcaa gtttggggga agataatatg ttcatagtga atcagggttg   6180
tggatttcct catctaacgg cattgtaact agtcctggag ggtctttttt atggataacc   6240
tccatgtacg atgtatccaa gatctccacg tactgtgttc tgtttcctaa gtaataccca   6300
acaacctctc caacaaacac ttgggaagat gcacttgtgc tgagatgtca agatgttagt   6360
actgtactgg atggagagaa tattaataaa taattgttac ccaactacat cttgtcgatt   6420
gaaagagata cccctaagac agataggata tctgcaaccc gaggaatgaa ccccccagca   6480
ccggcaccct ttctattaac aaaatgccaa ctgaaatttg aaaagttcaa ctaaacttat   6540
ttgacccaca aaaactcgtc aaaagtggcg gcgaaagctg gcaaatgatg acatcccctt   6600
ggaactatga tatcccctcg gaatcttcgt ccccatttgc cacatctact tgcaacgcca   6660
cgtctgctta ctaagcaacc caaatctgcc tcggctcaaa atgtggggaa gttcacatgc   6720
attcgctggt gaatctgatc tgacactaca actacacacc aggtccaaca tgagcgacaa   6780
tacgacaatc aaaaagccga tccgacccaa accgatccgg acggaacgcc tgccttacgc   6840
tggggccgca gaaatcatcc gagccaacca gaaagaccac tactttgagt ccgtgcttga   6900
acagcatctc gtcacgtttc tgcagaaatg gaagggagta cgatttatcc accagtacaa   6960
ggaggagctg gagacggcgt ccaagtttgc atatctcggt ttgtgtacgc ttgtgggctc   7020
caagactctc ggagaagagt acaccaatct catgtacact atcagagacc gaacagctct   7080
accgggggtg gtgagacggt ttggctacgt gctttccaac actctgtttc catacctgtt   7140
```

```
tgtgcgctac atgggcaagt tgcgcgccaa actgatgcgc gagtatcccc atctggtgga   7200

gtacgacgaa gatgagcctg tgcccagccc ggaaacatgg aaggagcggg tcatcaagac   7260

gtttgtgaac aagtttgaca agttcacggc gctggagggg tttaccgcga tccacttggc   7320

gattttctac gtctacggct cgtactacca gctcagtaag cggatctggg gcatgcgtta   7380

tgtatttgga caccgactgg acaagaatga gcctcgaatc ggttacgaga tgctcggtct   7440

gctgattttc gcccggtttg ccacgtcatt tgtgcagacg ggaagagagt acctcggagc   7500

gctgctggaa aagagcgtgg agaaagaggc aggggagaag gaagatgaaa aggaagcggt   7560

tgtgccgaaa aagaagtcgt caattccgtt cattgaggat acagaagggg agacggaaga   7620

caagatcgat ctggaggacc ctcgacagct caagttcatt cctgaggcgt ccagagcgtg   7680

cactctgtgt ctgtcataca ttagtgcgcc ggcatgtacg ccatgtggac actttttctg   7740

ttgggactgt atttccgaat gggtgagaga gaagcccgag tgtcccttgt gtcggcaggg   7800

tgtgagagag cagaacttgt tgcctatcag ataatgacga ggtctggatg gaaggactag   7860

tcagcgagac acagagcatc agggaccaga cacgaccaat tcaatcgaca acactgtgct   7920

gcatagcagt gcacagaggt cctgggcatg aatatatttt agcattggag atatgagtgg   7980

tagagcgtat acagtattaa ttgtggaggt atctcgtcgc attgatagag caatacagtt   8040

actgctgaag c                                                        8051
```

<210> SEQ ID NO 54
<211> LENGTH: 15877
<212> TYPE: DNA
<213> ORGANISM: Artificial Sequence
<220> FEATURE:
<223> OTHER INFORMATION: Plasmid pZKL1-2SP98C

<400> SEQUENCE: 54

```
aaatgatgtc gacgcagtag gatgtcctgc acgggtcttt ttgtggggtg tggagaaagg     60

ggtgcttgga tcgatggaag ccggtagaac cgggctgctt gtgcttggag atggaagccg    120

gtagaaccgg gctgcttggg gggatttggg gccgctgggc tccaaagagg ggtaggcatt    180

tcgttggggt tacgtaattg cggcatttgg gtcctgcgcg catgtcccat tggtcagaat    240

tagtccggat aggagactta tcagccaatc acagcgccgg atccacctgt aggttgggtt    300

gggtgggagc acccctccac agagtagagt caaacagcag cagcaacatg atagttgggg    360

gtgtgcgtgt taaaggaaaa aaaagaagct tgggttatat tcccgctcta tttagaggtt    420

gcgggataga cgccgacgga gggcaatggc gctatggaac cttgcggata tccatacgcc    480

gcggcggact gcgtccgaac cagctccagc agcgtttttt ccgggccatt gagccgactg    540

cgaccccgcc aacgtgtctt ggcccacgca ctcatgtcat gttggtgttg ggaggccact    600

ttttaagtag cacaaggcac ctagctcgca gcaaggtgtc cgaaccaaag aagcggctgc    660

agtggtgcaa acggggcgga aacggcggga aaaagccacg ggggcacgaa ttgaggcacg    720

ccctcgaatt tgagacgagt cacggcccca ttcgcccgcg caatggctcg ccaacgcccg    780

gtcttttgca ccacatcagg ttaccccaag ccaaaccttt gtgttaaaaa gcttaacata    840

ttataccgaa cgtaggtttg ggcgggcttg ctccgtctgt ccaaggcaac atttatataa    900

gggtctgcat cgccggctca attgaatctt ttttcttctt ctcttctcta tattcattct    960

tgaattaaac acacatcaac catgggcgta ttcattaaac aggagcagct tccggctctc   1020

aagaagtaca agtactccgc cgaggatcac tcgttcatct ccaacaacat tctgcgcccc   1080

ttctggcgac agtttgtcaa aatcttccct ctgtggatgg cccccaacat ggtgactctg   1140
```

```
ctgggcttct tctttgtcat tgtgaacttc atcaccatgc tcattgttga tcccacccac   1200
gaccgcgagc ctcccagatg ggtctacctc acctacgctc tgggtctgtt cctttaccag   1260
acatttgatg cctgtgacgg atcccatgcc cgacgaactg gccagagtgg acccccttgga   1320
gagctgtttg accactgtgt cgacgccatg aatacctctc tgattctcac ggtggtggtg   1380
tccaccaccc atatgggata taacatgaag ctactgattg tgcagattgc cgctctcgga   1440
aacttctacc tgtcgacctg ggagacctac cataccggaa ctctgtacct ttctggcttc   1500
tctggtcctg ttgaaggtat cttgattctg gtggctcttt tcgtcctcac cttcttcact   1560
ggtcccaacg tgtacgctct gaccgtctac gaggctcttc ccgagtccat cacttcgctg   1620
ctgcctgcca gcttcctgga cgtcaccatc acccagatct acattggatt cggagtgctg   1680
ggcatggtgt tcaacatcta cggcgcctgc ggaaacgtga tcaagtacta caacaacaag   1740
ggcaagagcg ctctccccgc cattctcgga atcgcccccct ttggcatctt ctacgtcggc   1800
gtctttgcct gggcccatgt tgctcctctg cttctctcca agtacgccat cgtctatctg   1860
tttgccattg gggctgcctt tgccatgcaa gtcggccaga tgattcttgc ccatctcgtg   1920
cttgctccct ttccccactg gaacgtgctg ctcttcttcc cctttgtggg actggcagtg   1980
cactacattg cacccgtgtt tggctgggac gccgatatcg tgtcggttaa cactctcttc   2040
acctgttttg gcgccacccct ctccatttac gccttctttg tgcttgagat catcgacgag   2100
atcaccaact acctcgatat ctggtgtctg cgaatcaagt accctcagga gaagaagacc   2160
gaataagcgg ccgcatggag cgtgtgttct gagtcgatgt tttctatgga gttgtgagtg   2220
ttagtagaca tgatgggttt atatatgatg aatgaataga tgtgattttg atttgcacga   2280
tggaattgag aactttgtaa acgtacatgg gaatgtatga atgtgggggt tttgtgactg   2340
gataactgac ggtcagtgga cgccgttgtt caaatatcca agagatgcga gaaactttgg   2400
gtcaagtgaa catgtcctct ctgttcaagt aaaccatcaa ctatgggtag tatatttagt   2460
aaggacaaga gttgagattc tttggagtcc tagaaacgta ttttcgcgtt ccaagatcaa   2520
attagtagag taatacgggc acgggaatcc attcatagtc tcaatcctgc aggtgagtta   2580
attaatcgag cttggcgtaa tcatggtcat agctgtttcc tgtgtgaaat tgttatccgc   2640
tcacaattcc acacaacgta cgatagttag tagacaacaa tcagaacatc tccctcctta   2700
tataatcaca caggccagaa cgcgctaaac taaagcgctt tggacactat gttacattgg   2760
cattgattga actgaaacca cagtctccct cgcctgaatc gagcaatgga tgttgtcgga   2820
agtcaacttc actagaagag cggttctatg ccttgtcaag atcatatcat aaactcactc   2880
tgtattaccc catctataga acacttgtta tgaatgggcg gaaacattcc gctatatgca   2940
cctttccaca ctaatgcaaa gatgtgcatc ttcaacgggt agtaagactg gttccgactt   3000
ccgttgcatg gagagcaatg acctcgataa tgcgaacatc cccccacatat acactcttac   3060
acaggccaat ataatctgtg catttactaa atatttaagt ctatgcacct gcttgatgaa   3120
aagcggcacg gatggtatca tctagtttcc gccaatccaa gaaccaactg tgttggcagt   3180
ggtgtagccc atggcacaca gaccaaagat gaaaatacag acatcggcgg ttcgagccgt   3240
ggtgcctcga gcaacaccct tgtaatgcaa aagaggaggg taaatgtaca ccagaggcac   3300
acatgcaaac gatccggtga gagcgacgaa ccgatcgaga tcgtcggcac ctccccatgc   3360
aacaaaggcg gtgacaaaca caaggaagaa ccggaaaatg ttcttctgcc acttgatggt   3420
agagttgtac ttgcctgatc gggtgaagag accattctcg atgattcgga tggcgcgcca   3480
```

-continued

```
gctgcattaa tgaatcggcc aacgcgcggg gagaggcggt ttgcgtattg ggcgctcttc   3540
cgcttcctcg ctcactgact cgctgcgctc ggtcgttcgg ctgcggcgag cggtatcagc   3600
tcactcaaag gcggtaatac ggttatccac agaatcaggg gataacgcag gaaagaacat   3660
gtgagcaaaa ggccagcaaa aggccaggaa ccgtaaaaag gccgcgttgc tggcgttttt   3720
ccataggctc cgcccccctg acgagcatca caaaaatcga cgctcaagtc agaggtggcg   3780
aaacccgaca ggactataaa gataccaggc gtttccccct ggaagctccc tcgtgcgctc   3840
tcctgttccg accctgccgc ttaccggata cctgtccgcc tttctccctt cgggaagcgt   3900
ggcgctttct catagctcac gctgtaggta tctcagttcg gtgtaggtcg ttcgctccaa   3960
gctgggctgt gtgcacgaac cccccgttca gcccgaccgc tgcgccttat ccggtaacta   4020
tcgtcttgag tccaacccgg taagacacga cttatcgcca ctggcagcag ccactggtaa   4080
caggattagc agagcgaggt atgtaggcgg tgctacagag ttcttgaagt ggtggcctaa   4140
ctacggctac actagaagaa cagtatttgg tatctgcgct ctgctgaagc cagttacctt   4200
cggaaaaaga gttggtagct cttgatccgg caaacaaacc accgctggta gcggtggttt   4260
ttttgtttgc aagcagcaga ttacgcgcag aaaaaaagga tctcaagaag atcctttgat   4320
cttttctacg gggtctgacg ctcagtggaa cgaaaactca cgttaaggga ttttggtcat   4380
gagattatca aaaaggatct tcacctagat ccttttaaat taaaaatgaa gttttaaatc   4440
aatctaaagt atatatgagt aaacttggtc tgacagttac caatgcttaa tcagtgaggc   4500
acctatctca gcgatctgtc tatttcgttc atccatagtt gcctgactcc ccgtcgtgta   4560
gataactacg atacgggagg gcttaccatc tggccccagt gctgcaatga taccgcgaga   4620
cccacgctca ccggctccag atttatcagc aataaaccag ccagccggaa gggccgagcg   4680
cagaagtggt cctgcaactt tatccgcctc catccagtct attaattgtt gccgggaagc   4740
tagagtaagt agttcgccag ttaatagttt gcgcaacgtt gttgccattg ctacaggcat   4800
cgtggtgtca cgctcgtcgt ttggtatggc ttcattcagc tccggttccc aacgatcaag   4860
gcgagttaca tgatccccca tgttgtgcaa aaaagcggtt agctccttcg gtcctccgat   4920
cgttgtcaga agtaagttgg ccgcagtgtt atcactcatg gttatggcag cactgcataa   4980
ttctcttact gtcatgccat ccgtaagatg cttttctgtg actggtgagt actcaaccaa   5040
gtcattctga gaatagtgta tgcggcgacc gagttgctct tgcccggcgt caatacggga   5100
taataccgcg ccacatagca gaactttaaa agtgctcatc attggaaaac gttcttcggg   5160
gcgaaaactc tcaaggatct taccgctgtt gagatccagt tcgatgtaac ccactcgtgc   5220
acccaactga tcttcagcat cttttacttt caccagcgtt tctgggtgag caaaaacagg   5280
aaggcaaaat gccgcaaaaa agggaataag ggcgacacgg aaatgttgaa tactcatact   5340
cttccttttt caatattatt gaagcattta tcagggttat tgtctcatga gcggatacat   5400
atttgaatgt atttagaaaa ataaacaaat aggggttccg cgcacatttc cccgaaaagt   5460
gccacctgat gcggtgtgaa ataccgcaca gatgcgtaag gagaaaatac cgcatcagga   5520
aattgtaagc gttaatattt tgttaaaatt cgcgttaaat ttttgttaaa tcagctcatt   5580
ttttaaccaa taggccgaaa tcggcaaaat cccttataaa tcaaaagaat agaccgagat   5640
agggttgagt gttgttccag tttggaacaa gagtccacta ttaaagaacg tggactccaa   5700
cgtcaaaggg cgaaaaaccg tctatcaggg cgatggccca ctacgtgaac catcacccta   5760
atcaagtttt ttggggtcga ggtgccgtaa agcactaaat cggaacccta aagggagccc   5820
ccgatttaga gcttgacggg gaaagccggc gaacgtggcg agaaaggaag ggaagaaagc   5880
```

-continued gaaaggagcg ggcgctaggg cgctggcaag tgtagcggtc acgctgcgcg taaccaccac 5940
acccgccgcg cttaatgcgc cgctacaggg cgcgtccatt cgccattcag gctgcgcaac 6000
tgttgggaag ggcgatcggt gcgggcctct tcgctattac gccagctggc gaaaggggga 6060
tgtgctgcaa ggcgattaag ttgggtaacg ccagggtttt cccagtcacg acgttgtaaa 6120
acgacggcca gtgaattgta atacgactca ctatagggcg aattgggccc gacgtcgcat 6180
gcttagaagt gaggattaca agaagcctct ggatatcaat gatgaacgta ctcagcggct 6240
ggtcaagcat ttcgaccgtc gaatcgacga ggtgttcacc tttgacaagc gagggttccc 6300
aattgatcac gttctcgagt tgttcaaatc ttctctcaac atctctctgc atgaactatc 6360
tctgttgacg aacgtgtcac ccactgttcc tcgaacgccc ttctccgagt ttggtctgaa 6420
catcttcgat ctcaaactga cccccgcagt gatcaatagt gccatgccac tgccgatgcg 6480
gtgcgaacat ccctggaggg attctcggag ctctacacaa tgcagattct gtcgtcgagt 6540
actctctacc ttgctcgaat gacttattgt gctactactg cactcatgct tcgatcatgt 6600
gccctactgc accccaaatt tggtgatctg attgagacag agtaccctct tcagctgatt 6660
cagaagatca tcagcaacat gaatgatgtg gttgaccagg caggctgttg tagtcacgtc 6720
cttcacttca agttcattct tcatctgctt ctgttttact ttgacaggca aatgaagaca 6780
tggtacgact tgatggaggc caagaacgcc atttcacccc gagacaccga agtgcctgaa 6840
atcctggctg cccccattga taacatcgga aactacggta ttccggaaag tgtatataga 6900
acctttcccc agcttgtgtc tgtggatatg gatggtgtaa tccccttaat taactcacct 6960
gcaggattga gactatgaat ggattcccgt gcccgtatta ctctactaat ttgatcttgg 7020
aacgcgaaaa tacgtttcta ggactccaaa gaatctcaac tcttgtcctt actaaatata 7080
ctacccatag ttgatggttt acttgaacag agaggacatg ttcacttgac ccaaagtttc 7140
tcgcatctct tggatatttg aacaacggcg tccactgacc gtcagttatc cagtcacaaa 7200
acccccacat tcatacattc ccatgtacgt ttacaaagtt ctcaattcca tcgtgcaaat 7260
caaaatcaca tctattcatt catcatatat aaacccatca tgtctactaa cactcacaac 7320
tccatagaaa acatcgactc agaacacacg ctccatgcgg ccgcttaggc aacgggcttg 7380
atgacagcgg gaggagtgcc cacattgttt cggtttcgaa agaacaggac acccttgcca 7440
gctccctcgg caccagcgga gggttcaacc cactggcaca ttcgtgcaga tcggtacatg 7500
gctcgaatga atcctcgagg accgtcctgg acatcagctc gatagtgctt gcccatgata 7560
ggtttgatgg cctcggtagc ttcgtccgca ttgtagaagg gaatggaaga gacgtagtga 7620
tgcaggacgt gagtctcgat aatgccgtgg agcagatgac gtccaatgaa gcccatctct 7680
cggtcgatgg ttgcagcggc acctcgcaca aagttccact cgtcgttggt gtagtgggga 7740
agagtaggat ctgtgtgctg cagaaaggta atggcgacga gccagtggtt aacccacaag 7800
tagggaacga agtaccagat ggccatgttg tagaatccga acttctgaac gagaaagtac 7860
agagcggtgg ccataagacc aatgccaatg tcggagagca cgatgagctt ggcgtcgctg 7920
ttctcgtaca gaggagatcg gggatcgaaa tggttaactc caccgccaag accgttgtgc 7980
tttcccttgc ctcgaccctc tcgctgccgc tcatggtagt tgtgtccagt aacgttggta 8040
atgagatagt tgggccaacc gaccagttgc tgaagcacaa gcatgagcag ggtgaaagca 8100
ggagtttcct cggtaagatg ggcgagttcg tgggtcatct tgccgagtcg agtagcttgc 8160
tgctctcggg ttcgaggaac gaagaccatg tctcgctcca tgtttccagt ggccttgtga 8220

-continued

```
tgcttccggt gggagatttg ccagctgaag tagggaacaa gcagggaaga gtgaagcacc   8280
cagccagtaa tgtcgttgat gattcgggaa tcggagaaag caccatgtcc acactcgtgg   8340
gcaatgaccc acagtccagt accgaagagt ccctgaagaa cggtgtacac agcccacaga   8400
ccggctcgag caggagtgga gggaatgtac tcgggtgtca caaagttgta ccagatgctg   8460
aaagtggtag tcaggaggac aatgtctcga agaatgtagc cgtatccctt gagagcagat   8520
cgcttgaagc agtgcttggg aatagcgttg tagatgtcct tgatggtgaa gtcgggaact   8580
tcgaactggt tgccgtaggt atccagcatg acaccgtact cggacttggg cttggcaatg   8640
tccacctcgg acatggaaga cagcgatgta gaggaggccg agtgtctggg agaatcggag   8700
ggagagacgg cagcagactc cgagtcggtc acagtggtgg aagtgacggt tcgtcggagg   8760
gcagggttct gcttgggcag agccgaggtg gaggccatgg ccattgctgt agatatgtct   8820
tgtgtgtaag gggttggggg tggttgtttg tgttcttgac ttttgtgtta gcaagggaag   8880
acgggcaaaa aagtgagtgt ggttgggagg gagagacgag ccttatatat aatgcttgtt   8940
tgtgtttgtg caagtggacg ccgaaacggg caggagccaa actaaacaag gcagacaatg   9000
cgagcttaat tggattgcct gatgggcagg ggttagggct cgatcaatgg gggtgcgaag   9060
tgacaaaatt gggaattagg ttcgcaagca aggctgacaa gactttggcc caaacatttg   9120
tacgcggtgg acaacaggag ccacccatcg tctgtcacgg gctagccggt cgtgcgtcct   9180
gtcaggctcc acctaggctc catgccactc catacaatcc cactagtgta ccgctaggcc   9240
gcttttagct cccatctaag acccccccaa aacctccact gtacagtgca ctgtactgtg   9300
tggcgatcaa gggcaaggga aaaaaggcgc aaacatgcac gcatggaatg acgtaggtaa   9360
ggcgttacta gactgaaaag tggcacattt cggcgtgcca aagggtccta ggtgcgtttc   9420
gcgagctggg cgccaggcca agccgctcca aaacgcctct ccgactccct ccagcggcct   9480
ccatatcccc atccctctcc acagcaatgt tgttaagcct tgcaaacgaa aaaatagaaa   9540
ggctaataag cttccaatat tgtggtgtac gctgcataac gcaacaatga gcgccaaaca   9600
acacacacac acagcacaca gcagcattaa ccacgatgaa cagcatgaat tcctttacct   9660
gcaggataac ttcgtataat gtatgctata cgaagttatg atctctctct tgagcttttc   9720
cataacaagt tcttctgcct ccaggaagtc catgggtggt ttgatcatgg ttttggtgta   9780
gtggtagtgc agtggtggta ttgtgactgg ggatgtagtt gagaataagt catacacaag   9840
tcagctttct tcgagcctca tataagtata agtagttcaa cgtattagca ctgtacccag   9900
catctccgta tcgagaaaca caacaacatg ccccattgga cagatcatgc ggatacacag   9960
gttgtgcagt atcatacata ctcgatcaga caggtcgtct gaccatcata caagctgaac  10020
aagcgctcca tacttgcacg ctctctatat acacagttaa attacatatc catagtctaa  10080
cctctaacag ttaatcttct ggtaagcctc ccagccagcc ttctggtatc gcttggcctc  10140
ctcaatagga tctcggttct ggccgtacag acctcggccg acaattatga tatccgttcc  10200
ggtagacatg acatcctcaa cagttcggta ctgctgtccg agagcgtctc ccttgtcgtc  10260
aagacccacc ccgggggtca gaataagcca gtcctcagag tcgcccttag gtcggttctg  10320
ggcaatgaag ccaaccacaa actcggggtc ggatcgggca agctcaatgg tctgcttgga  10380
gtactcgcca gtggccagag agcccttgca agacagctcg gccagcatga gcagacctct  10440
ggccagcttc tcgttgggag aggggactag gaactccttg tactgggagt tctcgtagtc  10500
agagacgtcc tccttcttct gttcagagac agtttcctcg gcaccagctc gcaggccagc  10560
aatgattccg gttccgggta caccgtgggc gttggtgata tcggaccact cggcgattcg  10620
```

gtgacaccgg tactggtgct tgacagtgtt gccaatatct gcgaactttc tgtcctcgaa 10680
caggaagaaa ccgtgcttaa gagcaagttc cttgaggggg agcacagtgc cggcgtaggt 10740
gaagtcgtca atgatgtcga tatgggtttt gatcatgcac acataaggtc cgaccttatc 10800
ggcaagctca atgagctcct tggtggtggt aacatccaga gaagcacaca ggttggtttt 10860
cttggctgcc acgagcttga gcactcgagc ggcaaaggcg gacttgtgga cgttagctcg 10920
agcttcgtag gagggcattt tggtggtgaa gaggagactg aaataaattt agtctgcaga 10980
actttttatc ggaaccttat ctggggcagt gaagtatatg ttatggtaat agttacgagt 11040
tagttgaact tatagataga ctggactata cggctatcgg tccaaattag aaagaacgtc 11100
aatggctctc tgggcgtcgc ctttgccgac aaaaatgtga tcatgatgaa agccagcaat 11160
gacgttgcag ctgatattgt tgtcggccaa ccgcgccgaa aacgcagctg tcagacccac 11220
agcctccaac gaagaatgta tcgtcaaagt gatccaagca cactcatagt tggagtcgta 11280
ctccaaaggc ggcaatgacg agtcagacag atactcgtcg acgcgataac ttcgtataat 11340
gtatgctata cgaagttatc gtacgatagt tagtagacaa caatcgatcg aggaagagga 11400
caagcggctg cttcttaagt ttgtgacatc agtatccaag gcaccattgc aaggattcaa 11460
ggctttgaac ccgtcatttg ccattcgtaa cgctggtaga caggttgatc ggttccctac 11520
ggcctccacc tgtgtcaatc ttctcaagct gcctgactat caggacattg atcaacttcg 11580
gaagaaactt ttgtatgcca ttcgatcaca tgctggtttc gatttgtctt agaggaacgc 11640
atatacagta atcatagaga ataaacgata ttcatttatt aaagtagata gttgaggtag 11700
aagttgtaaa gagtgataaa tagcggccgc tcactgaatc tttttggctc ccttgtgctt 11760
tcggacgatg taggtctgca cgtagaagtt gaggaacaga cacaggacag taccaacgta 11820
gaagtagttg aaaaaccagc caaacattct cattccatct tgtcggtagc agggaatgtt 11880
ccggtacttc cagacgatgt agaagccaac gttgaactga atgatctgca tagaagtaat 11940
cagggacttg ggcataggga acttgagctt gatcagtcgg gtccaatagt agccgtacat 12000
gatccagtga atgaagccgt tgagcagcac aaagatccaa acggcttcgt ttcggtagtt 12060
gtagaacagc cacatgtcca taggagctcc gagatggtga aagaactgca accaggtcag 12120
aggcttgccc atgaggggca gatagaagga gtcaatgtac tcgaggaact tgctgaggta 12180
gaacagctga gtggtgattc ggaagacatt gttgtcgaaa gccttctcgc agttgtcgga 12240
catgacacca atggtgtaca tggcgtaggc catagagagg aaggagccca gcgagtagat 12300
ggacatgagc aggttgtagt tggtgaacac aaacttcatt cgagactgac ccttgggtcc 12360
gagaggacca agggtgaact tcaggatgac gaaggcgatg gagaggtaca gcacctcgca 12420
gtgcgaggca tcagaccaga gctgagcata gtcgaccttg ggaagaacct cctggccaat 12480
ggagacgatt tcgttcacga cctccatggt tgtgaattag ggtggtgaga atggttggtt 12540
gtagggaaga atcaaaggcc ggtctcggga tccgtgggta tatatatata tatatatata 12600
tacgatcctt cgttacctcc ctgttctcaa aactgtggtt tttcgttttt cgtttttttgc 12660 ttttttttgat ttttttaggg ccaactaagc ttccagattt cgctaatcac ctttgtacta 12720
attacaagaa aggaagaagc tgattagagt tgggcttttt atgcaactgt gctactcctt 12780
atctctgata tgaaagtgta gacccaatca catcatgtca tttagagttg gtaatactgg 12840
gaggatagat aaggcacgaa aacgagccat agcagacatg ctgggtgtag ccaagcagaa 12900
gaaagtagat gggagccaat tgacgagcga gggagctacg ccaatccgac atacgacacg 12960

```
ctgagatcgt cttggccggg gggtacctac agatgtccaa gggtaagtgc ttgactgtaa  13020
ttgtatgtct gaggacaaat atgtagtcag ccgtataaag tcataccagg caccagtgcc  13080
atcatcgaac cactaactct ctatgataca tgcctccggt attattgtac catgcgtcgc  13140
tttgttacat acgtatcttg ccttttctc tcagaaactc cagactttgg ctattggtcg  13200
agataagccc ggaccatagt gagtctttca cactctgttt aaacaccact aaaaccccac  13260
aaaatatatc ttaccgaata tacagatcta ctatagagga acaattgccc cggagaagac  13320
ggccaggccg cctagatgac aaattcaaca actcacagct gactttctgc cattgccact  13380
aggggggggc ctttttatat ggccaagcca agctctccac gtcggttggg ctgcacccaa  13440
caataaatgg gtagggttgc accaacaaag ggatgggatg gggggtagaa gatacgagga  13500
taacggggct caatggcaca aataagaacg aatactgcca ttaagactcg tgatccagcg  13560
actgacacca ttgcatcatc taagggcctc aaaactacct cggaactgct gcgctgatct  13620
ggacaccaca gaggttccga gcactttagg ttgcaccaaa tgtcccacca ggtgcaggca  13680
gaaaacgctg gaacagcgtg tacagtttgt cttaacaaaa agtgagggcg ctgaggtcga  13740
gcagggtggt gtgacttgtt atagccttta gagctgcgaa agcgcgtatg gatttggctc  13800
atcaggccag attgagggtc tgtggacaca tgtcatgtta gtgtacttca atcgcccccct  13860
ggatatagcc ccgacaatag gccgtggcct catttttttg ccttccgcac atttccattg  13920
ctcggtaccc acaccttgct tctcctgcac ttgccaacct taatactggt ttacattgac  13980
caacatctta caagcggggg gcttgtctag ggtatatata aacagtggct ctcccaatcg  14040
gttgccagtc tcttttttcc tttctttccc cacagattcg aaatctaaac tacacatcac  14100
acaatgcctg ttactgacgt ccttaagcga aagtccggtg tcatcgtcgg cgacgatgtc  14160
cgagccgtga gtatccacga caagatcagt gtcgagacga cgcgttttgt gtaatgacac  14220
aatccgaaag tcgctagcaa cacacactct ctacacaaac taacccagct ctccatggtg  14280
aaggcttctc gacaggctct gcccctcgtc atcgacggaa aggtgtacga cgtctccgct  14340
tgggtgaact tccaccctgg tggagctgaa atcattgaga actaccaggg acgagatgct  14400
actgacgcct tcatggttat gcactctcag gaagccttcg acaagctcaa gcgaatgccc  14460
aagatcaacc aggcttccga gctgcctccc caggctgccg tcaacgaagc tcaggaggat  14520
ttccgaaagc tccgagaaga gctgatcgcc actggcatgt ttgacgcctc tcccctctgg  14580
tactcgtaca agatcttgac caccctgggt cttggcgtgc ttgccttctt catgctggtc  14640
cagtaccacc tgtacttcat tggtgctctc gtgctcggta tgcactacca gcaaatggga  14700
tggctgtctc atgacatctg ccaccaccag accttcaaga accgaaactg gaataacgtc  14760
ctgggtctgg tctttggcaa cggactccag ggcttctccg tgacctggtg gaaggacaga  14820
cacaacgccc atcattctgc taccaacgtt cagggtcacg atcccgacat tgataacctg  14880
cctctgctcg cctggtccga ggacgatgtc actcgagctt ctcccatctc ccgaaagctc  14940
attcagttcc aacagtacta tttcctggtc atctgtattc tcctgcgatt catctggtgt  15000
ttccagtctg tgctgaccgt tcgatccctc aaggaccgag acaaccagtt ctaccgatct  15060
cagtacaaga aagaggccat tggactcgct ctgcactgga ctctcaagac cctgttccac  15120
ctcttcttta tgccctccat cctgacctcg atgctggtgt tctttgtttc cgagctcgtc  15180
ggtggcttcg gaattgccat cgtggtcttc atgaaccact accctctgga gaagatcggt  15240
gattccgtct gggacggaca tggcttctct gtgggtcaga tccatgagac catgaacatt  15300
cgacgaggca tcattactga ctggttcttt ggaggcctga actaccagat cgagcaccat  15360
```

ctctggccca ccctgcctcg acacaacctc actgccgttt cctaccaggt ggaacagctg 15420
tgccagaagc acaacctccc ctaccgaaac cctctgcccc atgaaggtct cgtcatcctg 15480
ctccgatacc tgtcccagtt cgctcgaatg gccgagaagc agcccggtgc caaggctcag 15540
taagcggccg catgagaaga taaatatata aatacattga gatattaaat gcgctagatt 15600
agagagcctc atactgctcg gagagaagcc aagacgagta ctcaaagggg attacaccat 15660
ccatatccac agacacaagc tggggaaagg ttctatatac actttccgga ataccgtagt 15720
ttccgatgtt atcaatgggg gcagccagga tttcaggcac ttcggtgtct cggggtgaaa 15780
tggcgttctt ggcctccatc aagtcgtacc atgtcttcat ttgcctgtca aagtaaaaca 15840
gaagcagatg aagaatgaac ttgaagtgaa ggaattt 15877

<210> SEQ ID NO 55
<211> LENGTH: 15812
<212> TYPE: DNA
<213> ORGANISM: Artificial Sequence
<220> FEATURE:
<223> OTHER INFORMATION: Plasmid pZKL2-5U89GC

<400> SEQUENCE: 55
gtacgttatc atttgaacag tgaaaggcta cagtaacaga agcagttgta aacttcattc 60
cgttgattct gtactacagt accccactac gccgcttccg ctgacactgt tcaacccaaa 120
aactacatct gcgtgcgctg tgtaaggcta tcatcagata catactgtag attctgtaga 180
tgcgaacctg cttgtatcat atacatcccc ctccccctga cctgcacaag caagcaatgt 240
gacattgata ttgctgctta tctagtgccg aggatgtgaa agccgagact caaacatttc 300
ttttactctc ttgttcctga ccagacctgg cggagattac gccagtatga ttcttgcagg 360
tctgagacaa gcctggaaca gccaacattt atttttcgaa gcgagaaaca tgccacaccc 420
cggcacgttc agagatgcat atgatttgtt tttcgagtaa cagtaccccc cccccccccc 480
ccaatgaaac cagtattact cacaccatcc tcattcaaag cgttacactg attacgcgcc 540
catcaacgac agcatgaggg gactgctgat ctgatctaat caaatgacta caaaaatcgc 600
aataatgaag agcaaacgac aaaaaagaaa caggttaacc aatcccgctt caatgtctca 660
ccacaatcca gcactgtttc tcattacctc ctccctctaa tttcagagtt gcatcagggt 720
ccttgatggc gcgccagctg cattaatgaa tcggccaacg cgcggggaga ggcggtttgc 780
gtattgggcg ctcttccgct tcctcgctca ctgactcgct gcgctcggtc gttcggctgc 840
ggcgagcggt atcagctcac tcaaaggcgg taatacggtt atccacagaa tcaggggata 900
acgcaggaaa gaacatgtga gcaaaaggcc agcaaaaggc caggaaccgt aaaaaggccg 960
cgttgctggc gtttttccat aggctccgcc cccctgacga gcatcacaaa aatcgacgct 1020
caagtcagag gtggcgaaac ccgacaggac tataaagata ccaggcgttt ccccctggaa 1080
gctccctcgt gcgctctcct gttccgaccc tgccgcttac cggatacctg tccgcctttc 1140
tcccttcggg aagcgtggcg ctttctcata gctcacgctg taggtatctc agttcggtgt 1200
aggtcgttcg ctccaagctg ggctgtgtgc acgaaccccc cgttcagccc gaccgctgcg 1260
ccttatccgg taactatcgt cttgagtcca acccggtaag acacgactta tcgccactgg 1320
cagcagccac tggtaacagg attagcagag cgaggtatgt aggcggtgct acagagttct 1380
tgaagtggtg gcctaactac ggctacacta gaagaacagt atttggtatc tgcgctctgc 1440
tgaagccagt taccttcgga aaaagagttg gtagctcttg atccggcaaa caaaccaccg 1500

-continued ctggtagcgg tggttttttt gtttgcaagc agcagattac gcgcagaaaa aaaggatctc 1560
aagaagatcc tttgatcttt tctacggggt ctgacgctca gtggaacgaa aactcacgtt 1620
aagggatttt ggtcatgaga ttatcaaaaa ggatcttcac ctagatcctt ttaaattaaa 1680
aatgaagttt taaatcaatc taaagtatat atgagtaaac ttggtctgac agttaccaat 1740
gcttaatcag tgaggcacct atctcagcga tctgtctatt tcgttcatcc atagttgcct 1800
gactccccgt cgtgtagata actacgatac gggagggctt accatctggc cccagtgctg 1860
caatgatacc gcgagaccca cgctcaccgg ctccagattt atcagcaata aaccagccag 1920
ccggaagggc cgagcgcaga agtggtcctg caactttatc cgcctccatc cagtctatta 1980
attgttgccg ggaagctaga gtaagtagtt cgccagttaa tagtttgcgc aacgttgttg 2040
ccattgctac aggcatcgtg gtgtcacgct cgtcgtttgg tatggcttca ttcagctccg 2100
gttcccaacg atcaaggcga gttacatgat cccccatgtt gtgcaaaaaa gcggttagct 2160
ccttcggtcc tccgatcgtt gtcagaagta agttggccgc agtgttatca ctcatggtta 2220
tggcagcact gcataattct cttactgtca tgccatccgt aagatgcttt tctgtgactg 2280
gtgagtactc aaccaagtca ttctgagaat agtgtatgcg gcgaccgagt tgctcttgcc 2340
cggcgtcaat acgggataat accgcgccac atagcagaac tttaaaagtg ctcatcattg 2400
gaaaacgttc ttcggggcga aaactctcaa ggatcttacc gctgttgaga tccagttcga 2460
tgtaacccac tcgtgcaccc aactgatctt cagcatcttt tactttcacc agcgtttctg 2520
ggtgagcaaa aacaggaagg caaaatgccg caaaaaaggg aataagggcg acacggaaat 2580
gttgaatact catactcttc ctttttcaat attattgaag catttatcag ggttattgtc 2640
tcatgagcgg atacatattt gaatgtattt agaaaaataa acaaataggg gttccgcgca 2700
catttccccg aaaagtgcca cctgatgcgg tgtgaaatac cgcacagatg cgtaaggaga 2760
aaataccgca tcaggaaatt gtaagcgtta atattttgtt aaaattcgcg ttaaattttt 2820
gttaaatcag ctcatttttt aaccaatagg ccgaaatcgg caaaatccct tataaatcaa 2880
aagaatagac cgagataggg ttgagtgttg ttccagtttg gaacaagagt ccactattaa 2940
agaacgtgga ctccaacgtc aaagggcgaa aaaccgtcta tcagggcgat ggcccactac 3000
gtgaaccatc accctaatca agttttttgg ggtcgaggtg ccgtaaagca ctaaatcgga 3060
accctaaagg gagcccccga tttagagctt gacggggaaa gccggcgaac gtggcgagaa 3120
aggaagggaa gaaagcgaaa ggagcgggcg ctagggcgct ggcaagtgta gcggtcacgc 3180
tgcgcgtaac caccacaccc gccgcgctta atgcgccgct acagggcgcg tccattcgcc 3240
attcaggctg cgcaactgtt gggaagggcg atcggtgcgg gcctcttcgc tattacgcca 3300
gctggcgaaa gggggatgtg ctgcaaggcg attaagttgg gtaacgccag ggttttccca 3360
gtcacgacgt tgtaaaacga cggccagtga attgtaatac gactcactat agggcgaatt 3420
gggcccgacg tcgcatgctg gtttcgattt gtcttagagg aacgcatata cagtaatcat 3480
agagaataaa cgatattcat ttattaaagt agatagttga ggtagaagtt gtaaagagtg 3540
ataaatagct tagataccac agacaccctc ggtgacgaag tactgcagat ggtttccaat 3600
cacattgacc tgctggagca gagtgttacc ggcagagcac tgtttattgc tctggccctg 3660
gcacatgaca acgttggaga gaggagggtg gatcaggggc cagtcaataa agacctcacc 3720
agagcagtgc tggtaaccgt cccagaaggg cacttgaggg acgatatctc ctcggtgggt 3780
gattcggtag agctttcggt ctttggacac cttggagaca tcggggttct cctggccaaa 3840
gaagagttta tcgacccagt tagcaaagcc agcgttaccg acaatgggct gaccaagagt 3900

```
aacaacgagg ggatcgtggc cgttaacctt gaggttgatt ccgaacagaa gggctgcagc   3960
tcctccgaga gagtgaccgg tgacagcaat ctggtagtcg ggatactgct caatcacaga   4020
gtcgagcttg gggccgatct gattgtaggt gttgttgtag gactggatga agccattgtg   4080
gacaagacag tcatcacaag tagcagtaga agagatgtta gcagcaagat caaagttaat   4140
taactcacct gcaggattga gactatgaat ggattcccgt gcccgtatta ctctactaat   4200
ttgatcttgg aacgcgaaaa tacgtttcta ggactccaaa gaatctcaac tcttgtcctt   4260
actaaatata ctacccatag ttgatggttt acttgaacag agaggacatg ttcacttgac   4320
ccaaagtttc tcgcatctct tggatatttg aacaacggcg tccactgacc gtcagttatc   4380
cagtcacaaa acccccacat tcatacattc ccatgtacgt ttacaaagtt ctcaattcca   4440
tcgtgcaaat caaaatcaca tctattcatt catcatatat aaacccatca tgtctactaa   4500
cactcacaac tccatagaaa acatcgactc agaacacacg ctccatgcgg ccgcttagga   4560
atcctgagcg tccttgacac agtgaaccac accgactttg tgcatgtact tgagggtgga   4620
aatgatgttg cccacaatgg tagggtagaa gacgtaccga actccgtgtc gttcgcaaca   4680
ctctcggaca gcttgctgca cgaagggata gtgccaagac gacattcgag gaaagaggtg   4740
atgctcgatc tggaagttga gaccgccagt aaagaacatg gcaatgggtc caccgtaggt   4800
ggaagaggtc tccacctgag ctctgtacca gtcgatctga tcggcttcaa cgtccttctc   4860
ggagctcttg accttgcagt tcttgtcggg gattcgctcc gagccatcga agttgtgaga   4920
caagatgaaa aagaaggtga ggaaggcacc ggtagcagtg ggcaccagag gaatggtgat   4980
gagcagggag gttccagtga gataccaggg caagaaggcg gttcgaaaga tgaagaaagc   5040
tcgcataacg aatgcaaggg ttcggtaccg tcgcagaaag ccgttctctc gcatggctgt   5100
gacagactcg ggaatggtgt cgttgtgctg cattcggaag atgtagagag ggttgtacac   5160
cagcgaaacg ccgtaggctc caagcacgag gtacatgtac caggcctgga atcggtgaaa   5220
ccactttcga gcagtgttgg cagcagggta gttgtggaac acaaggaatg gttctgcgga   5280
ctcggcatcc aggtcgagac catgctgatt ggtgtaggtg tgatgtcgca tgatgtgaga   5340
ctgcagccag atccatctgg acgatccaat gacgtcgatg ccgtaggcaa agagagcgtt   5400
gacccagggc tttttgctga tggcaccatg agaggcatcg tgctgaatgg acaggccgat   5460
ctgcatgtgc atgaatccag tcaagagacc ccacagcacc attccggtag tagcccagtg   5520
ccactcgcaa aaggcggtga cagcaatgat gccaacggtt cgcagccaga atccaggtgt   5580
ggcataccag ttccgacctt tcatgacctc tcgcatagtt cgcttgacgt cctgtgcaaa   5640
gggagagtcg taggtgtaga caatgtcctt ggaggttcgg tcgtgcttgc ctcgcacgaa   5700
ctgttgaagc agcttcgagt tctcgggctt gacgtaaggg tgcatggagt agaacagagg   5760
agaagcatcg gaggcaccag aagcgaggat caagtcgcct ccgggatgga ccttggcaag   5820
accttccaga tcgtagagaa tgccgtcgat ggcaaccagg tcgggtcgct cgagcagctg   5880
ctcggtagta agggagagag ccatggttgt gaattagggt ggtgagaatg gttggttgta   5940
gggaagaatc aaaggccggt ctcgggatcc gtgggtatat atatatatat atatatatac   6000
gatccttcgt tacctccctg ttctcaaaac tgtggttttt cgtttttcgt tttttgcttt   6060
ttttgatttt tttagggcca actaagcttc cagatttcgc taatcacctt tgtactaatt   6120
acaagaaagg aagaagctga ttagagttgg gctttttatg caactgtgct actccttatc   6180
tctgatatga aagtgtagac ccaatcacat catgtcattt agagttggta atactgggag   6240
```

-continued

```
gatagataag gcacgaaaac gagccatagc agacatgctg ggtgtagcca agcagaagaa   6300
agtagatggg agccaattga cgagcgaggg agctacgcca atccgacata cgacacgctg   6360
agatcgtctt ggccgggggg tacctacaga tgtccaaggg taagtgcttg actgtaattg   6420
tatgtctgag gacaaatatg tagtcagccg tataaagtca taccaggcac cagtgccatc   6480
atcgaaccac taactctcta tgatacatgc ctccggtatt attgtaccat gcgtcgcttt   6540
gttacatacg tatcttgcct ttttctctca gaaactccag aattctctct cttgagcttt   6600
tccataacaa gttcttctgc ctccaggaag tccatgggtg gtttgatcat ggttttggtg   6660
tagtggtagt gcagtggtgg tattgtgact ggggatgtag ttgagaataa gtcatacaca   6720
agtcagcttt cttcgagcct catataagta taagtagttc aacgtattag cactgtaccc   6780
agcatctccg tatcgagaaa cacaacaaca tgccccattg gacagatcat gcggatacac   6840
aggttgtgca gtatcataca tactcgatca gacaggtcgt ctgaccatca tacaagctga   6900
acaagcgctc catacttgca cgctctctat atacacagtt aaattacata tccatagtct   6960
aacctctaac agttaatctt ctggtaagcc tcccagccag ccttctggta tcgcttggcc   7020
tcctcaatag gatctcggtt ctggccgtac agacctcggc cgacaattat gatatccgtt   7080
ccggtagaca tgacatcctc aacagttcgg tactgctgtc cgagagcgtc tcccttgtcg   7140
tcaagaccca ccccgggggt cagaataagc cagtcctcag agtcgccctt aggtcggttc   7200
tgggcaatga agccaaccac aaactcgggg tcggatcggg caagctcaat ggtctgcttg   7260
gagtactcgc cagtggccag agagcccttg caagacagct cggccagcat gagcagacct   7320
ctggccagct tctcgttggg agaggggact aggaactcct tgtactggga gttctcgtag   7380
tcagagacgt cctccttctt ctgttcagag acagtttcct cggcaccagc tcgcaggcca   7440
gcaatgattc cggttccggg tacaccgtgg gcgttggtga tatcggacca ctcggcgatt   7500
cggtgacacc ggtactggtg cttgacagtg ttgccaatat ctgcgaactt tctgtcctcg   7560
aacaggaaga aaccgtgctt aagagcaagt tccttgaggg ggagcacagt gccggcgtag   7620
gtgaagtcgt caatgatgtc gatatgggtt ttgatcatgc acacataagg tccgacctta   7680
tcggcaagct caatgagctc cttggtggtg gtaacatcca gagaagcaca caggttggtt   7740
ttcttggctg ccacgagctt gagcactcga gcggcaaagg cggacttgtg gacgttagct   7800
cgagcttcgt aggagggcat tttggtggtg aagaggagac tgaaataaat ttagtctgca   7860
gaacttttta tcggaacctt atctggggca gtgaagtata tgttatggta atagttacga   7920
gttagttgaa cttatagata gactggacta tacggctatc ggtccaaatt agaaagaacg   7980
tcaatggctc tctgggcgtc gcctttgccg acaaaaatgt gatcatgatg aaagccagca   8040
atgacgttgc agctgatatt gttgtcggcc aaccgcgccg aaaacgcagc tgtcagaccc   8100
acagcctcca acgaagaatg tatcgtcaaa gtgatccaag cacactcata gttggagtcg   8160
tactccaaag gcggcaatga cgagtcagac agatactcgt cgaccttttc cttgggaacc   8220
accaccgtca gcccttctga ctcacgtatt gtagccaccg acacaggcaa cagtccgtgg   8280
atagcagaat atgtcttgtc ggtccatttc tcaccaactt taggcgtcaa gtgaatgttg   8340
cagaagaagt atgtgccttc attgagaatc ggtgttgctg atttcaataa agtcttgaga   8400
tcagtttggc cagtcatgtt gtggggggta attggattga gttatcgcct acagtctgta   8460
caggtatact cgctgcccac tttatacttt ttgattccgc tgcacttgaa gcaatgtcgt   8520
ttaccaaaag tgagaatgct ccacagaaca caccccaggg tatggttgag caaaaaaataa   8580
acactccgat acggggaatc gaaccccggt ctccacggtt ctcaagaagt attcttgatg   8640
```

agagcgtatc gatcgaggaa gaggacaagc ggctgcttct taagtttgtg acatcagtat 8700
ccaaggcacc attgcaagga ttcaaggctt tgaacccgtc atttgccatt cgtaacgctg 8760
gtagacaggt tgatcggttc cctacggcct ccacctgtgt caatcttctc aagctgcctg 8820
actatcagga cattgatcaa cttcggaaga aacttttgta tgccattcga tcacatgctg 8880
gtttcgattt gtcttagagg aacgcatata cagtaatcat agagaataaa cgatattcat 8940
ttattaaagt agatagttga ggtagaagtt gtaaagagtg ataaatagcg gccgctcact 9000
gaatcttttt ggctcccttg tgctttcgga cgatgtaggt ctgcacgtag aagttgagga 9060
acagacacag gacagtacca acgtagaagt agttgaaaaa ccagccaaac attctcattc 9120
catcttgtcg gtagcaggga atgttccggt acttccagac gatgtagaag ccaacgttga 9180
actgaatgat ctgcatagaa gtaatcaggg acttgggcat agggaacttg agcttgatca 9240
gtcgggtcca atagtagccg tacatgatcc agtgaatgaa gccgttgagc agcacaaaga 9300
tccaaacggc ttcgtttcgg tagttgtaga acagccacat gtccatagga gctccgagat 9360
ggtgaaagaa ctgcaaccag gtcagaggct tgcccatgag ggcagatag aaggagtcaa 9420
tgtactcgag gaacttgctg aggtagaaca gctgagtggt gattcggaag acattgttgt 9480
cgaaagcctt ctcgcagttg tcggacatga caccaatggt gtacatggcg taggccatag 9540
agaggaagga gcccagcgag tagatggaca tgagcaggtt gtagttggtg aacacaaact 9600
tcattcgaga ctgacccttg ggtccgagag gaccaagggt gaacttcagg atgacgaagg 9660
cgatggagag gtacagcacc tcgcagtgcg aggcatcaga ccagagctga gcatagtcga 9720
ccttgggaag aacctcctgg ccaatggaga cgatttcgtt cacgacctcc atggttgatg 9780
tgtgtttaat tcaagaatga atatagagaa gagaagaaga aaaaagattc aattgagccg 9840
gcgatgcaga cccttatata aatgttgcct tggacagacg gagcaagccc gcccaaacct 9900
acgttcggta taatatgtta agctttttaa cacaaaggtt tggcttgggg taacctgatg 9960
tggtgcaaaa gaccgggcgt tggcgagcca ttgcgcgggc gaatggggcc gtgactcgtc 10020
tcaaattcga gggcgtgcct caattcgtgc ccccgtggct ttttcccgcc gtttccgccc 10080
cgtttgcacc actgcagccg cttctttggt tcggacacct tgctgcgagc taggtgcctt 10140
gtgctactta aaaagtggcc tcccaacacc aacatgacat gagtgcgtgg gccaagacac 10200
gttggcgggg tcgcagtcgg ctcaatggcc cggaaaaaac gctgctggag ctggttcgga 10260
cgcagtccgc cgcggcgtat ggatatccgc aaggttccat agcgccattg ccctccgtcg 10320
gcgtctatcc cgcaacctct aaatagagcg ggaatataac ccaagcttct tttttttcct 10380
ttaacacgca cacccccaac tatcatgttg ctgctgctgt ttgactctac tctgtggagg 10440
ggtgctccca cccaacccaa cctacaggtg gatccggcgc tgtgattggc tgataagtct 10500
cctatccgga ctaattctga ccaatgggac atgcgcgcag gacccaaatg ccgcaattac 10560
gtaaccccaa cgaaatgcct acccctcttt ggagcccagc ggccccaaat ccccccaagc 10620
agcccggttc taccggcttc catctccaag cacaagcagc ccggttctac cggcttccat 10680
ctccaagcac ccctttctcc acaccccaca aaaagacccg tgcaggacat cctactgcgt 10740
gtttaaacac cactaaaacc ccacaaaata tatcttaccg aatatacaga tctactatag 10800
aggaacaatt gccccggaga agacggccag gccgcctaga tgacaaattc aacaactcac 10860
agctgacttt ctgccattgc cactaggggg gggccttttt atatggccaa gccaagctct 10920
ccacgtcggt tgggctgcac ccaacaataa atgggtaggg ttgcaccaac aaagggatgg 10980

-continued gatggggggt agaagatacg aggataacgg ggctcaatgg cacaaataag aacgaatact 11040
gccattaaga ctcgtgatcc agcgactgac accattgcat catctaaggg cctcaaaact 11100
acctcggaac tgctgcgctg atctggacac cacagaggtt ccgagcactt taggttgcac 11160
caaatgtccc accaggtgca ggcagaaaac gctggaacag cgtgtacagt ttgtcttaac 11220
aaaaagtgag ggcgctgagg tcgagcaggg tggtgtgact tgttatagcc tttagagctg 11280
cgaaagcgcg tatggatttg gctcatcagg ccagattgag ggtctgtgga cacatgtcat 11340
gttagtgtac ttcaatcgcc ccctggatat agccccgaca ataggccgtg gcctcatttt 11400
tttgccttcc gcacatttcc attgctcggt acccacacct tgcttctcct gcacttgcca 11460
accttaatac tggtttacat tgaccaacat cttacaagcg gggggcttgt ctagggtata 11520
tataaacagt ggctctccca atcggttgcc agtctctttt ttcctttctt tccccacaga 11580
ttcgaaatct aaactacaca tcacacaatg cctgttactg acgtccttaa gcgaaagtcc 11640
ggtgtcatcg tcggcgacga tgtccgagcc gtgagtatcc acgacaagat cagtgtcgag 11700
acgacgcgtt ttgtgtaatg acacaatccg aaagtcgcta gcaacacaca ctctctacac 11760
aaactaaccc agctctccat ggtgaaggct tctcgacagg ctctgcccct cgtcatcgac 11820
ggaaaggtgt acgacgtctc cgcttgggtg aacttccacc ctggtggagc tgaaatcatt 11880
gagaactacc agggacgaga tgctactgac gccttcatgg ttatgcactc tcaggaagcc 11940
ttcgacaagc tcaagcgaat gcccaagatc aaccaggctt ccgagctgcc tccccaggct 12000
gccgtcaacg aagctcagga ggatttccga aagctccgag aagagctgat cgccactggc 12060
atgtttgacg cctctcccct ctggtactcg tacaagatct tgaccaccct gggtcttggc 12120
gtgcttgcct tcttcatgct ggtccagtac cacctgtact tcattggtgc tctcgtgctc 12180
ggtatgcact accagcaaat gggatggctg tctcatgaca tctgccacca ccagaccttc 12240
aagaaccgaa actggaataa cgtcctgggt ctggtctttg gcaacggact ccagggcttc 12300
tccgtgacct ggtggaagga cagacacaac gcccatcatt ctgctaccaa cgttcagggt 12360
cacgatcccg acattgataa cctgcctctg ctcgcctggt ccgaggacga tgtcactcga 12420
gcttctccca tctcccgaaa gctcattcag ttccaacagt actatttcct ggtcatctgt 12480
attctcctgc gattcatctg gtgtttccag tctgtgctga ccgttcgatc cctcaaggac 12540
cgagacaacc agttctaccg atctcagtac aagaaagagg ccattggact cgctctgcac 12600
tggactctca agaccctgtt ccacctcttc tttatgccct ccatcctgac ctcgatgctg 12660
gtgttctttg tttccgagct cgtcggtggc ttcggaattg ccatcgtggt cttcatgaac 12720
cactaccctc tggagaagat cggtgattcc gtctgggacg gacatggctt ctctgtgggt 12780
cagatccatg agaccatgaa cattcgacga ggcatcatta ctgactggtt ctttggaggc 12840
ctgaactacc agatcgagca ccatctctgg cccaccctgc ctcgacacaa cctcactgcc 12900
gtttcctacc aggtggaaca gctgtgccag aagcacaacc tcccctaccg aaaccctctg 12960
ccccatgaag gtctcgtcat cctgctccga tacctgtccc agttcgctcg aatggccgag 13020
aagcagcccg gtgccaaggc tcagtaagcg gccgcatgag aagataaata tataaataca 13080
ttgagatatt aaatgcgcta gattagagag cctcatactg ctcggagaga agccaagacg 13140
agtactcaaa ggggattaca ccatccatat ccacagacac aagctgggga aaggttctat 13200
atacactttc cggaataccg tagtttccga tgttatcaat gggggcagcc aggatttcag 13260
gcacttcggt gtctcggggt gaaatggcgt tcttggcctc catcaagtcg taccatgtct 13320
tcatttgcct gtcaaagtaa aacagaagca gatgaagaat gaacttgaag tgaaggaatt 13380

-continued

```
taaatagttg gagcaaggga gaaatgtaga gtgtgaaaga ctcactatgg tccgggctta  13440
tctcgaccaa tagccaaagt ctggagtttc tgagagaaaa aggcaagata cgtatgtaac  13500
aaagcgacgc atggtacaat aataccggag gcatgtatca tagagagtta gtggttcgat  13560
gatggcactg gtgcctggta tgactttata cggctgacta catatttgtc ctcagacata  13620
caattacagt caagcactta cccttggaca tctgtaggta ccccccggcc aagacgatct  13680
cagcgtgtcg tatgtcggat tggcgtagct ccctcgctcg tcaattggct cccatctact  13740
ttcttctgct tggctacacc cagcatgtct gctatggctc gttttcgtgc cttatctatc  13800
ctcccagtat taccaactct aaatgacatg atgtgattgg gtctacactt tcatatcaga  13860
gataaggagt agcacagttg cataaaaagc ccaactctaa tcagcttctt cctttcttgt  13920
aattagtaca aaggtgatta gcgaaatctg gaagcttagt tggccctaaa aaaatcaaaa  13980
aaagcaaaaa acgaaaaacg aaaaaccaca gttttgagaa cagggaggta acgaaggatc  14040
gtatatatat atatatatat atatacccac ggatcccgag accggccttt gattcttccc  14100
tacaaccaac cattctcacc accctaattc acaaccatgg gcgtattcat taaacaggag  14160
cagcttccgg ctctcaagaa gtacaagtac tccgccgagg atcactcgtt catctccaac  14220
aacattctgc gccccttctg gcgacagttt gtcaaaatct tccctctgtg gatggccccc  14280
aacatggtga ctctgctggg cttcttcttt gtcattgtga acttcatcac catgctcatt  14340
gttgatccca cccacgaccg cgagcctccc agatgggtct acctcaccta cgctctgggt  14400
ctgttccttt accagacatt tgatgcctgt gacggatccc atgcccgacg aactggccag  14460
agtggacccc ttggagagct gtttgaccac tgtgtcgacg ccatgaatac ctctctgatt  14520
ctcacggtgg tggtgtccac cacccatatg ggatataaca tgaagctact gattgtgcag  14580
attgccgctc tcggaaactt ctacctgtcg acctgggaga cctaccatac cggaactctg  14640
tacctttctg gcttctctgg tcctgttgaa ggtatcttga ttctggtggc tcttttcgtc  14700
ctcaccttct tcactggtcc caacgtgtac gctctgaccg tctacgaggc tcttcccgag  14760
tccatcactt cgctgctgcc tgccagcttc ctggacgtca ccatcaccca gatctacatt  14820
ggattcggag tgctgggcat ggtgttcaac atctacggcg cctgcggaaa cgtgatcaag  14880
tactacaaca acaagggcaa gagcgctctc cccgccattc tcggaatcgc cccctttggc  14940
atcttctacg tcggcgtctt tgcctgggcc catgttgctc ctctgcttct ctccaagtac  15000
gccatcgtct atctgtttgc cattggggct gcctttgcca tgcaagtcgg ccagatgatt  15060
cttgcccatc tcgtgcttgc tccctttccc cactggaacg tgctgctctt cttccccttt  15120
gtgggactgg cagtgcacta cattgcaccc gtgtttggct gggacgccga tatcgtgtcg  15180
gttaacactc tcttcacctg ttttggcgcc accctctcca tttacgcctt ctttgtgctt  15240
gagatcatcg acgagatcac caactacctc gatatctggt gtctgcgaat caagtaccct  15300
caggagaaga agaccgaata agcggccgca tggagcgtgt gttctgagtc gatgttttct  15360
atggagttgt gagtgttagt agacatgatg ggtttatata tgatgaatga atagatgtga  15420
ttttgatttg cacgatggaa ttgagaactt tgtaaacgta catgggaatg tatgaatgtg  15480
ggggttttgt gactggataa ctgacggtca gtggacgccg ttgttcaaat atccaagaga  15540
tgcgagaaac tttgggtcaa gtgaacatgt cctctctgtt caagtaaacc atcaactatg  15600
ggtagtatat ttagtaagga caagagttga gattctttgg agtcctagaa acgtattttc  15660
gcgttccaag atcaaattag tagagtaata cgggcacggg aatccattca tagtctcaat  15720
```

-continued cctgcaggtg agttaattaa tcgagcttgg cgtaatcatg gtcatagctg tttcctgtgt 15780
gaaattgtta tccgctcaca attccacaca ac 15812

<210> SEQ ID NO 56
<211> LENGTH: 7966
<212> TYPE: DNA
<213> ORGANISM: Artificial Sequence
<220> FEATURE:
<223> OTHER INFORMATION: Plasmid pYPS161

<400> SEQUENCE: 56
aaatgtaacg aaactgaaat ttgaccagat attgtgtccg cggtggagct ccagcttttg 60
ttccctttag tgagggttaa tttcgagctt ggcgtaatca tggtcatagc tgtttcctgt 120
gtgaaattgt tatccgctca caagcttcca cacaacgtac gttctggttg gctcggatga 180
tttctgcggc cccagcgtaa ggcaggcgtt ccgtccggat cggtttgggt cggatcggct 240
ttttgattgt cgtattgtcg ctcatgttgg acctggtgtg tagttgtagt gtcagatcag 300
attcaccagc gaatgcatgt gaacttcccc acattttgag ccgaggcaga tttgggttgc 360
ttagtaagca gacgtggcgt tgcaagtaga tgtggcaaat ggggacgaag attccgaggg 420
gatatcatag ttccaagggg atgtcatcat ttgccagctt tcgccgccac ttttgacgag 480
tttttgtggg tcaaataagt ttagttgaac ttttcaaatt tcagttggca ttttgttaat 540
agaaagggtg ccggtgctgg ggggttcatt cctcgggttg cagatatcct atctgtctta 600
ggggtatctc tttcaatcga caagatgtag ttgggtaaca attatttatt aatattctct 660
ccatccagta cagtactaac atcttgacat ctcagcacaa gtgcatcttc ccaagtgttt 720
gttggagagg ttgttgggta ttacttagga aacagaacac agtacgtgga gatcttggat 780
acatcgtaca tggaggttat ccataaaaaa gaccctccag gactagttac aatgccgtta 840
gatgaggaaa tccacaaccc tgattcacta tgaacatatt atcttccccc aaacttgcga 900
tatatggccc ttgatgatag ccttgatttt acccttgatg gtacctccac gaccaaccga 960
tctgctgttt gaagagatat tttcaaattt gaagtgctca gatctactaa acatgagtcc 1020
agtaattctt tccgtctttc cgatttccga tattcccttt tttagcccga cttttcactg 1080
ctcccatgtc aaacgattag gacttgggag acaatcccac tgtcaaaatc accccgatat 1140
tctctgtaaa acaagtactt cttccacgtg atcttcaaat acctcttcca cgtgaccttc 1200
aaatacctct tcaagtacct cttccacgcg accttcaaag tcccttcaaa tacccttctc 1260
aattctcccc ttctcctcca tagtccttct ctctgactaa gcttgagaat acatgacgct 1320
aagacgaaaa cacactagag accctgagag cctgaacatg catccactct gcagttgcgc 1380
acgtgcctac agcaactatc gggtccagtg ctggatctga cactgcgtct ccctatgaag 1440
aaactgataa acagatctgc actcataaca atgatctgag cgatgaaaac gtgacctcca 1500
cagccacaag tcataatcgg cgcgccagct gcattaatga atcggccaac gcgcggggag 1560
aggcggtttg cgtattgggc gctcttccgc ttcctcgctc actgactcgc tgcgctcggt 1620
cgttcggctg cggcgagcgg tatcagctca ctcaaaggcg gtaatacggt tatccacaga 1680
atcaggggat aacgcaggaa agaacatgtg agcaaaaggc cagcaaaagg ccaggaaccg 1740
taaaaaggcc gcgttgctgg cgtttttcca taggctccgc ccccctgacg agcatcacaa 1800
aaatcgacgc tcaagtcaga ggtggcgaaa cccgacagga ctataaagat accaggcgtt 1860
tccccctgga agctccctcg tgcgctctcc tgttccgacc ctgccgctta ccggatacct 1920
gtccgccttt ctcccttcgg gaagcgtggc gctttctcat agctcacgct gtaggtatct 1980

```
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaagaacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac cgcgagaccc acgctcaccg gctccagatt tatcagcaat   2700
aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
attcagctcc ggttcccaac gatcaaggcg agttacatga tcccccatgt tgtgcaaaaa   2940
agcggttagc tccttcggtc ctccgatcgt tgtcagaagt aagttggccg cagtgttatc   3000
actcatggtt atggcagcac tgcataattc tcttactgtc atgccatccg taagatgctt   3060
ttctgtgact ggtgagtact caaccaagtc attctgagaa tagtgtatgc ggcgaccgag   3120
ttgctcttgc ccggcgtcaa tacgggataa taccgcgcca catagcagaa ctttaaaagt   3180
gctcatcatt ggaaaacgtt cttcggggcg aaaactctca aggatcttac cgctgttgag   3240
atccagttcg atgtaaccca ctcgtgcacc caactgatct tcagcatctt ttactttcac   3300
cagcgtttct gggtgagcaa aaacaggaag gcaaaatgcc gcaaaaaagg gaataagggc   3360
gacacggaaa tgttgaatac tcatactctt cctttttcaa tattattgaa gcatttatca   3420
gggttattgt ctcatgagcg gatacatatt tgaatgtatt tagaaaaata aacaaatagg   3480
ggttccgcgc acatttcccc gaaaagtgcc acctgatgcg gtgtgaaata ccgcacagat   3540
gcgtaaggag aaaataccgc atcaggaaat tgtaagcgtt aatattttgt taaaattcgc   3600
gttaaatttt tgttaaatca gctcattttt taaccaatag gccgaaatcg gcaaaatccc   3660
ttataaatca aaagaataga ccgagatagg gttgagtgtt gttccagttt ggaacaagag   3720
tccactatta aagaacgtgg actccaacgt caaagggcga aaaaccgtct atcagggcga   3780
tggcccacta cgtgaaccat caccctaatc aagttttttg gggtcgaggt gccgtaaagc   3840
actaaatcgg aaccctaaag ggagcccccg atttagagct tgacggggaa agccggcgaa   3900
cgtggcgaga aaggaaggga agaaagcgaa aggagcgggc gctagggcgc tggcaagtgt   3960
agcggtcacg ctgcgcgtaa ccaccacacc cgccgcgctt aatgcgccgc tacagggcgc   4020
gtccattcgc cattcaggct gcgcaactgt tgggaagggc gatcggtgcg ggcctcttcg   4080
ctattacgcc agctggcgaa aggggatgt gctgcaaggc gattaagttg ggtaacgcca    4140
gggttttccc agtcacgacg ttgtaaaacg acggccagtg aattgtaata cgactcacta   4200
tagggcgaat tgggcccgac gtcgcatgca actattagtg aggcttcggg agtggttgtc   4260
tcggttgtct cattcagact cgttgtgttg tatctatatc tatataaaca ctcttgtccc   4320
```

-continued

```
tcaatcccac tgccatcttt tgctaaactt gccgccaata tgaaactcat ctccctcatc   4380
accgtcgcta ccaccgctct ggcggctgtc ggagacaagt acaagctgac ctataccaga   4440
tcagacgccc aatcggtcga atctctgccc gtcacctacc aagatgacct gatcaccgcc   4500
tccaccgacg gcgaacccat caccatcacc gagggcgagg gcaacacctt ctctgttaac   4560
gacatgccca tcgcctatct ggagctgcag gctttgttct ggaccggcga ctacggctac   4620
aagctccagg gctcggtctt tgacattgcc gccgatggaa cctttgagct gagagacggc   4680
cccaaggagt actactattg cactcctcac cctgagcgaa acgtcatcta cgtcatcaac   4740
agccccgact actccaagtg tcggttcaag cgtaccatca agttccacgc tgaaaagatc   4800
taagtggtaa tcgaccgact aaccattttt agctgacaaa cacttgctaa ctcctataac   4860
gaatgaatga ctaacttggc atattgttac caagtattac ttgggatata gttgagtgta   4920
accattgcta agaatccaaa ctggagcttc taaaggtctg ggagtcgccg tatgtgttca   4980
tatcgaaatc aaagaaatca taatcgcaac agaattcaaa atcaagcaga ttaatatcca   5040
ttattgtact cggatcgtga catatctgat atgatctcgg atatgatctc tgactgttta   5100
ctgggagatt tgttgaagat ttgttgaggt tatctgaaaa gtagacaata gagacaaaat   5160
gacgatatca agaactgaat cggccgaaa tactcggtat cattcccttc agcagtaact   5220
gtattgctct atcaatgcga cgagatacct ccacaattaa tactgtatac gctctaccac   5280
tcatatctcc aatgctaaaa tatattcatg cccaggacct ctgtgcactg ctatgcagca   5340
cagtgttgtc gattgaattg gtcgtgtctg gtccctgatg ctctgtgtct cgctgactag   5400
tccttccatc cagacctcgt cattatctga taggcaacaa gttctgctct ctcacaccct   5460
gccgacacaa gggacactcg ggcttctctc tcacccattc ggaaatacag tccttaatta   5520
agttgcgaca catgtcttga tagtatcttg aattctctct cttgagcttt tccataacaa   5580
gttcttctgc ctccaggaag tccatgggtg gtttgatcat ggttttggtg tagtggtagt   5640
gcagtggtgg tattgtgact ggggatgtag ttgagaataa gtcatacaca agtcagcttt   5700
cttcgagcct catataagta taagtagttc aacgtattag cactgtaccc agcatctccg   5760
tatcgagaaa cacaacaaca tgccccattg gacagatcat gcggatacac aggttgtgca   5820
gtatcataca tactcgatca gacaggtcgt ctgaccatca tacaagctga acaagcgctc   5880
catacttgca cgctctctat atacacagtt aaattacata tccatagtct aacctctaac   5940
agttaatctt ctggtaagcc tcccagccag ccttctggta tcgcttggcc tcctcaatag   6000
gatctcggtt ctggccgtac agacctcggc cgacaattat gatatccgtt ccggtagaca   6060
tgacatcctc aacagttcgg tactgctgtc cgagagcgtc tcccttgtcg tcaagaccca   6120
ccccgggggt cagaataagc cagtcctcag agtcgccctt aggtcggttc tgggcaatga   6180
agccaaccac aaactcgggg tcggatcggg caagctcaat ggtctgcttg gagtactcgc   6240
cagtggccag agagcccttg caagacagct cggccagcat gagcagacct ctggccagct   6300
tctcgttggg agaggggact aggaactcct tgtactggga gttctcgtag tcagagacgt   6360
cctccttctt ctgttcagag acagtttcct cggcaccagc tcgcaggcca gcaatgattc   6420
cggttccggg tacaccgtgg gcgttggtga tatcggacca ctcggcgatt cggtgacacc   6480
ggtactggtg cttgacagtg ttgccaatat ctgcgaactt tctgtcctcg aacaggaaga   6540
aaccgtgctt aagagcaagt tccttgaggg ggagcacagt gccggcgtag gtgaagtcgt   6600
caatgatgtc gatatgggtt ttgatcatgc acacataagg tccgacctta tcggcaagct   6660
caatgagctc cttggtggtg gtaacatcca gagaagcaca caggttggtt ttcttggctg   6720
```

ccacgagctt gagcactcga gcggcaaagg cggacttgtg gacgttagct cgagcttcgt 6780
aggagggcat tttggtggtg aagaggagac tgaaataaat ttagtctgca gaacttttta 6840
tcggaacctt atctggggca gtgaagtata tgttatggta atagttacga gttagttgaa 6900
cttatagata gactggacta tacggctatc ggtccaaatt agaaagaacg tcaatggctc 6960
tctgggcgtc gcctttgccg acaaaaatgt gatcatgatg aaagccagca atgacgttgc 7020
agctgatatt gttgtcggcc aaccgcgccg aaaacgcagc tgtcagaccc acagcctcca 7080
acgaagaatg tatcgtcaaa gtgatccaag cacactcata gttggagtcg tactccaaag 7140
gcggcaatga cgagtcagac agatactcgt cgaccttttc cttgggaacc accaccgtca 7200
gcccttctga ctcacgtatt gtagccaccg acacaggcaa cagtccgtgg atagcagaat 7260
atgtcttgtc ggtccatttc tcaccaactt taggcgtcaa gtgaatgttg cagaagaagt 7320
atgtgccttc attgagaatc ggtgttgctg atttcaataa agtcttgaga tcagtttggc 7380
cagtcatgtt gtggggggta attggattga gttatcgcct acagtctgta caggtatact 7440
cgctgcccac tttatacttt ttgattccgc tgcacttgaa gcaatgtcgt ttaccaaaag 7500
tgagaatgct ccacagaaca caccccaggg tatggttgag caaaaaataa acactccgat 7560
acggggaatc gaaccccggt ctccacggtt ctcaagaagt attcttgatg agagcgtatc 7620
gatgagccta aaatgaaccc gagtatatct cataaaattc tcggtgagag gtctgtgact 7680
gtcagtacaa ggtgccttca ttatgccctc aaccttacca tacctcactg aatgtagtgt 7740
acctctaaaa atgaaataca gtgccaaaag ccaaggcact gagctcgtct aacggacttg 7800
atatacaacc aattaaaaca aatgaaaaga aatacagttc tttgtatcat ttgtaacaat 7860
taccctgtac aaactaaggt attgaaatcc cacaatattc ccaaagtcca cccctttcca 7920
aattgtcatg cctacaactc atataccaag cactaaccta ccgttt 7966

<210> SEQ ID NO 57
<211> LENGTH: 20
<212> TYPE: DNA
<213> ORGANISM: Artificial Sequence
<220> FEATURE:
<223> OTHER INFORMATION: Primer Pex-10del1 3'.Forward

<400> SEQUENCE: 57
ccaacatgag cgacaatacg 20

<210> SEQ ID NO 58
<211> LENGTH: 20
<212> TYPE: DNA
<213> ORGANISM: Artificial Sequence
<220> FEATURE:
<223> OTHER INFORMATION: Primer Pex-10del2 5'.Reverse

<400> SEQUENCE: 58
caagttctgc tctctcacac 20

<210> SEQ ID NO 59
<211> LENGTH: 8673
<212> TYPE: DNA
<213> ORGANISM: Artificial Sequence
<220> FEATURE:
<223> OTHER INFORMATION: Plasmid pYRH13

<400> SEQUENCE: 59
taagcgattg atgattggaa acacacacat gggttatatc taggtgagag ttagttggac 60

-continued

```
agttatatat taaatcagct atgccaacgg taacttcatt catgtcaacg aggaaccagt    120
gactgcaagt aatatagaat ttgaccacct tgccattctc ttgcactcct ttactatatc    180
tcatttattt cttatataca aatcacttct tcttcccagc atcgagctcg gaaacctcat    240
gagcaataac atcgtggatc tcgtcaatag agggcttttt ggactccttg ctgttggcca    300
ccttgtcctt gctgtctggc tcattctgtt tcaacgcctt tcgcgccaga ccatcaacct    360
tgttgagctc tccgtcagca gcctcgacca gatcatcaaa accagaaccc ttggctcgag    420
ttcgggcttc tcgaagcttg tctttagcct cttcataatc gcccttcttg atagcaatca    480
caccgactcc atatgtgcat agagcctggg cctcctcgac ttccttggtc cgtcggacat    540
cgggctcaag agaaggaatg gccttgagaa cacgcttgta acatgactcg gatcgagcca    600
gggcgttatt actgctcgtc ttcattgtgt ccagaggaat ctcgccgcct gtgtcagctt    660
tgatggtggt gccctcgttc ttttcggcag tgtgaacaat cacctccagc tgttcagaca    720
tgaggtagaa catggaggct aggttggctt gggctaacaa cagatctccc actccacatc    780
cggaagcaag catgatctga taagtgattt gcttctctct gagagcaacg ttggcgaggg    840
cgtcagagag gttgtgagtt gtgagcacat cacgagcagc aataagctcg tctctgaagg    900
gcatccaggc gtcgtaattg ccggaagcac gcagcagacg agcatgagac gcacttttag    960
tcagctgggt catgaactcc cgctcgctct gtgtcggggg cgtgctggcg agtttcagca   1020
gatctgtggc ctcggggcac cgtcgacaga cctcttcttg agccagcagg atctgcagca   1080
gtagcgctcg tgataccaca tcatttttct cggttccaga aatgtgagcg agcttgagag   1140
cgatccgcag acctctctgg atcacctggg gccggacatc ctgggcgatt ttgttattct   1200
ggaaggcgtc aacgtaggca gcacaaatct ccatgtacac gtcgtgggca gcgtccgggt   1260
agttgagcat ctcgtagatc tctgccagtt tgagctggat gcctgtgtat tcgtccgaca   1320
agggagacag gccttgggcc tcggcctcca taagtgcctc aatgtaatac ttgacggcat   1380
gcgacgtcgg gcccaattcg ccctatagtg agtcgtatta caattcactg gccgtcgttt   1440
tacaacgtcg tgactgggaa aaccctggcg ttacccaact taatcgcctt gcagcacatc   1500
ccccttttcgc cagctggcgt aatagcgaag aggcccgcac cgatcgccct tcccaacagt   1560
tgcgcagcct gaatggcgaa tggacgcgcc ctgtagcggc gcattaagcg cggcgggtgt   1620
ggtggttacg cgcagcgtga ccgctacact tgccagcgcc ctagcgcccg ctcctttcgc   1680
tttcttccct tcctttctcg ccacgttcgc cggctttccc cgtcaagctc taaatcgggg   1740
gctcccttta gggttccgat ttagtgcttt acggcacctc gaccccaaaa aacttgatta   1800
gggtgatggt tcacgtagtg ggccatcgcc ctgatagacg gtttttcgcc ctttgacgtt   1860
ggagtccacg ttctttaata gtggactctt gttccaaact ggaacaacac tcaaccctat   1920
ctcggtctat tcttttgatt tataagggat tttgccgatt tcggcctatt ggttaaaaaa   1980
tgagctgatt taacaaaaat ttaacgcgaa ttttaacaaa atattaacgc ttacaatttc   2040
ctgatgcggt attttctcct tacgcatctg tgcggtattt cacaccgcat caggtggcac   2100
ttttcgggga aatgtgcgcg gaacccctat ttgtttattt ttctaaatac attcaaatat   2160
gtatccgctc atgagacaat aaccctgata aatgcttcaa taatattgaa aaaggaagag   2220
tatgagtatt caacatttcc gtgtcgccct tattcccttt tttgcggcat tttgccttcc   2280
tgtttttgct cacccagaaa cgctggtgaa agtaaaagat gctgaagatc agttgggtgc   2340
acgagtgggt tacatcgaac tggatctcaa cagcggtaag atccttgaga gttttcgccc   2400
cgaagaacgt tttccaatga tgagcacttt taaagttctg ctatgtggcg cggtattatc   2460
```

-continued

```
ccgtattgac gccgggcaag agcaactcgg tcgccgcata cactattctc agaatgactt   2520
ggttgagtac tcaccagtca cagaaaagca tcttacggat ggcatgacag taagagaatt   2580
atgcagtgct gccataacca tgagtgataa cactgcggcc aacttacttc tgacaacgat   2640
cggaggaccg aaggagctaa ccgctttttt gcacaacatg ggggatcatg taactcgcct   2700
tgatcgttgg gaaccggagc tgaatgaagc cataccaaac gacgagcgtg acaccacgat   2760
gcctgtagca atggcaacaa cgttgcgcaa actattaact ggcgaactac ttactctagc   2820
ttcccggcaa caattaatag actggatgga ggcggataaa gttgcaggac cacttctgcg   2880
ctcggccctt ccggctggct ggtttattgc tgataaatct ggagccggtg agcgtgggtc   2940
tcgcggtatc attgcagcac tggggccaga tggtaagccc tcccgtatcg tagttatcta   3000
cacgacgggg agtcaggcaa ctatggatga acgaaataga cagatcgctg agataggtgc   3060
ctcactgatt aagcattggt aactgtcaga ccaagtttac tcatatatac tttagattga   3120
tttaaaactt catttttaat ttaaaaggat ctaggtgaag atcctttttg ataatctcat   3180
gaccaaaatc ccttaacgtg agttttcgtt ccactgagcg tcagaccccg tagaaaagat   3240
caaaggatct tcttgagatc ctttttttct gcgcgtaatc tgctgcttgc aaacaaaaaa   3300
accaccgcta ccagcggtgg tttgtttgcc ggatcaagag ctaccaactc tttttccgaa   3360
ggtaactggc ttcagcagag cgcagatacc aaatactgtt cttctagtgt agccgtagtt   3420
aggccaccac ttcaagaact ctgtagcacc gcctacatac ctcgctctgc taatcctgtt   3480
accagtggct gctgccagtg gcgataagtc gtgtcttacc gggttggact caagacgata   3540
gttaccggat aaggcgcagc ggtcgggctg aacggggggt tcgtgcacac agcccagctt   3600
ggagcgaacg acctacaccg aactgagata cctacagcgt gagctatgag aaagcgccac   3660
gcttcccgaa gggagaaagg cggacaggta tccggtaagc ggcagggtcg gaacaggaga   3720
gcgcacgagg gagcttccag ggggaaacgc ctggtatctt tatagtcctg tcgggtttcg   3780
ccacctctga cttgagcgtc gatttttgtg atgctcgtca ggggggcgga gcctatggaa   3840
aaacgccagc aacgcggcct ttttacggtt cctggccttt tgctggcctt ttgctcacat   3900
gttctttcct gcgttatccc ctgattctgt ggataaccgt attaccgcct ttgagtgagc   3960
tgataccgct cgccgcagcc gaacgaccga gcgcagcgag tcagtgagcg aggaagcgga   4020
agagcgccca atacgcaaac cgcctctccc cgcgcgttgg ccgattcatt aatgcagctg   4080
gcgcgccggt ttctgtctct cgtcgtgtca cagatggtgt tgttgttgat gagttcctgg   4140
ttgccctgtt tcgcacaagg tggtgcgtga ggttgtgtgg agaggggctt gaaggagggg   4200
ggtcgaggtg caggagcgtc ccccgagggg ccctaggccg tcacatgacc ggcataatgg   4260
tgtggagtcg ggttttggtt ttcctggcgg gttccacact tgtcaagtct cgtttttcag   4320
gcttttttttc actcgctctt tttgcacttt ggcatctttt tacctttggt gcttaccacc   4380
tttgtatgca ggaaatctat tgggtttggt gtataggtga aaaaaaaaaa gccaaaggtg   4440
actgtttttt tccgactcgg tcatgttgca ttttgtgcga tattataagt ggggaacgaa   4500
tggaggcgag ctggtgtgat acgggagctg ctgtttctca cgattctgcc cagccattta   4560
tcacgcgcac gctgacatct tgcacttagt catcaagagc tacagtacga cgagtacata   4620
ctagagccaa ccactcctga agtgcttcca tgagttcagt tgagtgctga accaactctc   4680
gacactctcg acagcctgtg aaaaggaatg agtgtgtgga aagggattca atactggaga   4740
agagagggga gagatcgaga gggtgatgtt acatccccaa gcgtcgtagt ctcgcgttga   4800
```

tgactggaac ggactgttga acgacgatca acatggtgtg caagctgatg gacagttggg 4860
ccaatggttc agaagcgtta gttgagcttc taacgaccta ctactcgcct gtcaagtgag 4920
gtgtgtactt gttcatactc ctactcgtct cactggcgtc tagggttgtg agcaccgtcg 4980
cttatgaaag acgccgtcgc ctatgaaaga caccgtcgct cattgaagac tagatccata 5040
atataaacaa aagagtattt ctctgaatgg cgacggattg gccagcccca tcgttacaca 5100
atttgtccaa aaacaccatc tctgccgtcc atcgatatct ttcgaaatca tccggaccag 5160
acagtagagc tttgagaacc ccgaaggagg aatactgcag tgaagtgttc tttgaaactc 5220
tgactggagt atctccattt ctatatctcc attagtaatc actccaaaca gatgtcttcc 5280
agcttgagtc agccgagacc acggtcacgt atggtgattc cttcaaacat ataactccat 5340
tgacctaaca agacactggc agttgtaaat acgtaaatac attcttgatg taagttttaa 5400
tctgattgga gactcttctg agtaacacac tctcttccaa gcagtcattt tggccttttt 5460
ttcttccaaa cccgtctcga ttactcatca ggttttatct gagaaccaaa acgtctcaat 5520
cattgacata ttgtaccatc aactctgtaa aaacttgaca gatgtgctac ttgtgtcatt 5580
atgaatcgat tttccaaata tccattatca ttatcccatt tcttccccga tatcacctcc 5640
ccatctacca cctccattta ccaaccacca tgctcagtaa tcagaaactc ctcttcacag 5700
accacaattg ccaataattg accaccaaaa gtcgtaccat gtgtttctcc ggtgaccagg 5760
tctcgctttc acccatttat tccctcaaaa acacccctac agtaatttca gcgcctttcc 5820
atcaaactcc atacttgcaa caaaatcaca atggcccccct gcctaaacta cgcccgccca 5880
taattgagta tatttgtatg acaatcccgc tcgaaatttg gcccacttgt tccccgagct 5940
ccaaatattc actattcacc ttcacctcgt gcccaccctg gcccccccaat gcccccgtg 6000
ctcgtaacgt ctccctcccc cacaccccac acacgtgaca taaagtgtaa agtgcgagta 6060
cccgtacgtt gtgtggaagc ttgtgagcgg ataacaattt cacacaggaa acagctatga 6120
ccatgattac gccaagctcg aaattaaccc tcactaaagg gaacaaaagc tggagctcca 6180
ccgcggacac aatatctggt caaatttcag tttcgttaca tttaaacggt aggttagtgc 6240
ttggtatatg agttgtaggc atgacaattt ggaaaggggt ggactttggg aatattgtgg 6300
gatttcaata ccttagtttg tacagggtaa ttgttacaaa tgatacaaag aactgtattt 6360
cttttcattt gttttaattg gttgtatatc aagtccgtta gacgagctca gtgccttggc 6420
ttttggcact gtatttcatt tttagaggta cactacattc agtgaggtat ggtaaggttg 6480
agggcataat gaaggcacct tgtactgaca gtcacagacc tctcaccgag aattttatga 6540
gatatactcg ggttcatttt aggctcatcg atacgctctc atcaagaata cttcttgaga 6600
accgtggaga ccggggttcg attccccgta tcggagtgtt tattttttgc tcaaccatac 6660
cctggggtgt gttctgtgga gcattctcac ttttggtaaa cgacattgct tcaagtgcag 6720
cggaatcaaa aagtataaag tgggcagcga gtatacctgt acagactgta ggcgataact 6780
caatccaatt accccccaca acatgactgg ccaaactgat ctcaagactt tattgaaatc 6840
agcaacaccg attctcaatg aaggcacata cttcttctgc aacattcact tgacgcctaa 6900
agttggtgag aaatggaccg acaagacata ttctgctatc cacggactgt tgcctgtgtc 6960
ggtggctaca atacgtgagt cagaagggct gacggtggtg gttcccaagg aaaaggtcga 7020
cgagtatctg tctgactcgt cattgccgcc tttggagtac gactccaact atgagtgtgc 7080
ttggatcact ttgacgatac attcttcgtt ggaggctgtg ggtctgacag ctgcgttttc 7140
ggcgcggttg gccgacaaca atatcagctg caacgtcatt gctggctttc atcatgatca 7200

```
catttttgtc ggcaaaggcg acgcccagag agccattgac gttctttcta atttggaccg   7260

atagccgtat agtccagtct atctataagt tcaactaact cgtaactatt accataacat   7320

atacttcact gccccagata aggttccgat aaaaagttct gcagactaaa tttatttcag   7380

tctcctcttc accaccaaaa tgccctccta cgaagctcga gctaacgtcc acaagtccgc   7440

ctttgccgct cgagtgctca agctcgtggc agccaagaaa accaacctgt gtgcttctct   7500

ggatgttacc accaccaagg agctcattga gcttgccgat aaggtcggac cttatgtgtg   7560

catgatcaaa acccatatcg acatcattga cgacttcacc tacgccggca ctgtgctccc   7620

cctcaaggaa cttgctctta agcacggttt cttcctgttc gaggacagaa agttcgcaga   7680

tattggcaac actgtcaagc accagtaccg gtgtcaccga atcgccgagt ggtccgatat   7740

caccaacgcc cacggtgtac ccggaaccgg aatcattgct ggcctgcgag ctggtgccga   7800

ggaaactgtc tctgaacaga agaaggagga cgtctctgac tacgagaact cccagtacaa   7860

ggagttccta gtcccctctc ccaacgagaa gctggccaga ggtctgctca tgctggccga   7920

gctgtcttgc aagggctctc tggccactgg cgagtactcc aagcagacca ttgagcttgc   7980

ccgatccgac cccgagtttg tggttggctt cattgcccag aaccgaccta agggcgactc   8040

tgaggactgg cttattctga cccccggggt gggtcttgac gacaagggag acgctctcgg   8100

acagcagtac cgaactgttg aggatgtcat gtctaccgga acggatatca taattgtcgg   8160

ccgaggtctg tacggccaga accgagatcc tattgaggag gccaagcgat accagaaggc   8220

tggctgggag gcttaccaga agattaactg ttagaggtta gactatggat atgtaattta   8280

actgtgtata tagagagcgt gcaagtatgg agcgcttgtt cagcttgtat gatggtcaga   8340

cgacctgtct gatcgagtat gtatgatact gcacaacctg tgtatccgca tgatctgtcc   8400

aatggggcat gttgttgtgt ttctcgatac ggagatgctg ggtacagtgc taatacgttg   8460

aactacttat acttatatga ggctcgaaga aagctgactt gtgtatgact tattctcaac   8520

tacatcccca gtcacaatac caccactgca ctaccactac accaaaacca tgatcaaacc   8580

acccatggac ttcctggagg cagaagaact tgttatggaa aagctcaaga gagagaattc   8640

aagatactat caagacatgt gtcgcaactt aat                                8673
```

<210> SEQ ID NO 60
<211> LENGTH: 38
<212> TYPE: DNA
<213> ORGANISM: Artificial Sequence
<220> FEATURE:
<223> OTHER INFORMATION: Primer PEX16Fii

<400> SEQUENCE: 60

```
ccaaccagat caccacccac tacaccttcc aggaaccc                             38
```

<210> SEQ ID NO 61
<211> LENGTH: 34
<212> TYPE: DNA
<213> ORGANISM: Artificial Sequence
<220> FEATURE:
<223> OTHER INFORMATION: Primer PEX16Rii

<400> SEQUENCE: 61

```
ctggtagaac tcgcctcgga acaaccacca tccc                                 34
```

<210> SEQ ID NO 62
<211> LENGTH: 34
<212> TYPE: DNA

<213> ORGANISM: Artificial Sequence
<220> FEATURE:
<223> OTHER INFORMATION: Primer 3UTR-URA3

<400> SEQUENCE: 62
gagagaattc aagatactat caagacatgt gtcg 34

<210> SEQ ID NO 63
<211> LENGTH: 33
<212> TYPE: DNA
<213> ORGANISM: Artificial Sequence
<220> FEATURE:
<223> OTHER INFORMATION: Primer Pex16-conf

<400> SEQUENCE: 63
cacaccttca ccccggaagt cgccaccatt ctg 33

<210> SEQ ID NO 64
<211> LENGTH: 20
<212> TYPE: DNA
<213> ORGANISM: Artificial Sequence
<220> FEATURE:
<223> OTHER INFORMATION: Real time PCR primer ef-324F

<400> SEQUENCE: 64
cgactgtgcc atcctcatca 20

<210> SEQ ID NO 65
<211> LENGTH: 21
<212> TYPE: DNA
<213> ORGANISM: Artificial Sequence
<220> FEATURE:
<223> OTHER INFORMATION: Real time PCR primer ef-392R

<400> SEQUENCE: 65
tgaccgtcct tggagatacc a 21

<210> SEQ ID NO 66
<211> LENGTH: 18
<212> TYPE: DNA
<213> ORGANISM: Artificial Sequence
<220> FEATURE:
<223> OTHER INFORMATION: Real time PCR primer Pex16-741F

<400> SEQUENCE: 66
gggagtggtg gccgagtt 18

<210> SEQ ID NO 67
<211> LENGTH: 21
<212> TYPE: DNA
<213> ORGANISM: Artificial Sequence
<220> FEATURE:
<223> OTHER INFORMATION: Real time PCR primer Pex16-802R

<400> SEQUENCE: 67
ggaaaagcaa gcatgcgtag a 21

<210> SEQ ID NO 68
<211> LENGTH: 21
<212> TYPE: DNA
<213> ORGANISM: Artificial Sequence
<220> FEATURE:
<223> OTHER INFORMATION: Nucleotide portion of primer ef-345T

<400> SEQUENCE: 68
tgctggtggt gttggtgagt t 21

<210> SEQ ID NO 69
<211> LENGTH: 21
<212> TYPE: DNA
<213> ORGANISM: Artificial Sequence
<220> FEATURE:
<223> OTHER INFORMATION: Nucleotide portion of TaqMan probe Pex16-760T

<400> SEQUENCE: 69
ctgtccattc tgcgacccct c 21

<210> SEQ ID NO 70
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 70
taatcgagct tggcgtaatc atggtcatag ctgtttcctg tgtgaaattg ttatccgctc 60
acaattccac acaacatacg agccggaagc ataaagtgta aagcctgggg tgcctaatga 120
gtgagctaac tcacattaat tgcgttgcgc tcactgcccg ctttccagtc gggaaacctg 180
tcgtgccagc tgcattaatg aatcggccaa cgcgcgggga gaggcggttt gcgtattggg 240
cgctcttccg cttcctcgct cactgactcg ctgcgctcgg tcgttcggct gcggcgagcg 300
gtatcagctc actcaaaggc ggtaatacgg ttatccacag aatcagggga taacgcagga 360
aagaacatgt gagcaaaagg ccagcaaaag gccaggaacc gtaaaaaggc cgcgttgctg 420
gcgtttttcc ataggctccg cccccctgac gagcatcaca aaaatcgacg ctcaagtcag 480
aggtggcgaa acccgacagg actataaaga taccaggcgt ttccccctgg aagctccctc 540
gtgcgctctc ctgttccgac cctgccgctt accggatacc tgtccgcctt tctcccttcg 600
ggaagcgtgg cgctttctca tagctcacgc tgtaggtatc tcagttcggt gtaggtcgtt 660
cgctccaagc tgggctgtgt gcacgaaccc cccgttcagc ccgaccgctg cgccttatcc 720
ggtaactatc gtcttgagtc caacccggta agacacgact tatcgccact ggcagcagcc 780
actggtaaca ggattagcag agcgaggtat gtaggcggtg ctacagagtt cttgaagtgg 840
tggcctaact acggctacac tagaaggaca gtatttggta tctgcgctct gctgaagcca 900
gttaccttcg gaaaaagagt tggtagctct tgatccggca aacaaaccac cgctggtagc 960
ggtggttttt ttgtttgcaa gcagcagatt acgcgcagaa aaaaaggatc tcaagaagat 1020
cctttgatct tttctacggg gtctgacgct cagtggaacg aaaactcacg ttaagggatt 1080
ttggtcatga gattatcaaa aaggatcttc acctagatcc ttttaaatta aaaatgaagt 1140
tttaaatcaa tctaaagtat atatgagtaa acttggtctg acagttacca atgcttaatc 1200
agtgaggcac ctatctcagc gatctgtcta tttcgttcat ccatagttgc ctgactcccc 1260
gtcgtgtaga taactacgat acgggagggc ttaccatctg gccccagtgc tgcaatgata 1320
ccgcgagacc cacgctcacc ggctccagat ttatcagcaa taaaccagcc agccggaagg 1380
gccgagcgca gaagtggtcc tgcaacttta tccgcctcca tccagtctat taattgttgc 1440
cgggaagcta gagtaagtag ttcgccagtt aatagtttgc gcaacgttgt tgccattgct 1500
acaggcatcg tggtgtcacg ctcgtcgttt ggtatggctt cattcagctc cggttcccaa 1560
cgatcaaggc gagttacatg atcccccatg ttgtgcaaaa aagcggttag ctccttcggt 1620
cctccgatcg ttgtcagaag taagttggcc gcagtgttat cactcatggt tatggcagca 1680

-continued

```
ctgcataatt ctcttactgt catgccatcc gtaagatgct tttctgtgac tggtgagtac   1740
tcaaccaagt cattctgaga atagtgtatg cggcgaccga gttgctcttg cccggcgtca   1800
atacgggata ataccgcgcc acatagcaga actttaaaag tgctcatcat tggaaaacgt   1860
tcttcggggc gaaaactctc aaggatctta ccgctgttga gatccagttc gatgtaaccc   1920
actcgtgcac ccaactgatc ttcagcatct tttactttca ccagcgtttc tgggtgagca   1980
aaaacaggaa ggcaaaatgc cgcaaaaaag ggaataaggg cgacacggaa atgttgaata   2040
ctcatactct tcctttttca atattattga agcatttatc agggttattg tctcatgagc   2100
ggatacatat ttgaatgtat ttagaaaaat aaacaaatag gggttccgcg cacatttccc   2160
cgaaaagtgc cacctgacgc gccctgtagc ggcgcattaa gcgcggcggg tgtggtggtt   2220
acgcgcagcg tgaccgctac acttgccagc gccctagcgc ccgctccttt cgctttcttc   2280
ccttcctttc tcgccacgtt cgccggcttt ccccgtcaag ctctaaatcg ggggctccct   2340
ttagggttcc gatttagtgc tttacggcac ctcgacccca aaaaacttga ttagggtgat   2400
ggttcacgta gtgggccatc gccctgatag acggtttttc gccctttgac gttggagtcc   2460
acgttcttta atagtggact cttgttccaa actggaacaa cactcaaccc tatctcggtc   2520
tattcttttg atttataagg gattttgccg atttcggcct attggttaaa aaatgagctg   2580
atttaacaaa aatttaacgc gaattttaac aaaatattaa cgcttacaat ttccattcgc   2640
cattcaggct gcgcaactgt tgggaagggc gatcggtgcg ggcctcttcg ctattacgcc   2700
agctggcgaa aggggggatgt gctgcaaggc gattaagttg ggtaacgcca gggttttccc   2760
agtcacgacg ttgtaaaacg acggccagtg aattgtaata cgactcacta tagggcgaat   2820
tgggtaccgg gccccccctc gaggtcgacg agtatctgtc tgactcgtca ttgccgcctt   2880
tggagtacga ctccaactat gagtgtgctt ggatcacttt gacgatacat tcttcgttgg   2940
aggctgtggg tctgacagct gcgttttcgg cgcggttggc cgacaacaat atcagctgca   3000
acgtcattgc tggctttcat catgatcaca tttttgtcgg caaaggcgac gcccagagag   3060
ccattgacgt tctttctaat ttggaccgat agccgtatag tccagtctat ctataagttc   3120
aactaactcg taactattac cataacatat acttcactgc cccagataag gttccgataa   3180
aaagttctgc agactaaatt tatttcagtc tcctcttcac caccaaaatg ccctcctacg   3240
aagctcgagt gctcaagctc gtggcagcca agaaaaccaa cctgtgtgct tctctggatg   3300
ttaccaccac caaggagctc attgagcttg ccgataaggt cggaccttat gtgtgcatga   3360
tcaaaaccca tatcgacatc attgacgact tcacctacgc cggcactgtg ctccccctca   3420
aggaacttgc tcttaagcac ggtttcttcc tgttcgagga cagaaagttc gcagatattg   3480
gcaacactgt caagcaccag taccggtgtc accgaatcgc cgagtggtcc gatatcacca   3540
acgcccacgg tgtacccgga accggaatcg attgctggcc tgcgagctgg tgcgtacgag   3600
gaaactgtct ctgaacagaa gaaggaggac gtctctgact acgagaactc ccagtacaag   3660
gagttcctag tcccctctcc caacgagaag ctggccagag gtctgctcat gctggccgag   3720
ctgtcttgca agggctctct ggccactggc gagtactcca agcagaccat tgagcttgcc   3780
cgatccgacc ccgagtttgt ggttggcttc attgcccaga accgacctaa gggcgactct   3840
gaggactggc ttattctgac ccccggggtg ggtcttgacg acaagggaga cgctctcgga   3900
cagcagtacc gaactgttga ggatgtcatg tctaccggaa cggatatcat aattgtcggc   3960
cgaggtctgt acggccagaa ccgagatcct attgaggagg ccaagcgata ccagaaggct   4020
ggctgggagg cttaccagaa gattaactgt tagaggttag actatggata tgtaatttaa   4080
```

ctgtgtatat agagagcgtg caagtatgga gcgcttgttc agcttgtatg atggtcagac 4140
gacctgtctg atcgagtatg tatgatactg cacaacctgt gtatccgcat gatctgtcca 4200
atggggcatg ttgttgtgtt tctcgatacg gagatgctgg gtacagtgct aatacgttga 4260
actacttata cttatatgag gctcgaagaa agctgacttg tgtatgactt aat 4313

<210> SEQ ID NO 71
<211> LENGTH: 15966
<212> TYPE: DNA
<213> ORGANISM: Artificial Sequence
<220> FEATURE:
<223> OTHER INFORMATION: Plasmid pZKD2-5U89A2

<400> SEQUENCE: 71
gtacgtttca tgaaggcggg cagaaagtac tcgatggtgg agatgattgc tcggaggtac 60
ttgttctgcg gccagtatct ctcagcaatc aggtgatact cctggacgtc cagagggtag 120
tatgtgtgcg tgggctccag atccaccgtc ttgtgcagag ttatggggaa gtagcggcca 180
aagagcttcc agatgaagaa gtttcttgaa ataggcgagt atcgcttgac cactcctccg 240
ttggacgggg agtcgtcttt aacagcgtac actacatacg caatcacaaa tggccagagc 300
agtggaattg cgcagcatag catgaaaatt gtgaggaaag tgggaatgct gaaaatgtgc 360
cagaccagag agaaggtctc acatcggttg agtaatggtg tcgatagcgg ggcatatcgg 420
attcccgcga ttttgggtgc cgtgtcgttt ttgtctcgcg acttgtagta ttgtgagtcg 480
atagtcatag cttttgtttt gtgtgacttg tctgttgcct gttgttagaa gaaaaagtgg 540
gagcttatca gtcacggtcc acgaacgatt tcgtacttgt acgtaattgg tcgtgagaac 600
tgttgcagag ccggtgcttt tttttgtggc caagtcgaca ggtcgatttc ggcgctgtgc 660
gaggttgctg ggatgtgctg gtttggctgc caaatgtggg gaagatttca acctcggatt 720
tgacgtgtgt agaggcgcgc cagctgcatt aatgaatcgg ccaacgcgcg gggagaggcg 780
gtttgcgtat tgggcgctct tccgcttcct cgctcactga ctcgctgcgc tcggtcgttc 840
ggctgcggcg agcggtatca gctcactcaa aggcggtaat acggttatcc acagaatcag 900
gggataacgc aggaaagaac atgtgagcaa aaggccagca aaaggccagg aaccgtaaaa 960
aggccgcgtt gctggcgttt ttccataggc tccgcccccc tgacgagcat cacaaaaatc 1020
gacgctcaag tcagaggtgg cgaaacccga caggactata aagataccag gcgtttcccc 1080
ctggaagctc cctcgtgcgc tctcctgttc cgaccctgcc gcttaccgga tacctgtccg 1140
cctttctccc ttcgggaagc gtggcgcttt ctcatagctc acgctgtagg tatctcagtt 1200
cggtgtaggt cgttcgctcc aagctgggct gtgtgcacga accccccgtt cagcccgacc 1260
gctgcgcctt atccggtaac tatcgtcttg agtccaaccc ggtaagacac gacttatcgc 1320
cactggcagc agccactggt aacaggatta gcagagcgag gtatgtaggc ggtgctacag 1380
agttcttgaa gtggtggcct aactacggct acactagaag aacagtattt ggtatctgcg 1440
ctctgctgaa gccagttacc ttcggaaaaa gagttggtag ctcttgatcc ggcaaacaaa 1500
ccaccgctgg tagcggtggt ttttttgttt gcaagcagca gattacgcgc agaaaaaaag 1560
gatctcaaga agatcctttg atcttttcta cggggtctga cgctcagtgg aacgaaaact 1620
cacgttaagg gattttggtc atgagattat caaaaaggat cttcacctag atccttttaa 1680
attaaaaatg aagttttaaa tcaatctaaa gtatatatga gtaaacttgg tctgacagtt 1740
accaatgctt aatcagtgag gcacctatct cagcgatctg tctatttcgt tcatccatag 1800

-continued

```
ttgcctgact ccccgtcgtg tagataacta cgatacggga gggcttacca tctggcccca   1860
gtgctgcaat gataccgcga gacccacgct caccggctcc agatttatca gcaataaacc   1920
agccagccgg aagggccgag cgcagaagtg gtcctgcaac tttatccgcc tccatccagt   1980
ctattaattg ttgccgggaa gctagagtaa gtagttcgcc agttaatagt ttgcgcaacg   2040
ttgttgccat tgctacaggc atcgtggtgt cacgctcgtc gtttggtatg gcttcattca   2100
gctccggttc ccaacgatca aggcgagtta catgatcccc catgttgtgc aaaaaagcgg   2160
ttagctcctt cggtcctccg atcgttgtca gaagtaagtt ggccgcagtg ttatcactca   2220
tggttatggc agcactgcat aattctctta ctgtcatgcc atccgtaaga tgcttttctg   2280
tgactggtga gtactcaacc aagtcattct gagaatagtg tatgcggcga ccgagttgct   2340
cttgcccggc gtcaatacgg gataataccg cgccacatag cagaacttta aaagtgctca   2400
tcattggaaa acgttcttcg gggcgaaaac tctcaaggat cttaccgctg ttgagatcca   2460
gttcgatgta acccactcgt gcacccaact gatcttcagc atcttttact ttcaccagcg   2520
tttctgggtg agcaaaaaca ggaaggcaaa atgccgcaaa aaagggaata agggcgacac   2580
ggaaatgttg aatactcata ctcttccttt ttcaatatta ttgaagcatt tatcagggtt   2640
attgtctcat gagcggatac atatttgaat gtatttagaa aaataaacaa ataggggttc   2700
cgcgcacatt tccccgaaaa gtgccacctg atgcggtgtg aaataccgca cagatgcgta   2760
aggagaaaat accgcatcag gaaattgtaa gcgttaatat tttgttaaaa ttcgcgttaa   2820
atttttgtta aatcagctca ttttttaacc aataggccga aatcggcaaa atcccttata   2880
aatcaaaaga atagaccgag atagggttga gtgttgttcc agtttggaac aagagtccac   2940
tattaaagaa cgtggactcc aacgtcaaag ggcgaaaaac cgtctatcag ggcgatggcc   3000
cactacgtga accatcaccc taatcaagtt ttttggggtc gaggtgccgt aaagcactaa   3060
atcggaaccc taaagggagc ccccgattta gagcttgacg gggaaagccg gcgaacgtgg   3120
cgagaaagga agggaagaaa gcgaaaggag cgggcgctag ggcgctggca agtgtagcgg   3180
tcacgctgcg cgtaaccacc acacccgccg cgcttaatgc gccgctacag ggcgcgtcca   3240
ttcgccattc aggctgcgca actgttggga agggcgatcg gtgcgggcct cttcgctatt   3300
acgccagctg gcgaaagggg gatgtgctgc aaggcgatta agttgggtaa cgccagggtt   3360
ttcccagtca cgacgttgta aaacgacggc cagtgaattg taatacgact cactataggg   3420
cgaattgggc ccgacgtcgc atgcatcaaa ggaagggtga atccaaggaa gttcttgaca   3480
aactgctgga atcggtacag cttggacgac ttgtcgttgc taacctggtc atagaggtcg   3540
ttctcaccaa aggccatgat gggaacaagg gcgacatttc cgacctccat accaagtcga   3600
acaaaaccct ttcgcttgag tagcaccagg tccatgacac cgggtctggc cagaagactt   3660
tcctgtgctc caccaacgac aatgcagata gactggtttc gcttgaggag ggccttgcag   3720
gacttcttgg agacagaagc gactcccaga ctcatgaggt actctctgta gagaggcact   3780
cggaagttgt tggtgagagt cataagagaa acagggatgc ccggaaagag cttggaccat   3840
ccagctccct cggtggcaat tccaccaaag gctcccatgc cgataatgcc gtgggggtgg   3900
tagccgaaga tgtattttct gccagtgggc ttgagttttg tgggcgacag ctgtgggtcg   3960
ttttcgccaa tgatctggtt ggcgtaggag ttgagggacc cgttaagaag cgtggaatca   4020
gatgcagtgg agccagcaga ggcggacgac aaaggtcgtc ggttagtggt gccattgttg   4080
ccgttgccgt taagttcgga gcccgaggcg tggccgttgg agccagatga ttctccacgg   4140
ctatatctgc tgtcgtggtt aattaactca cctgcaggat tgagactatg aatggattcc   4200
```

```
cgtgcccgta ttactctact aatttgatct tggaacgcga aaatacgttt ctaggactcc   4260
aaagaatctc aactcttgtc cttactaaat atactaccca tagttgatgg tttacttgaa   4320
cagagaggac atgttcactt gacccaaagt ttctcgcatc tcttggatat ttgaacaacg   4380
gcgtccactg accgtcagtt atccagtcac aaaacccccca cattcataca ttcccatgta   4440
cgtttacaaa gttctcaatt ccatcgtgca aatcaaaatc acatctattc attcatcata   4500
tataaaccca tcatgtctac taacactcac aactccatag aaaacatcga ctcagaacac   4560
acgctccatg cggccgctta ggaatcctga gcgtccttga cacagtgaac cacaccgact   4620
ttgtgcatgt acttgagggt ggaaatgatg ttgcccacaa tggtagggta gaagacgtac   4680
cgaactccgt gtcgttcgca acactctcgg acagcttgct gcacgaaggg atagtgccaa   4740
gacgacattc gaggaaagag gtgatgctcg atctggaagt tgagaccgcc agtaaagaac   4800
atggcaatgg gtccaccgta ggtggaagag gtctccacct gagctctgta ccagtcgatc   4860
tgatcggctt caacgtcctt ctcggagctc ttgaccttgc agttcttgtc ggggattcgc   4920
tccgagccat cgaagttgtg agacaagatg aaaaagaagg tgaggaaggc accggtagca   4980
gtgggcacca gaggaatggt gatgagcagg gaggttccag tgagatacca gggcaagaag   5040
gcggttcgaa agatgaagaa agctcgcata acgaatgcaa gggttcggta ccgtcgcaga   5100
aagccgttct ctcgcatggc tgtgacagac tcgggaatgg tgtcgttgtg ctgcattcgg   5160
aagatgtaga gagggttgta caccagcgaa acgccgtagg ctccaagcac gaggtacatg   5220
taccaggcct ggaatcggtg aaaccacttt cgagcagtgt tggcagcagg gtagttgtgg   5280
aacacaagga atggttctgc ggactcggca tccaggtcga gaccatgctg attggtgtag   5340
gtgtgatgtc gcatgatgtg agactgcagc cagatccatc tggacgatcc aatgacgtcg   5400
atgccgtagg caaagagagc gttgacccag ggctttttgc tgatggcacc atgagaggca   5460
tcgtgctgaa tggacaggcc gatctgcatg tgcatgaatc cagtcaagag accccacagc   5520
accattccgg tagtagccca gtgccactcg caaaaggcgg tgacagcaat gatgccaacg   5580
gttcgcagcc agaatccagg tgtggcatac cagttccgac ctttcatgac ctctcgcata   5640
gttcgcttga cgtcctgtgc aaagggagag tcgtaggtgt agacaatgtc cttggaggtt   5700
cggtcgtgct tgcctcgcac gaactgttga agcagcttcg agttctcggg cttgacgtaa   5760
gggtgcatgg agtagaacag aggagaagca tcggaggcac cagaagcgag gatcaagtcg   5820
cctccgggat ggaccttggc aagaccttcc agatcgtaga gaatgccgtc gatggcaacc   5880
aggtcgggtc gctcgagcag ctgctcggta gtaagggaga gagccatggc cattgctgta   5940
gatatgtctt gtgtgtaagg gggttggggt ggttgtttgt gttcttgact tttgtgttag   6000
caagggaaga cgggcaaaaa agtgagtgtg gttgggaggg agagacgagc cttatatata   6060
atgcttgttt gtgtttgtgc aagtggacgc cgaaacgggc aggagccaaa ctaaacaagg   6120
cagacaatgc gagcttaatt ggattgcctg atgggcaggg gttagggctc gatcaatggg   6180
ggtgcgaagt gacaaaattg ggaattaggt tcgcaagcaa ggctgacaag actttggccc   6240
aaacatttgt acgcggtgga caacaggagc cacccatcgt ctgtcacggg ctagccggtc   6300
gtgcgtcctg tcaggctcca cctaggctcc atgccactcc atacaatccc actagtgtac   6360
cgctaggccg cttttagctc ccatctaaga ccccccccaaa acctccactg tacagtgcac   6420
tgtactgtgt ggcgatcaag ggcaagggaa aaaaggcgca aacatgcacg catggaatga   6480
cgtaggtaag gcgttactag actgaaaagt ggcacatttc ggcgtgccaa agggtcctag   6540
```

-continued gtgcgtttcg cgagctgggc gccaggccaa gccgctccaa aacgcctctc cgactccctc 6600
cagcggcctc catatcccca tccctctcca cagcaatgtt gttaagcctt gcaaacgaaa 6660
aaatagaaag gctaataagc ttccaatatt gtggtgtacg ctgcataacg caacaatgag 6720
cgccaaacaa cacacacaca cagcacacag cagcattaac cacgatgaac agcatgaatt 6780
ctctctcttg agcttttcca taacaagttc ttctgcctcc aggaagtcca tgggtggttt 6840
gatcatggtt ttggtgtagt ggtagtgcag tggtggtatt gtgactgggg atgtagttga 6900
gaataagtca tacacaagtc agctttcttc gagcctcata taagtataag tagttcaacg 6960
tattagcact gtacccagca tctccgtatc gagaaacaca acaacatgcc ccattggaca 7020
gatcatgcgg atacacaggt tgtgcagtat catacatact cgatcagaca ggtcgtctga 7080
ccatcataca agctgaacaa gcgctccata cttgcacgct ctctatatac acagttaaat 7140
tacatatcca tagtctaacc tctaacagtt aatcttctgg taagcctccc agccagcctt 7200
ctggtatcgc ttggcctcct caataggatc tcggttctgg ccgtacagac ctcggccgac 7260
aattatgata tccgttccgg tagacatgac atcctcaaca gttcggtact gctgtccgag 7320
agcgtctccc ttgtcgtcaa gacccacccc gggggtcaga ataagccagt cctcagagtc 7380
gcccttaggt cggttctggg caatgaagcc aaccacaaac tcggggtcgg atcgggcaag 7440
ctcaatggtc tgcttggagt actcgccagt ggccagagag cccttgcaag acagctcggc 7500
cagcatgagc agacctctgg ccagcttctc gttgggagag gggactagga actccttgta 7560
ctgggagttc tcgtagtcag agacgtcctc cttcttctgt tcagagacag tttcctcggc 7620
accagctcgc aggccagcaa tgattccggt tccgggtaca ccgtgggcgt tggtgatatc 7680
ggaccactcg gcgattcggt gacaccggta ctggtgcttg acagtgttgc caatatctgc 7740
gaactttctg tcctcgaaca ggaagaaacc gtgcttaaga gcaagttcct tgagggggag 7800
cacagtgccg gcgtaggtga agtcgtcaat gatgtcgata tgggttttga tcatgcacac 7860
ataaggtccg accttatcgg caagctcaat gagctccttg gtggtggtaa catccagaga 7920
agcacacagg ttggttttct tggctgccac gagcttgagc actcgagcgg caaaggcgga 7980
cttgtggacg ttagctcgag cttcgtagga gggcattttg gtggtgaaga ggagactgaa 8040
ataaatttag tctgcagaac tttttatcgg aaccttatct ggggcagtga agtatatgtt 8100
atggtaatag ttacgagtta gttgaactta tagatagact ggactatacg gctatcggtc 8160
caaattagaa agaacgtcaa tggctctctg ggcgtcgcct ttgccgacaa aaatgtgatc 8220
atgatgaaag ccagcaatga cgttgcagct gatattgttg tcggccaacc gcgccgaaaa 8280
cgcagctgtc agacccacag cctccaacga agaatgtatc gtcaaagtga tccaagcaca 8340
ctcatagttg gagtcgtact ccaaaggcgg caatgacgag tcagacagat actcgtcgac 8400
cttttccttg ggaaccacca ccgtcagccc ttctgactca cgtattgtag ccaccgacac 8460
aggcaacagt ccgtggatag cagaatatgt cttgtcggtc catttctcac caactttagg 8520
cgtcaagtga atgttgcaga agaagtatgt gccttcattg agaatcggtg ttgctgattt 8580
caataaagtc ttgagatcag tttggccagt catgttgtgg ggggtaattg gattgagtta 8640
tcgcctacag tctgtacagg tatactcgct gcccacttta tactttttga ttccgctgca 8700
cttgaagcaa tgtcgtttac caaaagtgag aatgctccac agaacacacc ccagggtatg 8760
gttgagcaaa aaataaacac tccgatacgg ggaatcgaac cccggtctcc acggttctca 8820
agaagtattc ttgatgagag cgtatcgata gttggagcaa gggagaaatg tagagtgtga 8880
aagactcact atggtccggg cttatctcga ccaatagcca aagtctggag tttctgagag 8940

```
aaaaaggcaa gatacgtatg taacaaagcg acgcatggta caataatacc ggaggcatgt   9000
atcatagaga gttagtggtt cgatgatggc actggtgcct ggtatgactt tatacggctg   9060
actacatatt tgtcctcaga catacaatta cagtcaagca cttacccttg gacatctgta   9120
ggtacccccc ggccaagacg atctcagcgt gtcgtatgtc ggattggcgt agctccctcg   9180
ctcgtcaatt ggctcccatc tactttcttc tgcttggcta cacccagcat gtctgctatg   9240
gctcgttttc gtgccttatc tatcctccca gtattaccaa ctctaaatga catgatgtga   9300
ttgggtctac actttcatat cagagataag gagtagcaca gttgcataaa aagcccaact   9360
ctaatcagct tcttcctttc ttgtaattag tacaaaggtg attagcgaaa tctggaagct   9420
tagttggccc taaaaaaatc aaaaaaagca aaaaacgaaa aacgaaaaac cacagttttg   9480
agaacaggga ggtaacgaag gatcgtatat atatatatat atatatatac ccacggatcc   9540
cgagaccggc ctttgattct tccctacaac caaccattct caccacccta attcacaacc   9600
atggctgccg tcatcgaggt ggccaacgag ttcgtcgcta tcactgccga gacccttccc   9660
aaggtggact atcagcgact ctggcgagac atctactcct gcgagctcct gtacttctcc   9720
attgctttcg tcatcctcaa gtttaccctt ggcgagctct cggattctgg caaaaagatt   9780
ctgcgagtgc tgttcaagtg gtacaacctc ttcatgtccg tcttttcgct ggtgtccttc   9840
ctctgtatgg gttacgccat ctacaccgtt ggactgtact ccaacgaatg cgacagagct   9900
ttcgacaaca gcttgttccg atttgccacc aaggtcttct actattccaa gtttctggag   9960
tacatcgact ctttctacct tcccctcatg gccaagcctc tgtcctttct gcagttcttt  10020
catcacttgg gagctcctat ggacatgtgg ctcttcgtgc agtactctgg cgaatccatt  10080
tggatctttg tgttcctgaa cggattcatt cactttgtca tgtacggcta ctattggaca  10140
cggctgatga agttcaactt tcccatgccc aagcagctca ttaccgcaat gcagatcacc  10200
cagttcaacg ttggcttcta cctcgtgtgg tggtacaagg acattccctg ttaccgaaag  10260
gatcccatgc gaatgctggc ctggatcttc aactactggt acgtcggtac cgttcttctg  10320
ctcttcatca acttctttgt caagtcctac gtgtttccca agcctaagac tgccgacaaa  10380
aaggtccagt agcggccgca tgtacataca agattattta tagaaatgaa tcgcgatcga  10440
acaaagagta cgagtgtacg agtaggggat gatgataaaa gtggaagaag ttccgcatct  10500
ttggatttat caacgtgtag gacgatactt cctgtaaaaa tgcaatgtct ttaccatagg  10560
ttctgctgta gatgttatta actaccatta acatgtctac ttgtacagtt gcagaccagt  10620
tggagtatag aatggtacac ttaccaaaaa gtgttgatgg ttgtaactac gatatataaa  10680
actgttgacg ggatctgtat attcggtaag atatattttg tggggtttta gtggtgttta  10740
aacaccacta aaaccccaca aaatatatct taccgaatat acagatctac tatagaggaa  10800
caattgcccc ggagaagacg gccaggccgc ctagatgaca aattcaacaa ctcacagctg  10860
actttctgcc attgccacta gggggggcc tttttatatg gccaagccaa gctctccacg  10920
tcggttgggc tgcacccaac aataaatggg tagggttgca ccaacaaagg gatgggatgg  10980
ggggtagaag atacgaggat aacggggctc aatggcacaa ataagaacga atactgccat  11040
taagactcgt gatccagcga ctgacaccat tgcatcatct aagggcctca aaactacctc  11100
ggaactgctg cgctgatctg gacaccacag aggttccgag cactttaggt tgcaccaaat  11160
gtcccaccag gtgcaggcag aaaacgctgg aacagcgtgt acagtttgtc ttaacaaaaa  11220
gtgagggcgc tgaggtcgag cagggtggtg tgacttgtta tagcctttag agctgcgaaa  11280
```

-continued

```
gcgcgtatgg atttggctca tcaggccaga ttgagggtct gtggacacat gtcatgttag  11340
tgtacttcaa tcgccccctg gatatagccc cgacaatagg ccgtggcctc atttttttgc  11400
cttccgcaca tttccattgc tcggtaccca caccttgctt ctcctgcact tgccaacctt  11460
aatactggtt tacattgacc aacatcttac aagcgggggg cttgtctagg gtatatataa  11520
acagtggctc tcccaatcgg ttgccagtct ctttttttcct ttctttcccc acagattcga  11580
aatctaaact acacatcaca caatgcctgt tactgacgtc cttaagcgaa agtccggtgt  11640
catcgtcggc gacgatgtcc gagccgtgag tatccacgac aagatcagtg tcgagacgac  11700
gcgttttgtg taatgacaca atccgaaagt cgctagcaac acacactctc tacacaaact  11760
aacccagctc tccatggtga aggcttctcg acaggctctg cccctcgtca tcgacggaaa  11820
ggtgtacgac gtctccgctt gggtgaactt ccaccctggt ggagctgaaa tcattgagaa  11880
ctaccaggga cgagatgcta ctgacgcctt catggttatg cactctcagg aagccttcga  11940
caagctcaag cgaatgccca agatcaacca ggcttccgag ctgcctcccc aggctgccgt  12000
caacgaagct caggaggatt tccgaaagct ccgagaagag ctgatcgcca ctggcatgtt  12060
tgacgcctct cccctctggt actcgtacaa gatcttgacc accctgggtc ttggcgtgct  12120
tgccttcttc atgctggtcc agtaccacct gtacttcatt ggtgctctcg tgctcggtat  12180
gcactaccag caaatgggat ggctgtctca tgacatctgc caccaccaga ccttcaagaa  12240
ccgaaactgg aataacgtcc tgggtctggt ctttggcaac ggactccagg gcttctccgt  12300
gacctggtgg aaggacagac acaacgccca tcattctgct accaacgttc agggtcacga  12360
tcccgacatt gataacctgc ctctgctcgc ctggtccgag gacgatgtca ctcgagcttc  12420
tcccatctcc cgaaagctca ttcagttcca acagtactat ttcctggtca tctgtattct  12480
cctgcgattc atctggtgtt tccagtctgt gctgaccgtt cgatccctca aggaccgaga  12540
caaccagttc taccgatctc agtacaagaa agaggccatt ggactcgctc tgcactggac  12600
tctcaagacc ctgttccacc tcttctttat gccctccatc ctgacctcga tgctggtgtt  12660
ctttgtttcc gagctcgtcg gtggcttcgg aattgccatc gtggtcttca tgaaccacta  12720
ccctctggag aagatcggtg attccgtctg ggacggacat ggcttctctg tgggtcagat  12780
ccatgagacc atgaacattc gacgaggcat cattactgac tggttctttg gaggcctgaa  12840
ctaccagatc gagcaccatc tctggcccac cctgcctcga cacaacctca ctgccgtttc  12900
ctaccaggtg gaacagctgt gccagaagca caacctcccc taccgaaacc ctctgcccca  12960
tgaaggtctc gtcatcctgc tccgatacct gtcccagttc gctcgaatgg ccgagaagca  13020
gcccggtgcc aaggctcagt aagcggccgc atgagaagat aaatatataa atacattgag  13080
atattaaatg cgctagatta gagagcctca tactgctcgg agagaagcca agacgagtac  13140
tcaaagggga ttacaccatc catatccaca gacacaagct ggggaaaggt tctatataca  13200
ctttccggaa taccgtagtt tccgatgtta tcaatggggg cagccaggat ttcaggcact  13260
tcggtgtctc ggggtgaaat ggcgttcttg gcctccatca agtcgtacca tgtcttcatt  13320
tgcctgtcaa agtaaaacag aagcagatga agaatgaact tgaagtgaag gaatttaaat  13380
agttggagca agggagaaat gtagagtgtg aaagactcac tatggtccgg gcttatctcg  13440
accaatagcc aaagtctgga gtttctgaga gaaaaaggca agatacgtat gtaacaaagc  13500
gacgcatggt acaataatac cggaggcatg tatcatagag agttagtggt tcgatgatgg  13560
cactggtgcc tggtatgact ttatacggct gactacatat ttgtcctcag acatacaatt  13620
acagtcaagc acttaccctt ggacatctgt aggtaccccc cggccaagac gatctcagcg  13680
```

-continued

```
tgtcgtatgt cggattggcg tagctccctc gctcgtcaat tggctcccat ctactttctt  13740
ctgcttggct acacccagca tgtctgctat ggctcgtttt cgtgccttat ctatcctccc  13800
agtattacca actctaaatg acatgatgtg attgggtcta cactttcata tcagagataa  13860
ggagtagcac agttgcataa aaagcccaac tctaatcagc ttcttccttt cttgtaatta  13920
gtacaaaggt gattagcgaa atctggaagc ttagttggcc ctaaaaaaat caaaaaaagc  13980
aaaaaacgaa aaacgaaaaa ccacagtttt gagaacaggg aggtaacgaa ggatcgtata  14040
tatatatata tatatatata cccacggatc ccgagaccgg cctttgattc ttccctacaa  14100
ccaaccattc tcaccaccct aattcacaac catggcctcc acctcggctc tgcccaagca  14160
gaaccctgcc ctccgacgaa ccgtcacttc caccactgtg accgactcgg agtctgctgc  14220
cgtctctccc tccgattctc ccagacactc ggcctcctct acatcgctgt cttccatgtc  14280
cgaggtggac attgccaagc ccaagtccga gtacggtgtc atgctggata cctacggcaa  14340
ccagttcgaa gttcccgact tcaccatcaa ggacatctac aacgctattc ccaagcactg  14400
cttcaagcga tctgctctca agggatacgg ctacattctt cgagacattg tcctcctgac  14460
taccactttc agcatctggt acaactttgt gacacccgag tacattccct ccactcctgc  14520
tcgagccggt ctgtgggctg tgtacaccgt tcttcaggga ctcttcggta ctggactgtg  14580
ggtcattgcc cacgagtgtg gacatggtgc tttctccgat tcccgaatca tcaacgacat  14640
tactggctgg gtgcttcact cttccctgct tgttccctac ttcagctggc aaatctccca  14700
ccggaagcat cacaaggcca ctggaaacat ggagcgagac atggtcttcg ttcctcgaac  14760
ccgagagcag caagctactc gactcggcaa gatgacccac gaactcgccc atcttaccga  14820
ggaaactcct gctttcaccc tgctcatgct tgtgcttcag caactggtcg gttggcccaa  14880
ctatctcatt accaacgtta ctggacacaa ctaccatgag cggcagcgag agggtcgagg  14940
caagggaaag cacaacggtc ttggcggtgg agttaaccat ttcgatcccc gatctcctct  15000
gtacgagaac agcgacgcca agctcatcgt gctctccgac attggcattg gtcttatggc  15060
caccgctctg tactttctcg ttcagaagtt cggattctac aacatggcca tctggtactt  15120
cgttccctac ttgtgggtta accactggct cgtcgccatt acctttctgc agcacacaga  15180
tcctactctt ccccactaca ccaacgacga gtggaacttt gtgcgaggtg ccgctgcaac  15240
catcgaccga gagatgggct tcattggacg tcatctgctc cacggcatta tcgagactca  15300
cgtcctgcat cactacgtct cttccattcc cttctacaat gcggacgaag ctaccgaggc  15360
catcaaacct atcatgggca agcactatcg agctgatgtc caggacggtc ctcgaggatt  15420
cattcgagcc atgtaccgat ctgcacgaat gtgccagtgg gttgaaccct ccgctggtgc  15480
cgagggagct ggcaagggtg tcctgttctt tcgaaaccga aacaatgtgg gcactcctcc  15540
cgctgtcatc aagcccgttg cctaagcggc cgctatttat cactctttac aacttctacc  15600
tcaactatct actttaataa atgaatatcg tttattctct atgattactg tatatgcgtt  15660
cctctaagac aaatcgaaac cagcatgtga tcgaatggca tacaaaagtt tcttccgaag  15720
ttgatcaatg tcctgatagt caggcagctt gagaagattg acacaggtgg aggccgtagg  15780
gaaccgatca acctgtctac cagcgttacg aatggcaaat gacgggttca aagccttgaa  15840
tccttgcaat ggtgccttgg atactgatgt cacaaactta agaagcagcc gcttgtcctc  15900
ttcctcgatc gatggtcata gctgtttcct gtgtgaaatt gttatccgct cacaattcca  15960
cacaac                                                             15966
```

```
<210> SEQ ID NO 72
<211> LENGTH: 2119
<212> TYPE: DNA
<213> ORGANISM: Yarrowia lipolytica
<220> FEATURE:
<221> NAME/KEY: CDS
<222> LOCATION: (291)..(1835)
<223> OTHER INFORMATION: DGAT2 opening reading frame
<220> FEATURE:
<221> NAME/KEY: misc_feature
<222> LOCATION: (291)..(293)
<223> OTHER INFORMATION: initiation codon ('ATG')
<220> FEATURE:
<221> NAME/KEY: misc_feature
<222> LOCATION: (456)..(458)
<223> OTHER INFORMATION: initiation codon ('ATG')
<220> FEATURE:
<221> NAME/KEY: misc_feature
<222> LOCATION: (768)..(770)
<223> OTHER INFORMATION: initiation codon ('ATG')
<300> PUBLICATION INFORMATION:
<302> TITLE: ACYLTRANSFERASES FOR ALTERATION OF POLYUNSATURATED FATTY
      ACIDS AND OIL CONTENT IN OLEAGINOUS YEASTS
<310> PATENT DOCUMENT NUMBER: U.S. Patent 7,267,976
<311> PATENT FILING DATE: 2004-07-01
<312> PUBLICATION DATE: 2007-09-11
<313> RELEVANT RESIDUES IN SEQ ID NO: (1)..(2119)

<400> SEQUENCE: 72

aaacgcaccc actgctcgtc ctccttgctc ctcgaaaccg actcctctac acacgtcaaa      60

tccgaggttg aaatcttccc cacatttggc agccaaacca gcacatccca gcaacctcgc     120

acagcgccga aatcgacctg tcgacttggc cacaaaaaaa agcaccggct ctgcaacagt     180

tctcacgacc aattacgtac aagtacgaaa tcgttcgtgg accgtgactg ataagctccc     240

actttttctt ctaacaacag gcaacagaca agtcacacaa aacaaaagct atg act       296
                                                      Met Thr
                                                      1

atc gac tca caa tac tac aag tcg cga gac aaa aac gac acg gca ccc      344
Ile Asp Ser Gln Tyr Tyr Lys Ser Arg Asp Lys Asn Asp Thr Ala Pro
        5                   10                  15

aaa atc gcg gga atc cga tat gcc ccg cta tcg aca cca tta ctc aac      392
Lys Ile Ala Gly Ile Arg Tyr Ala Pro Leu Ser Thr Pro Leu Leu Asn
    20                  25                  30

cga tgt gag acc ttc tct ctg gtc tgg cac att ttc agc att ccc act      440
Arg Cys Glu Thr Phe Ser Leu Val Trp His Ile Phe Ser Ile Pro Thr
35                  40                  45                  50

ttc ctc aca att ttc atg cta tgc tgc gca att cca ctg ctc tgg cca      488
Phe Leu Thr Ile Phe Met Leu Cys Cys Ala Ile Pro Leu Leu Trp Pro
                55                  60                  65

ttt gtg att gcg tat gta gtg tac gct gtt aaa gac gac tcc ccg tcc      536
Phe Val Ile Ala Tyr Val Val Tyr Ala Val Lys Asp Asp Ser Pro Ser
            70                  75                  80

aac gga gga gtg gtc aag cga tac tcg cct att tca aga aac ttc ttc      584
Asn Gly Gly Val Val Lys Arg Tyr Ser Pro Ile Ser Arg Asn Phe Phe
        85                  90                  95

atc tgg aag ctc ttt ggc cgc tac ttc ccc ata act ctg cac aag acg      632
Ile Trp Lys Leu Phe Gly Arg Tyr Phe Pro Ile Thr Leu His Lys Thr
    100                 105                 110

gtg gat ctg gag ccc acg cac aca tac tac cct ctg gac gtc cag gag      680
Val Asp Leu Glu Pro Thr His Thr Tyr Tyr Pro Leu Asp Val Gln Glu
115                 120                 125                 130

tat cac ctg att gct gag aga tac tgg ccg cag aac aag tac ctc cga      728
Tyr His Leu Ile Ala Glu Arg Tyr Trp Pro Gln Asn Lys Tyr Leu Arg
                135                 140                 145
```

-continued

```
gca atc atc tcc acc atc gag tac ttt ctg ccc gcc ttc atg aaa cgg      776
Ala Ile Ile Ser Thr Ile Glu Tyr Phe Leu Pro Ala Phe Met Lys Arg
            150                 155                 160

tct ctt tct atc aac gag cag gag cag cct gcc gag cga gat cct ctc      824
Ser Leu Ser Ile Asn Glu Gln Glu Gln Pro Ala Glu Arg Asp Pro Leu
        165                 170                 175

ctg tct ccc gtt tct ccc agc tct ccg ggt tct caa cct gac aag tgg      872
Leu Ser Pro Val Ser Pro Ser Ser Pro Gly Ser Gln Pro Asp Lys Trp
    180                 185                 190

att aac cac gac agc aga tat agc cgt gga gaa tca tct ggc tcc aac      920
Ile Asn His Asp Ser Arg Tyr Ser Arg Gly Glu Ser Ser Gly Ser Asn
195                 200                 205                 210

ggc cac gcc tcg ggc tcc gaa ctt aac ggc aac ggc aac aat ggc acc      968
Gly His Ala Ser Gly Ser Glu Leu Asn Gly Asn Gly Asn Asn Gly Thr
                215                 220                 225

act aac cga cga cct ttg tcg tcc gcc tct gct ggc tcc act gca tct     1016
Thr Asn Arg Arg Pro Leu Ser Ser Ala Ser Ala Gly Ser Thr Ala Ser
            230                 235                 240

gat tcc acg ctt ctt aac ggg tcc ctc aac tcc tac gcc aac cag atc     1064
Asp Ser Thr Leu Leu Asn Gly Ser Leu Asn Ser Tyr Ala Asn Gln Ile
        245                 250                 255

att ggc gaa aac gac cca cag ctg tcg ccc aca aaa ctc aag ccc act     1112
Ile Gly Glu Asn Asp Pro Gln Leu Ser Pro Thr Lys Leu Lys Pro Thr
    260                 265                 270

ggc aga aaa tac atc ttc ggc tac cac ccc cac ggc att atc ggc atg     1160
Gly Arg Lys Tyr Ile Phe Gly Tyr His Pro His Gly Ile Ile Gly Met
275                 280                 285                 290

gga gcc ttt ggt gga att gcc acc gag gga gct gga tgg tcc aag ctc     1208
Gly Ala Phe Gly Gly Ile Ala Thr Glu Gly Ala Gly Trp Ser Lys Leu
                295                 300                 305

ttt ccg ggc atc cct gtt tct ctt atg act ctc acc aac aac ttc cga     1256
Phe Pro Gly Ile Pro Val Ser Leu Met Thr Leu Thr Asn Asn Phe Arg
            310                 315                 320

gtg cct ctc tac aga gag tac ctc atg agt ctg gga gtc gct tct gtc     1304
Val Pro Leu Tyr Arg Glu Tyr Leu Met Ser Leu Gly Val Ala Ser Val
        325                 330                 335

tcc aag aag tcc tgc aag gcc ctc ctc aag cga aac cag tct atc tgc     1352
Ser Lys Lys Ser Cys Lys Ala Leu Leu Lys Arg Asn Gln Ser Ile Cys
    340                 345                 350

att gtc gtt ggt gga gca cag gaa agt ctt ctg gcc aga ccc ggt gtc     1400
Ile Val Val Gly Gly Ala Gln Glu Ser Leu Leu Ala Arg Pro Gly Val
355                 360                 365                 370

atg gac ctg gtg cta ctc aag cga aag ggt ttt gtt cga ctt ggt atg     1448
Met Asp Leu Val Leu Leu Lys Arg Lys Gly Phe Val Arg Leu Gly Met
                375                 380                 385

gag gtc gga aat gtc gcc ctt gtt ccc atc atg gcc ttt ggt gag aac     1496
Glu Val Gly Asn Val Ala Leu Val Pro Ile Met Ala Phe Gly Glu Asn
            390                 395                 400

gac ctc tat gac cag gtt agc aac gac aag tcg tcc aag ctg tac cga     1544
Asp Leu Tyr Asp Gln Val Ser Asn Asp Lys Ser Ser Lys Leu Tyr Arg
        405                 410                 415

ttc cag cag ttt gtc aag aac ttc ctt gga ttc acc ctt cct ttg atg     1592
Phe Gln Gln Phe Val Lys Asn Phe Leu Gly Phe Thr Leu Pro Leu Met
    420                 425                 430

cat gcc cga ggc gtc ttc aac tac gat gtc ggt ctt gtc ccc tac agg     1640
His Ala Arg Gly Val Phe Asn Tyr Asp Val Gly Leu Val Pro Tyr Arg
435                 440                 445                 450

cga ccc gtc aac att gtg gtt ggt tcc ccc att gac ttg cct tat ctc     1688
Arg Pro Val Asn Ile Val Val Gly Ser Pro Ile Asp Leu Pro Tyr Leu
                455                 460                 465
```

```
cca cac ccc acc gac gaa gaa gtg tcc gaa tac cac gac cga tac atc      1736
Pro His Pro Thr Asp Glu Glu Val Ser Glu Tyr His Asp Arg Tyr Ile
            470                 475                 480

gcc gag ctg cag cga atc tac aac gag cac aag gat gaa tat ttc atc      1784
Ala Glu Leu Gln Arg Ile Tyr Asn Glu His Lys Asp Glu Tyr Phe Ile
        485                 490                 495

gat tgg acc gag gag ggc aaa gga gcc cca gag ttc cga atg att gag      1832
Asp Trp Thr Glu Glu Gly Lys Gly Ala Pro Glu Phe Arg Met Ile Glu
    500                 505                 510

taa ggaaaactgc ctgggttagg caaatagcta atgagtattt ttttgatggc          1885

aaccaaatgt agaaagaaaa aaaaaaaaaa agaaaaaaaa aagagaatat tatatctatg   1945

taattctatt aaaagctctg ttgagtgagc ggaataaata ctgttgaaga ggggattgtg   2005

tagagatctg tttactcaat ggcaaactca tctgggggag atccttccac tgtgggaagc   2065

tcctggatag cctttgcatc ggggttcaag aagaccattg tgaacagccc ttga         2119


<210> SEQ ID NO 73
<211> LENGTH: 514
<212> TYPE: PRT
<213> ORGANISM: Yarrowia lipolytica

<400> SEQUENCE: 73

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255
```

```
Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu


<210> SEQ ID NO 74
<211> LENGTH: 1434
<212> TYPE: DNA
<213> ORGANISM: Fusarium moniliforme
<220> FEATURE:
<221> NAME/KEY: CDS
<222> LOCATION: (1)..(1434)
<223> OTHER INFORMATION: synthetic delta-12 desaturase
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES IN SEQ ID NO: (1)..(1434)
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES IN SEQ ID NO: (1)..(1434)

<400> SEQUENCE: 74

atg gcc tcc acc tcg gct ctg ccc aag cag aac cct gcc ctc cga cga       48
Met Ala Ser Thr Ser Ala Leu Pro Lys Gln Asn Pro Ala Leu Arg Arg
1               5                   10                  15
```

```
acc gtc act tcc acc act gtg acc gac tcg gag tct gct gcc gtc tct       96
Thr Val Thr Ser Thr Thr Val Thr Asp Ser Glu Ser Ala Ala Val Ser
            20                  25                  30

ccc tcc gat tct ccc aga cac tcg gcc tcc tct aca tcg ctg tct tcc      144
Pro Ser Asp Ser Pro Arg His Ser Ala Ser Ser Thr Ser Leu Ser Ser
        35                  40                  45

atg tcc gag gtg gac att gcc aag ccc aag tcc gag tac ggt gtc atg      192
Met Ser Glu Val Asp Ile Ala Lys Pro Lys Ser Glu Tyr Gly Val Met
    50                  55                  60

ctg gat acc tac ggc aac cag ttc gaa gtt ccc gac ttc acc atc aag      240
Leu Asp Thr Tyr Gly Asn Gln Phe Glu Val Pro Asp Phe Thr Ile Lys
65                  70                  75                  80

gac atc tac aac gct att ccc aag cac tgc ttc aag cga tct gct ctc      288
Asp Ile Tyr Asn Ala Ile Pro Lys His Cys Phe Lys Arg Ser Ala Leu
                85                  90                  95

aag gga tac ggc tac att ctt cga gac att gtc ctc ctg act acc act      336
Lys Gly Tyr Gly Tyr Ile Leu Arg Asp Ile Val Leu Leu Thr Thr Thr
            100                 105                 110

ttc agc atc tgg tac aac ttt gtg aca ccc gag tac att ccc tcc act      384
Phe Ser Ile Trp Tyr Asn Phe Val Thr Pro Glu Tyr Ile Pro Ser Thr
        115                 120                 125

cct gct cga gcc ggt ctg tgg gct gtg tac acc gtt ctt cag gga ctc      432
Pro Ala Arg Ala Gly Leu Trp Ala Val Tyr Thr Val Leu Gln Gly Leu
    130                 135                 140

ttc ggt act gga ctg tgg gtc att gcc cac gag tgt gga cat ggt gct      480
Phe Gly Thr Gly Leu Trp Val Ile Ala His Glu Cys Gly His Gly Ala
145                 150                 155                 160

ttc tcc gat tcc cga atc atc aac gac att act ggc tgg gtg ctt cac      528
Phe Ser Asp Ser Arg Ile Ile Asn Asp Ile Thr Gly Trp Val Leu His
                165                 170                 175

tct tcc ctg ctt gtt ccc tac ttc agc tgg caa atc tcc cac cgg aag      576
Ser Ser Leu Leu Val Pro Tyr Phe Ser Trp Gln Ile Ser His Arg Lys
            180                 185                 190

cat cac aag gcc act gga aac atg gag cga gac atg gtc ttc gtt cct      624
His His Lys Ala Thr Gly Asn Met Glu Arg Asp Met Val Phe Val Pro
        195                 200                 205

cga acc cga gag cag caa gct act cga ctc ggc aag atg acc cac gaa      672
Arg Thr Arg Glu Gln Gln Ala Thr Arg Leu Gly Lys Met Thr His Glu
    210                 215                 220

ctc gcc cat ctt acc gag gaa act cct gct ttc acc ctg ctc atg ctt      720
Leu Ala His Leu Thr Glu Glu Thr Pro Ala Phe Thr Leu Leu Met Leu
225                 230                 235                 240

gtg ctt cag caa ctg gtc ggt tgg ccc aac tat ctc att acc aac gtt      768
Val Leu Gln Gln Leu Val Gly Trp Pro Asn Tyr Leu Ile Thr Asn Val
                245                 250                 255

act gga cac aac tac cat gag cgg cag cga gag ggt cga ggc aag gga      816
Thr Gly His Asn Tyr His Glu Arg Gln Arg Glu Gly Arg Gly Lys Gly
            260                 265                 270

aag cac aac ggt ctt ggc ggt gga gtt aac cat ttc gat ccc cga tct      864
Lys His Asn Gly Leu Gly Gly Gly Val Asn His Phe Asp Pro Arg Ser
        275                 280                 285

cct ctg tac gag aac agc gac gcc aag ctc atc gtg ctc tcc gac att      912
Pro Leu Tyr Glu Asn Ser Asp Ala Lys Leu Ile Val Leu Ser Asp Ile
    290                 295                 300

ggc att ggt ctt atg gcc acc gct ctg tac ttt ctc gtt cag aag ttc      960
Gly Ile Gly Leu Met Ala Thr Ala Leu Tyr Phe Leu Val Gln Lys Phe
305                 310                 315                 320

gga ttc tac aac atg gcc atc tgg tac ttc gtt ccc tac ttg tgg gtt     1008
Gly Phe Tyr Asn Met Ala Ile Trp Tyr Phe Val Pro Tyr Leu Trp Val
```

```
                325                 330                 335

aac cac tgg ctc gtc gcc att acc ttt ctg cag cac aca gat cct act      1056
Asn His Trp Leu Val Ala Ile Thr Phe Leu Gln His Thr Asp Pro Thr
            340                 345                 350

ctt ccc cac tac acc aac gac gag tgg aac ttt gtg cga ggt gcc gct      1104
Leu Pro His Tyr Thr Asn Asp Glu Trp Asn Phe Val Arg Gly Ala Ala
        355                 360                 365

gca acc atc gac cga gag atg ggc ttc att gga cgt cat ctg ctc cac      1152
Ala Thr Ile Asp Arg Glu Met Gly Phe Ile Gly Arg His Leu Leu His
    370                 375                 380

ggc att atc gag act cac gtc ctg cat cac tac gtc tct tcc att ccc      1200
Gly Ile Ile Glu Thr His Val Leu His His Tyr Val Ser Ser Ile Pro
385                 390                 395                 400

ttc tac aat gcg gac gaa gct acc gag gcc atc aaa cct atc atg ggc      1248
Phe Tyr Asn Ala Asp Glu Ala Thr Glu Ala Ile Lys Pro Ile Met Gly
                405                 410                 415

aag cac tat cga gct gat gtc cag gac ggt cct cga gga ttc att cga      1296
Lys His Tyr Arg Ala Asp Val Gln Asp Gly Pro Arg Gly Phe Ile Arg
            420                 425                 430

gcc atg tac cga tct gca cga atg tgc cag tgg gtt gaa ccc tcc gct      1344
Ala Met Tyr Arg Ser Ala Arg Met Cys Gln Trp Val Glu Pro Ser Ala
        435                 440                 445

ggt gcc gag gga gct ggc aag ggt gtc ctg ttc ttt cga aac cga aac      1392
Gly Ala Glu Gly Ala Gly Lys Gly Val Leu Phe Phe Arg Asn Arg Asn
    450                 455                 460

aat gtg ggc act cct ccc gct gtc atc aag ccc gtt gcc taa              1434
Asn Val Gly Thr Pro Pro Ala Val Ile Lys Pro Val Ala
465                 470                 475


<210> SEQ ID NO 75
<211> LENGTH: 477
<212> TYPE: PRT
<213> ORGANISM: Fusarium moniliforme

<400> SEQUENCE: 75

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175
```

```
Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475
```

<210> SEQ ID NO 76
<211> LENGTH: 1272
<212> TYPE: DNA
<213> ORGANISM: Artificial Sequence
<220> FEATURE:
<223> OTHER INFORMATION: mutant EgD8M delta-8 desaturase ("EgD8S-23")
<220> FEATURE:
<221> NAME/KEY: CDS
<222> LOCATION: (2)..(1270)
<300> PUBLICATION INFORMATION:
<302> TITLE: MUTANT DELTA-8 DESATURASE GENES ENGINEERED BY TARGETED
      MUTAGENESIS AND THEIR USE IN MAKING POLYUNSATURATED FATTY ACIDS
<310> PATENT DOCUMENT NUMBER: WO 2008/073271
<311> PATENT FILING DATE: 2007-12-05
<312> PUBLICATION DATE: 2008-06-19
<313> RELEVANT RESIDUES IN SEQ ID NO: (1)..(1272)
<300> PUBLICATION INFORMATION:
<302> TITLE: MUTANT DELTA-8 DESATURASE GENES ENGINEERED BY TARGETED
      MUTAGENESIS AND THEIR USE IN MAKING POLYUNSATURATED FATTY ACIDS
<310> PATENT DOCUMENT NUMBER: US 2008-0138868-A1
<311> PATENT FILING DATE: 2006-12-07

<312> PUBLICATION DATE: 2008-06-12
<313> RELEVANT RESIDUES IN SEQ ID NO: (1)..(1272)

<400> SEQUENCE: 76

```
c atg gtg aag gct tct cga cag gct ctg ccc ctc gtc atc gac gga aag      49
  Met Val Lys Ala Ser Arg Gln Ala Leu Pro Leu Val Ile Asp Gly Lys
  1               5                   10                  15

gtg tac gac gtc tcc gct tgg gtg aac ttc cac cct ggt gga gct gaa        97
Val Tyr Asp Val Ser Ala Trp Val Asn Phe His Pro Gly Gly Ala Glu
            20                  25                  30

atc att gag aac tac cag gga cga gat gct act gac gcc ttc atg gtt       145
Ile Ile Glu Asn Tyr Gln Gly Arg Asp Ala Thr Asp Ala Phe Met Val
        35                  40                  45

atg cac tct cag gaa gcc ttc gac aag ctc aag cga atg ccc aag atc       193
Met His Ser Gln Glu Ala Phe Asp Lys Leu Lys Arg Met Pro Lys Ile
    50                  55                  60

aac cag gct tcc gag ctg cct ccc cag gct gcc gtc aac gaa gct cag       241
Asn Gln Ala Ser Glu Leu Pro Pro Gln Ala Ala Val Asn Glu Ala Gln
65                  70                  75                  80

gag gat ttc cga aag ctc cga gaa gag ctg atc gcc act ggc atg ttt       289
Glu Asp Phe Arg Lys Leu Arg Glu Glu Leu Ile Ala Thr Gly Met Phe
                85                  90                  95

gac gcc tct ccc ctc tgg tac tcg tac aag atc ttg acc acc ctg ggt       337
Asp Ala Ser Pro Leu Trp Tyr Ser Tyr Lys Ile Leu Thr Thr Leu Gly
            100                 105                 110

ctt ggc gtg ctt gcc ttc ttc atg ctg gtc cag tac cac ctg tac ttc       385
Leu Gly Val Leu Ala Phe Phe Met Leu Val Gln Tyr His Leu Tyr Phe
        115                 120                 125

att ggt gct ctc gtg ctc ggt atg cac tac cag caa atg gga tgg ctg       433
Ile Gly Ala Leu Val Leu Gly Met His Tyr Gln Gln Met Gly Trp Leu
    130                 135                 140

tct cat gac atc tgc cac cac cag acc ttc aag aac cga aac tgg aat       481
Ser His Asp Ile Cys His His Gln Thr Phe Lys Asn Arg Asn Trp Asn
145                 150                 155                 160

aac gtc ctg ggt ctg gtc ttt ggc aac gga ctc cag ggc ttc tcc gtg       529
Asn Val Leu Gly Leu Val Phe Gly Asn Gly Leu Gln Gly Phe Ser Val
                165                 170                 175

acc tgg tgg aag gac aga cac aac gcc cat cat tct gct acc aac gtt       577
Thr Trp Trp Lys Asp Arg His Asn Ala His His Ser Ala Thr Asn Val
            180                 185                 190

cag ggt cac gat ccc gac att gat aac ctg cct ctg ctc gcc tgg tcc       625
Gln Gly His Asp Pro Asp Ile Asp Asn Leu Pro Leu Leu Ala Trp Ser
        195                 200                 205

gag gac gat gtc act cga gct tct ccc atc tcc cga aag ctc att cag       673
Glu Asp Asp Val Thr Arg Ala Ser Pro Ile Ser Arg Lys Leu Ile Gln
    210                 215                 220

ttc caa cag tac tat ttc ctg gtc atc tgt att ctc ctg cga ttc atc       721
Phe Gln Gln Tyr Tyr Phe Leu Val Ile Cys Ile Leu Leu Arg Phe Ile
225                 230                 235                 240

tgg tgt ttc cag tct gtg ctg acc gtt cga tcc ctc aag gac cga gac       769
Trp Cys Phe Gln Ser Val Leu Thr Val Arg Ser Leu Lys Asp Arg Asp
                245                 250                 255

aac cag ttc tac cga tct cag tac aag aaa gag gcc att gga ctc gct       817
Asn Gln Phe Tyr Arg Ser Gln Tyr Lys Lys Glu Ala Ile Gly Leu Ala
            260                 265                 270

ctg cac tgg act ctc aag acc ctg ttc cac ctc ttc ttt atg ccc tcc       865
Leu His Trp Thr Leu Lys Thr Leu Phe His Leu Phe Phe Met Pro Ser
        275                 280                 285

atc ctg acc tcg atg ctg gtg ttc ttt gtt tcc gag ctc gtc ggt ggc       913
Ile Leu Thr Ser Met Leu Val Phe Phe Val Ser Glu Leu Val Gly Gly
```

```
    290                 295                 300

ttc gga att gcc atc gtg gtc ttc atg aac cac tac cct ctg gag aag      961
Phe Gly Ile Ala Ile Val Val Phe Met Asn His Tyr Pro Leu Glu Lys
305                 310                 315                 320

atc ggt gat tcc gtc tgg gac gga cat ggc ttc tct gtg ggt cag atc     1009
Ile Gly Asp Ser Val Trp Asp Gly His Gly Phe Ser Val Gly Gln Ile
                325                 330                 335

cat gag acc atg aac att cga cga ggc atc att act gac tgg ttc ttt     1057
His Glu Thr Met Asn Ile Arg Arg Gly Ile Ile Thr Asp Trp Phe Phe
            340                 345                 350

gga ggc ctg aac tac cag atc gag cac cat ctc tgg ccc acc ctg cct     1105
Gly Gly Leu Asn Tyr Gln Ile Glu His His Leu Trp Pro Thr Leu Pro
        355                 360                 365

cga cac aac ctc act gcc gtt tcc tac cag gtg gaa cag ctg tgc cag     1153
Arg His Asn Leu Thr Ala Val Ser Tyr Gln Val Glu Gln Leu Cys Gln
    370                 375                 380

aag cac aac ctc ccc tac cga aac cct ctg ccc cat gaa ggt ctc gtc     1201
Lys His Asn Leu Pro Tyr Arg Asn Pro Leu Pro His Glu Gly Leu Val
385                 390                 395                 400

atc ctg ctc cga tac ctg tcc cag ttc gct cga atg gcc gag aag cag     1249
Ile Leu Leu Arg Tyr Leu Ser Gln Phe Ala Arg Met Ala Glu Lys Gln
                405                 410                 415

ccc ggt gcc aag gct cag taa gc                                      1272
Pro Gly Ala Lys Ala Gln
            420


<210> SEQ ID NO 77
<211> LENGTH: 422
<212> TYPE: PRT
<213> ORGANISM: Artificial Sequence
<220> FEATURE:
<223> OTHER INFORMATION: Synthetic Construct

<400> SEQUENCE: 77

Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190
```

```
Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420


<210> SEQ ID NO 78
<211> LENGTH: 792
<212> TYPE: DNA
<213> ORGANISM: Eutreptiella sp. CCMP389
<220> FEATURE:
<221> NAME/KEY: CDS
<222> LOCATION: (1)..(792)
<223> OTHER INFORMATION: synthetic delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(792)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 2007-0117190-A1
<311> PATENT FILING DATE: 2006-11-16
<312> PUBLICATION DATE: 2007-05-24
<313> RELEVANT RESIDUES IN SEQ ID NO: (1)..(792)

<400> SEQUENCE: 78

atg gct gcc gtc atc gag gtg gcc aac gag ttc gtc gct atc act gcc       48
Met Ala Ala Val Ile Glu Val Ala Asn Glu Phe Val Ala Ile Thr Ala
1               5                   10                  15

gag acc ctt ccc aag gtg gac tat cag cga ctc tgg cga gac atc tac       96
Glu Thr Leu Pro Lys Val Asp Tyr Gln Arg Leu Trp Arg Asp Ile Tyr
            20                  25                  30
```

```
tcc tgc gag ctc ctg tac ttc tcc att gct ttc gtc atc ctc aag ttt      144
Ser Cys Glu Leu Leu Tyr Phe Ser Ile Ala Phe Val Ile Leu Lys Phe
        35                  40                  45

acc ctt ggc gag ctc tcg gat tct ggc aaa aag att ctg cga gtg ctg      192
Thr Leu Gly Glu Leu Ser Asp Ser Gly Lys Lys Ile Leu Arg Val Leu
    50                  55                  60

ttc aag tgg tac aac ctc ttc atg tcc gtc ttt tcg ctg gtg tcc ttc      240
Phe Lys Trp Tyr Asn Leu Phe Met Ser Val Phe Ser Leu Val Ser Phe
65                  70                  75                  80

ctc tgt atg ggt tac gcc atc tac acc gtt gga ctg tac tcc aac gaa      288
Leu Cys Met Gly Tyr Ala Ile Tyr Thr Val Gly Leu Tyr Ser Asn Glu
                85                  90                  95

tgc gac aga gct ttc gac aac agc ttg ttc cga ttt gcc acc aag gtc      336
Cys Asp Arg Ala Phe Asp Asn Ser Leu Phe Arg Phe Ala Thr Lys Val
            100                 105                 110

ttc tac tat tcc aag ttt ctg gag tac atc gac tct ttc tac ctt ccc      384
Phe Tyr Tyr Ser Lys Phe Leu Glu Tyr Ile Asp Ser Phe Tyr Leu Pro
        115                 120                 125

ctc atg gcc aag cct ctg tcc ttt ctg cag ttc ttt cat cac ttg gga      432
Leu Met Ala Lys Pro Leu Ser Phe Leu Gln Phe Phe His His Leu Gly
    130                 135                 140

gct cct atg gac atg tgg ctc ttc gtg cag tac tct ggc gaa tcc att      480
Ala Pro Met Asp Met Trp Leu Phe Val Gln Tyr Ser Gly Glu Ser Ile
145                 150                 155                 160

tgg atc ttt gtg ttc ctg aac gga ttc att cac ttt gtc atg tac ggc      528
Trp Ile Phe Val Phe Leu Asn Gly Phe Ile His Phe Val Met Tyr Gly
                165                 170                 175

tac tat tgg aca cgg ctg atg aag ttc aac ttt ccc atg ccc aag cag      576
Tyr Tyr Trp Thr Arg Leu Met Lys Phe Asn Phe Pro Met Pro Lys Gln
            180                 185                 190

ctc att acc gca atg cag atc acc cag ttc aac gtt ggc ttc tac ctc      624
Leu Ile Thr Ala Met Gln Ile Thr Gln Phe Asn Val Gly Phe Tyr Leu
        195                 200                 205

gtg tgg tgg tac aag gac att ccc tgt tac cga aag gat ccc atg cga      672
Val Trp Trp Tyr Lys Asp Ile Pro Cys Tyr Arg Lys Asp Pro Met Arg
    210                 215                 220

atg ctg gcc tgg atc ttc aac tac tgg tac gtc ggt acc gtt ctt ctg      720
Met Leu Ala Trp Ile Phe Asn Tyr Trp Tyr Val Gly Thr Val Leu Leu
225                 230                 235                 240

ctc ttc atc aac ttc ttt gtc aag tcc tac gtg ttt ccc aag cct aag      768
Leu Phe Ile Asn Phe Phe Val Lys Ser Tyr Val Phe Pro Lys Pro Lys
                245                 250                 255

act gcc gac aaa aag gtc cag tag                                      792
Thr Ala Asp Lys Lys Val Gln
            260


<210> SEQ ID NO 79
<211> LENGTH: 263
<212> TYPE: PRT
<213> ORGANISM: Eutreptiella sp. CCMP389

<400> SEQUENCE: 79

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
```

```
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260


<210> SEQ ID NO 80
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: synthetic delta-5 desaturase

<400> SEQUENCE: 80

atg gct ctc tcc ctt act acc gag cag ctg ctc gag cga ccc gac ctg       48
Met Ala Leu Ser Leu Thr Thr Glu Gln Leu Leu Glu Arg Pro Asp Leu
1               5                   10                  15

gtt gcc atc gac ggc att ctc tac gat ctg gaa ggt ctt gcc aag gtc       96
Val Ala Ile Asp Gly Ile Leu Tyr Asp Leu Glu Gly Leu Ala Lys Val
            20                  25                  30

cat ccc gga ggc gac ttg atc ctc gct tct ggt gcc tcc gat gct tct      144
His Pro Gly Gly Asp Leu Ile Leu Ala Ser Gly Ala Ser Asp Ala Ser
        35                  40                  45

cct ctg ttc tac tcc atg cac cct tac gtc aag ccc gag aac tcg aag      192
Pro Leu Phe Tyr Ser Met His Pro Tyr Val Lys Pro Glu Asn Ser Lys
    50                  55                  60

ctg ctt caa cag ttc gtg cga ggc aag cac gac cga acc tcc aag gac      240
Leu Leu Gln Gln Phe Val Arg Gly Lys His Asp Arg Thr Ser Lys Asp
65                  70                  75                  80

att gtc tac acc tac gac tct ccc ttt gca cag gac gtc aag cga act      288
Ile Val Tyr Thr Tyr Asp Ser Pro Phe Ala Gln Asp Val Lys Arg Thr
                85                  90                  95

atg cga gag gtc atg aaa ggt cgg aac tgg tat gcc aca cct gga ttc      336
Met Arg Glu Val Met Lys Gly Arg Asn Trp Tyr Ala Thr Pro Gly Phe
```

-continued

```
            100                 105                 110

tgg ctg cga acc gtt ggc atc att gct gtc acc gcc ttt tgc gag tgg      384
Trp Leu Arg Thr Val Gly Ile Ile Ala Val Thr Ala Phe Cys Glu Trp
        115                 120                 125

cac tgg gct act acc gga atg gtg ctg tgg ggt ctc ttg act gga ttc      432
His Trp Ala Thr Thr Gly Met Val Leu Trp Gly Leu Leu Thr Gly Phe
    130                 135                 140

atg cac atg cag atc ggc ctg tcc att cag cac gat gcc tct cat ggt      480
Met His Met Gln Ile Gly Leu Ser Ile Gln His Asp Ala Ser His Gly
145                 150                 155                 160

gcc atc agc aaa aag ccc tgg gtc aac gct ctc ttt gcc tac ggc atc      528
Ala Ile Ser Lys Lys Pro Trp Val Asn Ala Leu Phe Ala Tyr Gly Ile
                165                 170                 175

gac gtc att gga tcg tcc aga tgg atc tgg ctg cag tct cac atc atg      576
Asp Val Ile Gly Ser Ser Arg Trp Ile Trp Leu Gln Ser His Ile Met
            180                 185                 190

cga cat cac acc tac acc aat cag cat ggt ctc gac ctg gat gcc gag      624
Arg His His Thr Tyr Thr Asn Gln His Gly Leu Asp Leu Asp Ala Glu
        195                 200                 205

tcc gca gaa cca ttc ctt gtg ttc cac aac tac cct gct gcc aac act      672
Ser Ala Glu Pro Phe Leu Val Phe His Asn Tyr Pro Ala Ala Asn Thr
    210                 215                 220

gct cga aag tgg ttt cac cga ttc cag gcc tgg tac atg tac ctc gtg      720
Ala Arg Lys Trp Phe His Arg Phe Gln Ala Trp Tyr Met Tyr Leu Val
225                 230                 235                 240

ctt gga gcc tac ggc gtt tcg ctg gtg tac aac cct ctc tac atc ttc      768
Leu Gly Ala Tyr Gly Val Ser Leu Val Tyr Asn Pro Leu Tyr Ile Phe
                245                 250                 255

cga atg cag cac aac gac acc att ccc gag tct gtc aca gcc atg cga      816
Arg Met Gln His Asn Asp Thr Ile Pro Glu Ser Val Thr Ala Met Arg
            260                 265                 270

gag aac ggc ttt ctg cga cgg tac cga acc ctt gca ttc gtt atg cga      864
Glu Asn Gly Phe Leu Arg Arg Tyr Arg Thr Leu Ala Phe Val Met Arg
        275                 280                 285

gct ttc ttc atc ttt cga acc gcc ttc ttg ccc tgg tat ctc act gga      912
Ala Phe Phe Ile Phe Arg Thr Ala Phe Leu Pro Trp Tyr Leu Thr Gly
    290                 295                 300

acc tcc ctg ctc atc acc att cct ctg gtg ccc act gct acc ggt gcc      960
Thr Ser Leu Leu Ile Thr Ile Pro Leu Val Pro Thr Ala Thr Gly Ala
305                 310                 315                 320

ttc ctc acc ttc ttt ttc atc ttg tct cac aac ttc gat ggc tcg gag     1008
Phe Leu Thr Phe Phe Phe Ile Leu Ser His Asn Phe Asp Gly Ser Glu
                325                 330                 335

cga atc ccc gac aag aac tgc aag gtc aag agc tcc gag aag gac gtt     1056
Arg Ile Pro Asp Lys Asn Cys Lys Val Lys Ser Ser Glu Lys Asp Val
            340                 345                 350

gaa gcc gat cag atc gac tgg tac aga gct cag gtg gag acc tct tcc     1104
Glu Ala Asp Gln Ile Asp Trp Tyr Arg Ala Gln Val Glu Thr Ser Ser
        355                 360                 365

acc tac ggt gga ccc att gcc atg ttc ttt act ggc ggt ctc aac ttc     1152
Thr Tyr Gly Gly Pro Ile Ala Met Phe Phe Thr Gly Gly Leu Asn Phe
    370                 375                 380

cag atc gag cat cac ctc ttt cct cga atg tcg tct tgg cac tat ccc     1200
Gln Ile Glu His His Leu Phe Pro Arg Met Ser Ser Trp His Tyr Pro
385                 390                 395                 400

ttc gtg cag caa gct gtc cga gag tgt tgc gaa cga cac gga gtt cgg     1248
Phe Val Gln Gln Ala Val Arg Glu Cys Cys Glu Arg His Gly Val Arg
                405                 410                 415

tac gtc ttc tac cct acc att gtg ggc aac atc att tcc acc ctc aag     1296
```

```
Tyr Val Phe Tyr Pro Thr Ile Val Gly Asn Ile Ile Ser Thr Leu Lys
            420                 425                 430

tac atg cac aaa gtc ggt gtg gtt cac tgt gtc aag gac gct cag gat      1344
Tyr Met His Lys Val Gly Val Val His Cys Val Lys Asp Ala Gln Asp
        435                 440                 445

tcc taa                                                              1350
Ser
```

<210> SEQ ID NO 81
<211> LENGTH: 449
<212> TYPE: PRT
<213> ORGANISM: Euglena gracilis

<400> SEQUENCE: 81

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
```

```
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser


<210> SEQ ID NO 82
<211> LENGTH: 6356
<212> TYPE: DNA
<213> ORGANISM: Artificial Sequence
<220> FEATURE:
<223> OTHER INFORMATION: Plasmid pY157

<400> SEQUENCE: 82

ttgagaagcc cattgtatat tattaggatc gtagcattat tgtggcaaaa aatattcaag     60

tgctcatgtg aattgacacg atcacgtaaa tacctggtga aattgctagt attcgtgatg    120

ttctaataca actctgttca atatttccgg cgctctcttg tatacaagag cacaagacat    180

gcaccccaca ttaaccgagg tcaagtgttt atgtatgaaa agtgacataa atcgtccaaa    240

aaaaagtagc acatagttgt atggctgtaa gttatgtgat tgtcagttct tcggccttcc    300

aactcctatg caccgtcttc aatcatctac ccccgtgccc cacaccccgc actattagag    360

tttatcacag tcagctaaac tgcttgcaca tctacacctc tgactacacc accatggatt    420

tcttcagacg gcaccagaaa aaggtgctgg cactggtagg tgtggcgctg agttcctacc    480

tgtttatcga ctatgtgaag aaaaagttct tcgagatcca gggtcgtttg agctcggagc    540

gaaccgctaa acagaatctc cggcgccgat ttgaacagaa ccagcaggat gcagatttta    600

caatcatggc tctgctatcc agcttgacga caccggtaat ggagcgttac cccgtcgacc    660

agatcaaggc agagttacag agcaagagac gccccacaga ccgggttttg gctctcgaga    720

gctccacctc gtcctcagct accgcacaaa ccgtgcccac catgacaagt ggcgccacag    780

aggagggcga gaagttaatt aactttggcc ggcctttacc tgcaggataa cttcgtataa    840

tgtatgctat acgaagttat gaattctctc tcttgagctt ttccataaca agttcttctg    900

cctccaggaa gtccatgggt ggtttgatca tggttttggt gtagtggtag tgcagtggtg    960

gtattgtgac tggggatgta gttgagaata agtcatacac aagtcagctt tcttcgagcc   1020

tcatataagt ataagtagtt caacgtatta gcactgtacc cagcatctcc gtatcgagaa   1080

acacaacaac atgccccatt ggacagatca tgcggataca caggttgtgc agtatcatac   1140

atactcgatc agacaggtcg tctgaccatc atacaagctg aacaagcgct ccatacttgc   1200

acgctctcta tatacacagt taaattacat atccatagtc taacctctaa cagttaatct   1260

tctggtaagc ctcccagcca gccttctggt atcgcttggc ctcctcaata ggatctcggt   1320
```

-continued

```
tctggccgta cagacctcgg ccgacaatta tgatatccgt tccggtagac atgacatcct   1380
caacagttcg gtactgctgt ccgagagcgt ctcccttgtc gtcaagaccc accccggggg   1440
tcagaataag ccagtcctca gagtcgccct taggtcggtt ctgggcaatg aagccaacca   1500
caaactcggg gtcggatcgg gcaagctcaa tggtctgctt ggagtactcg ccagtggcca   1560
gagagccctt gcaagacagc tcggccagca tgagcagacc tctggccagc ttctcgttgg   1620
gagaggggac taggaactcc ttgtactggg agttctcgta gtcagagacg tcctccttct   1680
tctgttcaga gacagtttcc tcggcaccag ctcgcaggcc agcaatgatt ccggttccgg   1740
gtacaccgtg ggcgttggtg atatcggacc actcggcgat tcggtgacac cggtactggt   1800
gcttgacagt gttgccaata tctgcgaact ttctgtcctc gaacaggaag aaaccgtgct   1860
taagagcaag ttccttgagg gggagcacag tgccggcgta ggtgaagtcg tcaatgatgt   1920
cgatatgggt tttgatcatg cacacataag gtccgacctt atcggcaagc tcaatgagct   1980
ccttggtggt ggtaacatcc agagaagcac acaggttggt tttcttggct gccacgagct   2040
tgagcactcg agcggcaaag gcggacttgt ggacgttagc tcgagcttcg taggagggca   2100
ttttggtggt gaagaggaga ctgaaataaa tttagtctgc agaacttttt atcggaacct   2160
tatctggggc agtgaagtat atgttatggt aatagttacg agttagttga acttatagat   2220
agactggact atacggctat cggtccaaat tagaaagaac gtcaatggct ctctgggcgt   2280
cgcctttgcc gacaaaaatg tgatcatgat gaaagccagc aatgacgttg cagctgatat   2340
tgttgtcggc caaccgcgcc gaaaacgcag ctgtcagacc cacagcctcc aacgaagaat   2400
gtatcgtcaa agtgatccaa gcacactcat agttggagtc gtactccaaa ggcggcaatg   2460
acgagtcaga cagatactcg tcgactcatc gatataactt cgtataatgt atgctatacg   2520
aagttatcct aggtatagat cttgcacttc ttattttctt cacgcgtttg cagctcaaca   2580
ttctaggacg acgaaactac gtcaacagtg ttgtcgctct ggcgcagcag ggccgagagg   2640
gtaatgccga gggtcgagtg gcgccctcgt ttggtgatct tgcagatatg ggctatttcg   2700
gcgacctttc aggctcgtcc agcttcggag aaactattgt cgatcccgat ctggacgaac   2760
agtaccttac cttttcgtgg tggctgctga acgagggatg ggtgtcgctg agcgagcgag   2820
tggaggaagc ggttcgtcga gtgtgggacc ccgtgtcacc caaggccgaa cttggatttg   2880
acgagttgtc ggaactcatt ggacgaacac agatgctcat tgatcgacct ctcaatccct   2940
cgtcgccact caactttctg agccagctgc tgccaccacg ggagcaggag gagtacgtgc   3000
ttgcccagaa ccccagcgat actgctgccc ccattgtagg acctaccctc cgacggcttc   3060
tggacgagac tgccgacttc atcgagtccc ctaatgccgc agaggtgatt gagcgacttg   3120
ttcactccgg tctctctgtg ttcatggaca agctggctgt cacgtttgga gccacacctg   3180
ctgattcggg ttcgccttat cctgtggtgc tgcctactgc aaaggtcaag ctgccctcca   3240
ttcttgccaa catggctcga caggctggag gcatggccca gggatcgccg ggcgtggaaa   3300
acgagtacat tgacgtgatg aaccaagtgc aggagctgac ctcctttagt gctgtggtct   3360
attcatcttt tgattgggct ctctagaggc tcattcacga aagacacgaa gaacgaagat   3420
ggggactgaa tacagcgctc tcatttgtac acaaatgatt tatgacagag taacttgtac   3480
atcatgtaga gcatacatac tgaaggtgtg atctcacggg atatcttgaa gaccactcgt   3540
agctggaggc ataggtagtg ctagtacgga tacttgcacc gtatccaaca taagtagagg   3600
agcctcctag tggctattgg tacaccgata aagatacaca tacatggcgc gccagctgca   3660
ttaatgaatc ggccaacgcg cggggagagg cggtttgcgt attgggcgct cttccgcttc   3720
```

-continued ctcgctcact gactcgctgc gctcggtcgt tcggctgcgg cgagcggtat cagctcactc 3780
aaaggcggta atacggttat ccacagaatc aggggataac gcaggaaaga acatgtgagc 3840
aaaaggccag caaaaggcca ggaaccgtaa aaaggccgcg ttgctggcgt ttttccatag 3900
gctccgcccc cctgacgagc atcacaaaaa tcgacgctca agtcagaggt ggcgaaaccc 3960
gacaggacta taaagatacc aggcgtttcc ccctggaagc tccctcgtgc gctctcctgt 4020
tccgaccctg ccgcttaccg gatacctgtc cgcctttctc ccttcgggaa gcgtggcgct 4080
ttctcatagc tcacgctgta ggtatctcag ttcggtgtag gtcgttcgct ccaagctggg 4140
ctgtgtgcac gaaccccccg ttcagcccga ccgctgcgcc ttatccggta actatcgtct 4200
tgagtccaac ccggtaagac acgacttatc gccactggca gcagccactg gtaacaggat 4260
tagcagagcg aggtatgtag gcggtgctac agagttcttg aagtggtggc ctaactacgg 4320
ctacactaga agaacagtat ttggtatctg cgctctgctg aagccagtta ccttcggaaa 4380
aagagttggt agctcttgat ccggcaaaca aaccaccgct ggtagcggtg gtttttttgt 4440
ttgcaagcag cagattacgc gcagaaaaaa aggatctcaa gaagatcctt tgatcttttc 4500
tacggggtct gacgctcagt ggaacgaaaa ctcacgttaa gggattttgg tcatgagatt 4560
atcaaaaagg atcttcacct agatcctttt aaattaaaaa tgaagtttta aatcaatcta 4620
aagtatatat gagtaaactt ggtctgacag ttaccaatgc ttaatcagtg aggcacctat 4680
ctcagcgatc tgtctatttc gttcatccat agttgcctga ctccccgtcg tgtagataac 4740
tacgatacgg gagggcttac catctggccc cagtgctgca atgataccgc gagacccacg 4800
ctcaccggct ccagatttat cagcaataaa ccagccagcc ggaagggccg agcgcagaag 4860
tggtcctgca actttatccg cctccatcca gtctattaat tgttgccggg aagctagagt 4920
aagtagttcg ccagttaata gtttgcgcaa cgttgttgcc attgctacag gcatcgtggt 4980
gtcacgctcg tcgtttggta tggcttcatt cagctccggt tcccaacgat caaggcgagt 5040
tacatgatcc cccatgttgt gcaaaaaagc ggttagctcc ttcggtcctc cgatcgttgt 5100
cagaagtaag ttggccgcag tgttatcact catggttatg gcagcactgc ataattctct 5160
tactgtcatg ccatccgtaa gatgcttttc tgtgactggt gagtactcaa ccaagtcatt 5220
ctgagaatag tgtatgcggc gaccgagttg ctcttgcccg gcgtcaatac gggataatac 5280
cgcgccacat agcagaactt taaaagtgct catcattgga aaacgttctt cggggcgaaa 5340
actctcaagg atcttaccgc tgttgagatc cagttcgatg taacccactc gtgcacccaa 5400
ctgatcttca gcatctttta ctttcaccag cgtttctggg tgagcaaaaa caggaaggca 5460
aaatgccgca aaaaagggaa taagggcgac acggaaatgt tgaatactca tactcttcct 5520
ttttcaatat tattgaagca tttatcaggg ttattgtctc atgagcggat acatatttga 5580
atgtatttag aaaaataaac aaataggggt tccgcgcaca tttccccgaa aagtgccacc 5640
tgatgcggtg tgaaataccg cacagatgcg taaggagaaa ataccgcatc aggaaattgt 5700
aagcgttaat attttgttaa aattcgcgtt aaatttttgt taaatcagct cattttttaa 5760
ccaataggcc gaaatcggca aaatccctta taaatcaaaa gaatagaccg agatagggtt 5820
gagtgttgtt ccagtttgga acaagagtcc actattaaag aacgtggact ccaacgtcaa 5880
agggcgaaaa accgtctatc agggcgatgg cccactacgt gaaccatcac cctaatcaag 5940
ttttttgggg tcgaggtgcc gtaaagcact aaatcggaac cctaaaggga gcccccgatt 6000
tagagcttga cggggaaagc cggcgaacgt ggcgagaaag gaagggaaga aagcgaaagg 6060

```
agcgggcgct agggcgctgg caagtgtagc ggtcacgctg cgcgtaacca ccacacccgc   6120

cgcgcttaat gcgccgctac agggcgcgtc cattcgccat tcaggctgcg caactgttgg   6180

gaagggcgat cggtgcgggc ctcttcgcta ttacgccagc tggcgaaagg gggatgtgct   6240

gcaaggcgat taagttgggt aacgccaggg ttttcccagt cacgacgttg taaaacgacg   6300

gccagtgaat tgtaatacga ctcactatag ggcgaattgg gcccgacgtc gcatgc       6356


<210> SEQ ID NO 83
<211> LENGTH: 5910
<212> TYPE: DNA
<213> ORGANISM: Artificial Sequence
<220> FEATURE:
<223> OTHER INFORMATION: Plasmid pY87

<400> SEQUENCE: 83

catcaaagga agggtgaatc caaggaagtt cttgacaaac tgctggaatc ggtacagctt     60

ggacgacttg tcgttgctaa cctggtcata gaggtcgttc tcaccaaagg ccatgatggg    120

aacaagggcg acatttccga cctccatacc aagtcgaaca aaccctttc gcttgagtag     180

caccaggtcc atgacaccgg gtctggccag aagactttcc tgtgctccac caacgacaat    240

gcagatagac tggtttcgct tgaggagggc cttgcaggac ttcttggaga cagaagcgac    300

tcccagactc atgaggtact ctctgtagag aggcactcgg aagttgttgg tgagagtcat    360

aagagaaaca gggatgcccg gaaagagctt ggaccatcca gctccctcgg tggcaattcc    420

accaaaggct cccatgccga taatgccgtg ggggtggtag ccgaagatgt attttctgcc    480

agtgggcttg agttttgtgg gcgacagctg tgggtcgttt tcgccaatga tctggttggc    540

gtaggagttg agggacccgt taagaagcgt ggaatcagat gcagtggagc cagcagaggc    600

ggacgacaaa ggtcgtcggt tagtggtgcc attgttgccg ttgccgttaa gttcggagcc    660

cgaggcgtgg ccgttggagc cagatgattc tccacggcta tatctgctgt cgtggttaat    720

taactttggc cggcctttac ctgcaggata acttcgtata atgtatgcta tacgaagtta    780

tgaattctct ctcttgagct tttccataac aagttcttct gcctccagga agtccatggg    840

tggtttgatc atggttttgg tgtagtggta gtgcagtggt ggtattgtga ctggggatgt    900

agttgagaat aagtcataca caagtcagct ttcttcgagc ctcatataag tataagtagt    960

tcaacgtatt agcactgtac ccagcatctc cgtatcgaga aacacaacaa catgccccat   1020

tggacagatc atgcggatac acaggttgtg cagtatcata catactcgat cagacaggtc   1080

gtctgaccat catacaagct gaacaagcgc tccatacttg cacgctctct atatacacag   1140

ttaaattaca tatccatagt ctaacctcta acagttaatc ttctggtaag cctcccagcc   1200

agccttctgg tatcgcttgg cctcctcaat aggatctcgg ttctggccgt acagacctcg   1260

gccgacaatt atgatatccg ttccggtaga catgacatcc tcaacagttc ggtactgctg   1320

tccgagagcg tctcccttgt cgtcaagacc caccccgggg gtcagaataa gccagtcctc   1380

agagtcgccc ttaggtcggt tctgggcaat gaagccaacc acaaactcgg ggtcggatcg   1440

ggcaagctca atggtctgct tggagtactc gccagtggcc agagagccct tgcaagacag   1500

ctcggccagc atgagcagac ctctggccag cttctcgttg ggagagggga ctaggaactc   1560

cttgtactgg gagttctcgt agtcagagac gtcctccttc ttctgttcag agacagtttc   1620

ctcggcacca gctcgcaggc cagcaatgat tccggttccg ggtacaccgt gggcgttggt   1680

gatatcggac cactcggcga ttcggtgaca ccggtactgg tgcttgacag tgttgccaat   1740

atctgcgaac tttctgtcct cgaacaggaa gaaaccgtgc ttaagagcaa gttccttgag   1800
```

-continued gggggagcaca gtgccggcgt aggtgaagtc gtcaatgatg tcgatatggg ttttgatcat 1860
gcacacataa ggtccgacct tatcggcaag ctcaatgagc tccttggtgg tggtaacatc 1920
cagagaagca cacaggttgg ttttcttggc tgccacgagc ttgagcactc gagcggcaaa 1980
ggcggacttg tggacgttag ctcgagcttc gtaggagggc attttggtgg tgaagaggag 2040
actgaaataa atttagtctg cagaactttt tatcggaacc ttatctgggg cagtgaagta 2100
tatgttatgg taatagttac gagttagttg aacttataga tagactggac tatacggcta 2160
tcggtccaaa ttagaaagaa cgtcaatggc tctctgggcg tcgcctttgc cgacaaaaat 2220
gtgatcatga tgaaagccag caatgacgtt gcagctgata ttgttgtcgg ccaaccgcgc 2280
cgaaaacgca gctgtcagac ccacagcctc caacgaagaa tgtatcgtca aagtgatcca 2340
agcacactca tagttggagt cgtactccaa aggcggcaat gacgagtcag acagatactc 2400
gtcgactcat cgatataact tcgtataatg tatgctatac gaagttatcc taggtataga 2460
tctcaccgta cgtttcatga aggcgggcag aaagtactcg atggtggaga tgattgctcg 2520
gaggtacttg ttctgcggcc agtatctctc agcaatcagg tgatactcct ggacgtccag 2580
agggtagtat gtgtgcgtgg gctccagatc caccgtcttg tgcagagtta tggggaagta 2640
gcggccaaag agcttccaga tgaagaagtt tcttgaaata ggcgagtatc gcttgaccac 2700
tcctccgttg gacggggagt cgtctttaac agcgtacact acatacgcaa tcacaaatgg 2760
ccagagcagt ggaattgcgc agcatagcat gaaaattgtg aggaaagtgg gaatgctgaa 2820
aatgtgccag accagagaga aggtctcaca tcggttgagt aatggtgtcg atagcggggc 2880
atatcggatt cccgcgattt tgggtgccgt gtcgtttttg tctcgcgact tgtagtattg 2940
tgagtcgata gtcatagctt ttgttttgtg tgacttgtct gttgcctgtt gttagaagaa 3000
aaagtgggag cttatcagtc acggtccacg aacgatttcg tacttgtacg taattggtcg 3060
tgagaactgt tgcagagccg gtgctttttt ttgtggccaa gtcgacaggt cgatttcggc 3120
gctgtgcgag gttgctggga tgtgctggtt tggctgccaa atgtggggaa gatttcaacc 3180
tcggatttga cgtgtgtaga ggcgcgccag ctgcattaat gaatcggcca acgcgcgggg 3240
agaggcggtt tgcgtattgg gcgctcttcc gcttcctcgc tcactgactc gctgcgctcg 3300
gtcgttcggc tgcggcgagc ggtatcagct cactcaaagg cggtaatacg gttatccaca 3360
gaatcagggg ataacgcagg aaagaacatg tgagcaaaag gccagcaaaa ggccaggaac 3420
cgtaaaaagg ccgcgttgct ggcgtttttc cataggctcc gcccccctga cgagcatcac 3480
aaaaatcgac gctcaagtca gaggtggcga aacccgacag gactataaag ataccaggcg 3540
tttccccctg gaagctccct cgtgcgctct cctgttccga ccctgccgct taccggatac 3600
ctgtccgcct ttctcccttc gggaagcgtg gcgctttctc atagctcacg ctgtaggtat 3660
ctcagttcgg tgtaggtcgt tcgctccaag ctgggctgtg tgcacgaacc ccccgttcag 3720
cccgaccgct gcgccttatc cggtaactat cgtcttgagt ccaacccggt aagacacgac 3780
ttatcgccac tggcagcagc cactggtaac aggattagca gagcgaggta tgtaggcggt 3840
gctacagagt tcttgaagtg gtggcctaac tacggctaca ctagaagaac agtatttggt 3900
atctgcgctc tgctgaagcc agttaccttc ggaaaaagag ttggtagctc ttgatccggc 3960
aaacaaacca ccgctggtag cggtggtttt tttgtttgca agcagcagat tacgcgcaga 4020
aaaaaaggat ctcaagaaga tcctttgatc ttttctacgg ggtctgacgc tcagtggaac 4080
gaaaactcac gttaagggat tttggtcatg agattatcaa aaaggatctt cacctagatc 4140

```
cttttaaatt aaaaatgaag ttttaaatca atctaaagta tatatgagta aacttggtct   4200

gacagttacc aatgcttaat cagtgaggca cctatctcag cgatctgtct atttcgttca   4260

tccatagttg cctgactccc cgtcgtgtag ataactacga tacgggaggg cttaccatct   4320

ggccccagtg ctgcaatgat accgcgagac ccacgctcac cggctccaga tttatcagca   4380

ataaaccagc cagccggaag ggccgagcgc agaagtggtc ctgcaacttt atccgcctcc   4440

atccagtcta ttaattgttg ccgggaagct agagtaagta gttcgccagt taatagtttg   4500

cgcaacgttg ttgccattgc tacaggcatc gtggtgtcac gctcgtcgtt tggtatggct   4560

tcattcagct ccggttccca acgatcaagg cgagttacat gatcccccat gttgtgcaaa   4620

aaagcggtta gctccttcgg tcctccgatc gttgtcagaa gtaagttggc cgcagtgtta   4680

tcactcatgg ttatggcagc actgcataat tctcttactg tcatgccatc cgtaagatgc   4740

ttttctgtga ctggtgagta ctcaaccaag tcattctgag aatagtgtat gcggcgaccg   4800

agttgctctt gcccggcgtc aatacgggat aataccgcgc cacatagcag aactttaaaa   4860

gtgctcatca ttggaaaacg ttcttcgggg cgaaaactct caaggatctt accgctgttg   4920

agatccagtt cgatgtaacc cactcgtgca cccaactgat cttcagcatc ttttactttc   4980

accagcgttt ctgggtgagc aaaaacagga aggcaaaatg ccgcaaaaaa gggaataagg   5040

gcgacacgga aatgttgaat actcatactc ttcctttttc aatattattg aagcatttat   5100

cagggttatt gtctcatgag cggatacata tttgaatgta tttagaaaaa taaacaaata   5160

ggggttccgc gcacatttcc ccgaaaagtg ccacctgatg cggtgtgaaa taccgcacag   5220

atgcgtaagg agaaaatacc gcatcaggaa attgtaagcg ttaatatttt gttaaaattc   5280

gcgttaaatt tttgttaaat cagctcattt tttaaccaat aggccgaaat cggcaaaatc   5340

ccttataaat caaaagaata gaccgagata gggttgagtg ttgttccagt ttggaacaag   5400

agtccactat taaagaacgt ggactccaac gtcaaagggc gaaaaaccgt ctatcagggc   5460

gatggcccac tacgtgaacc atcaccctaa tcaagttttt tggggtcgag gtgccgtaaa   5520

gcactaaatc ggaaccctaa agggagcccc cgatttagag cttgacgggg aaagccggcg   5580

aacgtggcga gaaaggaagg gaagaaagcg aaaggagcgg gcgctagggc gctggcaagt   5640

gtagcggtca cgctgcgcgt aaccaccaca cccgccgcgc ttaatgcgcc gctacagggc   5700

gcgtccattc gccattcagg ctgcgcaact gttgggaagg gcgatcggtg cgggcctctt   5760

cgctattacg ccagctggcg aaagggggat gtgctgcaag gcgattaagt tgggtaacgc   5820

cagggttttc ccagtcacga cgttgtaaaa cgacggccag tgaattgtaa tacgactcac   5880

tatagggcga attgggcccg acgtcgcatg                                     5910
```

<210> SEQ ID NO 84
<211> LENGTH: 34
<212> TYPE: DNA
<213> ORGANISM: Escherichia coli

<400> SEQUENCE: 84

```
ataacttcgt ataatgtatg ctatacgaag ttat                                  34
```

<210> SEQ ID NO 85
<211> LENGTH: 20
<212> TYPE: DNA
<213> ORGANISM: Artificial Sequence
<220> FEATURE:
<223> OTHER INFORMATION: Primer UP 768

<400> SEQUENCE: 85

-continued

```
acccgtgttt cgtctaaaag                                              20


<210> SEQ ID NO 86
<211> LENGTH: 22
<212> TYPE: DNA
<213> ORGANISM: Artificial Sequence
<220> FEATURE:
<223> OTHER INFORMATION: Primer LP 769

<400> SEQUENCE: 86

ggtagataca agtggcaata ac                                           22
```